US010676752B2

(12) United States Patent
Ren et al.

(10) Patent No.: US 10,676,752 B2
(45) Date of Patent: Jun. 9, 2020

(54) METHODS CONTROLLING GENE EXPRESSION

(71) Applicant: BASF Plant Science GmbH, Ludwigshafen (DE)

(72) Inventors: Peifeng Ren, Cary, NC (US); Hee-Sook Song, Raleigh, NC (US); John McMillan, Raleigh, NC (US)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 465 days.

(21) Appl. No.: 14/737,789

(22) Filed: Jun. 12, 2015

(65) Prior Publication Data
US 2016/0152994 A1   Jun. 2, 2016

Related U.S. Application Data

(62) Division of application No. 11/918,554, filed as application No. PCT/EP2006/061604 on Apr. 13, 2006, now Pat. No. 9,085,774.

(60) Provisional application No. 60/672,976, filed on Apr. 19, 2005.

(51) Int. Cl.
*C12N 15/82* (2006.01)
*C12N 15/79* (2006.01)

(52) U.S. Cl.
CPC ......... *C12N 15/8218* (2013.01); *C12N 15/79* (2013.01); *C12N 15/8216* (2013.01)

(58) Field of Classification Search
None
See application file for complete search history.

(56) References Cited

U.S. PATENT DOCUMENTS

| | | | |
|---|---|---|---|
| 2002/0022018 | A1 | 2/2002 | Curiel et al. |
| 2004/0268441 | A1 | 12/2004 | Vance et al. |
| 2015/0144669 | A1 | 5/2015 | Chang |

FOREIGN PATENT DOCUMENTS

| | | |
|---|---|---|
| NZ | 260511 | 7/1995 |
| WO | WO-98/44138 A1 | 10/1998 |
| WO | WO-00/77223 A1 | 12/2000 |
| WO | WO-03/093441 A2 | 11/2003 |
| WO | WO-2004/009779 A2 | 1/2004 |
| WO | WO-2005/035769 A2 | 4/2005 |
| WO | WO-2006/073727 A2 | 7/2006 |
| WO | WO-2006/074400 A2 | 7/2006 |
| WO | WO-2006/138638 A1 | 12/2006 |
| WO | WO-2007/047016 A2 | 4/2007 |

OTHER PUBLICATIONS

Parizotto et al, Genes and Dev. (2004) 18:2237-2242.*
Pasquinelli, A.E., Nature Reviews Genetics (2012) 13:271-282.*
Zhang et al, The Plant Journal (2006) 46:243-259.*
Mansfield, J. H., et al., "MicroRNA-responsive 'sensor' transgenes uncover Hox-like and other developmentally regulated patterns of vertebrate microRNA expression", Nature Genetics, 2004, vol. 36, No. 10, pp. 1079-1083.
Stark, A., et al., "Identification of *Drosophila* microRNA targets", PLOS Biology, 2003, vol. 1, Issue 3, pp. 397-409.
Brennecke, J., et al., "*bantam* encodes a developmentally regulated microRNA that controls cell proliferation and regulates the proapoptotic gene *hid* in *Drosophila*", Cell, 2003, vol. 113, pp. 25-36.
Laufs, P., et al., "MicroRNA regulation of the CUC genes is required for boundary size control in *Arabidopsis* meristems", Development, 2004, vol. 131, No. 17, pp. 4311-4322.
Palatnik, J. F., et al., "Control of leaf morphogenesis by microRNAs", Nature, 2003, vol. 425, pp. 257-263.
Mallory, A. C., et al., "MicroRNA regulation of NAC-domain targets is required for proper formation and separation of adjacent embryonic, vegetative, and floral organs", Current Biology, 2004, vol. 14, pp. 1035-1046.
Chen, X., "A microRNA as a translational repressor of *APETALA2* in *Arabidopsis* flower development", Science, 2004, vol. 303, pp. 2022-2025.
Zeng, Y., et al., "Both natural and designed micro RNAs can inhibit the expression of cognate mRNAs when expressed in human cells", Molecular Cell, 2002, vol. 9, pp. 1327-1333.
Lim, L. P., et al., "Microarray analysis shows that some microRNAs downregulate large numbers of target mRNAs", Nature, 2005, vol. 433, pp. 769-773.
Berger, E. M., et al., "Inhibition of micro-RNA-induced RNA silencing by 2'-O-methyl oligonucleotides in *Drosophila* S2 cells", In Vitro Cell. Dev. Biol.—Animal, 2005, vol. 41, pp. 12-18.
Carrington, J. C., et al., "Role of microRNAs in plant and animal development", Science, 2003, vol. 301, pp. 336-338.
He, L., et al., "MicroRNAs: small RNAs with a big role in gene regulation", Nature Reviews, 2004, vol. 5, pp. 522-531.
Bartel, D. P., et al., "Micromanagers of gene expression: the potentially widespread influence of metazoan microRNAs", Nature Review, 2004, vol. 5, pp. 396-400.
Brown, B. D., et al., "Endogenous microRNA regulation suppresses transgene expression in hematopoietic lineages and enables stable gene transfer", Nature Medicine, 2006, vol. 12, No. 5, pp. 585-591.

(Continued)

*Primary Examiner* — Mykola V. Kovalenko
(74) *Attorney, Agent, or Firm* — Marshall, Gerstein & Borun LLP

(57) ABSTRACT

The present invention is in the field of genetics, especially plant genetics, and provides agents capable of controlling gene expression. The present invention specifically provides sequences of naturally occurring, tissue-specifically expressed microRNAs. The invention further provides for transgenic expression constructs comprising sequences encoding such microRNAs. By incorporation of the microRNA encoding sequence the expression from the expression construct is specifically silenced in the tissue where the naturally occurring microRNA is naturally expressed. Thereby the expression profile resulting from the promoter is modulated and leakiness is reduced. The invention further provides for a method for modulating transgenic expression by incorporating sequences encoding the microRNAs into transgenic expression constructs. The compositions and methods of the invention can be used to enhance performance of agricultural relevant crops and for therapy, prophylaxis, research and diagnostics in diseases and disorders, which afflict mammalian species.

16 Claims, 5 Drawing Sheets

Specification includes a Sequence Listing.

(56) References Cited

OTHER PUBLICATIONS

Vance, V., et al., "RNA silencing in plants—defense and counterdefense", Science, 2001, vol. 292, pp. 2277-2280.
Zamore, P. D., "RNA interference: listening to the sound of silence", Nature Structural Biology, 2001, vol. 8, No. 9, pp. 746-749.
Lee, R. C., et al., "An extensive class of small RNAs in *Caenorhabditis elegans*", Science, 2001, vol. 294, pp. 862-864.
Mallory, A. C., et al., "MicroRNA control of *PHABULOSA* in leaf development: importance of pairing to the microRNA 5' region", The EMBO Journal, 2004, vol. 23, pp. 3356-3364.
Doench, J. G., et al., "Specificity of microRNA target selection in translational repression", Genes & Development, 2004, vol. 18, pp. 504-511.
McManus, M. T., et al., "Gene silencing using micro-RNA designed hairpins", RNA, 2002, vol. 8, pp. 842-850.
Juarez, M. T., et al., "MicroRNA-mediated repression of *rolled leaf1* specifies maize leaf polarity", Nature, 2004, vol. 428, pp. 84-88.
Kidner, C. A., et al., "Spatially restricted microRNA directs leaf polarity through ARGONAUTE1", Nature, 2004, vol. 428, pp. 81-84.
Jones-Rhoades, M. W., et al., "Computational identification of plant microRNAs and their targets, including a stress-induced miRNA", Molecular Cell, 2004, vol. 14, pp. 787-799.
Sunkar, R., et al., "Novel and stress-regulated microRNAs and other small RNAs from *Arabidopsis*", The Plant Cell, 2004, vol. 16, pp. 2001-2019.
Yekta, S., et al., "MicroRNA-directed cleavage of *HOXB8* mRNA", Science, 2004, vol. 304, pp. 594-596.
Sempere, L. F., et al., "Expression profiling of mammalian microRNAs uncovers a subset of brain-expressed microRNAs with pos murine and human neuronal differentiation", Genome Biology, 2004, vol. 5, R.13.
Opperman, C. H., et al., "Root-knot nematode-directed expression of a plant root-specific gene", Science, 1994, vol. 263, pp. 221-223.
Lagos-Quintana, M., et al., "Identification of novel genes coding for small expressed RNAs", Science, 2001, vol. 294, pp. 853-858.
Lagos-Quintana, M., et al., "Identification of tissue-specific microRNAs from mouse", Current Biology, 2002, vol. 12, pp. 735-739.
Lim, L. P., et al., "Vertebrate microRNA genes", Science, 2003, vol. 299, p. 1540.
Mourelatos, Z., et al., "miRNPs: a novel class of ribonucleoproteins containing numerous microRNAs", Genes & Development, 2002, vol. 16, pp. 720-728.
Dostie, J., et al., "Numerous microRNPs in neuronal cells containing novel microRNAs", RNA, 2003, vol. 9, pp. 180-186.
Parizotto, E. A., et al., "In Vivo Investigation of the Transcription, Processing, Endonucleolytic Activity, and Functional Relevance of the Spatial Distribution of a Plant miRNA", Genes & Development, 2004, vol. 18. pp. 2237-2242.
Office Communication Issued in EP Application No. 06754739.8, dated Oct. 21, 2009.
Park, W., et al., "Carpel Factory, a Dicer Homolog, and HEN1, a Novel Protein, Act in microRNA Metabolism in *Arabidopsis thaliana*", Current Biology, 2002, vol. 12, pp. 1484-1495.
Himber, C., et al., "Transitivity-Dependent and -Independent Cell-to-Cell Movement of RNA Silencing", The EMBO Journal, 2003, vol. 22, No. 17, pp. 4523-4533.
Llave, C., et al., "Cleavage of Scarecrow-Like mRNA Targets Directed by a Class of *Arabidopsis* miRNA", Science, 2002, vol. 297, pp. 2053-2056.
Miki, D., et al., "RNA Silencing of Single and Multiple Members in a Gene Family of Rice", Plant Physiology, 2005, vol. 138, pp. 1903-1913.
Wang, J.-F., et al., "Identification of 20 microRNAs from *Oryza sativa*", Nucleic Acids Research, 2004, vol. 32, No. 5, pp. 1688-1695.
Opposition Filed in EP 1 874 936 B1 by Boult Wade Tennant, Jul. 28, 2014.
Mallory, A. C., et al., "MicroRNA-Directed Regulation of *Arabidopsis* Auxin Response FACTOR17 Is Essential for Proper Development and Modulates Expression of Early Auxin Response Genes", Plant Cell, 2005, vol. 17, No. 5, pp. 1360-1375.

\* cited by examiner

SEQUENCE LISTING

```
<160> NUMBER OF SEQ ID NOS: 270

<210> SEQ ID NO 1
<211> LENGTH: 21
<212> TYPE: RNA
<213> ORGANISM: Arabidopsis thaliana

<400> SEQUENCE: 1
ugccuggcuc ccuguaugcc a                                            21

<210> SEQ ID NO 2
<211> LENGTH: 24
<212> TYPE: RNA
<213> ORGANISM: Arabidopsis thaliana

<400> SEQUENCE: 2
uugaagagga cuuggaacuu cgau                                         24

<210> SEQ ID NO 3
<211> LENGTH: 21
<212> TYPE: RNA
<213> ORGANISM: Arabidopsis thaliana

<400> SEQUENCE: 3
ugaagcugcc agcaugaucu a                                            21

<210> SEQ ID NO 4
<211> LENGTH: 21
<212> TYPE: RNA
<213> ORGANISM: Arabidopsis thaliana

<400> SEQUENCE: 4
agaaucuuga ugaugcugca u                                            21
```

```
<210> SEQ ID NO 5
<211> LENGTH: 20
<212> TYPE: RNA
<213> ORGANISM: Arabidopsis thaliana

<400> SEQUENCE: 5
uuggacugaa gggagcuccc                                              20

<210> SEQ ID NO 6
<211> LENGTH: 21
<212> TYPE: RNA
<213> ORGANISM: Oryza sativa

<400> SEQUENCE: 6
ugacagaaga gagugagcac a                                            21

<210> SEQ ID NO 7
<211> LENGTH: 21
<212> TYPE: RNA
<213> ORGANISM: Oryza sativa

<400> SEQUENCE: 7
cgacagaaga gagugagcau a                                            21

<210> SEQ ID NO 8
<211> LENGTH: 21
<212> TYPE: RNA
<213> ORGANISM: Oryza sativa

<400> SEQUENCE: 8
uuuggauuga agggagcucu g                                            21

<210> SEQ ID NO 9
<211> LENGTH: 21
<212> TYPE: RNA
<213> ORGANISM: Oryza sativa

<400> SEQUENCE: 9
ugccuggcuc ccugaaugcc a                                            21

<210> SEQ ID NO 10
<211> LENGTH: 21
<212> TYPE: RNA
<213> ORGANISM: Oryza sativa

<400> SEQUENCE: 10
ucgauaaacc ucugcaucca g                                            21

<210> SEQ ID NO 11
<211> LENGTH: 21
<212> TYPE: RNA
<213> ORGANISM: Oryza sativa

<400> SEQUENCE: 11
uggagaagca gggcacgugc a                                            21

<210> SEQ ID NO 12
<211> LENGTH: 21
<212> TYPE: RNA
<213> ORGANISM: Oryza sativa

<400> SEQUENCE: 12
uggagaagca gggcacgugc u                                            21
```

```
<210> SEQ ID NO 13
<211> LENGTH: 21
<212> TYPE: RNA
<213> ORGANISM: Oryza sativa

<400> SEQUENCE: 13
ucggaccagg cuucauuccc c                                              21

<210> SEQ ID NO 14
<211> LENGTH: 21
<212> TYPE: RNA
<213> ORGANISM: Oryza sativa

<400> SEQUENCE: 14
ugaagcugcc agcaugaucu g                                              21

<210> SEQ ID NO 15
<211> LENGTH: 21
<212> TYPE: RNA
<213> ORGANISM: Oryza sativa

<400> SEQUENCE: 15
ucgcuuggug cagaucggga c                                              21

<210> SEQ ID NO 16
<211> LENGTH: 21
<212> TYPE: RNA
<213> ORGANISM: Oryza sativa

<400> SEQUENCE: 16
uagccaagga ugacuugccu a                                              21

<210> SEQ ID NO 17
<211> LENGTH: 21
<212> TYPE: RNA
<213> ORGANISM: Oryza sativa

<400> SEQUENCE: 17
uagccaagga ugacuugccu g                                              21

<210> SEQ ID NO 18
<211> LENGTH: 21
<212> TYPE: RNA
<213> ORGANISM: Oryza sativa

<400> SEQUENCE: 18
ugauugagcc gugccaauau c                                              21

<210> SEQ ID NO 19
<211> LENGTH: 21
<212> TYPE: RNA
<213> ORGANISM: Oryza sativa

<400> SEQUENCE: 19
uuauugagug cagcguugau g                                              21

<210> SEQ ID NO 20
<211> LENGTH: 21
<212> TYPE: RNA
<213> ORGANISM: Oryza sativa

<400> SEQUENCE: 20
uguguucuca ggucacccu u                                               21
```

```
<210> SEQ ID NO 21
<211> LENGTH: 21
<212> TYPE: RNA
<213> ORGANISM: Oryza sativa

<400> SEQUENCE: 21
ugccaaagga aauuugcccc g                                             21

<210> SEQ ID NO 22
<211> LENGTH: 20
<212> TYPE: RNA
<213> ORGANISM: Zea mays

<400> SEQUENCE: 22
ugacagaaga gagugagcac                                               20

<210> SEQ ID NO 23
<211> LENGTH: 21
<212> TYPE: RNA
<213> ORGANISM: Zea mays

<400> SEQUENCE: 23
uuuggauuga agggagcucu a                                             21

<210> SEQ ID NO 24
<211> LENGTH: 21
<212> TYPE: RNA
<213> ORGANISM: Zea mays

<400> SEQUENCE: 24
ugccuggcuc ccuguaugcc a                                             21

<210> SEQ ID NO 25
<211> LENGTH: 21
<212> TYPE: RNA
<213> ORGANISM: Zea mays

<400> SEQUENCE: 25
ucggaccagg cuucauuccc c                                             21

<210> SEQ ID NO 26
<211> LENGTH: 22
<212> TYPE: RNA
<213> ORGANISM: Zea mays

<400> SEQUENCE: 26
ugaagcugcc agcaugaucu gg                                            22

<210> SEQ ID NO 27
<211> LENGTH: 21
<212> TYPE: RNA
<213> ORGANISM: Zea mays

<400> SEQUENCE: 27
ugauugagcc gcgccaauau c                                             21

<210> SEQ ID NO 28
<211> LENGTH: 20
<212> TYPE: RNA
<213> ORGANISM: Zea mays

<400> SEQUENCE: 28
```

```
agcucaggag ggauagcgcc                                                    20

<210> SEQ ID NO 29
<211> LENGTH: 20
<212> TYPE: RNA
<213> ORGANISM: Zea mays

<400> SEQUENCE: 29
aagcucagga gggauagcgc                                                    20

<210> SEQ ID NO 30
<211> LENGTH: 21
<212> TYPE: RNA
<213> ORGANISM: Zea mays

<400> SEQUENCE: 30
agcucaggag ggauagcgcc a                                                  21

<210> SEQ ID NO 31
<211> LENGTH: 20
<212> TYPE: RNA
<213> ORGANISM: Zea mays

<400> SEQUENCE: 31
ugacagaaga gagugagcac                                                    20

<210> SEQ ID NO 32
<211> LENGTH: 21
<212> TYPE: RNA
<213> ORGANISM: Zea mays

<400> SEQUENCE: 32
uugacagaag agagugagca c                                                  21

<210> SEQ ID NO 33
<211> LENGTH: 21
<212> TYPE: RNA
<213> ORGANISM: Zea mays

<400> SEQUENCE: 33
gugacagaag agagugagca c                                                  21

<210> SEQ ID NO 34
<211> LENGTH: 21
<212> TYPE: RNA
<213> ORGANISM: Zea mays

<400> SEQUENCE: 34
ugacagaaga gagugagcac a                                                  21

<210> SEQ ID NO 35
<211> LENGTH: 21
<212> TYPE: RNA
<213> ORGANISM: Zea mays

<400> SEQUENCE: 35
uuuggauuga agggagcucu a                                                  21

<210> SEQ ID NO 36
<211> LENGTH: 21
<212> TYPE: RNA
<213> ORGANISM: Zea mays

<400> SEQUENCE: 36
```

```
uuuggauuga agggagcucu u                                              21

<210> SEQ ID NO 37
<211> LENGTH: 21
<212> TYPE: RNA
<213> ORGANISM: Zea mays

<400> SEQUENCE: 37
ucuuuggauu gaagggagcu c                                              21

<210> SEQ ID NO 38
<211> LENGTH: 20
<212> TYPE: RNA
<213> ORGANISM: Zea mays

<400> SEQUENCE: 38
uuuggauuga agggagcucu                                                20

<210> SEQ ID NO 39
<211> LENGTH: 21
<212> TYPE: RNA
<213> ORGANISM: Zea mays

<400> SEQUENCE: 39
ugccuggcuc ccuguaugcc a                                              21

<210> SEQ ID NO 40
<211> LENGTH: 22
<212> TYPE: RNA
<213> ORGANISM: Zea mays

<400> SEQUENCE: 40
ugccuggcuc ccuguaugcc au                                             22

<210> SEQ ID NO 41
<211> LENGTH: 20
<212> TYPE: RNA
<213> ORGANISM: Zea mays

<400> SEQUENCE: 41
gccuggcucc cuguaugcca                                                20

<210> SEQ ID NO 42
<211> LENGTH: 21
<212> TYPE: RNA
<213> ORGANISM: Zea mays

<400> SEQUENCE: 42
ucggaccagg cuucauuccc c                                              21

<210> SEQ ID NO 43
<211> LENGTH: 22
<212> TYPE: RNA
<213> ORGANISM: Zea mays

<400> SEQUENCE: 43
ucggaccagg cuucauuccc cc                                             22

<210> SEQ ID NO 44
<211> LENGTH: 22
<212> TYPE: RNA
<213> ORGANISM: Zea mays
```

```
<400> SEQUENCE: 44
uucggaccag gcuucauucc cc                                            22

<210> SEQ ID NO 45
<211> LENGTH: 21
<212> TYPE: RNA
<213> ORGANISM: Zea mays

<400> SEQUENCE: 45
uucggaccag gcuucauucc c                                             21

<210> SEQ ID NO 46
<211> LENGTH: 22
<212> TYPE: RNA
<213> ORGANISM: Zea mays

<400> SEQUENCE: 46
ugaagcugcc agcaugaucu gg                                            22

<210> SEQ ID NO 47
<211> LENGTH: 20
<212> TYPE: RNA
<213> ORGANISM: Zea mays

<400> SEQUENCE: 47
ugaagcugcc agcaugaucu                                               20

<210> SEQ ID NO 48
<211> LENGTH: 21
<212> TYPE: RNA
<213> ORGANISM: Zea mays

<400> SEQUENCE: 48
ugaagcugcc agcaugaucu g                                             21

<210> SEQ ID NO 49
<211> LENGTH: 22
<212> TYPE: RNA
<213> ORGANISM: Zea mays

<400> SEQUENCE: 49
ugaagcugcc agcaugaucu au                                            22

<210> SEQ ID NO 50
<211> LENGTH: 22
<212> TYPE: RNA
<213> ORGANISM: Zea mays

<400> SEQUENCE: 50
augaagcugc cagcaugauc ua                                            22

<210> SEQ ID NO 51
<211> LENGTH: 22
<212> TYPE: RNA
<213> ORGANISM: Zea mays

<400> SEQUENCE: 51
gugaagcugc cagcaugauc ua                                            22

<210> SEQ ID NO 52
<211> LENGTH: 21
<212> TYPE: RNA
<213> ORGANISM: Zea mays
```

```
<400> SEQUENCE: 52
ugauugagcc gugccaauau c                                              21

<210> SEQ ID NO 53
<211> LENGTH: 21
<212> TYPE: RNA
<213> ORGANISM: Zea mays

<400> SEQUENCE: 53
ugauugagcc gcgccaauau c                                              21

<210> SEQ ID NO 54
<211> LENGTH: 20
<212> TYPE: RNA
<213> ORGANISM: Zea mays

<400> SEQUENCE: 54
ugauugagcc gcgccaauau                                                20

<210> SEQ ID NO 55
<211> LENGTH: 21
<212> TYPE: RNA
<213> ORGANISM: Zea mays

<400> SEQUENCE: 55
aagcucagga gggauagcgc c                                              21

<210> SEQ ID NO 56
<211> LENGTH: 21
<212> TYPE: RNA
<213> ORGANISM: Mus musculus

<400> SEQUENCE: 56
uggaauguaa agaaguaugu a                                              21

<210> SEQ ID NO 57
<211> LENGTH: 23
<212> TYPE: RNA
<213> ORGANISM: Mus musculus

<400> SEQUENCE: 57
ucuuugguua ucuagcugua uga                                            23

<210> SEQ ID NO 58
<211> LENGTH: 23
<212> TYPE: RNA
<213> ORGANISM: Mus musculus

<400> SEQUENCE: 58
uggaguguga caaugguguu ugu                                            23

<210> SEQ ID NO 59
<211> LENGTH: 22
<212> TYPE: RNA
<213> ORGANISM: Mus musculus

<400> SEQUENCE: 59
uuaaggcacg cggugaaugc ca                                             22

<210> SEQ ID NO 60
<211> LENGTH: 22
<212> TYPE: RNA
```

```
<213> ORGANISM: Mus musculus

<400> SEQUENCE: 60
ucacagugaa ccggucucuu uu                                        22

<210> SEQ ID NO 61
<211> LENGTH: 22
<212> TYPE: RNA
<213> ORGANISM: Mus musculus

<400> SEQUENCE: 61
uguaacagca acuccaugug ga                                        22

<210> SEQ ID NO 62
<211> LENGTH: 22
<212> TYPE: RNA
<213> ORGANISM: Mus musculus

<400> SEQUENCE: 62
uggaauguaa ggaagugugu gg                                        22

<210> SEQ ID NO 63
<211> LENGTH: 21
<212> TYPE: RNA
<213> ORGANISM: Homo sapiens

<400> SEQUENCE: 63
uugugcuuga ucuaaccaug u                                         21

<210> SEQ ID NO 64
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 64
caactactgc acggtaaaag tgatagg                                   27

<210> SEQ ID NO 65
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 65
gcagcttgct tcgatctctc gctcgcc                                   27

<210> SEQ ID NO 66
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 66
tgcctcgatt cgaccgtgta atggaat                                   27

<210> SEQ ID NO 67
<211> LENGTH: 27
<212> TYPE: DNA
<213> ORGANISM: Artificial sequence
<220> FEATURE:
<223> OTHER INFORMATION: Oligonucleotide primer
```

```
<400> SEQUENCE: 67
actcctggct tccttccgat ctggact                                         27

<210> SEQ ID NO 68
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 68
ccggtgacct tcttgcttct tcgatcg                                         27

<210> SEQ ID NO 69
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 69
cctctctctc acacacactc tcagtaa                                         27

<210> SEQ ID NO 70
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 70
aacaaatggc gtacttatat aaccaca                                         27

<210> SEQ ID NO 71
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 71
cgggcggaat gggatgggat tacgtgt                                         27

<210> SEQ ID NO 72
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 72
tttgtattta ggtccctaac gccctc                                          26

<210> SEQ ID NO 73
<211> LENGTH: 26
<212> TYPE: DNA
<213> ORGANISM: Artificial sequence
<220> FEATURE:
<223> OTHER INFORMATION: Oligonucleotide primer

<400> SEQUENCE: 73
tgttgatgcg gatttctgcg tgtgat                                          26

<210> SEQ ID NO 74
```

```
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 74
gccgatgccc aagaactagt cattttα                                    27

<210> SEQ ID NO 75
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 75
attaacacgt caaccaaacc gccgtcc                                    27

<210> SEQ ID NO 76
<211> LENGTH: 27
<212> TYPE: DNA
<213> ORGANISM: Artificial sequence
<220> FEATURE:
<223> OTHER INFORMATION: Oligonucleotide primer

<400> SEQUENCE: 76
aaagcgatgc ctaccatacc acactgc                                    27

<210> SEQ ID NO 77
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 77
tgcccacatt tattatggtt ttacaccc                                   28

<210> SEQ ID NO 78
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 78
tgatcacatc accgtctctc ttcattaa                                   28

<210> SEQ ID NO 79
<211> LENGTH: 28
<212> TYPE: DNA
<213> ORGANISM: Artificial sequence
<220> FEATURE:
<223> OTHER INFORMATION: Oligonucleotide primer

<400> SEQUENCE: 79
tatcccagtc tcgatattgt catccgct                                   28

<210> SEQ ID NO 80
<211> LENGTH: 22
<212> TYPE: DNA
<213> ORGANISM: Artificial sequence
<220> FEATURE:
<223> OTHER INFORMATION: miRNA-tag

<400> SEQUENCE: 80
```

-continued

| acagatcatg ctggcagctt ca | 22 |

<210> SEQ ID NO 81
<211> LENGTH: 21
<212> TYPE: DNA
<213> ORGANISM: Artificial sequence
<220> FEATURE:
<223> OTHER INFORMATION: miRNA-tag

<400> SEQUENCE: 81

| tagagctccc ttcaatccaa a | 21 |

<210> SEQ ID NO 82
<211> LENGTH: 21
<212> TYPE: DNA
<213> ORGANISM: Artificial sequence
<220> FEATURE:
<223> OTHER INFORMATION: miRNA-tag

<400> SEQUENCE: 82

| ggggaatgaa gcctggtccg a | 21 |

<210> SEQ ID NO 83
<211> LENGTH: 21
<212> TYPE: DNA
<213> ORGANISM: Artificial sequence
<220> FEATURE:
<223> OTHER INFORMATION: miRNA-tag

<400> SEQUENCE: 83

| ggggaatgaa gcgtggaccg a | 21 |

<210> SEQ ID NO 84
<211> LENGTH: 4880
<212> TYPE: DNA
<213> ORGANISM: Artificial sequence
<220> FEATURE:
<223> OTHER INFORMATION: expression construct pBPSMM232
<220> FEATURE:
<221> NAME/KEY: promoter
<222> LOCATION: (298)..(2278)
<223> OTHER INFORMATION: Zm ubiquitin promoter and intron (1981bp)
<220> FEATURE:
<221> NAME/KEY: misc_feature
<222> LOCATION: (2305)..(4305)
<223> OTHER INFORMATION: beta-glucuronidase GUS(2001bp)
<220> FEATURE:
<221> NAME/KEY: misc_feature
<222> LOCATION: (4365)..(4365)
<223> OTHER INFORMATION: MiRNA tag insertion site (Sac I)
<220> FEATURE:
<221> NAME/KEY: terminator
<222> LOCATION: (4376)..(4628)
<223> OTHER INFORMATION: NOS terminator (253 bp)

<400> SEQUENCE: 84

| cgttcttccg aatagcatcg gtaacatgag caaagtctgc cgccttacaa cggctctccc | 60 |
| gctgacgccg tcccggactg atgggctgcc tgtatcgagt ggtgattttg tgccgagctg | 120 |
| ccggtcgggg agctgttggc tggctggtgg caggatatat tgtggtgtaa acaaattgac | 180 |
| gcttagacaa cttaataaca cattgcggac gtttttaatg tactgaattg actagtggcg | 240 |
| cgccaagctt gcatgcctgc aggtcgactc tagaggatcc ccatcgaatt cctgcagtgc | 300 |
| agcgtgaccc ggtcgtgccc ctctctagag ataatgagca ttgcatgtct aagttataaa | 360 |
| aaattaccac atatttttt tgtcacactt gtttgaagtg cagtttatct atctttatac | 420 |

-continued

| | | | | |
|---|---|---|---|---|
| atatatttaa | actttactct | acgaataata | taatctatag | tactacaata | atatcagtgt | 480 |
| tttagagaat | catataaatg | aacagttaga | catggtctaa | aggacaattg | agtattttga | 540 |
| caacaggact | ctacagtttt | atcttttag | tgtgcatgtg | ttctcctttt | ttttgcaaa | 600 |
| tagcttcacc | tatataatac | ttcatccatt | ttattagtac | atccatttag | ggtttagggt | 660 |
| taatggtttt | tatagactaa | tttttttagt | acatctattt | tattctattt | tagcctctaa | 720 |
| attaagaaaa | ctaaaactct | attttagttt | ttttatttaa | taatttagat | ataaaataga | 780 |
| ataaaataaa | gtgactaaaa | attaaacaaa | tacccttaa | gaaattaaaa | aaactaagga | 840 |
| aacatttttc | ttgtttcgag | tagataatgc | cagcctgtta | aacgccgtcg | acgagtctaa | 900 |
| cggacaccaa | ccagcgaacc | agcagcgtcg | cgtcgggcca | agcgaagcag | acggcacggc | 960 |
| atctctgtcg | ctgcctctgg | accctctcg | agagttccgc | tccaccgttg | gacttgctcc | 1020 |
| gctgtcggca | tccagaaatt | gcgtggcgga | gcggcagacg | tgagccggca | cggcaggcgg | 1080 |
| cctcctcctc | ctctcacggc | accggcagct | acggggatt | cctttcccac | cgctccttcg | 1140 |
| ctttcccttc | ctcgcccgcc | gtaataaata | gacaccccct | ccacccctc | tttccccaac | 1200 |
| ctcgtgttgt | tcggagcgca | cacacacaca | accagatctc | ccccaaatcc | acccgtcggc | 1260 |
| acctccgctt | caaggtacgc | cgctcgtcct | ccccccccc | ccctctctac | cttctctaga | 1320 |
| tcggcgttcc | ggtccatggt | tagggcccgg | tagttctact | tctgttcatg | tttgtgttag | 1380 |
| atccgtgttt | gtgttagatc | cgtgctgcta | gcgttcgtac | acggatgcga | cctgtacgtc | 1440 |
| agacacgttc | tgattgctaa | cttgccagtg | tttctctttg | gggaatcctg | ggatggctct | 1500 |
| agccgttccg | cagacgggat | cgatttcatg | attttttttg | tttcgttgca | tagggtttgg | 1560 |
| tttgcccttt | tcctttattt | caatatatgc | cgtgcacttg | tttgtcgggt | catcttttca | 1620 |
| tgcttttttt | tgtcttggtt | gtgatgatgt | ggtctggttg | ggcggtcgtt | ctagatcgga | 1680 |
| gtagaattct | gtttcaaact | acctggtgga | tttattaatt | ttggatctgt | atgtgtgtgc | 1740 |
| catacatatt | catagttacg | aattgaagat | gatggatgga | aatatcgatc | taggataggt | 1800 |
| atacatgttg | atgcgggttt | tactgatgca | tatacagaga | tgcttttgt | tcgcttggtt | 1860 |
| gtgatgatgt | ggtgtggttg | ggcggtcgtt | cattcgttct | agatcggagt | agaatactgt | 1920 |
| ttcaaactac | ctggtgtatt | tattaattt | ggaactgtat | gtgtgtgtca | tacatcttca | 1980 |
| tagttacgag | tttaagatgg | atggaaatat | cgatctagga | taggtataca | tgttgatgtg | 2040 |
| ggttttactg | atgcatatac | atgatggcat | atgcagcatc | tattcatatg | ctctaacctt | 2100 |
| gagtacctat | ctattataat | aaacaagtat | gttttataat | tattttgatc | ttgatatact | 2160 |
| tggatgatgg | catatgcagc | agctatatgt | ggattttttt | agccctgcct | tcatacgcta | 2220 |
| tttatttgct | tggtactgtt | tcttttgtcg | atgctcaccc | tgttgtttgg | tgttacttct | 2280 |
| gcagcccggg | taggtcagtc | ccttatgtta | cgtcctgtag | aaaccccaac | ccgtgaaatc | 2340 |
| aaaaaactcg | acggcctgtg | ggcattcagt | ctggatcgcg | aaaactgtgg | aattggtcag | 2400 |
| cgttggtggg | aaagcgcgtt | acaagaaagc | cgggcaattg | ctgtgccagg | cagtttaac | 2460 |
| gatcagttcg | ccgatgcaga | tattcgtaat | tatgcgggca | acgtctggta | tcagcgcgaa | 2520 |
| gtctttatac | cgaaaggttg | gcaggccag | cgtatcgtgc | tgcgtttcga | tgcggtcact | 2580 |
| cattacggca | aagtgtgggt | caataatcag | gaagtgatgg | agcatcaggg | cggctatacg | 2640 |
| ccatttgaag | ccgatgtcac | gccgtatgtt | attgccggga | aaagtgtacg | taagtttctg | 2700 |
| cttctacctt | tgatatatat | ataataatta | tcattaatta | gtagtaatat | aatatttcaa | 2760 |
| atatttttt | caaaataaaa | gaatgtagta | tatagcaatt | gcttttctgt | agtttataag | 2820 |

```
tgtgtatatt ttaatttata acttttctaa tatatgacca aaatttgttg atgtgcaggt    2880
atcaccgttt gtgtgaacaa cgaactgaac tggcagacta tcccgccggg aatggtgatt    2940
accgacgaaa acggcaagaa aaagcagtct tacttccatg atttctttaa ctatgccgga    3000
atccatcgca gcgtaatgct ctacaccacg ccgaacacct gggtggacga tatcaccgtg    3060
gtgacgcatg tcgcgcaaga ctgtaaccac gcgtctgttg actggcaggt ggtggccaat    3120
ggtgatgtca gcgttgaact gcgtgatgcg gatcaacagg tggttgcaac tggacaaggc    3180
actagcggga ctttgcaagt ggtgaatccg cacctctggc aaccgggtga aggttatctc    3240
tatgaactgt gcgtcacagc caaaagccag acagagtgtg atatctaccc gcttcgcgtc    3300
ggcatccggt cagtggcagt gaagggcgaa cagttcctga ttaaccacaa accgttctac    3360
tttactggct ttggtcgtca tgaagatgcg gacttgcgtg gcaaaggatt cgataacgtg    3420
ctgatggtgc acgaccacgc attaatggac tggattgggg ccaactccta ccgtacctcg    3480
cattacccctt acgctgaaga gatgctcgac tgggcagatg aacatggcat cgtggtgatt    3540
gatgaaactg ctgctgtcgg ctttaacctc tctttaggca ttggtttcga agcgggcaac    3600
aagccgaaag aactgtacag cgaagaggca gtcaacgggg aaactcagca agcgcactta    3660
caggcgatta aagagctgat agcgcgtgac aaaaaccacc aagcgtggt gatgtggagt    3720
attgccaacg aaccggatac ccgtccgcaa ggtgcacggg aatatttcgc gccactggcg    3780
gaagcaacgc gtaaactcga cccgacgcgt ccgatcacct gcgtcaatgt aatgttctgc    3840
gacgctcaca ccgataccat cagcgatctc tttgatgtgc tgtgcctgaa ccgttattac    3900
ggatggtatg tccaaagcgg cgatttggaa acggcagaga aggtactgga aaaagaactt    3960
ctggcctggc aggagaaact gcatcagccg attatcatca ccgaatacgg cgtggatacg    4020
ttagccgggc tgcactcaat gtacaccgac atgtggagtg aagagtatca gtgtgcatgg    4080
ctggatatgt atcaccgcgt cttttgatcgc gtcagcgccg tcgtcggtga acaggtatgg    4140
aatttcgccg attttgcgac ctcgcaaggc atattgcgcg ttggcggtaa caagaaaggg    4200
atcttcactc gcgaccgcaa accgaagtcg gcggcttttc tgctgcaaaa acgctggact    4260
ggcatgaact tcggtgaaaa accgcagcag ggaggcaaac aatgaatcaa caactctcct    4320
ggcgcaccat cgtcggctac agcctcggga attgctaccg agctcgaatt tccccgatcg    4380
ttcaaacatt tggcaataaa gtttcttaag attgaatcct gttgccggtc ttgcgatgat    4440
tatcatataa tttctgttga attacgttaa gcatgtaata attaacatgt aatgcatgac    4500
gttatttatg agatgggttt ttatgattag agtcccgcaa ttatacattt aatacgcgat    4560
agaaaacaaa atatagcgcg caaactagga taaattatcg cgcgcggtgt catctatgtt    4620
actagatcgg gaattggcat gcaagcttgg cactggccgt cgttttacaa cgtcgtgact    4680
gggaaaaccc tggcgttacc caacttaatc gccttgcagc acatcccccct ttcgccagct    4740
ggcgtaatag cgaagaggcc cgcaccgatc gcccttccca acagttgcgc agcctgaatg    4800
gcgaatgcta gagcagcttg agcttggatc agattgtcgt ttcccgcctt cagtttgtgt    4860
taattaacgg tccgaggcct                                                4880
```

<210> SEQ ID NO 85
<211> LENGTH: 4960
<212> TYPE: DNA
<213> ORGANISM: Artificial sequence
<220> FEATURE:
<223> OTHER INFORMATION: expression construct pBPSMM271
<220> FEATURE:

```
<221> NAME/KEY: promoter
<222> LOCATION: (227)..(1260)
<223> OTHER INFORMATION: Os CCoAMT1 promoter (1034bp)
<220> FEATURE:
<221> NAME/KEY: Intron
<222> LOCATION: (1319)..(2369)
<223> OTHER INFORMATION: Zm ubiquitin intron (1051bp)
<220> FEATURE:
<221> NAME/KEY: misc_feature
<222> LOCATION: (2389)..(4389)
<223> OTHER INFORMATION: beta-glucuronidase gene GUS (2001bp)
<220> FEATURE:
<221> NAME/KEY: misc_feature
<222> LOCATION: (4450)..(4450)
<223> OTHER INFORMATION: MiRNA tag insertion site (Sac I)
<220> FEATURE:
<221> NAME/KEY: terminator
<222> LOCATION: (4461)..(4713)
<223> OTHER INFORMATION: NOS terminator (253 bp)

<400> SEQUENCE: 85
gatgggctgc ctgtatcgag tggtgatttt gtgccgagct gccggtcggg gagctgttgg    60
ctggctggtg gcaggatata ttgtggtgta aacaaattga cgcttagaca acttaataac   120
acattgcgga cgttttaat gtactgaatt gactagtggc gcgccaagct tgcatgcctg    180
caggtcgact ctagtaacgg ccgccagtgt gctggaattc gcccttcaac tactgcacgg   240
taaaagtgat aggaatcggt cggaaacagt attaatgttt ttattatttt tacaaaaacg   300
aattgaaata attggaaatt tcatatttta tatattaaac tattcagtat caacttcaat   360
tcgacgtcaa tagaaattag aaaagcataa ttatacacag taataggcgt tcaagatatt   420
attgttatta tttagttttg tggaaatggt atcaacgtga tcggaaaatt ttgtacatgt   480
tttcaccctg cgggatatct caattccttc tcctccctct accgccatat cagcacacgt   540
tttagagcac caatcataac ccataaatcc gtgggctact cacttattta atttatatgt   600
gaattcgtga cctgactcac tcacatacta tcaaaaattt gtctcagtca cccatctcct   660
tctttcctgg tccgataagg gtttatccta cggttcgacg gttatcacga tagtcgtgcg   720
gttactgagg tataccgtga tttaaaaata tgataaagtt accgcaggtt taactgcgc    780 ggtttggtaa acctgttcct cctcaccaac cttctcctcc ggtctcctta tgtgtctcac   840
cgaggcgagc cgccgcgaga ccgcatggac gcggtccacg cacctggcgg tgcacctcct   900 cctcccggc gaagaagacg tggaggagag taaatgagca atcaggccca cggcccaatc    960
gccgtccacc acccaccacc ctcagcgacc caaaaccacc tcaccaaccc aactctgtac  1020
cgtactgtac ccgccctccc ctcccactga cactccgggc ccacctgtcg gcgcgactct  1080
tccacggtcc ccttctctcc tcagagattt tttccacgca tttttaatt tttttttctg   1140 cagttcacat gctcttctcc cactcttccg ccgcgctata taaccgcgc gaggcgtcgt   1200 tgcctcgtcg gcgaagtcaa tccggcgatc cccggcgagc gagagatcga agcaagctgc  1260
aagggcgaat tctgcagata tccatcacac tggcggccgc tcgagcatgc atctagagga  1320
tctcccccaa atccacccgt cggcacctcc gcttcaaggt acgccgctcg tcctccccc   1380 cccccctct ctaccttctc tagatcggcg ttccggtcca tggttagggc ccggtagttc   1440
tacttctgtt catgtttgtg ttagatccgt gtttgtgtta gatccgtgct gctagcgttc  1500
gtacacggat gcgacctgta cgtcagacac gttctgattg ctaacttgcc agtgtttctc  1560
tttggggaat cctgggatgg ctctagccgt tccgcagacg ggatcgattt catgattttt  1620
tttgtttcgt tgcataggggt ttggtttgcc cttttccttt atttcaatat atgccgtgca  1680
cttgtttgtc gggtcatctt ttcatgcttt ttttttgtctt ggttgtgatg atgtggtctg  1740
```

-continued

```
gttgggcggt cgttctagat cggagtagaa ttctgtttca aactacctgg tggatttatt    1800
aattttggat ctgtatgtgt gtgccataca tattcatagt tacgaattga agatgatgga    1860
tggaaatatc gatctaggat aggtatacat gttgatgcgg gttttactga tgcatataca    1920
gagatgcttt ttgttcgctt ggttgtgatg atgtggtgtg gttgggcggt cgttcattcg    1980
ttctagatcg gagtagaata ctgtttcaaa ctacctggtg tatttattaa ttttggaact    2040
gtatgtgtgt gtcatacatc ttcatagtta cgagtttaag atggatggaa atatcgatct    2100
aggataggta tacatgttga tgtgggtttt actgatgcat atacatgatg gcatatgcag    2160
catctattca tatgctctaa ccttgagtac ctatctatta aataaacaa gtatgtttta    2220 taattatttt gatcttgata tacttggatg atggcatatg cagcagctat atgtggattt    2280
ttttagccct gccttcatac gctatttatt tgcttggtac tgtttctttt gtcgatgctc    2340
accctgttgt ttggtgttac ttctgcagcc cgggtaggtc agtcccttat gttacgtcct    2400
gtagaaaccc caacccgtga aatcaaaaaa ctcgacggcc tgtgggcatt cagtctggat    2460
cgcgaaaact gtggaattgg tcagcgttgg tgggaaagcg cgttacaaga aagccgggca    2520
attgctgtgc caggcagttt taacgatcag ttcgccgatg cagatattcg taattatgcg    2580
ggcaacgtct ggtatcagcg cgaagtcttt ataccgaaag gttgggcagg ccagcgtatc    2640
gtgctgcgtt tcgatgcggt cactcattac ggcaaagtgt gggtcaataa tcaggaagtg    2700
atggagcatc agggcggcta tacgccattt gaagccgatg tcacgccgta tgttattgcc    2760
gggaaaagtg tacgtaagtt tctgcttcta cctttgatat atatataata attatcatta    2820
attagtagta atataatatt tcaaatattt ttttcaaaat aaaagaatgt agtatatagc    2880
aattgctttt ctgtagttta taagtgtgta tattttaatt tataacttttt ctaatatatg    2940 accaaaattt gttgatgtgc aggtatcacc gtttgtgtga caacgaact gaactggcag    3000 actatcccgc cggaatggt gattaccgac gaaaacggca agaaaaagca gtcttacttc    3060
catgatttct ttaactatgc cggaatccat cgcagcgtaa tgctctacac cacgccgaac    3120
acctgggtgg acgatatcac cgtggtgacg catgtcgcgc aagactgtaa ccacgcgtct    3180
gttgactggc aggtggtggc caatggtgat gtcagcgttg aactgcgtga tgcggatcaa    3240
caggtggttg caactggaca aggcactagc gggactttgc aagtggtgaa tccgcacctc    3300
tggcaaccgg gtgaaggtta tctctatgaa ctgtgcgtca cagccaaaag ccagacagag    3360
tgtgatatct acccgcttcg cgtcggcatc cggtcagtgg cagtgaaggg cgaacagttc    3420
ctgattaacc acaaaccgtt ctactttact ggctttggtc gtcatgaaga tgcggacttg    3480
cgtggcaaag gattcgataa cgtgctgatg gtgcacgacc acgcattaat ggactggatt    3540
ggggccaact cctaccgtac ctcgcattac ccttacgctg aagagatgct cgactgggca    3600
gatgaacatg gcatcgtggt gattgatgaa actgctgctg tcggctttaa cctctcttta    3660
ggcattggtt tcgaagcggg caacaagccg aaagaactgt acagcgaaga ggcagtcaac    3720
ggggaaactc agcaagcgca cttacaggcg attaaagagc tgatagcgcg tgacaaaaac    3780
cacccaagcg tggtgatgtg gagtattgcc aacgaaccgg ataccgtcc gcaaggtgca    3840 cgggaatatt tcgcgccact ggcggaagca acgcgtaaac tcgacccgac gcgtccgatc    3900
acctgcgtca atgtaatgtt ctgcgacgct cacaccgata ccatcagcga tctctttgat    3960
gtgctgtgcc tgaaccgtta ttacggatgg tatgtccaaa gcggcgattt ggaaacggca    4020
gagaaggtac tggaaaaaga acttctggcc tggcaggaga aactgcatca gccgattatc    4080
```

```
atcaccgaat acggcgtgga tacgttagcc gggctgcact caatgtacac cgacatgtgg    4140
agtgaagagt atcagtgtgc atggctggat atgtatcacc gcgtctttga tcgcgtcagc    4200
gccgtcgtcg gtgaacaggt atggaatttc gccgattttg cgacctcgca aggcatattg    4260
cgcgttggcg gtaacaagaa agggatcttc actcgcgacc gcaaaccgaa gtcggcggct    4320
tttctgctgc aaaaacgctg gactggcatg aacttcggtg aaaaaccgca gcagggaggc    4380
aaacaatgaa tcaacaactc tcctggcgca ccatcgtcgg ctacagcctc gggaattgcg    4440
taccgagctc gaatttcccc gatcgttcaa acatttggca ataaagtttc ttaagattga    4500
atcctgttgc cggtcttgcg atgattatca tataatttct gttgaattac gttaagcatg    4560
taataattaa catgtaatgc atgacgttat ttatgagatg ggttttatg attagagtcc     4620 cgcaattata catttaatac gcatagaaa acaaaatata gcgcgcaaac taggataaat      4680
tatcgcgcgc ggtgtcatct atgttactag atcgggaatt ggcatgcaag cttggcactg    4740
gccgtcgttt tacaacgtcg tgactgggaa accctggcg ttacccaact taatcgcctt      4800
gcagcacatc ccccttttcgc cagctggcgt aatagcgaag aggcccgcac cgatcgccct    4860
tcccaacagt tgcgcagcct gaatggcgaa tgctagagca gcttgagctt ggatcagatt    4920
gtcgtttccc gccttcagtt tgtgttaatt aacggtccga                          4960

<210> SEQ ID NO 86
<211> LENGTH: 5000
<212> TYPE: DNA
<213> ORGANISM: Artificial sequence
<220> FEATURE:
<223> OTHER INFORMATION: expression construct pBPSMM272
<220> FEATURE:
<221> NAME/KEY: promoter
<222> LOCATION: (255)..(1316)
<223> OTHER INFORMATION: Zm LDH Promoter (1062bp)
<220> FEATURE:
<221> NAME/KEY: Intron
<222> LOCATION: (1355)..(2405)
<223> OTHER INFORMATION: ubiquitin Intron (1051bp)
<220> FEATURE:
<221> NAME/KEY: misc_feature
<222> LOCATION: (2425)..(4425)
<223> OTHER INFORMATION: beta-glucuronidase GUS (2001bp)
<220> FEATURE:
<221> NAME/KEY: misc_feature
<222> LOCATION: (4486)..(4486)
<223> OTHER INFORMATION: MiRNA tag insertion site (SacI)
<220> FEATURE:
<221> NAME/KEY: terminator
<222> LOCATION: (4497)..(4749)
<223> OTHER INFORMATION: NOS terminator (253 bp): 4497-4749

<400> SEQUENCE: 86
cccggactga tgggctgcct gtatcgagtg gtgattttgt gccgagctgc cggtcgggga     60
gctgttggct ggctggtggc aggatatatt gtggtgtaaa caaattgacg cttagacaac    120
ttaataacac attgcggacg ttttttaatgt actgaattga ctagtggcgc gccaagcttg   180
catgcctgca ggtcgactct agatgcatgc tcgagcggcc gccagtgtga tggatatctg    240
cagaattcgc ccttaacaaa tggcgtactt atataaccac aatgtactgg tgctgcgtca    300 ttatttttata ctacgcatat attattataa gtagagaaag ctcacaaaac catgcgcgcg   360 ccccccctgtt tgtttcggtc gctaattaca cccttttgtat cgttggttga tgatggtctc  420
caccggccgt acgagtcatc gatcgttgat ttatttttat caccgacttg cacgcctttc    480
gaacaaagac gcaacaaagg aaagcgaaag cgtcacgaac gaggttgttc cctgacagtt    540
gttcgactaa tacaactgca agacactgaa taagcagtaa aaatcaatat agattaaagt    600
```

```
taaacgaaca tgctcaacat cgaatactac tcatatgtgt tattattaag agaataccac    660
caaggtagaa aagttaaagg acctaaactg ttgtgccggg agagttgtgc gacgaacaga    720
tgtaaatatg ataaaataag ttcaaagttc atatagatag cacgatcaca cttagggcta    780
gtttgaagcc ataaaaatgg aagagattaa atgagataaa attcacttat ttaattttaa    840
ataagaagag agttttaacc cctctaattc tctccagtat tttagctcct aaactagctc    900
ttacagcagt aaaagaccct tgatggtagc gtatgcaaag agaaggaact attcaatgaa    960
ttgttttttt aatcactagt agtatggtgg gtaactgtcg tcaaccggcc ctatctactt   1020
cagtttagtg aagcactaaa ccgcaccttg gtatgttcaa atttaagatt tttttttgaaa  1080 cgaaacaatt ttaaccagcg gctccaaacc ggtgaagtgg tttggtcttt ggtgtggggc   1140
cagggtatta atggaattga atatataaag agcagggtgg tggacctttc cctcccacg    1200 agtcgagtag ccattgccca ttgccattcc ttccttcctc cacagagaaa tccgatccgc   1260
ggagatttga cccaaccaga tcatatcaca cacgtaatcc catcccattc cgcccgaagg   1320
gcgaattcca gcacactggc ggccgttact agtggatctc ccccaaatcc accgtcggc    1380 acctccgctt caaggtacgc cgctcgtcct cccccccccc ccctctctac cttctctaga   1440
tcggcgttcc ggtccatggt tagggcccgg tagttctact tctgttcatg tttgtgttag   1500
atccgtgttt gtgttagatc cgtgctgcta gcgttcgtac acggatgcga cctgtacgtc   1560
agacacgttc tgattgctaa cttgccagtg tttctctttg gggaatcctg ggatggctct   1620
agccgttccg cagacgggat cgatttcatg atttttttg tttcgttgca tagggtttgg    1680
tttgcccttt tcctttattt caatatatgc cgtgcacttg tttgtcgggt catcttttca   1740 tgctttttt tgtcttggtt gtgatgatgt ggtctggttg ggcggtcgtt ctagatcgga   1800
gtagaattct gtttcaaact acctggtgga tttattaatt ttggatctgt atgtgtgtgc   1860
catacatatt catagttacg aattgaagat gatggatgga aatatcgatc taggataggt   1920
atacatgttg atgcgggttt tactgatgca tatacagaga tgcttttttgt tcgcttggtt  1980 gtgatgatgt ggtgtggttg ggcggtcgtt cattcgttct agatcggagt agaatactgt   2040
ttcaaactac ctggtgtatt tattaatttt ggaactgtat gtgtgtgtca tacatcttca   2100
tagttacgag tttaagatgg atggaaatat cgatctagga taggtataca tgttgatgtg   2160
ggttttactg atgcatatac atgatggcat atgcagcatc tattcatatg ctctaacctt   2220
gagtacctat ctattataat aaacaagtat gttttataat tattttgatc ttgatatact   2280
tggatgatgg catatgcagc agctatatgt ggattttttt agccctgcct tcatacgcta   2340
tttatttgct tggtactgtt tcttttgtcg atgctcaccc tgttgtttgg tgttacttct   2400
gcagcccggg taggtcagtc ccttatgtta cgtcctgtag aaacccccaac ccgtgaaatc   2460 aaaaaactcg acggcctgtg ggcattcagt ctggatcgcg aaaactgtgg aattggtcag   2520
cgttggtggg aaagcgcgtt acaagaaagc cgggcaattg ctgtgccagg cagttttaac   2580
gatcagttcg ccgatgcaga tattcgtaat tatgcgggca acgtctggta tcagcgcgaa   2640
gtctttatac cgaaaggttg ggcaggccag cgtatcgtgc tgcgtttcga tgcggtcact   2700
cattacggca aagtgtgggt caataatcag gaagtgatga gcatcagggg cggctatacg   2760
ccatttgaag ccgatgtcac gccgtatgtt attgccggga aaagtgtacg taagtttctg   2820
cttctacctt tgatatatat ataataatta tcattaatta gtagtaatat aatatttcaa   2880
atattttttt caaaataaaa gaatgtagta tatagcaatt gcttttctgt agtttataag   2940
```

```
tgtgtatatt ttaatttata acttttctaa tatatgacca aaatttgttg atgtgcaggt    3000
atcaccgttt gtgtgaacaa cgaactgaac tggcagacta tcccgccggg aatggtgatt    3060
accgacgaaa acggcaagaa aaagcagtct tacttccatg atttctttaa ctatgccgga    3120
atccatcgca gcgtaatgct ctacaccacg ccgaacacct gggtggacga tatcaccgtg    3180
gtgacgcatg tcgcgcaaga ctgtaaccac gcgtctgttg actggcaggt ggtggccaat    3240
ggtgatgtca gcgttgaact gcgtgatgcg atcaacagg tggttgcaac tggacaaggc    3300
actagcggga ctttgcaagt ggtgaatccg cacctctggc aaccgggtga aggttatctc    3360
tatgaactgt gcgtcacagc caaaagccag acagagtgtg atatctaccc gcttcgcgtc    3420
ggcatccggt cagtggcagt gaagggcgaa cagttcctga ttaaccacaa accgttctac    3480
tttactggct ttggtcgtca tgaagatgcg gacttgcgtg gcaaaggatt cgataacgtg    3540
ctgatggtgc acgaccacgc attaatggac tggattgggg ccaactccta ccgtacctcg    3600
cattaccctt acgctgaaga gatgctcgac tgggcagatg aacatggcat cgtggtgatt    3660
gatgaaactg ctgctgtcgg ctttaacctc tctttaggca ttggtttcga agcgggcaac    3720
aagccgaaag aactgtacag cgaagaggca gtcaacgggg aaactcagca agcgcactta    3780
caggcgatta aagagctgat agcgcgtgac aaaaaccacc caagcgtggt gatgtggagt    3840
attgccaacg aaccggatac ccgtccgcaa ggtgcacggg aatatttcgc gccactggcg    3900
gaagcaacgc gtaaactcga cccgacgcgt ccgatcacct gcgtcaatgt aatgttctgc    3960
gacgctcaca ccgataccat cagcgatctc tttgatgtgc tgtgcctgaa ccgttattac    4020
ggatggtatg tccaaagcgg cgatttggaa acggcagaga aggtactgga aaagaacttt    4080
ctggcctggc aggagaaact gcatcagccg attatcatca ccgaatacgg cgtggatacg    4140
ttagccgggc tgcactcaat gtacaccgac atgtggagtg aagagtatca gtgtgcatgg    4200
ctggatatgt atcaccgcgt ctttgatcgc gtcagcgccg tcgtcggtga acaggtatgg    4260
aatttcgccg attttgcgac ctcgcaaggc atattgcgcg ttggcggtaa caagaaaggg    4320
atcttcactc gcgaccgcaa accgaagtcg gcggcttttc tgctgcaaaa acgctggact    4380
ggcatgaact tcggtgaaaa accgcagcag ggaggcaaac aatgaatcaa caactctcct    4440
ggcgcaccat cgtcggctac agcctcggga attgcgtacc gagctcgaat tccccgatc    4500 gttcaaacat ttggcaataa agtttcttaa gattgaatcc tgttgccggt cttgcgatga    4560
ttatcatata atttctgttg aattacgtta agcatgtaat aattaacatg taatgcatga    4620
cgttatttat gagatgggtt tttatgatta gagtcccgca attatacatt taatacgcga    4680
tagaaaacaa aatatagcgc gcaaactagg ataaattatc gcgcgcggtg tcatctatgt    4740
tactagatcg ggaattggca tgcaagcttg gcactggccg tcgttttaca acgtcgtgac    4800
tgggaaaacc ctggcgttac ccaacttaat cgccttgcag cacatccccc tttcgccagc    4860
tggcgtaata gcgaagaggc ccgcaccgat cgcccttccc aacagttgcg cagcctgaat    4920
ggcgaatgct agagcagctt gagcttggat cagattgtcg tttcccgcct tcagtttgtg    4980
ttaattaacg gtccgaggcc                                                5000
```

<210> SEQ ID NO 87
<211> LENGTH: 4857
<212> TYPE: DNA
<213> ORGANISM: Artificial sequence
<220> FEATURE:
<223> OTHER INFORMATION: expression construct pBPSMM304
<220> FEATURE:
<221> NAME/KEY: terminator

```
<222> LOCATION: (426)..(678)
<223> OTHER INFORMATION: NOS terminator (253 bp) complement
<220> FEATURE:
<221> NAME/KEY: misc_feature
<222> LOCATION: (694)..(694)
<223> OTHER INFORMATION: MiRNA tag insertion site (Sac I)
<220> FEATURE:
<221> NAME/KEY: misc_feature
<222> LOCATION: (749)..(2749)
<223> OTHER INFORMATION: beta-glucuronidase GUS (2001bp) complement
<220> FEATURE:
<221> NAME/KEY: Intron
<222> LOCATION: (2769)..(3819)
<223> OTHER INFORMATION: Zm ubiquitin intron (1051bp) complement
<220> FEATURE:
<221> NAME/KEY: promoter
<222> LOCATION: (3859)..(4856)
<223> OTHER INFORMATION: Os CP12 promoter (998bp) (complement)

<400> SEQUENCE: 87
tacaacggct ctcccgctga cgccgtcccg gactgatggg ctgcctgtat cgagtggtga        60
ttttgtgccg agctgccggt cggggagctg ttggctggct ggtggcagga tatattgtgg       120
tgtaaacaaa ttgacgctta gacaacttaa taacacattg cggacgtttt taatgtactg       180
aattgactag tggcgcgccc acaaactgaa ggcgggaaac gacaatctga tccaagctca       240
agctgctcta gcattcgcca ttcaggctgc gcaactgttg ggaagggcga tcggtgcggg       300
cctcttcgct attacgccag ctgcgaaagg ggatgtgctg caagcgatta agttggtaac       360
gccagggttt cccagtcacg acgttgtaaa acgacggcca gtgccaagct tgcatgccaa       420
ttcccgatct agtaacatag atgacaccgc gcgcgataat ttatcctagt ttgcgcgcta       480
tattttgttt tctatcgcgt attaaatgta taattgcggg actctaatca taaaaaccca       540
tctcataaat aacgtcatgc attacatgtt aattattaca tgcttaacgt aattcaacag       600
aaattatatg ataatcatcg caagaccggc aacaggattc aatcttaaga aactttattg       660
ccaaatgttt gaacgatcgg ggaaattcga gctcggtagc aattcccgag ctgtagccg        720 acgatggtgc gccaggagag ttgttgattc attgtttgcc tccctgctgc ggttttttcac      780 cgaagttcat gccagtccag cgttttttgca gcagaaaagc cgccgacttc ggtttgcggt      840
cgcgagtgaa gatcccttc ttgttaccgc caacgcgcaa tatgccttgc gaggtcgcaa       900
aatcggcgaa attccatacc tgttcaccga cgacggcgct gacgcgatca agacgcggt       960 gatacatatc cagccatgca cactgatact cttcactcca catgtcggtg tacattgagt      1020
gcagcccggc taacgtatcc acgccgtatt cggtgatgat aatcggctga tgcagtttct      1080
cctgccaggc cagaagttct ttttccagta cctctctgc cgtttccaaa tcgccgcttt      1140
ggacatacca tccgtaataa cggttcaggc acagcacatc aaagagatcg ctgatggtat      1200
cggtgtgagc gtcgcagaac attcattga cgcaggtgat cggacgcgtc gggtcgagtt      1260
tacgcgttgc ttccgccagt ggcgcgaaat attcccgtgc accttgcgga cgggtatccg      1320
gttcgttggc aatactccac atcaccacgc ttgggtggtt tttgtcacgc gctatcagct      1380
ctttaatcgc ctgtaagtgc gcttgctgag tttccccgtt gactgcctct tcgctgtaca      1440
gttctttcgg cttgttgccc gcttcgaaac caatgcctaa agagaggtta aagccgacag      1500
cagcagtttc atcaatcacc acgatgccat gttcatctgc ccagtcgagc atctcttcag      1560
cgtaagggta atgcgaggta cggtaggagt tggccccaat ccagtccatt aatgcgtggt      1620
cgtgcaccat cagcacgtta tcgaatcctt tgccacgcaa gtccgcatct tcatgacgac      1680
caaagccagt aaagtagaac ggtttgtggt taatcaggaa ctgttcgccc ttcactgcca      1740
```

```
ctgaccggat gccgacgcga agcgggtaga tatcacactc tgtctggctt ttggctgtga    1800
cgcacagttc atagagataa ccttcacccg gttgccagag gtgcggattc accacttgca    1860
aagtcccgct agtgccttgt ccagttgcaa ccacctgttg atccgcatca cgcagttcaa    1920
cgctgacatc accattggcc accacctgcc agtcaacaga cgcgtggtta cagtcttgcg    1980
cgacatgcgt caccacggtg atatcgtcca cccaggtgtt cggcgtggtg tagagcatta    2040
cgctgcgatg gattccggca tagttaaaga aatcatggaa gtaagactgc ttttcttgc     2100
cgttttcgtc ggtaatcacc attcccggcg ggatagtctg ccagttcagt tcgttgttca    2160
cacaaacggt gatacctgca catcaacaaa ttttggtcat atattagaaa agttataaat    2220
taaaatatac acacttataa actacagaaa agcaattgct atatactaca ttcttttatt    2280
ttgaaaaaaa tatttgaaat attatattac tactaattaa tgataattat tatatatata    2340
tcaaaggtag aagcagaaac ttacgtacac ttttcccggc aataacatac ggcgtgacat    2400
cggcttcaaa tggcgtatag ccgccctgat gctccatcac ttcctgatta ttgacccaca    2460
cttttgccgta atgagtgacc gcatcgaaac gcagcacgat acgctggcct gcccaacctt    2520
tcggtataaa gacttcgcgc tgataccaga cgttgcccgc ataattacga atatctgcat    2580
cggcgaactg atcgttaaaa ctgcctggca cagcaattgc ccggctttct tgtaacgcgc    2640
tttcccacca acgctgacca attccacagt tttcgcgatc cagactgaat gcccacaggc    2700
cgtcgagttt tttgatttca cgggttgggg tttctacagg acgtaacata agggactgac    2760
ctacccgggc tgcagaagta acaccaaaca acagggtgag catcgacaaa agaaacagta    2820
ccaagcaaat aaatagcgta tgaaggcagg gctaaaaaaa tccacatata gctgctgcat    2880
atgccatcat ccaagtatat caagatcaaa ataattataa acatacttg tttattataa     2940
tagataggta ctcaaggtta gagcatatga atagatgctg catatgccat catgtatatg    3000
catcagtaaa acccacatca acatgtatac ctatcctaga tcgatatttc catccatctt    3060
aaactcgtaa ctatgaagat gtatgacaca cacatacagt tccaaaatta ataaatacac    3120
caggtagttt gaaacagtat tctactccga tctagaacga atgaacgacc gcccaaccac    3180
accacatcat cacaaccaag cgaacaaaaa gcatctctgt atatgcatca gtaaaacccg    3240
catcaacatg tatacctatc ctagatcgat atttccatcc atcatcttca attcgtaact    3300
atgaatatgt atggcacaca catacagatc caaaattaat aaatccacca ggtagtttga    3360
aacagaattc tactccgatc tagaacgacc gcccaaccag accacatcat cacaaccaag    3420
acaaaaaaaa gcatgaaaag atgacccgac aaacaagtgc acggcatata ttgaaataaa    3480
ggaaaagggc aaaccaaacc ctatgcaacg aaacaaaaaa aatcatgaaa tcgatcccgt    3540
ctgcggaacg gctagagcca tcccaggatt ccccaaagag aaacactggc aagttagcaa    3600
tcagaacgtg tctgacgtac aggtcgcatc cgtgtacgaa cgctagcagc acggatctaa    3660
cacaaacacg gatctaacac aaacatgaac agaagtagaa ctaccgggcc ctaaccatgg    3720
accggaacgc cgatctagag aaggtagaga gggggggggg gggaggacga gcggcgtacc    3780
ttgaagcgga ggtgccgacg ggtggatttg ggggagatcc tctagagtcg acctgcaggc    3840
atgcaagctt ggcgcgcctg ttgatgcgga tttctgcgtg tgatgtgggc gtttgtagct    3900
gttgcgacga ggcgttcgtt gcacggattg aagagatggg gtttatatat atatagctcc    3960
gtggggtggg ggagaagggg agagaggatt cgacgacgtg cactcgtttc ttatcgcctc    4020
ctcagccaat cgtcgtgtgc cacgtgggct gtatttgag atatttcatg cgaaatgggg    4080
acttggcaaa ggagatcttt ttcttttccc ttgggtgaat ctaaggtgag agaagcagtt    4140
```

```
ttaatttgac cgtgaaaaca tgagcagatg actgtgggtg tgtacatgta tgcagaagtt      4200
caggttggat acgaaattga tgtagaggtt cgtgttgtgc cagcaaagaa tggcttgtag      4260
ggaagtgaac tcggtctaag gccagaaaga tcactttcgg tctcgaaaat atctgagata      4320
ctatggaaaa gtttggtgaa gaacggacaa aatgaaacgt cctagatatc tcaactattt      4380
tggtggaaca gagttattta gtgtacaggt gcagaggtgc tcaaattatt tggtgagtag      4440
caaattattt ttcattttgc ccaataggtg cgtatggttc tttctttgta aagtttttag      4500
attgggacta agctagctcg gatcaagagc ggaattgagg tggtaagaga agtggaaacc      4560
agatggcctt gaagttgtcc ccgcaacctg gacttcctga gttcggacca acaagacaag      4620
cctcttgcaa ggcccagtta cagccggatt agtcgcttat aggcccacag ttgactgggc      4680
cttaggccca tgctgccacc ctgccgagaa ttttttttat ttttacattt tttgattaaa      4740
atatttaaaa ataattttc attccgaaaa tttacaaatc tagtcgtgcc tcacgtcctc       4800
ctagagggct tttttcaaat caccttcca gagggcgtta gggacctaaa tacaaag          4857
```

<210> SEQ ID NO 88
<211> LENGTH: 4725
<212> TYPE: DNA
<213> ORGANISM: Artificial sequence
<220> FEATURE:
<223> OTHER INFORMATION: expression construct pBPSMM331
<220> FEATURE:
<221> NAME/KEY: terminator
<222> LOCATION: (481)..(733)
<223> OTHER INFORMATION: NOS terminator (253 bp) complement
<220> FEATURE:
<221> NAME/KEY: misc_feature
<222> LOCATION: (749)..(749)
<223> OTHER INFORMATION: MiRNA tag insertion site (Sac I)
<220> FEATURE:
<221> NAME/KEY: misc_feature
<222> LOCATION: (804)..(2804)
<223> OTHER INFORMATION: GUS (2001bp): complement
<220> FEATURE:
<221> NAME/KEY: Intron
<222> LOCATION: (2824)..(3874)
<223> OTHER INFORMATION: Zm ubiquitin intron (1051bp): complement
<220> FEATURE:
<221> NAME/KEY: promoter
<222> LOCATION: (3912)..(4725)
<223> OTHER INFORMATION: Os SI promoter (814bp) complement

<400> SEQUENCE: 88

```
gttgccgttc ttccgaatag catcggtaac atgagcaaag tctgccgcct tacaacggct        60
ctcccgctga cgccgtcccg gactgatggg ctgcctgtat cgagtggtga ttttgtgccg       120
agctgccggt cggggagctg ttggctggct ggtggcagga tatattgtgg tgtaaacaaa       180
ttgacgctta gacaacttaa taacacattg cggacgtttt taatgtactg aattgactag       240
tggcgcgccc acaaactgaa ggcgggaaac gacaatctga tccaagctca agctgctcta       300
gcattcgcca ttcaggctgc gcaactgttg ggaagggcga tcggtgcggg cctcttcgct       360
attacgccag ctggcgaaag ggggatgtgc tgcaaggcga ttaagttggg taacgccagg       420
gttttcccag tcacgacgtt gtaaaacgac ggccagtgcc aagcttgcat gccaattccc       480
gatctagtaa catagatgac accgcgcgcg ataatttatc ctagtttgcg cgctatattt       540
tgttttctat cgcgtattaa atgtataatt gcgggactct aatcataaaa acccatctca       600
taaataacgt catgcattac atgttaatta ttacatgctt aacgtaattc aacagaaatt      660
atatgataat catcgcaaga ccggcaacag gattcaatct taagaaactt tattgccaaa      720
```

```
tgtttgaacg atcggggaaa ttcgagctcg gtagcaattc ccgaggctgt agccgacgat    780
ggtgcgccag gagagttgtt gattcattgt ttgcctccct gctgcggttt ttcaccgaag    840
ttcatgccag tccagcgttt ttgcagcaga aaagccgccg acttcggttt gcggtcgcga    900
gtgaagatcc ctttcttgtt accgccaacg cgcaatatgc cttgcgaggt cgcaaaatcg    960
gcgaaattcc atacctgttc accgacgacg cgcgctgacgc gatcaaagac gcggtgatac   1020
atatccagcc atgcacactg atactcttca ctccacatgt cggtgtacat tgagtgcagc   1080
ccggctaacg tatccacgcc gtattcggtg atgataatcg gctgatgcag tttctcctgc   1140
caggccagaa gttcttttc cagtaccttc tctgccgttt ccaaatcgcc gctttggaca   1200
taccatccgt aataacggtt caggcacagc acatcaaaga gatcgctgat ggtatcggtg   1260
tgagcgtcgc agaacattac attgacgcag gtgatcggac cgtcgggtc gagtttacgc   1320
gttgcttccg ccagtggcgc gaaatattcc cgtgcacctt gcggacgggt atccggttcg   1380
ttggcaatac tccacatcac cacgcttggg tggttttgt cacgcgctat cagctctta   1440
atcgcctgta agtgcgcttg ctgagtttcc ccgttgactg cctcttcgct gtacagttct   1500
ttcggcttgt tgcccgcttc gaaaccaatg cctaaagaga ggttaaagcc gacagcagca   1560
gtttcatcaa tcaccacgat gccatgttca tctgcccagt cgagcatctc ttcagcgtaa   1620
gggtaatgcg aggtacggta ggagttggcc ccaatccagt ccattaatgc gtggtcgtgc   1680
accatcagca cgttatcgaa tcctttgcca cgcaagtccg catcttcatg acgaccaaag   1740
ccagtaaagt agaacggttt gtggttaatc aggaactgtt cgcccttcac tgccactgac   1800
cggatgccga cgcgaagcgg gtagatatca cactctgtct ggcttttggc tgtgacgcac   1860
agttcataga gataaccttc acccggttgc cagaggtgcg gattcaccac ttgcaaagtc   1920
ccgctagtgc cttgtccagt tgcaaccacc tgttgatccg catcacgcag ttcaacgctg   1980
acatcaccat tggccaccac ctgccagtca acagacgcgt ggttacagtc ttgcgcgaca   2040
tgcgtcacca cggtgatatc gtccacccag gtgttcggcg tggtgtagag cattacgctg   2100
cgatggattc cggcatagtt aaagaaatca tggaagtaag actgcttttt cttgccgttt   2160
tcgtcggtaa tcaccattcc cggcgggata gtctgccagt tcagttcgtt gttcacacaa   2220
acggtgatac ctgcacatca acaaattttg gtcatatatt agaaaagtta taattaaaa   2280
tatacacact tataaactac agaaaagcaa ttgctatata ctacattctt ttattttgaa   2340
aaaaatattt gaaatattat attactacta attaatgata attattatat atatatcaaa   2400
ggtagaagca gaaacttacg tacacttttc ccggcaataa catacggcgt gacatcggct   2460
tcaaatggcg tatagccgcc ctgatgctcc atcacttcct gattattgac ccacactttg   2520
ccgtaatgag tgaccgcatc gaaacgcagc acgatacgct ggcctgccca acctttcggt   2580
ataaagactt cgcgctgata ccagacgttg cccgcataat tacgaatatc tgcatcggcg   2640
aactgatcgt taaaactgcc tggcacagca attgcccggc tttcttgtaa cgcgcttttcc   2700
caccaacgct gaccaattcc acagttttcg cgatccagac tgaatgccca caggccgtcg   2760
agttttttga tttcacgggt tggggtttct acaggacgta acataaggga ctgacctacc   2820
cgggctgcag aagtaacacc aaacaacagg gtgagcatcg acaaaagaaa cagtaccaag   2880
caaataaata gcgtatgaag gcagggctaa aaaaatccac atatagctgc tgcatatgcc   2940
atcatccaag tatatcaaga tcaaaataat tataaaacat acttgtttat tataatagat   3000
aggtactcaa ggttagagca tatgaataga tgctgcatat gccatcatgt atatgcatca   3060
gtaaaaccca catcaacatg tataccctatc ctagatcgat atttccatcc atcttaaact   3120
```

-continued

```
cgtaactatg aagatgtatg acacacacat acagttccaa aattaataaa tacaccaggt    3180
agtttgaaac agtattctac tccgatctag aacgaatgaa cgaccgccca accacaccac    3240
atcatcacaa ccaagcgaac aaaaagcatc tctgtatatg catcagtaaa acccgcatca    3300
acatgtatac ctatcctaga tcgatatttc catccatcat cttcaattcg taactatgaa    3360
tatgtatggc acacacatac agatccaaaa ttaataaatc caccaggtag tttgaaacag    3420
aattctactc cgatctagaa cgaccgccca accagaccac atcatcacaa ccaagacaaa    3480
aaaaagcatg aaaagatgac ccgacaaaca agtgcacggc atatattgaa ataaaggaaa    3540
agggcaaacc aaacctatg caacgaaaca aaaaaaatca tgaaatcgat cccgtctgcg    3600
gaacggctag agccatccca ggattcccca agagaaaaca ctggcaagtt agcaatcaga    3660
acgtgtctga cgtacaggtc gcatccgtgt acgaacgcta gcagcacgga tctaacacaa    3720
acacggatct aacacaaaca tgaacagaag tagaactacc gggccctaac catggaccgg    3780
aacgccgatc tagagaaggt agagagggggg gggggggggag gacgagcggc gtaccttgaa    3840
gcggaggtgc cgacgggtgg atttgggggga gatcctctag agtcgacctg caggcatgca    3900
agcttggcgc gcctaactcc tggcttcctt ccgatctgga ctggagagga gctgattgga    3960
tcggatcgag caggtcgtcg gggaaggagt gaggggggagt ctctctctct ctctgccaag    4020
gaccaaggta ggtcaatgcc tcagccagat cccatagcca taaacccttg ttttgttaaa    4080
gggcattcac aatgggccga cgtggcattc agcctcaacc caaaaaagcg aagactagta    4140
ttcctttgcc tcgtcgtcca accgcgcgcc ctcctcagct cagtgggacc cacaccaccg    4200
ctagaggaga gaggagaggg ggcgaagcag ccgaactcca ggggaggagg gcgccgaccg    4260
ccgcctcgca tccgcccgtc gccgtctccc gctccaagtc gtctgcccgc cgccgacatg    4320
ccgccgccgc cctgctgctc cgagcagccc cgccgctcgg gggggagagg aggggggtggt    4380 gcgccggcga gcgcatcccg ccgctcggcg ctgtcgccct gccgtcgctc caccactgct    4440
tggtccggcg ccgtcgccgt ctccgcgcgc caggctctct gcggtggggg aaaggaagag    4500 agggggggaga gagagggggaa agtgaaagag aagtgaaaat gtggtagtcc accataccta    4560
cttgtatcgt ggtcttgtag attttgcact gtggaacata tggcttaaca tagttgttgg    4620
tctaggtgac ataccaggaa caccaaagtg tggagagtgg cttgtgggggg tgggggccca    4680 ccaccttcat tccattacac ggtcgaatcg aggcagcgat cgctt                   4725
```

<210> SEQ ID NO 89
<211> LENGTH: 7150
<212> TYPE: DNA
<213> ORGANISM: Artificial sequence
<220> FEATURE:
<223> OTHER INFORMATION: expression construct pBPSMM325
<220> FEATURE:
<221> NAME/KEY: promoter
<222> LOCATION: (305)..(1338)
<223> OTHER INFORMATION: Os CCoAMT1 promoter (1034bp)
<220> FEATURE:
<221> NAME/KEY: Intron
<222> LOCATION: (1345)..(2395)
<223> OTHER INFORMATION: Zm ubiquitin intron :(1051bp)
<220> FEATURE:
<221> NAME/KEY: misc_feature
<222> LOCATION: (2407)..(4407)
<223> OTHER INFORMATION: beta-glucuronidase GUS (2001bp)
<220> FEATURE:
<221> NAME/KEY: terminator
<222> LOCATION: (4446)..(5549)
<223> OTHER INFORMATION: CCoAMT1 terminator (1104 bp)
<220> FEATURE:

```
<221> NAME/KEY: misc_feature
<222> LOCATION: (4793)..(4793)
<223> OTHER INFORMATION: MiRNA tag insertion (AgeI)

<400> SEQUENCE: 89
gtttcaaacc cggcagctta gttgccgttc ttccgaatag catcggtaac atgagcaaag      60
tctgccgcct tacaacggct ctcccgctga cgccgtcccg gactgatggg ctgcctgtat     120
cgagtggtga ttttgtgccg agctgccggt cggggagctg ttggctggct ggtggcagga    180
tatattgtgg tgtaaacaaa ttgacgctta gacaacttaa taacacattg cggacgtttt    240
taatgtactg aattgactag tggcgcgccc acaaaccttaa aggcgatcgc gctgaggcgg    300
accgcaacta ctgcacggta aaagtgatag gaatcggtcg gaaacagtat taatgttttt    360
attattttta caaaaacgaa ttgaaataat tggaattttt catatttata tattaaacta    420
ttcagtatca acttcaattc gacgtcaata gaaattagaa aagcataatt atacacagta    480
ataggcgttc aagatattat tgttattatt tagttttgtg gaaatggtat caacgtgatc    540
ggaaaatttt gtacatgttt tcaccctgcg ggatatctca attccttctc ctccctctac    600
cgccatatca gcacacgttt tagagcacca atcataaccc ataaatccgt gggctactca    660
cttatttaat ttatatgtga attcgtgacc tgactcactc acatactatc aaaaatttgt    720
ctcagtcacc catctccttc tttcctggtc cgataagggt ttatcctacg gttcgacggt    780
tatcacgata gtcgtgcggt tactgaggta taccgtgatt taaaaatatg ataaagttac    840
cgcaggtttt aactgcgcgg tttggtaaac ctgttcctcc tcaccaacct tctcctccgg    900
tctccttatg tgtctcaccg aggcgagccg ccgcgagacc gcatgacgc ggtccacgca    960 cctggcggtg cacctcctcc tccccggcga agaagacgtg gaggagagta aatgagcaat   1020
caggcccacg gcccaatcgc cgtccaccac ccaccaccct cagcgaccca aaaccacctc   1080
accaacccaa ctctgtaccg tactgtaccc gccctcccct cccactgaca ctccgggccc   1140
acctgtcggc gcgactcttc cacggtcccc ttctctcctc agagattttt tccacgcatt   1200
ttttaatttt ttttttctgca gttcacatgc tcttctccca ctcttccgcc gcgctatata   1260
aaccgcgcga ggcgtcgttg cctcgtcggc gaagtcaatc cggcgatccc cggcgagcga   1320
gagatcgaag caagctgcga gctcgatctc ccccaaatcc acccgtcggc acctccgctt   1380
caaggtacgc cgctcgtcct ccccccccccc ccctctctac cttctctaga tcggcgttcc   1440
ggtccatggt tagggcccgg tagttctact tctgttcatg tttgtgttag atccgtgttt   1500
gtgttagatc cgtgctgcta gcgttcgtac acggatgcga cctgtacgtc agacacgttc   1560
tgattgctaa cttgccagtg tttctctttg gggaatcctg ggatggctct agccgttccg   1620
cagacgggat cgatttcatg attttttttg tttcgttgca tagggtttgg tttgcccttt   1680
tcctttattt caatatatgc cgtgcacttg tttgtcgggt catcttttca tgcttttttt   1740
tgtcttggtt gtgatgatgt ggtctggttg ggcggtcgtt ctagatcgga gtagaattct   1800
gtttcaaact acctggtgga tttattaatt ttggatctgt atgtgtgtgc catacatatt   1860
catagttacg aattgaagat gatggatgga aatatcgatc taggataggt atacatgttg   1920
atgcgggttt tactgatgca tatacagaga tgcttttgt tcgcttggtt gtgatgatgt   1980
ggtgtggttg ggcggtcgtt cattcgttct agatcggagt agaatactgt ttcaaactac   2040
ctggtgtatt tattaatttt ggaactgtat gtgtgtgtca tacatcttca tagttacgag   2100
tttaagatgg atgaaatat cgatctagga taggtataca tgttgatgtg ggttttactg   2160
atgcatatac atgatggcat atgcagcatc tattcatatg ctctaacctt gagtacctat   2220
```

```
ctattataat aaacaagtat gttttataat tattttgatc ttgatatact tggatgatgg    2280
catatgcagc agctatatgt ggattttttt agccctgcct tcatacgcta tttatttgct    2340
tggtactgtt tcttttgtcg atgctcaccc tgttgtttgg tgttacttct gcagccccgg    2400
ggatccatgt tacgtcctgt agaaacccca acccgtgaaa tcaaaaaact cgacggcctg    2460
tgggcattca gtctggatcg cgaaaactgt ggaattggtc agcgttggtg ggaaagcgcg    2520
ttacaagaaa gccgggcaat tgctgtgcca ggcagtttta acgatcagtt cgccgatgca    2580
gatattcgta attatgcggg caacgtctgg tatcagcgcg aagtctttat accgaaaggt    2640
tgggcaggcc agcgtatcgt gctgcgtttc gatgcggtca ctcattacgg caaagtgtgg    2700
gtcaataatc aggaagtgat ggagcatcag ggcggctata cgccatttga agccgatgtc    2760
acgccgtatg ttattgccgg gaaaagtgta cgtaagtttc tgcttctacc tttgatatat    2820
atataataat tatcattaat tagtagtaat ataatatttc aaatattttt ttcaaaataa    2880
aagaatgtag tatatagcaa ttgcttttct gtagtttata agtgtgtata ttttaattta    2940
taacttttct aatatatgac caaaatttgt tgatgtgcag gtatcaccgt ttgtgtgaac    3000
aacgaactga actggcagac tatcccgccg ggaatggtga ttaccgacga aaacggcaag    3060
aaaaagcagt cttacttcca tgatttcttt aactatgccg gaatccatcg cagcgtaatg    3120
ctctacacca cgccgaacac ctgggtggac gatatcaccg tggtgacgca tgtcgcgcaa    3180
gactgtaacc acgcgtctgt tgactggcag gtggtggcca atggtgatgt cagcgttgaa    3240
ctgcgtgatg cggatcaaca ggtggttgca actggacaag gcactagcgg gactttgcaa    3300
gtggtgaatc cgcacctctg gcaaccgggt gaaggttatc tctatgaact gtgcgtcaca    3360
gccaaaagcc agacagagtg tgatatctac ccgcttcgcg tcggcatccg gtcagtggca    3420
gtgaagggcg aacagttcct gattaaccac aaaccgttct actttactgg ctttggtcgt    3480
catgaagatg cggacttgcg tggcaaagga ttcgataacg tgctgatggt gcacgaccac    3540
gcattaatgg actggattgg ggccaactcc taccgtacct cgcattaccc ttacgctgaa    3600
gagatgctcg actgggcaga tgaacatggc atcgtggtga ttgatgaaac tgctgctgtc    3660
ggctttaacc tctctttagg cattggtttc gaagcgggca acaagccgaa agaactgtac    3720
agcgaagagg cagtcaacgg ggaaactcag caagcgcact tacaggcgat taaagagctg    3780
atagcgcgtg acaaaaacca cccaagcgtg gtgatgtgga gtattgccaa cgaaccggat    3840
acccgtccgc aaggtgcacg ggaatatttc gcgccactgg cggaagcaac gcgtaaactc    3900
gacccgacgc gtccgatcac ctgcgtcaat gtaatgttct gcgacgctca caccgatacc    3960
atcagcgatc tctttgatgt gctgtgcctg aaccgttatt acggatggta tgtccaaagc    4020
ggcgatttgg aaacggcaga gaaggtactg gaaaagaac ttctggcctg caggagaaa     4080 ctgcatcagc cgattatcat caccgaatac ggcgtggata cgttagccgg gctgcactca    4140
atgtacaccg acatgtggag tgaagagtat cagtgtgcat ggctggatat gtatcaccgc    4200
gtctttgatc gcgtcagcgc cgtcgtcggt gaacaggtat ggaatttcgc cgattttgcg    4260
acctcgcaag gcatattgcg cgttggcggt aacaagaaag ggatcttcac tcgcgaccgc    4320
aaaccgaagt cggcggcttt tctgctgcaa aaacgctgga ctggcatgaa cttcggtgaa    4380
aaaccgcagc agggaggcaa acaatgaaga tcctctagag tcgacctgca ggcatgcaag    4440
cttggcgcgc cgccgatgcc caagaactag tcattttaaa tttataaatt ataactaaat    4500
tgtataattt ttgcctttttt tttttaattt gcaagctact ggaaaatgtt atttaatata    4560
```

```
tgtataaatg tcgagacaat aatattattg cattataaat tgacctggtt tttgttagct    4620
ttcgttgcgc gtgagaatgg tgagtgtgtg ctgctgatga aactcgaatg ttcacttttg    4680
ttgtcttgtc cagctttgct aaactttggc agcattagca aagctgtttt gttctgtttc    4740
tgaattgttc ttggattgaa atctctaata ttgacttgat aattaaattt gaccggtttt    4800
tggcagtaaa ttccttcagt attggcagct caaactgaat tcttctacta atagtttagt    4860
gcttgtggag agtgtagtcg tgtagagtgg actggactaa ttcagatctt tacttggtta    4920
gctgaagatg gcatccgtta tctgaattct tcagtagttg gtggataatg acaactcgat    4980
gtagagagat aatttgctgc atgttagttt ggaagtagct tcaaaggatt taattctcag    5040
cgtccgaagt cttaagtaca gttggtttgg agagctgttc ctgtgaagac ttttatgatt    5100
tgtgctagtt atgtcatcac atgatcactt caattatcac ttatcgatct agtgagacca    5160
accatacata ccatacaaag gtaaaaagtg ttcaaactgg attgaacaag ttctgtctcc    5220
atatagatcc tactaaaatg catacatgtt gtagcaatcc catttcatcc aaaccaaaca    5280
aaatctcttt cattcggctc taaccaatca aacagagcca tttgtatccc ccgaaccaaa    5340
ccagccgagc atggatgagg gatcgagggc atccgagcaa ccaaacaggc caaagtgaa    5400 tgctttggtc gattttcgat ttgttcccta cgaatccaat tttagtcctt cagccagaag    5460
accagataca attgatccct caactatcaa aacaagtgca gatgagctcc ctcgacagtt    5520
tggacggcgg tttggttgac gtggttaatt aacggtccga ggcctcctca gcaagctgtt    5580
aacgcgatcg cagcgcctta aggggccgct ctagattagt gtacggaata aaagtcctaa    5640
ttcattcttt ttcttatacg tcaccgtttt ctacatttag aaaaatgaag tgggaatcaa    5700
ttgaaacaat tgatagcttt aaatatcaag ctgtcttctc caggaccagg ccccagcaca    5760
tcggcgtgga aagcgctagg ccccagaaca actcgtcaat cgtcatggca ataatgaca    5820 cattgagccg atttgatgca tggaacagac taataaggaa ctcaaatctc tttggagatt    5880
gaatgattga gatgaaaatg aattaatatt ttttctcaat cccctccaat gctaagaaag    5940
tttgagtttc caaattagct ttagagggcg tttagatccc ttcgttttag agaaattaga    6000
attcactcaa taaataaact tatttaattt ggaatttgat attcaaccac ttttcaaagt    6060
ttagatatag gtctatctca aattcatagg gtggatgatg gaaatgattt tatgcattaa    6120
tagaatttgt ttctactgtg taacttacat gacactcttc atctcactcc tgtatagtaa    6180
aaatgtagca tataaatatc tccgacatct tgataataat agtatacaaa tatattttgc    6240
ataaaaccga attaacttaa ttgatatatg ccaaaattac tattattaga atggaattta    6300
attccaatga tccaaaccac gaaaatggat caggtaacta attcagtcaa atgcctcatt    6360 tttttcact cccctcaaac cacgaaaatg ccattctggt ttgtaaaata gtttgaaatt    6420
gcagccctag cattattcca tacatcatat gttgagttga aattaccaat ataataataa    6480
ctaaaaaagg aaaaaaatag cgaaaacaaa agcaaggacc agttggacac ttaaatttgg    6540
caacagaagc caattcagaa ccactgcata gcagtgctta ttatcttatt tatatgtagc    6600
aaaaggcact taaatgatct cttatgacac atgccagaag gaaaacaaca gactacacaa    6660
ttacaaggtc ggaagctaca taggattacc ataacagata gctgacggcc tacaaaaaaa    6720
gatagaatac aggagaacat cacacagata aaaacatatc acccttgtac tagcagggag    6780
gcggtgcttg ctggatttta gatcagttgc ttgctggatt ttagatcagt acacagtcct    6840
gccatcacca tccaggatca tatccttgaa agccccacca ttagggatca taggcaacac    6900
atgctcctgg tgtgggacga ttatatccaa gaggtacggc cctggagtct cgagcatctt    6960
```

-continued

```
ctttatcgct gcgcggactt cgttcttctt tgtcacacgg accgctggaa tgttgaaccc    7020
tttggcgatc gtcacgaaat ctggatatat ctcactttca ttctctgggt ttcccaagta    7080
tgtgtgcgct ctgttggcct tatagaacct gtcctcccac tgcaccacca tccccaggtg    7140
ctggttgttt                                                            7150
```

<210> SEQ ID NO 90
<211> LENGTH: 23
<212> TYPE: DNA
<213> ORGANISM: Homo sapiens

<400> SEQUENCE: 90

```
tcagttttgc atagatttgc aca                                               23
```

<210> SEQ ID NO 91
<211> LENGTH: 22
<212> TYPE: DNA
<213> ORGANISM: Homo sapiens

<400> SEQUENCE: 91

```
aaccacacaa cctactacct ca                                                22
```

<210> SEQ ID NO 92
<211> LENGTH: 22
<212> TYPE: DNA
<213> ORGANISM: Homo sapiens

<400> SEQUENCE: 92

```
cacaagttcg gatctacggg tt                                                22
```

<210> SEQ ID NO 93
<211> LENGTH: 23
<212> TYPE: DNA
<213> ORGANISM: Homo sapiens

<400> SEQUENCE: 93

```
tcatagccct gtacaatgct gct                                               23
```

<210> SEQ ID NO 94
<211> LENGTH: 23
<212> TYPE: DNA
<213> ORGANISM: Homo sapiens

<400> SEQUENCE: 94

```
tgatagccct gtacaatgct gct                                               23
```

<210> SEQ ID NO 95
<211> LENGTH: 23
<212> TYPE: DNA
<213> ORGANISM: Homo sapiens

<400> SEQUENCE: 95

```
cacaaattcg gatctacagg gta                                               23
```

<210> SEQ ID NO 96
<211> LENGTH: 20
<212> TYPE: DNA
<213> ORGANISM: Homo sapiens

<400> SEQUENCE: 96

```
gcattcaccg cgtgccttaa                                                   20
```

```
<210> SEQ ID NO 97
<211> LENGTH: 21
<212> TYPE: DNA
<213> ORGANISM: Homo sapiens

<400> SEQUENCE: 97
gcaagcccag accgcaaaaa g                                              21

<210> SEQ ID NO 98
<211> LENGTH: 18
<212> TYPE: DNA
<213> ORGANISM: Homo sapiens

<400> SEQUENCE: 98
agacacgtgc actgtaga                                                  18

<210> SEQ ID NO 99
<211> LENGTH: 20
<212> TYPE: DNA
<213> ORGANISM: Homo sapiens

<400> SEQUENCE: 99
gcagaagcat ttccacacac                                                20

<210> SEQ ID NO 100
<211> LENGTH: 22
<212> TYPE: DNA
<213> ORGANISM: Homo sapiens

<400> SEQUENCE: 100
acaaagttct gtagtgcact ga                                             22

<210> SEQ ID NO 101
<211> LENGTH: 22
<212> TYPE: DNA
<213> ORGANISM: Homo sapiens

<400> SEQUENCE: 101
cacaaaccat tatgtgctgc ta                                             22

<210> SEQ ID NO 102
<211> LENGTH: 22
<212> TYPE: DNA
<213> ORGANISM: Homo sapiens

<400> SEQUENCE: 102
cgccaatatt tacgtgctgc ta                                             22

<210> SEQ ID NO 103
<211> LENGTH: 22
<212> TYPE: DNA
<213> ORGANISM: Homo sapiens

<400> SEQUENCE: 103
tatctgcact agatgcacct ta                                             22

<210> SEQ ID NO 104
<211> LENGTH: 21
<212> TYPE: DNA
<213> ORGANISM: Homo sapiens

<400> SEQUENCE: 104
ggctgtcaat tcataggtca g                                              21
```

```
<210> SEQ ID NO 105
<211> LENGTH: 21
<212> TYPE: DNA
<213> ORGANISM: Homo sapiens

<400> SEQUENCE: 105
ccaacaacat gaaactacct a                                              21

<210> SEQ ID NO 106
<211> LENGTH: 22
<212> TYPE: DNA
<213> ORGANISM: Homo sapiens

<400> SEQUENCE: 106
aacaggtagt ctgaacactg gg                                             22

<210> SEQ ID NO 107
<211> LENGTH: 22
<212> TYPE: DNA
<213> ORGANISM: Homo sapiens

<400> SEQUENCE: 107
aactatacaa cctactacct ca                                             22

<210> SEQ ID NO 108
<211> LENGTH: 22
<212> TYPE: DNA
<213> ORGANISM: Homo sapiens

<400> SEQUENCE: 108
ctgttcctgc tgaactgagc ca                                             22

<210> SEQ ID NO 109
<211> LENGTH: 22
<212> TYPE: DNA
<213> ORGANISM: Homo sapiens

<400> SEQUENCE: 109
tacctgcact ataagcactt ta                                             22

<210> SEQ ID NO 110
<211> LENGTH: 22
<212> TYPE: DNA
<213> ORGANISM: Homo sapiens

<400> SEQUENCE: 110
acaagctttt tgctcgtctt at                                             22

<210> SEQ ID NO 111
<211> LENGTH: 21
<212> TYPE: DNA
<213> ORGANISM: Homo sapiens

<400> SEQUENCE: 111
cagccgctgt cacacgcaca g                                              21

<210> SEQ ID NO 112
<211> LENGTH: 21
<212> TYPE: DNA
<213> ORGANISM: Homo sapiens

<400> SEQUENCE: 112
```

-continued ggccgtgact ggagactgtt a          21

<210> SEQ ID NO 113
<211> LENGTH: 24
<212> TYPE: DNA
<213> ORGANISM: Homo sapiens

<400> SEQUENCE: 113
aacccaccga cagcaatgaa tgtt          24

<210> SEQ ID NO 114
<211> LENGTH: 21
<212> TYPE: DNA
<213> ORGANISM: Homo sapiens

<400> SEQUENCE: 114
ctgcctgtct gtgcctgctg t          21

<210> SEQ ID NO 115
<211> LENGTH: 21
<212> TYPE: DNA
<213> ORGANISM: Homo sapiens

<400> SEQUENCE: 115
gtctgtcaat tcataggtca t          21

<210> SEQ ID NO 116
<211> LENGTH: 21
<212> TYPE: DNA
<213> ORGANISM: Homo sapiens

<400> SEQUENCE: 116
cacagttgcc agctgagatt a          21

<210> SEQ ID NO 117
<211> LENGTH: 24
<212> TYPE: DNA
<213> ORGANISM: Homo sapiens

<400> SEQUENCE: 117
atccaatcag ttcctgatgc agta          24

<210> SEQ ID NO 118
<211> LENGTH: 21
<212> TYPE: DNA
<213> ORGANISM: Artificial sequence
<220> FEATURE:
<223> OTHER INFORMATION: Nearly complementary to hsa-miR-218

<400> SEQUENCE: 118
acatggttag atcaagcaca a          21

<210> SEQ ID NO 119
<211> LENGTH: 21
<212> TYPE: DNA
<213> ORGANISM: Homo sapiens

<400> SEQUENCE: 119
agaattgcgt ttggacaatc a          21

<210> SEQ ID NO 120
<211> LENGTH: 22
<212> TYPE: DNA
<213> ORGANISM: Homo sapiens

```
<400> SEQUENCE: 120
acagttcttc aactggcagc tt                                    22

<210> SEQ ID NO 121
<211> LENGTH: 21
<212> TYPE: DNA
<213> ORGANISM: Homo sapiens

<400> SEQUENCE: 121
aaagtgtcag atacggtgtg g                                     21

<210> SEQ ID NO 122
<211> LENGTH: 23
<212> TYPE: DNA
<213> ORGANISM: Homo sapiens

<400> SEQUENCE: 122
gaaacccagc agacaatgta gct                                   23

<210> SEQ ID NO 123
<211> LENGTH: 24
<212> TYPE: DNA
<213> ORGANISM: Homo sapiens

<400> SEQUENCE: 123
gagacccagt agccagatgt agct                                  24

<210> SEQ ID NO 124
<211> LENGTH: 21
<212> TYPE: DNA
<213> ORGANISM: Homo sapiens

<400> SEQUENCE: 124
ggaaatccct ggcaatgtga t                                     21

<210> SEQ ID NO 125
<211> LENGTH: 23
<212> TYPE: DNA
<213> ORGANISM: Homo sapiens

<400> SEQUENCE: 125
tcagttttgc atggatttgc aca                                   23

<210> SEQ ID NO 126
<211> LENGTH: 22
<212> TYPE: DNA
<213> ORGANISM: Homo sapiens

<400> SEQUENCE: 126
gcaaaaatgt gctagtgcca aa                                    22

<210> SEQ ID NO 127
<211> LENGTH: 21
<212> TYPE: DNA
<213> ORGANISM: Homo sapiens

<400> SEQUENCE: 127
acctatcctg aattacttga a                                     21

<210> SEQ ID NO 128
<211> LENGTH: 22
<212> TYPE: DNA
```

<213> ORGANISM: Homo sapiens

<400> SEQUENCE: 128
ggcggaactt agccactgtg aa                                       22

<210> SEQ ID NO 129
<211> LENGTH: 22
<212> TYPE: DNA
<213> ORGANISM: Homo sapiens

<400> SEQUENCE: 129
ctcaatagac tgtgagctcc tt                                       22

<210> SEQ ID NO 130
<211> LENGTH: 22
<212> TYPE: DNA
<213> ORGANISM: Homo sapiens

<400> SEQUENCE: 130
aaccgatttc agatggtgct ag                                       22

<210> SEQ ID NO 131
<211> LENGTH: 20
<212> TYPE: DNA
<213> ORGANISM: Homo sapiens

<400> SEQUENCE: 131
actgatttca aatggtgcta                                          20

<210> SEQ ID NO 132
<211> LENGTH: 22
<212> TYPE: DNA
<213> ORGANISM: Homo sapiens

<400> SEQUENCE: 132
gctgcaaaca tccgactgaa ag                                       22

<210> SEQ ID NO 133
<211> LENGTH: 23
<212> TYPE: DNA
<213> ORGANISM: Homo sapiens

<400> SEQUENCE: 133
gctgagagtg taggatgttt aca                                      23

<210> SEQ ID NO 134
<211> LENGTH: 22
<212> TYPE: DNA
<213> ORGANISM: Homo sapiens

<400> SEQUENCE: 134
cttccagtcg gggatgttta ca                                       22

<210> SEQ ID NO 135
<211> LENGTH: 20
<212> TYPE: DNA
<213> ORGANISM: Homo sapiens

<400> SEQUENCE: 135
tccagtcaag gatgtttaca                                          20

<210> SEQ ID NO 136
<211> LENGTH: 21

<212> TYPE: DNA
<213> ORGANISM: Homo sapiens

<400> SEQUENCE: 136
gcaacttagt aatgtgcaat a                                              21

<210> SEQ ID NO 137
<211> LENGTH: 19
<212> TYPE: DNA
<213> ORGANISM: Homo sapiens

<400> SEQUENCE: 137
caatgcaact acaatgcac                                                 19

<210> SEQ ID NO 138
<211> LENGTH: 21
<212> TYPE: DNA
<213> ORGANISM: Homo sapiens

<400> SEQUENCE: 138
aacaaaatca ctagtcttcc a                                              21

<210> SEQ ID NO 139
<211> LENGTH: 24
<212> TYPE: DNA
<213> ORGANISM: Homo sapiens

<400> SEQUENCE: 139
actacctgca ctgtaagcac tttg                                           24

<210> SEQ ID NO 140
<211> LENGTH: 22
<212> TYPE: DNA
<213> ORGANISM: Homo sapiens

<400> SEQUENCE: 140
acaggccggg acaagtgcaa ta                                             22

<210> SEQ ID NO 141
<211> LENGTH: 22
<212> TYPE: DNA
<213> ORGANISM: Homo sapiens

<400> SEQUENCE: 141
ctacctgcac gaacagcact tt                                             22

<210> SEQ ID NO 142
<211> LENGTH: 22
<212> TYPE: DNA
<213> ORGANISM: Homo sapiens

<400> SEQUENCE: 142
tgctcaataa atacccgttg aa                                             22

<210> SEQ ID NO 143
<211> LENGTH: 22
<212> TYPE: DNA
<213> ORGANISM: homo sapiens

<400> SEQUENCE: 143
aacaatacaa cttactacct ca                                             22

<210> SEQ ID NO 144

```
<211> LENGTH: 22
<212> TYPE: DNA
<213> ORGANISM: Homo sapiens

<400> SEQUENCE: 144
agcctatcct ggattacttg aa                                              22

<210> SEQ ID NO 145
<211> LENGTH: 22
<212> TYPE: DNA
<213> ORGANISM: Mus musculus

<400> SEQUENCE: 145
ctacgcgtat tcttaagcaa ta                                              22

<210> SEQ ID NO 146
<211> LENGTH: 20
<212> TYPE: DNA
<213> ORGANISM: Mus musculus

<400> SEQUENCE: 146
tcagttatca cagtactgta                                                 20

<210> SEQ ID NO 147
<211> LENGTH: 22
<212> TYPE: DNA
<213> ORGANISM: Mus musculus

<400> SEQUENCE: 147
acacaaattc ggttctacag gg                                              22

<210> SEQ ID NO 148
<211> LENGTH: 23
<212> TYPE: DNA
<213> ORGANISM: Artificial sequence
<220> FEATURE:
<223> OTHER INFORMATION: Complementary to mmu-miT-122a

<400> SEQUENCE: 148
acaaacacca ttgtcacact cca                                             23

<210> SEQ ID NO 149
<211> LENGTH: 22
<212> TYPE: DNA
<213> ORGANISM: Artificial sequence
<220> FEATURE:
<223> OTHER INFORMATION: Complementary to mmu-miR-124a

<400> SEQUENCE: 149
tggcattcac cgcgtgcctt aa                                              22

<210> SEQ ID NO 150
<211> LENGTH: 23
<212> TYPE: DNA
<213> ORGANISM: Mus musculus

<400> SEQUENCE: 150
cacaggttaa agggtctcag gga                                             23

<210> SEQ ID NO 151
<211> LENGTH: 22
<212> TYPE: DNA
<213> ORGANISM: Mus musculus

<400> SEQUENCE: 151
```
tcacaagtta gggtctcagg ga                                    22

<210> SEQ ID NO 152
<211> LENGTH: 21
<212> TYPE: DNA
<213> ORGANISM: Mus musculus

<400> SEQUENCE: 152
gcattattac tcacggtacg a                                     21

<210> SEQ ID NO 153
<211> LENGTH: 22
<212> TYPE: DNA
<213> ORGANISM: Mus musculus

<400> SEQUENCE: 153
agccaagctc agacggatcc ga                                    22

<210> SEQ ID NO 154
<211> LENGTH: 22
<212> TYPE: DNA
<213> ORGANISM: Artificial sequence
<220> FEATURE:
<223> OTHER INFORMATION: Complementary to mmu-miR-128

<400> SEQUENCE: 154
aaaagagacc ggttcactgt ga                                    22

<210> SEQ ID NO 155
<211> LENGTH: 22
<212> TYPE: DNA
<213> ORGANISM: Mus musculus

<400> SEQUENCE: 155
agcaagccca gaccgcaaaa ag                                    22

<210> SEQ ID NO 156
<211> LENGTH: 20
<212> TYPE: DNA
<213> ORGANISM: Mus musculus

<400> SEQUENCE: 156
gcccttttaa cattgcactg                                       20

<210> SEQ ID NO 157
<211> LENGTH: 22
<212> TYPE: DNA
<213> ORGANISM: Mus musculus

<400> SEQUENCE: 157
cgaccatggc tgtagactgt ta                                    22

<210> SEQ ID NO 158
<211> LENGTH: 22
<212> TYPE: DNA
<213> ORGANISM: Mus musculus

<400> SEQUENCE: 158
acagctggtt gaaggggacc aa                                    22

<210> SEQ ID NO 159
<211> LENGTH: 21
<212> TYPE: DNA

<213> ORGANISM: Mus musculus

<400> SEQUENCE: 159
ccctctggtc aaccagtcac a                                    21

<210> SEQ ID NO 160
<211> LENGTH: 23
<212> TYPE: DNA
<213> ORGANISM: Mus musculus

<400> SEQUENCE: 160
tcacatagga ataaaaagcc ata                                  23

<210> SEQ ID NO 161
<211> LENGTH: 23
<212> TYPE: DNA
<213> ORGANISM: Mus musculus

<400> SEQUENCE: 161
tccatcatca aaacaaatgg agt                                  23

<210> SEQ ID NO 162
<211> LENGTH: 22
<212> TYPE: DNA
<213> ORGANISM: Mus musculus

<400> SEQUENCE: 162
tgtgagttct accattgcca aa                                   22

<210> SEQ ID NO 163
<211> LENGTH: 21
<212> TYPE: DNA
<213> ORGANISM: Mus musculus

<400> SEQUENCE: 163
ccatctttac cagacagtgt t                                    21

<210> SEQ ID NO 164
<211> LENGTH: 22
<212> TYPE: DNA
<213> ORGANISM: Mus musculus

<400> SEQUENCE: 164
ccataaagta ggaaacacta ca                                   22

<210> SEQ ID NO 165
<211> LENGTH: 20
<212> TYPE: DNA
<213> ORGANISM: Mus musculus

<400> SEQUENCE: 165
gtagtgcttt ctactttatg                                      20

<210> SEQ ID NO 166
<211> LENGTH: 22
<212> TYPE: DNA
<213> ORGANISM: Mus musculus

<400> SEQUENCE: 166
tgagctacag tgcttcatct ca                                   22

<210> SEQ ID NO 167
<211> LENGTH: 22

```
<212> TYPE: DNA
<213> ORGANISM: Mus musculus

<400> SEQUENCE: 167
ctagtacatc atctatactg ta                                              22

<210> SEQ ID NO 168
<211> LENGTH: 24
<212> TYPE: DNA
<213> ORGANISM: Mus musculus

<400> SEQUENCE: 168
aagggattcc tgggaaaact ggac                                            24

<210> SEQ ID NO 169
<211> LENGTH: 22
<212> TYPE: DNA
<213> ORGANISM: Mus musculus

<400> SEQUENCE: 169
aacccatgga attcagttct ca                                              22

<210> SEQ ID NO 170
<211> LENGTH: 22
<212> TYPE: DNA
<213> ORGANISM: Mus musculus

<400> SEQUENCE: 170
ggagtgaaga cacggagcca ga                                              22

<210> SEQ ID NO 171
<211> LENGTH: 22
<212> TYPE: DNA
<213> ORGANISM: Mus musculus

<400> SEQUENCE: 171
cactggtaca agggttggga ga                                              22

<210> SEQ ID NO 172
<211> LENGTH: 21
<212> TYPE: DNA
<213> ORGANISM: Mus musculus

<400> SEQUENCE: 172
cctcaaggag cctcagtcta g                                               21

<210> SEQ ID NO 173
<211> LENGTH: 21
<212> TYPE: DNA
<213> ORGANISM: Mus musculus

<400> SEQUENCE: 173
ccaagttctg tcatgcactg a                                               21

<210> SEQ ID NO 174
<211> LENGTH: 20
<212> TYPE: DNA
<213> ORGANISM: Mus musculus

<400> SEQUENCE: 174 tcactttttgt gactatgcaa                                                20

<210> SEQ ID NO 175
```

```
<211> LENGTH: 22
<212> TYPE: DNA
<213> ORGANISM: Mus musculus

<400> SEQUENCE: 175
cgaaggcaac acggataacc ta                                              22

<210> SEQ ID NO 176
<211> LENGTH: 22
<212> TYPE: DNA
<213> ORGANISM: Mus musculus

<400> SEQUENCE: 176
cccctatcac aattagcatt aa                                              22

<210> SEQ ID NO 177
<211> LENGTH: 22
<212> TYPE: DNA
<213> ORGANISM: Mus musculus

<400> SEQUENCE: 177
tgtaaaccat gatgtgctgc ta                                              22

<210> SEQ ID NO 178
<211> LENGTH: 23
<212> TYPE: DNA
<213> ORGANISM: Mus musculus

<400> SEQUENCE: 178
actcaccgac agcgttgaat gtt                                             23

<210> SEQ ID NO 179
<211> LENGTH: 17
<212> TYPE: DNA
<213> ORGANISM: Mus musculus

<400> SEQUENCE: 179
gattcacaac accagct                                                    17

<210> SEQ ID NO 180
<211> LENGTH: 22
<212> TYPE: DNA
<213> ORGANISM: Mus musculus

<400> SEQUENCE: 180
tcttcccatg cgctatacct ct                                              22

<210> SEQ ID NO 181
<211> LENGTH: 22
<212> TYPE: DNA
<213> ORGANISM: Mus musculus

<400> SEQUENCE: 181
acccttatca gttctccgtc ca                                              22

<210> SEQ ID NO 182
<211> LENGTH: 18
<212> TYPE: DNA
<213> ORGANISM: Mus musculus

<400> SEQUENCE: 182
gaactgcctt tctctcca                                                   18
```

```
<210> SEQ ID NO 183
<211> LENGTH: 23
<212> TYPE: DNA
<213> ORGANISM: Mus musculus

<400> SEQUENCE: 183
aagcccaaaa ggagaattct ttg                                              23

<210> SEQ ID NO 184
<211> LENGTH: 22
<212> TYPE: DNA
<213> ORGANISM: Mus musculus

<400> SEQUENCE: 184
ccggctgcaa cacaagacac ga                                               22

<210> SEQ ID NO 185
<211> LENGTH: 22
<212> TYPE: DNA
<213> ORGANISM: Mus musculus

<400> SEQUENCE: 185
accctccacc atgcaaggga tg                                               22

<210> SEQ ID NO 186
<211> LENGTH: 23
<212> TYPE: DNA
<213> ORGANISM: Mus musculus

<400> SEQUENCE: 186
actgatatca gctcagtagg cac                                              23

<210> SEQ ID NO 187
<211> LENGTH: 22
<212> TYPE: DNA
<213> ORGANISM: Mus musculus

<400> SEQUENCE: 187
acctaatata tcaaacatat ca                                               22

<210> SEQ ID NO 188
<211> LENGTH: 22
<212> TYPE: DNA
<213> ORGANISM: Mus musculus

<400> SEQUENCE: 188
agctgctttt gggattccgt tg                                               22

<210> SEQ ID NO 189
<211> LENGTH: 21
<212> TYPE: DNA
<213> ORGANISM: Mus musculus

<400> SEQUENCE: 189
ctgggacttt gtaggccagt t                                                21

<210> SEQ ID NO 190
<211> LENGTH: 22
<212> TYPE: DNA
<213> ORGANISM: Artificial sequence
<220> FEATURE:
<223> OTHER INFORMATION: Complementary to mmu-miR-194

<400> SEQUENCE: 190
```

-continued

| tccacatgga gttgctgtta ca | 22 |

<210> SEQ ID NO 191
<211> LENGTH: 21
<212> TYPE: DNA
<213> ORGANISM: Mus musculus

<400> SEQUENCE: 191

| gccaatattt ctgtgctgct a | 21 |

<210> SEQ ID NO 192
<211> LENGTH: 22
<212> TYPE: DNA
<213> ORGANISM: Mus musculus

<400> SEQUENCE: 192

| aaccaatgtg cagactactg ta | 22 |

<210> SEQ ID NO 193
<211> LENGTH: 21
<212> TYPE: DNA
<213> ORGANISM: Artificial sequence
<220> FEATURE:
<223> OTHER INFORMATION: Complementary to mmu-miR-1b

<400> SEQUENCE: 193

| tacatacttc tttacattcc a | 21 |

<210> SEQ ID NO 194
<211> LENGTH: 23
<212> TYPE: DNA
<213> ORGANISM: Mus musculus

<400> SEQUENCE: 194

| aatacatact tctttacatt cca | 23 |

<210> SEQ ID NO 195
<211> LENGTH: 23
<212> TYPE: DNA
<213> ORGANISM: Mus musculus

<400> SEQUENCE: 195

| gtcatcatta ccaggcagta tta | 23 |

<210> SEQ ID NO 196
<211> LENGTH: 21
<212> TYPE: DNA
<213> ORGANISM: Mus musculus

<400> SEQUENCE: 196

| agaacaatgc cttactgagt a | 21 |

<210> SEQ ID NO 197
<211> LENGTH: 23
<212> TYPE: DNA
<213> ORGANISM: Mus musculus

<400> SEQUENCE: 197

| cagtgaattc taccagtgcc ata | 23 |

<210> SEQ ID NO 198
<211> LENGTH: 22
<212> TYPE: DNA
<213> ORGANISM: Mus musculus

<400> SEQUENCE: 198
cgcaaggtcg gttctacggg tg                                    22

<210> SEQ ID NO 199
<211> LENGTH: 22
<212> TYPE: DNA
<213> ORGANISM: Artificial sequence
<220> FEATURE:
<223> OTHER INFORMATION: Complementary to mmu-miR-206

<400> SEQUENCE: 199
ccacacactt ccttacattc ca                                    22

<210> SEQ ID NO 200
<211> LENGTH: 23
<212> TYPE: DNA
<213> ORGANISM: Mus musculus

<400> SEQUENCE: 200
gagggaggag agccaggaga agc                                   23

<210> SEQ ID NO 201
<211> LENGTH: 23
<212> TYPE: DNA
<213> ORGANISM: Mus musculus

<400> SEQUENCE: 201
gtggtaatcc ctggcaatgt gat                                   23

<210> SEQ ID NO 202
<211> LENGTH: 20
<212> TYPE: DNA
<213> ORGANISM: Mus musculus

<400> SEQUENCE: 202
cagaacttag ccactgtgaa                                       20

<210> SEQ ID NO 203
<211> LENGTH: 22
<212> TYPE: DNA
<213> ORGANISM: Mus musculus

<400> SEQUENCE: 203
taaccgattt caaatggtgc ta                                    22

<210> SEQ ID NO 204
<211> LENGTH: 21
<212> TYPE: DNA
<213> ORGANISM: Mus musculus

<400> SEQUENCE: 204
gctgagtgta ggatgtttac a                                     21

<210> SEQ ID NO 205
<211> LENGTH: 23
<212> TYPE: DNA
<213> ORGANISM: Artificial sequence
<220> FEATURE:
<223> OTHER INFORMATION: Complementary to mmu-miR-9

<400> SEQUENCE: 205
tcatacagct agataaccaa aga                                   23

```
<210> SEQ ID NO 206
<211> LENGTH: 21
<212> TYPE: DNA
<213> ORGANISM: Mus musculus

<400> SEQUENCE: 206
actttcggtt atctagcttt a                                              21

<210> SEQ ID NO 207
<211> LENGTH: 20
<212> TYPE: DNA
<213> ORGANISM: Mus musculus

<400> SEQUENCE: 207
acaagatcgg atctacgggt                                                20

<210> SEQ ID NO 208
<211> LENGTH: 21
<212> TYPE: DNA
<213> ORGANISM: Mus musculus

<400> SEQUENCE: 208
ctagtggtcc taaacatttc a                                              21

<210> SEQ ID NO 209
<211> LENGTH: 59
<212> TYPE: DNA
<213> ORGANISM: Artificial sequence
<220> FEATURE:
<223> OTHER INFORMATION: oligonucleotide primer

<400> SEQUENCE: 209
gggagctcgg ggaatgaagc ctggtccgag aatttccccg atcgttcaaa catttggca     59

<210> SEQ ID NO 210
<211> LENGTH: 30
<212> TYPE: DNA
<213> ORGANISM: Artificial sequence
<220> FEATURE:
<223> OTHER INFORMATION: oligonucleotide primer

<400> SEQUENCE: 210
tcggaccgtt aattaacaca aactgaaggc                                     30

<210> SEQ ID NO 211
<211> LENGTH: 25
<212> TYPE: DNA
<213> ORGANISM: Artificial sequence
<220> FEATURE:
<223> OTHER INFORMATION: oligonucleotide primer

<400> SEQUENCE: 211
gatctggccg gccgggcccg aattc                                          25

<210> SEQ ID NO 212
<211> LENGTH: 12587
<212> TYPE: DNA
<213> ORGANISM: Artificial sequence
<220> FEATURE:
<223> OTHER INFORMATION: vector construct pBPSLM185
<220> FEATURE:
<221> NAME/KEY: repeat_region
<222> LOCATION: (42)..(66)
<223> OTHER INFORMATION: Left T-DNA Border repeat region
<220> FEATURE:
<221> NAME/KEY: promoter
```

```
<222> LOCATION: (157)..(2144)
<223> OTHER INFORMATION: Maize Ubiquitin plus intron promoter
<220> FEATURE:
<221> NAME/KEY: CDS
<222> LOCATION: (2178)..(4094)
<223> OTHER INFORMATION: ZmAHAS L2 S653(At)N (XI12) cds. S621N.
<220> FEATURE:
<221> NAME/KEY: terminator
<222> LOCATION: (4095)..(5310)
<223> OTHER INFORMATION: Maize AHASL2 [XI12] 3'/UTR sequence with
      terminator.
<220> FEATURE:
<221> NAME/KEY: promoter
<222> LOCATION: (5368)..(6765)
<223> OTHER INFORMATION: Sugarcane bacilliform virus [ScBV] promoter
<220> FEATURE:
<221> NAME/KEY: CDS
<222> LOCATION: (6784)..(7461)
<223> OTHER INFORMATION: Discosoma sp. red fluorescent protein
      [drFP583;1]
<220> FEATURE:
<221> NAME/KEY: terminator
<222> LOCATION: (7493)..(7745)
<223> OTHER INFORMATION: Nopaline Synthase poly-A terminator
<220> FEATURE:
<221> NAME/KEY: repeat_region
<222> LOCATION: (7775)..(7919)
<223> OTHER INFORMATION: pSB11's full RB
<220> FEATURE:
<221> NAME/KEY: rep_origin
<222> LOCATION: (10197)..(10477)
<223> OTHER INFORMATION: pBR322 origin of replication [ecoli] from
      AF234316 pCambia2301
<220> FEATURE:
<221> NAME/KEY: CDS
<222> LOCATION: (11336)..(12151)
<223> OTHER INFORMATION: Kanamycin Resistance selection gene/CDS for
      microorganism.

<400> SEQUENCE: 212
tttgtgccga gctgccggtc ggggagctgt tggctggctg gtggcaggat atattgtggt     60
gtaaacaaat tgacgcttag acaacttaat aacacattgc ggacgttttt aatgtactga    120
attggatccg cccgggcggt accaagcttc cgcggctgca gtgcagcgtg acccggtcgt    180
gcccctctct agagataatg agcattgcat gtctaagtta taaaaaatta ccacatattt    240
tttttgtcac acttgtttga agtgcagttt atctatcttt atacatatat ttaaacttta    300
ctctacgaat aatataatct atagtactac aataatatca gtgttttaga gaatcatata    360
aatgaacagt tagacatggt ctaaaggaca attgagtatt ttgacaacag gactctacag    420
ttttatcttt ttagtgtgca tgtgttctcc ttttttttg caaatagctt cacctatata    480
atacttcatc cattttatta gtacatccat ttagggttta gggttaatgg tttttataga    540 ctaattttt tagtacatct attttattct attttagcct ctaaattaag aaaactaaaa    600
ctctatttta gttttttat ttaatagttt agatataaaa tagaataaaa taagtgact    660 aaaaattaaa caaataccct ttaagaaatt aaaaaaacta aggaaacatt tttcttgttt    720
cgagtagata atgccagcct gttaaacgcc gtcgacgagt ctaacggaca ccaaccagcg    780
aaccagcagc gtcgcgtcgg gccaagcgaa gcagacggca cggcatctct gtcgctgcct    840 ctggaccccct ctcgagagtt ccgctccacc gttggacttg ctccgctgtc ggcatccaga    900
aattgcgtgg cggagcggca gacgtgagcc ggcacggcag gcggcctcct cctcctctca    960
cggcaccggc agctacgggg gattcctttc ccaccgctcc ttcgctttcc cttcctcgcc   1020
cgccgtaata aatagacacc ccctccacac cctctttccc caacctcgtg ttgttcggag   1080
cgcacacaca cacaaccaga tctccccca atccacccgt cggcacctcc gcttcaaggt   1140
```

```
acgccgctcg tcctccccc cccccccct ctctaccttc tctagatcgg cgttccggtc      1200
catggttagg gcccggtagt tctacttctg ttcatgtttg tgttagatcc gtgtttgtgt    1260
tagatccgtg ctgctagcgt tcgtacacgg atgcgacctg tacgtcagac acgttctgat   1320
tgctaacttg ccagtgtttc tctttgggga atcctgggat ggctctagcc gttccgcaga   1380
cgggatcgat ttcatgattt tttttgtttc gttgcatagg gtttggtttg ccctttcct    1440
ttatttcaat atatgccgtg cacttgtttg tcgggtcatc ttttcatgct ttttttgtc   1500
ttggttgtga tgatgtggtc tggttgggcg gtcgttctag atcggagtag aattctgttt   1560
caaactacct ggtggattta ttaattttgg atctgtatgt gtgtgccata catattcata   1620
gttacgaatt gaagatgatg gatggaaata tcgatctagg ataggtatac atgttgatgc   1680
gggttttact gatgcatata cagagatgct ttttgttcgc ttggttgtga tgatgtggtg   1740
tggttgggcg gtcgttcatt cgttctagat cggagtagaa tactgtttca aactacctgg   1800
tgtatttatt aattttggaa ctgtatgtgt gtgtcataca tcttcatagt tacgagttta   1860
agatggatgg aaatatcgat ctaggatagg tatacatgtt gatgtgggtt ttactgatgc   1920
atatacatga tggcatatgc agcatctatt catatgctct aaccttgagt acctatctat   1980
tataataaac aagtatgttt tataattatt tcgatcttga tatacttgga tgatggcata   2040
tgcagcagct atatgtggat ttttttagcc ctgccttcat acgctattta tttgcttggt   2100
actgtttctt ttgtcgatgc tcaccctgtt gtttggtgtt acttctgcag ggtacggatc   2160
cactagttct agaaacc atg gcc acc gcc gcc gcc gcg tct acc gcg ctc      2210
                    Met Ala Thr Ala Ala Ala Ala Ser Thr Ala Leu
                      1               5                  10 act ggc gcc act acc gct gcg ccc aag gcg agg cgc cgg gcg cac ctc    2258
Thr Gly Ala Thr Thr Ala Ala Pro Lys Ala Arg Arg Arg Ala His Leu
         15                  20                  25 ctg gcc acc cgc cgc gcc ctc gcc gcg ccc atc agg tgc tca gcg gcg   2306
Leu Ala Thr Arg Arg Ala Leu Ala Ala Pro Ile Arg Cys Ser Ala Ala
         30                  35                  40 tca ccc gcc atg ccg atg gct ccc ccg gcc acc ccg ctc cgg ccg tgg   2354
Ser Pro Ala Met Pro Met Ala Pro Pro Ala Thr Pro Leu Arg Pro Trp
         45                  50                  55 ggc ccc acc gat ccc cgc aag ggc gcc gac atc ctc gtc gag tcc ctc   2402
Gly Pro Thr Asp Pro Arg Lys Gly Ala Asp Ile Leu Val Glu Ser Leu
 60                  65                  70                  75 gag cgc tgc ggc gtc cgc gac gtc ttc gcc tac ccc ggc ggc gcg tcc   2450
Glu Arg Cys Gly Val Arg Asp Val Phe Ala Tyr Pro Gly Gly Ala Ser
                 80                  85                  90 atg gag atc cac cag gca ctc acc cgc tcc ccc gtc atc gcc aac cac   2498
Met Glu Ile His Gln Ala Leu Thr Arg Ser Pro Val Ile Ala Asn His
             95                 100                 105 ctc ttc cgc cac gag caa ggg gag gcc ttt gcg gcc tcc ggc tac gcg   2546
Leu Phe Arg His Glu Gln Gly Glu Ala Phe Ala Ala Ser Gly Tyr Ala
            110                 115                 120 cgc tcc tcg ggc cgc gtc ggc gtc tgc atc gcc acc tcc ggc ccc ggc   2594
Arg Ser Ser Gly Arg Val Gly Val Cys Ile Ala Thr Ser Gly Pro Gly
        125                 130                 135 gcc acc aac ctt gtc tcc gcg ctc gcc gac gcg ctg ctc gat tcc gtc   2642
Ala Thr Asn Leu Val Ser Ala Leu Ala Asp Ala Leu Leu Asp Ser Val
140                 145                 150                 155 ccc atg gtc gcc atc acg gga cag gtg ccg cga cgc atg att ggc acc   2690
Pro Met Val Ala Ile Thr Gly Gln Val Pro Arg Arg Met Ile Gly Thr
                160                 165                 170
```

```
gac gcc ttc cag gag acg ccc atc gtc gag gtc acc cgc tcc atc acc      2738
Asp Ala Phe Gln Glu Thr Pro Ile Val Glu Val Thr Arg Ser Ile Thr
            175                 180                 185 aag cac aac tac ctg gtc ctc gac gtc gac gac atc ccc cgc gtc gtg      2786
Lys His Asn Tyr Leu Val Leu Asp Val Asp Asp Ile Pro Arg Val Val
        190                 195                 200 cag gag gct ttc ttc ctc gcc tcc tct ggt cga ccg ggg ccg gtg ctt      2834
Gln Glu Ala Phe Phe Leu Ala Ser Ser Gly Arg Pro Gly Pro Val Leu
    205                 210                 215 gtc gac atc ccc aag gac atc cag cag cag atg gcg gtg cct gtc tgg      2882
Val Asp Ile Pro Lys Asp Ile Gln Gln Gln Met Ala Val Pro Val Trp
220                 225                 230                 235 gac aag ccc atg agt ctg cct ggg tac att gcg cgc ctt ccc aag ccc      2930
Asp Lys Pro Met Ser Leu Pro Gly Tyr Ile Ala Arg Leu Pro Lys Pro
                240                 245                 250 cct gcg act gag ttg ctt gag cag gtg ctg cgt ctt gtt ggt gaa tcc      2978
Pro Ala Thr Glu Leu Leu Glu Gln Val Leu Arg Leu Val Gly Glu Ser
            255                 260                 265 cgg cgc cct gtt ctt tat gtt ggc ggt ggc tgc gca gca tct ggt gag      3026
Arg Arg Pro Val Leu Tyr Val Gly Gly Gly Cys Ala Ala Ser Gly Glu
        270                 275                 280 gag ttg cga cgc ttt gtg gag ctg act gga atc ccg gtc aca act act      3074
Glu Leu Arg Arg Phe Val Glu Leu Thr Gly Ile Pro Val Thr Thr Thr
    285                 290                 295 ctt atg ggc ctc ggc aac ttc ccc agc gac gac cca ctg tct ctg cgc      3122
Leu Met Gly Leu Gly Asn Phe Pro Ser Asp Asp Pro Leu Ser Leu Arg
300                 305                 310                 315 atg cta ggt atg cat ggc acg gtg tat gca aat tat gca gtg gat aag      3170
Met Leu Gly Met His Gly Thr Val Tyr Ala Asn Tyr Ala Val Asp Lys
                320                 325                 330 gcc gat ctg ttg ctt gca ctt ggt gtg cgg ttt gat gat cgt gtg aca      3218
Ala Asp Leu Leu Leu Ala Leu Gly Val Arg Phe Asp Asp Arg Val Thr
            335                 340                 345 ggg aag att gag gct ttt gca agc agg gct aag att gtg cac gtt gat      3266
Gly Lys Ile Glu Ala Phe Ala Ser Arg Ala Lys Ile Val His Val Asp
        350                 355                 360 att gat ccg gct gag att ggc aag aac aag cag cca cat gtg tcc atc      3314
Ile Asp Pro Ala Glu Ile Gly Lys Asn Lys Gln Pro His Val Ser Ile
    365                 370                 375 tgt gca gat gtt aag ctt gct ttg cag ggc atg aat gct ctt ctt gaa      3362
Cys Ala Asp Val Lys Leu Ala Leu Gln Gly Met Asn Ala Leu Leu Glu
380                 385                 390                 395 gga agc aca tca aag aag agc ttt gac ttt ggc tca tgg aac gat gag      3410
Gly Ser Thr Ser Lys Lys Ser Phe Asp Phe Gly Ser Trp Asn Asp Glu
                400                 405                 410 ttg gat cag cag aag agg gaa ttc ccc ctt ggg tat aaa aca tct aat      3458
Leu Asp Gln Gln Lys Arg Glu Phe Pro Leu Gly Tyr Lys Thr Ser Asn
            415                 420                 425 gag gag atc cag cca caa tat gct att cag gtt ctt gat gag ctg acg      3506
Glu Glu Ile Gln Pro Gln Tyr Ala Ile Gln Val Leu Asp Glu Leu Thr
        430                 435                 440 aaa ggc gag gcc atc atc ggc aca ggt gtt ggg cag cac cag atg tgg      3554
Lys Gly Glu Ala Ile Ile Gly Thr Gly Val Gly Gln His Gln Met Trp
    445                 450                 455 gcg gca cag tac tac act tac aag cgg cca agg cag tgg ttg tct tca      3602
Ala Ala Gln Tyr Tyr Thr Tyr Lys Arg Pro Arg Gln Trp Leu Ser Ser
460                 465                 470                 475 gct ggt ctt ggg gct atg gga ttt ggt ttg ccg gct gct gct ggt gct      3650
Ala Gly Leu Gly Ala Met Gly Phe Gly Leu Pro Ala Ala Ala Gly Ala
```

-continued

```
              480              485              490
tct gtg gcc aac cca ggt gtt act gtt gtt gac atc gat gga gat ggt    3698
Ser Val Ala Asn Pro Gly Val Thr Val Val Asp Ile Asp Gly Asp Gly
            495                  500              505 agc ttt ctc atg aac gtt cag gag cta gct atg atc cga att gag aac    3746
Ser Phe Leu Met Asn Val Gln Glu Leu Ala Met Ile Arg Ile Glu Asn
        510                  515                  520 ctc ccg gtg aag gtc ttt gtg cta aac aac cag cac ctg ggg atg gtg    3794
Leu Pro Val Lys Val Phe Val Leu Asn Asn Gln His Leu Gly Met Val
    525                  530                  535 gtg cag tgg gag gac agg ttc tat aag gcc aac aga gcg cac aca tac    3842
Val Gln Trp Glu Asp Arg Phe Tyr Lys Ala Asn Arg Ala His Thr Tyr
540                  545                  550                  555 ttg gga aac cca gag aat gaa agt gag ata tat cca gat ttc gtg acg    3890
Leu Gly Asn Pro Glu Asn Glu Ser Glu Ile Tyr Pro Asp Phe Val Thr
                560                  565                  570 atc gcc aaa ggg ttc aac att cca gcg gtc cgt gtg aca aag aag aac    3938
Ile Ala Lys Gly Phe Asn Ile Pro Ala Val Arg Val Thr Lys Lys Asn
            575                  580                  585 gaa gtc cgc gca gcg ata aag aag atg ctc gag act cca ggg ccg tac    3986
Glu Val Arg Ala Ala Ile Lys Lys Met Leu Glu Thr Pro Gly Pro Tyr
        590                  595                  600 ctc ttg gat ata atc gtc cca cac cag gag cat gtg ttg cct atg atc    4034
Leu Leu Asp Ile Ile Val Pro His Gln Glu His Val Leu Pro Met Ile
    605                  610                  615 cct aat ggt ggg gct ttc aag gat atg atc ctg gat ggt gat ggc agg    4082
Pro Asn Gly Gly Ala Phe Lys Asp Met Ile Leu Asp Gly Asp Gly Arg
620                  625                  630                  635 act gtg tac tga tctaaaatcc agcaagcaac tgatctaaaa tccagcaagc        4134
Thr Val Tyr accgcctccc tgctagtaca agggtgatat gttttttatct gtgtgatgtt ctcctgtatt  4194
ctatcttttt ttgtaggccg tcagctatct gttatggtaa tcctatgtag cttccgacct  4254
tgtaattgtg tagtctgttg ttttccttct ggcatgtgtc ataagagatc atttaagtgc  4314
cttttgctac atataaataa gataataagc actgctatgc agtggttctg aattggcttc  4374
tgttgccaaa tttaagtgtc caactggtcc ttgcttttgt tttcgctatt ttttccttt   4434 tttagttatt attatattgg taatttcaac tcaacatatg atgtatgaa taatgctagg   4494 gctgcaattt caaactattt tacaaaccag aatggcattt tcgtggtttg aggggagtga  4554
aaaaaaatga ggcatttgac tgaattagtt acctgatcca ttttcgtggt ttggatcatt  4614
ggaattaaat tccattctaa taatagtaat tttggcatat atcaattaag ttaattcggt  4674
tttatgcaaa atatatttgt atactattat tatcaagatg tcggagatat ttatatgcta  4734
catttttact atacaggagt gagatgaaga gtgtcatgta agttacacag tagaaacaaa  4794
ttctattaat gcataaaatc atttccatca tccaccctat gaatttgaga tagacctata  4854
tctaaacttt gaaagtggt tgaatatcaa attccaaatt aaataagtta ttttattgag   4914
tgaattctaa tttctctaaa acgaagggat ctaaacgccc tctaaagcta atttggaaac  4974
tcaaactttc ttagcattgg aggggattga gaaaaaatat taattcattt tcatctcaat  5034
cattcaatct ccaaagagat ttgagttcct tattagtctg ttccatgcat caaatcggct  5094
caatgtgtca ttatttgcca tgacgattga cgagttgttc tggggcctag cgctttccac  5154
gccgatgtgc tggggcctgg tcctggagaa gacagcttga tatttaaagc tatcaattgt  5214
ttcaattgat tcccacttca tttttctaaa tgtagaaaac ggtgacgtat aagaaaaaga  5274
```

| | |
|---|---:|
| atgaattagg acttttattc cgtacactaa tctagagcgg ccgcaagctt gtacaacgcg | 5334 |
| taccggttaa ttaaggtacc caattgcata tgtaatcctg gctagcaaca ctgaactatg | 5394 |
| ccagaaacca catcaaagat atgggcaagc ttcttggccc attatatcca aagacctcag | 5454 |
| agaaaggtga gcgaaggctc aattcagaag attggaagct gatcaatagg atcaagacaa | 5514 |
| tggtgagaac gcttccaaat ctcactattc caccagaaga tgcatacatt atcattgaaa | 5574 |
| cagatgcatg tgcaactgga tggggagcag tatgcaagtg gaagaaaaac aaggcagacc | 5634 |
| caagaaatac agagcaaatc tgtaggtatg ccagtggaaa atttgataag ccaaaaggaa | 5694 |
| cctgtgatgc agaaatctat ggggttatga atggcttaga aaagatgaga ttgttctact | 5754 |
| tggacaaaag agagatcaca gtcagaactg acagtagtgc aatcgaaagg ttctacaaca | 5814 |
| agagtgctga acacaagcct tctgagatca gatggatcag gttcatggac tacatcactg | 5874 |
| gtgcaggacc agagatagtc attgaacaca taaaagggaa gagcaatggt ttagctgaca | 5934 |
| tcttgtccag gctcaaagcc aaattagctc agaatgaacc aacggaagag atgatcctgc | 5994 |
| ttacacaagc cataagggaa gtaattcctt atccagatca tccatacact gagcaactca | 6054 |
| gagaatgggg aaacaaaatt ctggatccat tccccacatt caagaaggac atgttcgaaa | 6114 |
| gaacagagca agctttttatg ctaacagagg aaccagttct actctgtgca tgcaggaagc | 6174 |
| ctgcaattca gttagtgtcc agaacatctg ccaacccagg aaggaaattc ttcaagtgcg | 6234 |
| caatgaacaa atgccattgc tggtactggg cagatctcat tgaagaacac attcaagaca | 6294 |
| gaattgatga atttctcaag aatcttgaag ttctgaagac cggtggcgtg caaacaatgg | 6354 |
| aggaggaact tatgaaggaa gtcaccaagc tgaagataga agagcaggag ttcgaggaat | 6414 |
| accaggccac accaagggct atgtcgccag tagccgcaga agatgtgcta gatctccaag | 6474 |
| acgtaagcaa tgacgattga ggaggcattg acgtcaggga tgaccgcagc ggagagtact | 6534 |
| gggcccattc agtggatgct ccactgagtt gtattattgt gtgcttttcg gacaagtgtg | 6594 |
| ctgtccactt tcttttggca cctgtgccac tttattcctt gtctgccacg atgcctttgc | 6654 |
| ttagcttgta agcaaggatc gcagtgcgtg tgtgacacca ccccccttcc gacgctctgc | 6714 |
| ctatataagg caccgtctgt aagctcttac gatcatcggt agttcaccaa gggggtaccg | 6774 |
| gtcgccacc atg gcc tcc tcc gag aac gtc atc acc gag ttc atg cgc ttc | 6825 |
|            Met Ala Ser Ser Glu Asn Val Ile Thr Glu Phe Met Arg Phe | |
|               640                 645              650 | |
| aag gtg cgc atg gag ggc acc gtg aac ggc cac gag ttc gag atc gag | 6873 |
| Lys Val Arg Met Glu Gly Thr Val Asn Gly His Glu Phe Glu Ile Glu | |
|  655                 660              665 | |
| ggc gag ggc gag ggc cgc ccc tac gag ggc cac aac acc gtg aag ctg | 6921 |
| Gly Glu Gly Glu Gly Arg Pro Tyr Glu Gly His Asn Thr Val Lys Leu | |
|     670                 675             680 | |
| aag gtg acc aag ggc ggc ccc ctg ccc ttc gcc tgg gac atc ctg tcc | 6969 |
| Lys Val Thr Lys Gly Gly Pro Leu Pro Phe Ala Trp Asp Ile Leu Ser | |
| 685                690               695             700 | |
| ccc cag ttc cag tac ggc tcc aag gtg tac gtg aag cac ccc gcc gac | 7017 |
| Pro Gln Phe Gln Tyr Gly Ser Lys Val Tyr Val Lys His Pro Ala Asp | |
|            705                710              715 | |
| atc ccc gac tac aag aag ctg tcc ttc ccc gag ggc ttc aag tgg gag | 7065 |
| Ile Pro Asp Tyr Lys Lys Leu Ser Phe Pro Glu Gly Phe Lys Trp Glu | |
|                720              725            730 | |
| cgc gtg atg aac ttc gag gac ggc ggc gtg gcg acc gtg acc cag gac | 7113 |
| Arg Val Met Asn Phe Glu Asp Gly Gly Val Ala Thr Val Thr Gln Asp | |
|          735                740              745 | |

| | |
|---|---|
| tcc tcc ctg cag gac ggc tgc ttc atc tac aag gtg aag ttc atc ggc<br>Ser Ser Leu Gln Asp Gly Cys Phe Ile Tyr Lys Val Lys Phe Ile Gly<br>750 755 760 | 7161 |
| gtg aac ttc ccc tcc gac ggc ccc gtg atg cag aag aag acc atg ggc<br>Val Asn Phe Pro Ser Asp Gly Pro Val Met Gln Lys Lys Thr Met Gly<br>765 770 775 780 | 7209 |
| tgg gag gcc tcc acc gag cgc ctg tac ccc cgc gac ggc gtg ctg aag<br>Trp Glu Ala Ser Thr Glu Arg Leu Tyr Pro Arg Asp Gly Val Leu Lys<br>785 790 795 | 7257 |
| ggc gag acc cac aag gcc ctg aag ctg aag gac ggc ggc cac tac ctg<br>Gly Glu Thr His Lys Ala Leu Lys Leu Lys Asp Gly Gly His Tyr Leu<br>800 805 810 | 7305 |
| gtg gag ttc aag tcc atc tac atg gcc aag aag ccc gtg cag ctg ccc<br>Val Glu Phe Lys Ser Ile Tyr Met Ala Lys Lys Pro Val Gln Leu Pro<br>815 820 825 | 7353 |
| ggc tac tac tac gtg gac gcc aag ctg gac atc acc tcc cac aac gag<br>Gly Tyr Tyr Tyr Val Asp Ala Lys Leu Asp Ile Thr Ser His Asn Glu<br>830 835 840 | 7401 |
| gac tac acc atc gtg gag cag tac gag cgc acc gag ggc cgc cac cac<br>Asp Tyr Thr Ile Val Glu Gln Tyr Glu Arg Thr Glu Gly Arg His His<br>845 850 855 860 | 7449 |
| ctg ttc ctg tag cggccgccct gcagggagct cgaatttccc cgatcgttca<br>Leu Phe Leu | 7501 |
| aacatttggc aataaagttt cttaagattg aatcctgttg ccggtcttgc gatgattatc | 7561 |
| atataatttc tgttgaatta cgttaagcat gtaataatta acatgtaatg catgacgtta | 7621 |
| tttatgagat gggttttat gattagagtc ccgcaattat acatttaata cgcgatagaa | 7681 |
| aacaaaatat agcgcgcaaa ctaggataaa ttatcgcgcg cggtgtcatc tatgttacta | 7741 |
| gatcgggaat cgggcccgg ccggccagat cttgattgtc gtttcccgcc ttcagtttaa | 7801 |
| actatcagtg tttgacagga tatattggcg gtaaaccta agagaaaaga gcgtttatta | 7861 |
| gaataatcgg atatttaaaa gggcgtgaaa aggtttatcc gttcgtccat ttgtatgtgc | 7921 |
| atgccaacca cagggttccc ctcgggagtg cttggcattc cgtgcgataa tgacttctgt | 7981 |
| tcaaccaccc aaacgtcgga aagcctgacg acggagcagc attccaaaaa gatcccttgg | 8041 |
| ctcgtctggg tcggctagaa ggtcgagtgg gctgctgtgg cttgatccct caacgcggtc | 8101 |
| gcggacgtag cgcagcgccg aaaaatcctc gatcgcaaat ccgacgctgt cgaaaagcgt | 8161 |
| gatctgcttg tcgctctttc ggccgacgtc ctggccagtc atcacgcgcc aaagttccgt | 8221 |
| cacaggatga tctggcgcga gttgctggat ctcgccttca atccgggtct gtggcgggaa | 8281 |
| ctccacgaaa atatccgaac gcagcaagat cgtcgaccaa ttcttgaaga cgaaagggcc | 8341 |
| tcgtgatacg cctatttttta taggttaatg tcatgataat aatggtttct tagacgtcag | 8401 |
| gtggcacttt tcgggaaat gtgcgcggaa cccctatttg tttatttttc taaatacatt | 8461 |
| caaatatgta tccgctcatg agacaataac cctgataaat gcttcaataa tattgaaaaa | 8521 |
| ggaagagtat gagtattcaa catttccgtg tcgcccttat tcccttttt gcggcatttt | 8581 |
| gccttcctgt ttttgctcac ccagaaacgc tggtgaaagt aaaagatgct gaagatcagt | 8641 |
| tgggtgcacg agtgggttac atcgaactgg atctcaacag cggtaagatc cttgagagtt | 8701 |
| ttcgccccga agaacgtttt ccaatgatga gcacttttaa agttctgcta tgtggcgcgg | 8761 |
| tattatcccg tgttgacgcc gggcaagagc aactcggtcg ccgcatacac tattctcaga | 8821 |
| atgacttggt tgagtactca ccagtcacag aaaagcatct tacgcgatggc atgacagtaa | 8881 |
| gagaattatg cagtgctgcc ataaccatga gtgataacac tgcggccaac ttacttctga | 8941 |

```
caacgatcgg aggaccgaag gagctaaccg cttttttgca caacatgggg gatcatgtaa   9001
ctcgccttga tcgttgggaa ccggagctga atgaagccat accaaacgac gagcgtgaca   9061
ccacgatgcc gggggggggg gggggggaca tgaggttgcc ccgtattcag tgtcgctgat   9121
ttgtattgtc tgaagttgtt tttacgttaa gttgatgcag atcaattaat acgatacctg   9181
cgtcataatt gattatttga cgtggtttga tggcctccac gcacgttgtg atatgtagat   9241
gataatcatt atcactttac gggtcctttc cggtgatccg acaggttacg gggcggcgac   9301
ctcgcgggtt ttcgctattt atgaaaattt tccggtttaa ggcgtttccg ttcttcttcg   9361
tcataactta atgtttttat ttaaaatacc ctctgaaaag aaaggaaacg acaggtgctg   9421
aaagcgagct ttttggcctc tgtcgtttcc tttctctgtt tttgtccgtg aatgaacaa    9481
tggaacccccc ccccccccccc cctgcagcaa tggcaacaac gttgcgcaaa ctattaactg   9541
gcgaactact tactctagct tcccggcaac aattaataga ctggatggag gcggataaag   9601
ttgcaggacc acttctgcgc tcggcccttc cggctggctg gtttattgct gataaatctg   9661
gagccggtga gcgtgggtct cgcggtatca ttgcagcact ggggccagat ggtaagccct   9721
cccgtatcgt agttatctac acgacgggga gtcaggcaac tatggatgaa cgaaatagac   9781
agatcgctga gataggtgcc tcactgatta agcattggta actgtcagac caagtttact   9841
catatatact ttagattgat ttaaaacttc atttttaatt taaaaggatc taggtgaaga   9901
tcctttttga taatctcatg accaaaatcc cttaacgtga gttttcgttc cactgagcgt   9961
cagaccccgt agaaaagatc aaaggatctt cttgagatcc ttttttctg cgcgtaatct   10021
gctgcttgca aacaaaaaaa ccaccgctac cagcggtggt ttgtttgccg gatcaagagc   10081
taccaactct ttttccgaag gtaactggct tcagcagagc gcagatacca aatactgtcc   10141
ttctagtgta gccgtagtta ggccaccact tcaagaactc tgtagcaccg cctacatacc   10201
tcgctctgct aatcctgtta ccagtggctg ctgccagtgg cgataagtcg tgtcttaccg   10261
ggttggactc aagacgatag ttaccggata aggcgcagcg gtcgggctga acggggggtt   10321
cgtgcacaca gcccagcttg gagcgaacga cctacaccga actgagatac ctacagcgtg   10381
agctatgaga aagcgccacg cttcccgaag ggagaaaggc ggacaggtat ccggtaagcg   10441
gcagggtcgg aacaggagag cgcacgaggg agcttccagg gggaaacgcc tggtatcttt   10501
atagtcctgt cgggtttcgc cacctctgac ttgagcgtcg atttttgtga tgctcgtcag   10561
gggggcggag cctatggaaa aacgccagca acgcggcctt tttacggttc ctggccttt    10621
gctgccttt  tgctcacatg ttctttcctg cgttatcccc tgattctgtg gataaccgta   10681
ttaccgcctt tgagtgagct gataccgctc gccgcagccg aacgaccgag cgcagcgagt   10741
cagtgagcga ggaagcggaa gagcgcctga tgcggtattt tctccttacg catctgtgcg   10801
gtatttcaca ccgcatatgg tgcactctca gtacaatctg ctctgatgcc gcatagttaa   10861
gccagtatac actccgctat cgctacgtga ctgggtcatg gctgcgcccc gacacccgcc   10921
aacacccgct gacgcgccct gacgggcttg tctgctcccg gcatccgctt acagacaagc   10981
tgtgaccgtc tccgggagct gcatgtgtca gaggttttca ccgtcatcac cgaaacgcgc   11041
gaggcagcag atccccgat  caagtagata cactacatat atctacaata gacatcgagc   11101
cggaaggtga tgtttacttt cctgaaatcc ccagcaattt taggccagtt tttacccaag   11161
acttcgcctc taacataaat tatagttacc aaatctggca aaaggggtga ccggggggggg   11221
ggggaaagcc acgttgtgtc tcaaaatctc tgatgttaca ttgcacaaga taaaaatata   11281
tcatcatgaa caataaaact gtctgcttac ataaacagta atacaagggg tgtt atg      11338
```

```
                                                                    Met
agc cat att caa cgg gaa acg tct tgc tcg agg ccg cga tta aat tcc      11386
Ser His Ile Gln Arg Glu Thr Ser Cys Ser Arg Pro Arg Leu Asn Ser
865                 870                 875                 880 aac atg gat gct gat tta tat ggg tat aaa tgg gct cgc gat aat gtc      11434
Asn Met Asp Ala Asp Leu Tyr Gly Tyr Lys Trp Ala Arg Asp Asn Val
                    885                 890                 895 ggg caa tca ggt gcg aca atc tat cga ttg tat ggg aag ccc gat gcg      11482
Gly Gln Ser Gly Ala Thr Ile Tyr Arg Leu Tyr Gly Lys Pro Asp Ala
            900                 905                 910 cca gag ttg ttt ctg aaa cat ggc aaa ggt agc gtt gcc aat gat gtt      11530
Pro Glu Leu Phe Leu Lys His Gly Lys Gly Ser Val Ala Asn Asp Val
        915                 920                 925 aca gat gag atg gtc aga cta aac tgg ctg acg gaa ttt atg cct ctt      11578
Thr Asp Glu Met Val Arg Leu Asn Trp Leu Thr Glu Phe Met Pro Leu
    930                 935                 940 ccg acc atc aag cat ttt atc cgt act cct gat gat gca tgg tta ctc      11626
Pro Thr Ile Lys His Phe Ile Arg Thr Pro Asp Asp Ala Trp Leu Leu
945                 950                 955                 960 acc act gcg atc ccc ggg aaa aca gca ttc cag gta tta gaa gaa tat      11674
Thr Thr Ala Ile Pro Gly Lys Thr Ala Phe Gln Val Leu Glu Glu Tyr
                965                 970                 975 cct gat tca ggt gaa aat att gtt gat gcg ctg gca gtg ttc ctg cgc      11722
Pro Asp Ser Gly Glu Asn Ile Val Asp Ala Leu Ala Val Phe Leu Arg
                    980                 985                 990 cgg ttg cat tcg att cct gtt tgt  aat tgt cct ttt aac  agc gat cgc   11770
Arg Leu His Ser Ile Pro Val Cys  Asn Cys Pro Phe Asn  Ser Asp Arg
            995                 1000                 1005 gta ttt cgt ctc gct cag gcg  caa tca cga atg aat  aac ggt ttg       11815
Val Phe Arg Leu Ala Gln Ala  Gln Ser Arg Met Asn  Asn Gly Leu
        1010                 1015                 1020 gtt gat gcg agt gat ttt gat  gac gag cgt aat ggc  tgg cct gtt       11860
Val Asp Ala Ser Asp Phe Asp  Asp Glu Arg Asn Gly  Trp Pro Val
    1025                 1030                 1035 gaa caa gtc tgg aaa gaa atg  cat aag ctt ttg cca  ttc tca ccg       11905
Glu Gln Val Trp Lys Glu Met  His Lys Leu Leu Pro  Phe Ser Pro
    1040                 1045                 1050 gat tca gtc gtc act cat ggt  gat ttc tca ctt gat  aac ctt att       11950
Asp Ser Val Val Thr His Gly  Asp Phe Ser Leu Asp  Asn Leu Ile
    1055                 1060                 1065 ttt gac gag ggg aaa tta ata  ggt tgt att gat gtt  gga cga gtc       11995
Phe Asp Glu Gly Lys Leu Ile  Gly Cys Ile Asp Val  Gly Arg Val
    1070                 1075                 1080 gga atc gca gac cga tac cag  gat ctt gcc atc cta  tgg aac tgc       12040
Gly Ile Ala Asp Arg Tyr Gln  Asp Leu Ala Ile Leu  Trp Asn Cys
    1085                 1090                 1095 ctc ggt gag ttt tct cct tca  tta cag aaa cgg ctt  ttt caa aaa       12085
Leu Gly Glu Phe Ser Pro Ser  Leu Gln Lys Arg Leu  Phe Gln Lys
    1100                 1105                 1110 tat ggt att gat aat cct gat  atg aat aaa ttg cag  ttt cat ttg       12130
Tyr Gly Ile Asp Asn Pro Asp  Met Asn Lys Leu Gln  Phe His Leu
    1115                 1120                 1125 atg ctc gat gag ttt ttc taa tcagaattgg ttaattggtt gtaacactgg        12181
Met Leu Asp Glu Phe Phe
        1130 cagagcatta cgctgacttg acgggacggc ggctttgttg aataaatcga actttgtctg   12241 agttgaagga tcagatcacg catcttcccg acaacgcaga ccgttccgtg gcaaagcaaa   12301
```

-continued

```
agttcaaaat caccaactgg tccacctaca acaaagctct catcaaccgt ggctccctca    12361
ctttctggct ggatgatggg gcgattcagg gatcacaggc agcaacgctc tgtcatcgtt    12421
acaatcaaca tgctaccctc cgcgagatca tccgtgtttc aaacccggca gcttagttgc    12481
cgttcttccg aatagcatcg gtaacatgag caaagtctgc cgccttacaa cggctctccc    12541
gctgacgccg tcccggactg atgggctgcc tgtatcgagt ggtgat                    12587
```

<210> SEQ ID NO 213
<211> LENGTH: 638
<212> TYPE: PRT
<213> ORGANISM: Artificial sequence
<220> FEATURE:
<223> OTHER INFORMATION: Synthetic Construct

<400> SEQUENCE: 213

Met Ala Thr Ala Ala Ala Ser Thr Ala Leu Thr Gly Ala Thr Thr
1               5                   10                  15

Ala Ala Pro Lys Ala Arg Arg Ala His Leu Leu Ala Thr Arg Arg
                20                  25                  30

Ala Leu Ala Ala Pro Ile Arg Cys Ser Ala Ala Ser Pro Ala Met Pro
        35                  40                  45

Met Ala Pro Pro Ala Thr Pro Leu Arg Pro Trp Gly Pro Thr Asp Pro
    50                  55                  60

Arg Lys Gly Ala Asp Ile Leu Val Glu Ser Leu Glu Arg Cys Gly Val
65                  70                  75                  80

Arg Asp Val Phe Ala Tyr Pro Gly Gly Ala Ser Met Glu Ile His Gln
                85                  90                  95

Ala Leu Thr Arg Ser Pro Val Ile Ala Asn His Leu Phe Arg His Glu
            100                 105                 110

Gln Gly Glu Ala Phe Ala Ala Ser Gly Tyr Ala Arg Ser Ser Gly Arg
        115                 120                 125

Val Gly Val Cys Ile Ala Thr Ser Gly Pro Gly Ala Thr Asn Leu Val
    130                 135                 140

Ser Ala Leu Ala Asp Ala Leu Leu Asp Ser Val Pro Met Val Ala Ile
145                 150                 155                 160

Thr Gly Gln Val Pro Arg Arg Met Ile Gly Thr Asp Ala Phe Gln Glu
                165                 170                 175

Thr Pro Ile Val Glu Val Thr Arg Ser Ile Thr Lys His Asn Tyr Leu
            180                 185                 190

Val Leu Asp Val Asp Asp Ile Pro Arg Val Val Gln Glu Ala Phe Phe
        195                 200                 205

Leu Ala Ser Ser Gly Arg Pro Gly Pro Val Leu Val Asp Ile Pro Lys
    210                 215                 220

Asp Ile Gln Gln Gln Met Ala Val Pro Val Trp Asp Lys Pro Met Ser
225                 230                 235                 240

Leu Pro Gly Tyr Ile Ala Arg Leu Pro Lys Pro Pro Ala Thr Glu Leu
                245                 250                 255

Leu Glu Gln Val Leu Arg Leu Val Gly Glu Ser Arg Arg Pro Val Leu
            260                 265                 270

Tyr Val Gly Gly Gly Cys Ala Ala Ser Gly Glu Glu Leu Arg Arg Phe
        275                 280                 285

Val Glu Leu Thr Gly Ile Pro Val Thr Thr Thr Leu Met Gly Leu Gly
    290                 295                 300

Asn Phe Pro Ser Asp Asp Pro Leu Ser Leu Arg Met Leu Gly Met His
305                 310                 315                 320

```
Gly Thr Val Tyr Ala Asn Tyr Ala Val Asp Lys Ala Asp Leu Leu Leu
                325                 330                 335

Ala Leu Gly Val Arg Phe Asp Asp Arg Val Thr Gly Lys Ile Glu Ala
            340                 345                 350

Phe Ala Ser Arg Ala Lys Ile Val His Val Asp Ile Asp Pro Ala Glu
        355                 360                 365

Ile Gly Lys Asn Lys Gln Pro His Val Ser Ile Cys Ala Asp Val Lys
    370                 375                 380

Leu Ala Leu Gln Gly Met Asn Ala Leu Leu Glu Gly Ser Thr Ser Lys
385                 390                 395                 400

Lys Ser Phe Asp Phe Gly Ser Trp Asn Asp Glu Leu Asp Gln Gln Lys
                405                 410                 415

Arg Glu Phe Pro Leu Gly Tyr Lys Thr Ser Asn Glu Glu Ile Gln Pro
            420                 425                 430

Gln Tyr Ala Ile Gln Val Leu Asp Glu Leu Thr Lys Gly Glu Ala Ile
        435                 440                 445

Ile Gly Thr Gly Val Gly Gln His Gln Met Trp Ala Ala Gln Tyr Tyr
    450                 455                 460

Thr Tyr Lys Arg Pro Arg Gln Trp Leu Ser Ser Ala Gly Leu Gly Ala
465                 470                 475                 480

Met Gly Phe Gly Leu Pro Ala Ala Ala Gly Ala Ser Val Ala Asn Pro
                485                 490                 495

Gly Val Thr Val Val Asp Ile Asp Gly Asp Gly Ser Phe Leu Met Asn
            500                 505                 510

Val Gln Glu Leu Ala Met Ile Arg Ile Glu Asn Leu Pro Val Lys Val
        515                 520                 525

Phe Val Leu Asn Asn Gln His Leu Gly Met Val Val Gln Trp Glu Asp
    530                 535                 540

Arg Phe Tyr Lys Ala Asn Arg Ala His Thr Tyr Leu Gly Asn Pro Glu
545                 550                 555                 560

Asn Glu Ser Glu Ile Tyr Pro Asp Phe Val Thr Ile Ala Lys Gly Phe
                565                 570                 575

Asn Ile Pro Ala Val Arg Val Thr Lys Lys Asn Glu Val Arg Ala Ala
            580                 585                 590

Ile Lys Lys Met Leu Glu Thr Pro Gly Pro Tyr Leu Leu Asp Ile Ile
        595                 600                 605

Val Pro His Gln Glu His Val Leu Pro Met Ile Pro Asn Gly Gly Ala
    610                 615                 620

Phe Lys Asp Met Ile Leu Asp Gly Asp Gly Arg Thr Val Tyr
625                 630                 635

<210> SEQ ID NO 214
<211> LENGTH: 225
<212> TYPE: PRT
<213> ORGANISM: Artificial sequence
<220> FEATURE:
<223> OTHER INFORMATION: Synthetic Construct

<400> SEQUENCE: 214

Met Ala Ser Ser Glu Asn Val Ile Thr Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45
```

```
Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Thr His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ala Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 215
<211> LENGTH: 271
<212> TYPE: PRT
<213> ORGANISM: Artificial sequence
<220> FEATURE:
<223> OTHER INFORMATION: Synthetic Construct

<400> SEQUENCE: 215

Met Ser His Ile Gln Arg Glu Thr Ser Cys Ser Arg Pro Arg Leu Asn
1               5                   10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175
```

```
Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270

<210> SEQ ID NO 216
<211> LENGTH: 12590
<212> TYPE: DNA
<213> ORGANISM: Artificial sequence
<220> FEATURE:
<223> OTHER INFORMATION: binary vector for expressing dsRed in maize
<220> FEATURE:
<221> NAME/KEY: repeat_region
<222> LOCATION: (42)..(66)
<223> OTHER INFORMATION: Left T-DNA Border repeat region
<220> FEATURE:
<221> NAME/KEY: promoter
<222> LOCATION: (157)..(2144)
<223> OTHER INFORMATION: Maize Ubiquitin promoter:maize ubiquitin intron
<220> FEATURE:
<221> NAME/KEY: CDS
<222> LOCATION: (2178)..(4094)
<223> OTHER INFORMATION: ZmAHAS L2 S653(At)N (XI12) cds
<220> FEATURE:
<221> NAME/KEY: terminator
<222> LOCATION: (4095)..(5310)
<223> OTHER INFORMATION: Maize AHASL2 [XI12] 3'/UTR sequence with
      terminator
<220> FEATURE:
<221> NAME/KEY: promoter
<222> LOCATION: (5368)..(6765)
<223> OTHER INFORMATION: Sugarcane bacilliform virus [ScBV] promoter
<220> FEATURE:
<221> NAME/KEY: CDS
<222> LOCATION: (6784)..(7461)
<223> OTHER INFORMATION: Discosoma sp. red fluorescent protein
      [drFP583;1]
<220> FEATURE:
<221> NAME/KEY: terminator
<222> LOCATION: (7496)..(7748)
<223> OTHER INFORMATION: Nopaline Synthase poly-A terminator.
<220> FEATURE:
<221> NAME/KEY: repeat_region
<222> LOCATION: (7778)..(7922)
<223> OTHER INFORMATION: pSB11's full RB
<220> FEATURE:
<221> NAME/KEY: rep_origin
<222> LOCATION: (10200)..(10480)
<223> OTHER INFORMATION: pBR322 origin of replication [ecoli] from
      AF234316 pCambia2301
<220> FEATURE:
<221> NAME/KEY: CDS
<222> LOCATION: (11339)..(12154)
<223> OTHER INFORMATION: Kanamycin Resistance selection gene for
      microorganism.

<400> SEQUENCE: 216
tttgtgccga gctgccggtc ggggagctgt tggctggctg gtggcaggat atattgtggt      60
gtaaacaaat tgacgcttag acaacttaat aacacattgc ggacgttttt aatgtactga     120
attggatccg cccgggcggt accaagcttc cgcggctgca gtgcagcgtg acccggtcgt     180
```

| | |
|---|---|
| gcccctctct agagataatg agcattgcat gtctaagtta taaaaaatta ccacatattt | 240 |
| tttttgtcac acttgtttga agtgcagttt atctatcttt atacatatat ttaaacttta | 300 |
| ctctacgaat aatataatct atagtactac aataatatca gtgttttaga gaatcatata | 360 |
| aatgaacagt tagacatggt ctaaaggaca attgagtatt ttgacaacag gactctacag | 420 |
| ttttatcttt ttagtgtgca tgtgttctcc ttttttttg caaatagctt cacctatata | 480 |
| atacttcatc cattttatta gtacatccat ttagggttta gggttaatgg ttttttataga | 540 |
| ctaattttt tagtacatct atttttattct attttagcct ctaaattaag aaaactaaaa | 600 |
| ctctatttta gttttttttat ttaatagttt agatataaaa tagaataaaa taaagtgact | 660 |
| aaaaattaaa caaatacccct ttaagaaatt aaaaaaacta aggaaacatt tttcttgttt | 720 |
| cgagtagata atgccagcct gttaaacgcc gtcgacgagt ctaacggaca ccaaccagcg | 780 |
| aaccagcagc gtcgcgtcgg gccaagcgaa gcagacggca cggcatctct gtcgctgcct | 840 |
| ctggacccct ctcgagagtt ccgctccacc gttggacttg ctccgctgtc ggcatccaga | 900 |
| aattgcgtgg cggagcggca gacgtgagcc ggcacggcag gcggcctcct cctcctctca | 960 |
| cggcaccggc agctacgggg gattcctttc ccaccgctcc ttcgctttcc cttcctcgcc | 1020 |
| cgccgtaata aatagacacc ccctccacac cctctttccc caacctcgtg ttgttcggag | 1080 |
| cgcacacaca cacaaccaga tctccccccaa atccacccgt cggcacctcc gcttcaaggt | 1140 |
| acgccgctcg tcctcccccc ccccccccct ctctaccttc tctagatcgg cgttccggtc | 1200 |
| catggttagg gcccggtagt tctacttctg ttcatgtttg tgttagatcc gtgtttgtgt | 1260 |
| tagatccgtg ctgctagcgt tcgtacacgg atgcgacctg tacgtcagac acgttctgat | 1320 |
| tgctaacttg ccagtgtttc tctttgggga atcctgggat ggctctagcc gttccgcaga | 1380 |
| cgggatcgat ttcatgattt ttttttgtttc gttgcatagg gtttggtttg ccctttcct | 1440 |
| ttatttcaat atatgccgtg cacttgtttg tcgggtcatc ttttcatgct ttttttgtc | 1500 |
| ttggttgtga tgatgtggtc tggttgggcg gtcgttctag atcggagtag aattctgttt | 1560 |
| caaactacct ggtggattta ttaattttgg atctgtatgt gtgtgccata catattcata | 1620 |
| gttacgaatt gaagatgatg gatggaaata tcgatctagg ataggtatac atgttgatgc | 1680 |
| gggttttact gatgcatata cagagatgct ttttgttcgc ttggttgtga tgatgtggtg | 1740 |
| tggttgggcg gtcgttcatt cgttctagat cggagtagaa tactgtttca aactacctgg | 1800 |
| tgtatttatt aattttggaa ctgtatgtgt gtgtcataca tcttcatagt tacgagttta | 1860 |
| agatggatgg aaatatcgat ctaggatagg tatacatgtt gatgtgggtt ttactgatgc | 1920 |
| atatacatga tggcatatgc agcatctatt catatgctct aaccttgagt acctatctat | 1980 |
| tataataaac aagtatgttt tataattatt tcgatcttga tatacttgga tgatggcata | 2040 |
| tgcagcagct atatgtggat tttttagcc ctgccttcat acgctattta tttgcttggt | 2100 |
| actgtttctt ttgtcgatgc tcaccctgtt gtttggtgtt acttctgcag ggtacggatc | 2160 |
| cactagttct agaaacc atg gcc acc gcc gcc gcc gcg tct acc gcg ctc<br>                     Met Ala Thr Ala Ala Ala Ala Ser Thr Ala Leu<br>                      1            5                    10 | 2210 |
| act ggc gcc act acc gct gcg ccc aag gcg agg cgc cgg gcg cac ctc<br>Thr Gly Ala Thr Thr Ala Ala Pro Lys Ala Arg Arg Arg Ala His Leu<br>          15                  20                  25 | 2258 |
| ctg gcc acc cgc cgc gcc ctc gcc gcg ccc atc agg tgc tca gcg gcg<br>Leu Ala Thr Arg Arg Ala Leu Ala Ala Pro Ile Arg Cys Ser Ala Ala<br>      30                  35                  40 | 2306 |
| tca ccc gcc atg ccg atg gct ccc ccg gcc acc ccg ctc cgg ccg tgg | 2354 |

```
Ser Pro Ala Met Pro Met Ala Pro Pro Ala Thr Pro Leu Arg Pro Trp
    45                  50                  55 ggc ccc acc gat ccc cgc aag ggc gcc gac atc ctc gtc gag tcc ctc      2402
Gly Pro Thr Asp Pro Arg Lys Gly Ala Asp Ile Leu Val Glu Ser Leu
60                  65                  70                  75 gag cgc tgc ggc gtc cgc gac gtc ttc gcc tac ccc ggc ggc gcg tcc      2450
Glu Arg Cys Gly Val Arg Asp Val Phe Ala Tyr Pro Gly Gly Ala Ser
                80                  85                  90 atg gag atc cac cag gca ctc acc cgc tcc ccc gtc atc gcc aac cac      2498
Met Glu Ile His Gln Ala Leu Thr Arg Ser Pro Val Ile Ala Asn His
            95                  100                 105 ctc ttc cgc cac gag caa ggg gag gcc ttt gcg gcc tcc ggc tac gcg      2546
Leu Phe Arg His Glu Gln Gly Glu Ala Phe Ala Ala Ser Gly Tyr Ala
        110                 115                 120 cgc tcc tcg ggc cgc gtc ggc gtc tgc atc gcc acc tcc ggc ccc ggc      2594
Arg Ser Ser Gly Arg Val Gly Val Cys Ile Ala Thr Ser Gly Pro Gly
    125                 130                 135 gcc acc aac ctt gtc tcc gcg ctc gcc gac gcg ctg ctc gat tcc gtc      2642
Ala Thr Asn Leu Val Ser Ala Leu Ala Asp Ala Leu Leu Asp Ser Val
140                 145                 150                 155 ccc atg gtc gcc atc acg gga cag gtg ccg cga cgc atg att ggc acc      2690
Pro Met Val Ala Ile Thr Gly Gln Val Pro Arg Arg Met Ile Gly Thr
                160                 165                 170 gac gcc ttc cag gag acg ccc atc gtc gag gtc acc cgc tcc atc acc      2738
Asp Ala Phe Gln Glu Thr Pro Ile Val Glu Val Thr Arg Ser Ile Thr
            175                 180                 185 aag cac aac tac ctg gtc ctc gac gtc gac gac atc ccc cgc gtc gtg      2786
Lys His Asn Tyr Leu Val Leu Asp Val Asp Asp Ile Pro Arg Val Val
        190                 195                 200 cag gag gct ttc ttc ctc gcc tcc tct ggt cga ccg ggg ccg gtg ctt      2834
Gln Glu Ala Phe Phe Leu Ala Ser Ser Gly Arg Pro Gly Pro Val Leu
    205                 210                 215 gtc gac atc ccc aag gac atc cag cag cag atg gcg gtg cct gtc tgg      2882
Val Asp Ile Pro Lys Asp Ile Gln Gln Gln Met Ala Val Pro Val Trp
220                 225                 230                 235 gac aag ccc atg agt ctg cct ggg tac att gcg cgc ctt ccc aag ccc      2930
Asp Lys Pro Met Ser Leu Pro Gly Tyr Ile Ala Arg Leu Pro Lys Pro
                240                 245                 250 cct gcg act gag ttg ctt gag cag gtg ctg cgt ctt gtt ggt gaa tcc      2978
Pro Ala Thr Glu Leu Leu Glu Gln Val Leu Arg Leu Val Gly Glu Ser
            255                 260                 265 cgg cgc cct gtt ctt tat gtt ggc ggt ggc tgc gca gca tct ggt gag      3026
Arg Arg Pro Val Leu Tyr Val Gly Gly Gly Cys Ala Ala Ser Gly Glu
        270                 275                 280 gag ttg cga cgc ttt gtg gag ctg act gga atc ccg gtc aca act act      3074
Glu Leu Arg Arg Phe Val Glu Leu Thr Gly Ile Pro Val Thr Thr Thr
    285                 290                 295 ctt atg ggc ctc ggc aac ttc ccc agc gac gac cca ctg tct ctg cgc      3122
Leu Met Gly Leu Gly Asn Phe Pro Ser Asp Asp Pro Leu Ser Leu Arg
300                 305                 310                 315 atg cta ggt atg cat ggc acg gtg tat gca aat tat gca gtg gat aag      3170
Met Leu Gly Met His Gly Thr Val Tyr Ala Asn Tyr Ala Val Asp Lys
                320                 325                 330 gcc gat ctg ttg ctt gca ctt ggt gtg cgg ttt gat gat cgt gtg aca      3218
Ala Asp Leu Leu Leu Ala Leu Gly Val Arg Phe Asp Asp Arg Val Thr
            335                 340                 345 ggg aag att gag gct ttt gca agc agg gct aag att gtg cac gtt gat      3266
Gly Lys Ile Glu Ala Phe Ala Ser Arg Ala Lys Ile Val His Val Asp
        350                 355                 360
```

| | |
|---|---|
| att gat ccg gct gag att ggc aag aac aag cag cca cat gtg tcc atc<br>Ile Asp Pro Ala Glu Ile Gly Lys Asn Lys Gln Pro His Val Ser Ile<br>365                            370                           375 | 3314 |
| tgt gca gat gtt aag ctt gct ttg cag ggc atg aat gct ctt ctt gaa<br>Cys Ala Asp Val Lys Leu Ala Leu Gln Gly Met Asn Ala Leu Leu Glu<br>380                            385                           390                      395 | 3362 |
| gga agc aca tca aag aag agc ttt gac ttt ggc tca tgg aac gat gag<br>Gly Ser Thr Ser Lys Lys Ser Phe Asp Phe Gly Ser Trp Asn Asp Glu<br>                            400                           405                      410 | 3410 |
| ttg gat cag cag aag agg gaa ttc ccc ctt ggg tat aaa aca tct aat<br>Leu Asp Gln Gln Lys Arg Glu Phe Pro Leu Gly Tyr Lys Thr Ser Asn<br>                        415                           420                       425 | 3458 |
| gag gag atc cag cca caa tat gct att cag gtt ctt gat gag ctg acg<br>Glu Glu Ile Gln Pro Gln Tyr Ala Ile Gln Val Leu Asp Glu Leu Thr<br>                    430                           435                       440 | 3506 |
| aaa ggc gag gcc atc atc ggc aca ggt gtt ggg cag cac cag atg tgg<br>Lys Gly Glu Ala Ile Ile Gly Thr Gly Val Gly Gln His Gln Met Trp<br>445                            450                           455 | 3554 |
| gcg gca cag tac tac act tac aag cgg cca agg cag tgg ttg tct tca<br>Ala Ala Gln Tyr Tyr Thr Tyr Lys Arg Pro Arg Gln Trp Leu Ser Ser<br>460                            465                           470                      475 | 3602 |
| gct ggt ctt ggg gct atg gga ttt ggt ttg ccg gct gct gct ggt gct<br>Ala Gly Leu Gly Ala Met Gly Phe Gly Leu Pro Ala Ala Ala Gly Ala<br>                            480                           485                      490 | 3650 |
| tct gtg gcc aac cca ggt gtt act gtt gtt gac atc gat gga gat ggt<br>Ser Val Ala Asn Pro Gly Val Thr Val Val Asp Ile Asp Gly Asp Gly<br>                  495                           500                       505 | 3698 |
| agc ttt ctc atg aac gtt cag gag cta gct atg atc cga att gag aac<br>Ser Phe Leu Met Asn Val Gln Glu Leu Ala Met Ile Arg Ile Glu Asn<br>                        510                           515                       520 | 3746 |
| ctc ccg gtg aag gtc ttt gtg cta aac aac cag cac ctg ggg atg gtg<br>Leu Pro Val Lys Val Phe Val Leu Asn Asn Gln His Leu Gly Met Val<br>525                            530                           535 | 3794 |
| gtg cag tgg gag gac agg ttc tat aag gcc aac aga gcg cac aca tac<br>Val Gln Trp Glu Asp Arg Phe Tyr Lys Ala Asn Arg Ala His Thr Tyr<br>540                            545                           550                      555 | 3842 |
| ttg gga aac cca gag aat gaa agt gag ata tat cca gat ttc gtg acg<br>Leu Gly Asn Pro Glu Asn Glu Ser Glu Ile Tyr Pro Asp Phe Val Thr<br>                            560                           565                      570 | 3890 |
| atc gcc aaa ggg ttc aac att cca gcg gtc cgt gtg aca aag aag aac<br>Ile Ala Lys Gly Phe Asn Ile Pro Ala Val Arg Val Thr Lys Lys Asn<br>                        575                           580                       585 | 3938 |
| gaa gtc cgc gca gcg ata aag aag atg ctc gag act cca ggg ccg tac<br>Glu Val Arg Ala Ala Ile Lys Lys Met Leu Glu Thr Pro Gly Pro Tyr<br>                590                           595                      600 | 3986 |
| ctc ttg gat ata atc gtc cca cac cag gag cat gtg ttg cct atg atc<br>Leu Leu Asp Ile Ile Val Pro His Gln Glu His Val Leu Pro Met Ile<br>605                            610                           615 | 4034 |
| cct aat ggt ggg gct ttc aag gat atg atc ctg gat ggt gat ggc agg<br>Pro Asn Gly Gly Ala Phe Lys Asp Met Ile Leu Asp Gly Asp Gly Arg<br>620                            625                           630                      635 | 4082 |
| act gtg tac tga tctaaaatcc agcaagcaac tgatctaaaa tccagcaagc<br>Thr Val Tyr | 4134 |
| accgcctccc tgctagtaca agggtgatat gttttatct gtgtgatgtt ctcctgtatt | 4194 |
| ctatcttttt ttgtaggccg tcagctatct gttatggtaa tcctatgtag cttccgacct | 4254 |
| tgtaattgtg tagtctgttg ttttccttct ggcatgtgtc ataagagatc atttaagtgc | 4314 |
| cttttgctac atataaataa gataataagc actgctatgc agtggttctg aattggcttc | 4374 |

```
tgttgccaaa tttaagtgtc caactggtcc ttgcttttgt tttcgctatt ttttttcctttt   4434 tttagttatt attatattgg taatttcaac tcaacatatg atgtatggaa taatgctagg   4494
gctgcaattt caaactattt tacaaaccag aatggcattt tcgtggtttg aggggagtga   4554
aaaaaaatga ggcatttgac tgaattagtt acctgatcca ttttcgtggt ttggatcatt   4614
ggaattaaat tccattctaa taatagtaat tttggcatat atcaattaag ttaattcggt   4674
tttatgcaaa atatatttgt atactattat tatcaagatg tcggagatat ttatatgcta   4734
catttttact atacaggagt gagatgaaga gtgtcatgta agttacacag tagaaacaaa   4794
ttctattaat gcataaaatc atttccatca tccaccctat gaatttgaga tagacctata   4854
tctaaacttt gaaagtggt tgaatatcaa attccaaatt aaataagtta ttttattgag   4914
tgaattctaa tttctctaaa acgaagggat ctaaacgccc tctaaagcta atttggaaac   4974
tcaaactttc ttagcattgg agggggattga gaaaaaatat taattcattt tcatctcaat   5034
cattcaatct ccaaagagat ttgagttcct tattagtctg ttccatgcat caaatcggct   5094
caatgtgtca ttatttgcca tgacgattga cgagttgttc tggggcctag cgcttttccac   5154 gccgatgtgc tggggcctgg tcctggagaa gacagcttga tatttaaagc tatcaattgt   5214
ttcaattgat tcccacttca ttttttctaaa tgtagaaaac ggtgacgtat aagaaaaaga   5274
atgaattagg acttttattc cgtacactaa tctagagcgg ccgcaagctt gtacaacgcg   5334
taccggttaa ttaaggtacc caattgcata tgtaatcctg gctagcaaca ctgaactatg   5394
ccagaaacca catcaaagat atgggcaagc ttcttggccc attatatcca aagacctcag   5454
agaaaggtga gcgaaggctc aattcagaag attggaagct gatcaatagg atcaagacaa   5514
tggtgagaac gcttccaaat ctcactattc caccagaaga tgcatacatt atcattgaaa   5574
cagatgcatg tgcaactgga tgggagcag tatgcaagtg gaagaaaaac aaggcagacc   5634
caagaaatac agagcaaatc tgtaggtatg ccagtggaaa atttgataag ccaaaaggaa   5694
cctgtgatgc agaaatctat ggggttatga atggcttaga aaagatgaga ttgttctact   5754
tggacaaaag agagatcaca gtcagaactg acagtagtgc aatcgaaagg ttctacaaca   5814
agagtgctga acacaagcct tctgagatca gatggatcag gttcatggac tacatcactg   5874
gtgcaggacc agagatagtc attgaacaca taaaagggaa gagcaatggt ttagctgaca   5934
tcttgtccag gctcaaagcc aaattagctc agaatgaacc aacggaagag atgatcctgc   5994
ttacacaagc cataagggaa gtaattcctt atccagatca tccatacact gagcaactca   6054
gagaatgggg aaacaaaatt ctggatccat tccccacatt caagaaggac atgttcgaaa   6114
gaacagagca agcttttatg ctaacagagg aaccagttct actctgtgca tgcaggaagc   6174
ctgcaattca gttagtgtcc agaacatctg ccaacccagg aaggaaattc ttcaagtgcg   6234
caatgaacaa atgccattgc tggtactggg cagatctcat tgaagaacac attcaagaca   6294
gaattgatga atttctcaag aatcttgaag ttctgaagac cggtggcgtg caaacaatgg   6354
aggaggaact tatgaaggaa gtcaccaagc tgaagataga agagcaggag ttcgaggaat   6414
accaggccac accaagggct atgtcgccag tagccgcaga agatgtgcta gatctccaag   6474
acgtaagcaa tgacgattga ggaggcattg acgtcaggga tgaccgcagc ggagagtact   6534
gggcccattc agtggatgct ccactgagtt gtattattgt gtgcttttcg gacaagtgtg   6594
ctgtccactt tcttttggca cctgtgccac tttattcctt gtctgccacg atgcctttgc   6654
ttagcttgta agcaaggatc gcagtgcgtg tgtgacacca cccccccttcc gacgctctgc   6714
```

```
                                                                   -continued ctatataagg caccgtctgt aagctcttac gatcatcggt agttcaccaa ggggtaccg              6774 gtcgccacc atg gcc tcc tcc gag aac gtc atc acc gag ttc atg cgc ttc             6825
          Met Ala Ser Ser Glu Asn Val Ile Thr Glu Phe Met Arg Phe
              640                 645                 650 aag gtg cgc atg gag ggc acc gtg aac ggc cac gag ttc gag atc gag              6873
Lys Val Arg Met Glu Gly Thr Val Asn Gly His Glu Phe Glu Ile Glu
655                 660                 665 ggc gag ggc gag ggc cgc ccc tac gag ggc cac aac acc gtg aag ctg              6921
Gly Glu Gly Glu Gly Arg Pro Tyr Glu Gly His Asn Thr Val Lys Leu
        670                 675                 680 aag gtg acc aag ggc ggc ccc ctg ccc ttc gcc tgg gac atc ctg tcc              6969
Lys Val Thr Lys Gly Gly Pro Leu Pro Phe Ala Trp Asp Ile Leu Ser
685                 690                 695                 700 ccc cag ttc cag tac ggc tcc aag gtg tac gtg aag cac ccc gcc gac              7017
Pro Gln Phe Gln Tyr Gly Ser Lys Val Tyr Val Lys His Pro Ala Asp
                705                 710                 715 atc ccc gac tac aag aag ctg tcc ttc ccc gag ggc ttc aag tgg gag              7065
Ile Pro Asp Tyr Lys Lys Leu Ser Phe Pro Glu Gly Phe Lys Trp Glu
            720                 725                 730 cgc gtg atg aac ttc gag gac ggc ggc gtg gcg acc gtg acc cag gac              7113
Arg Val Met Asn Phe Glu Asp Gly Gly Val Ala Thr Val Thr Gln Asp
            735                 740                 745 tcc tcc ctg cag gac ggc tgc ttc atc tac aag gtg aag ttc atc ggc              7161
Ser Ser Leu Gln Asp Gly Cys Phe Ile Tyr Lys Val Lys Phe Ile Gly
750                 755                 760 gtg aac ttc ccc tcc gac ggc ccc gtg atg cag aag aag acc atg ggc              7209
Val Asn Phe Pro Ser Asp Gly Pro Val Met Gln Lys Lys Thr Met Gly
765                 770                 775                 780 tgg gag gcc tcc acc gag cgc ctg tac ccc cgc gac ggc gtg ctg aag              7257
Trp Glu Ala Ser Thr Glu Arg Leu Tyr Pro Arg Asp Gly Val Leu Lys
                785                 790                 795 ggc gag acc cac aag gcc ctg aag ctg aag gac ggc ggc cac tac ctg              7305
Gly Glu Thr His Lys Ala Leu Lys Leu Lys Asp Gly Gly His Tyr Leu
            800                 805                 810 gtg gag ttc aag tcc atc tac atg gcc aag aag ccc gtg cag ctg ccc              7353
Val Glu Phe Lys Ser Ile Tyr Met Ala Lys Lys Pro Val Gln Leu Pro
            815                 820                 825 ggc tac tac tac gtg gac gcc aag ctg gac atc acc tcc cac aac gag              7401
Gly Tyr Tyr Tyr Val Asp Ala Lys Leu Asp Ile Thr Ser His Asn Glu
830                 835                 840 gac tac acc atc gtg gag cag tac gag cgc acc gag ggc cgc cac cac              7449
Asp Tyr Thr Ile Val Glu Gln Tyr Glu Arg Thr Glu Gly Arg His His
845                 850                 855                 860 ctg ttc ctg tag cggccgccct gcagggagct cggatatccc tagggatcgt                  7501
Leu Phe Leu tcaaacattt ggcaataaag tttcttaaga ttgaatcctg ttgccggtct tgcgatgatt            7561
atcatataat ttctgttgaa ttacgttaag catgtaataa ttaacatgta atgcatgacg            7621
ttatttatga gatgggtttt tatgattaga gtcccgcaat tatacattta atacgcgata            7681
gaaaacaaaa tatagcgcgc aaactaggat aaattatcgc gcgcggtgtc atctatgtta            7741
ctagatcggg aattcgggcc cggccggcca gatcttgatt gtcgtttccc gccttcagtt            7801
taaactatca gtgtttgaca ggatatattg gcgggtaaac ctaagagaaa agagcgttta            7861
ttagaataat cggatatttta aagggcgtg aaaaggttta tccgttcgtc catttgtatg            7921
tgcatgccaa ccacagggtt cccctcggga gtgcttggca ttccgtgcga taatgacttc            7981
tgttcaacca cccaaacgtc ggaaagcctg acgacggagc agcattccaa aaagatccct            8041
```

```
tggctcgtct gggtcggcta aaggtcgag tgggctgctg tggcttgatc cctcaacgcg   8101
gtcgcggacg tagcgcagcg ccgaaaaatc ctcgatcgca aatccgacgc tgtcgaaaag   8161
cgtgatctgc ttgtcgctct ttcggccgac gtcctggcca gtcatcacgc gccaaagttc   8221
cgtcacagga tgatctggcg cgagttgctg gatctcgcct tcaatccggg tctgtggcgg   8281
gaactccacg aaaatatccg aacgcagcaa gatcgtcgac caattcttga agacgaaagg   8341
gcctcgtgat acgcctattt ttataggtta atgtcatgat aataatggtt tcttagacgt   8401
caggtggcac ttttcgggga aatgtgcgcg gaacccctat ttgtttattt ttctaaatac   8461
attcaaatat gtatccgctc atgagacaat aaccctgata aatgcttcaa taatattgaa   8521
aaaggaagag tatgagtatt caacatttcc gtgtcgccct tattccctt tttgcggcat    8581 tttgccttcc tgttttgct cacccagaaa cgctggtgaa agtaaaagat gctgaagatc     8641
agttgggtgc acgagtgggt tacatcgaac tggatctcaa cagcggtaag atccttgaga   8701
gttttcgccc cgaagaacgt tttccaatga tgagcacttt taaagttctg ctatgtggcg   8761
cggtattatc ccgtgttgac gccgggcaag agcaactcgg tcgccgcata cactattctc   8821
agaatgactt ggttgagtac tcaccagtca cagaaaagca tcttacggat ggcatgacag   8881
taagagaatt atgcagtgct gccataacca tgagtgataa cactgcggcc aacttacttc   8941
tgacaacgat cggaggaccg aaggagctaa ccgcttttt gcacaacatg ggggatcatg     9001
taactcgcct tgatcgttgg gaaccggagc tgaatgaagc cataccaaac gacgagcgtg   9061
acaccacgat gccggggggg gggggggggg acatgaggtt gccccgtatt cagtgtcgct   9121
gatttgtatt gtctgaagtt ggttttacgt taagttgatg cagatcaatt aatacgatac    9181
ctgcgtcata attgattatt tgacgtggtt tgatggcctc cacgcacgtt gtgatatgta   9241
gatgataatc attatcactt tacgggtcct ttccggtgat ccgacaggtt acggggcggc   9301
gacctcgcgg gttttcgcta tttatgaaaa ttttccggtt taaggcgttt ccgttcttct   9361
tcgtcataac ttaatgtttt tatttaaaat accctctgaa agaaaggaa acgacaggtg    9421 ctgaaagcga gcttttggc ctctgtcgtt cctttctct gttttgtcc gtggaatgaa     9481 caatggaacc cccccccccc cccctgcag caatggcaac aacgttgcgc aaactattaa   9541
ctggcgaact acttactcta gcttcccggc aacaattaat agactggatg gaggcggata   9601
aagttgcagg accacttctg cgctcggccc ttccggctgg ctggtttatt gctgataaat   9661
ctggagccgg tgagcgtggg tctcgcggta tcattgcagc actggggcca gatggtaagc   9721
cctcccgtat cgtagttatc tacacgacgg ggagtcaggc aactatggat gaacgaaata   9781
gacagatcgc tgagataggt gcctcactga ttaagcattg gtaactgtca gaccaagttt   9841
actcatatat actttagatt gatttaaaac ttcatttta atttaaaagg atctaggtga    9901 agatccttt tgataatctc atgaccaaaa tcccttaacg tgagttttcg ttccactgag   9961
cgtcagaccc cgtagaaaag atcaaaggat cttcttgaga tccttttttt ctgcgcgtaa  10021
tctgctgctt gcaaacaaaa aaaccaccgc taccagcggt ggtttgtttg ccggatcaag  10081
agctaccaac tcttttccg aaggtaactg gcttcagcag agcgcagata ccaaatactg    10141
tccttctagt gtagccgtag ttaggccacc acttcaagaa ctctgtagca ccgcctacat   10201
acctcgctct gctaatcctg ttaccagtgg ctgctgccag tggcgataag tcgtgtctta   10261
ccgggttgga ctcaagacga tagttaccgg ataaggcgca gcggtcgggc tgaacggggg   10321
gttcgtgcac acagcccagc ttggagcgaa cgacctacac cgaactgaga tacctacagc  10381
gtgagctatg agaaagcgcc acgcttcccg aagggagaaa ggcggacagg tatccggtaa  10441
```

-continued

```
gcggcagggt cggaacagga gagcgcacga gggagcttcc aggggaaaac gcctggtatc   10501
tttatagtcc tgtcgggttt cgccacctct gacttgagcg tcgattttg tgatgctcgt    10561 caggggggcg gagcctatgg aaaaacgcca gcaacgcggc cttttacgg ttcctggcct    10621 tttgctggcc ttttgctcac atgttctttc ctgcgttatc ccctgattct gtggataacc   10681
gtattaccgc ctttgagtga gctgataccg ctcgccgcag ccgaacgacc gagcgcagcg   10741
agtcagtgag cgaggaagcg gaagagcgcc tgatgcggta ttttctcctt acgcatctgt   10801
gcggtatttc acaccgcata tggtgcactc tcagtacaat ctgctctgat gccgcatagt   10861
taagccagta tacactccgc tatcgctacg tgactgggtc atggctgcgc ccgacaccc    10921 gccaacaccc gctgacgcgc cctgacgggc ttgtctgctc ccggcatccg cttacagaca   10981
agctgtgacc gtctccggga gctgcatgtg tcagaggttt tcaccgtcat caccgaaacg   11041
cgcgaggcag cagatccccc gatcaagtag atacactaca tatatctaca atagacatcg   11101
agccggaagg tgatgtttac tttcctgaaa tccccagcaa ttttaggcca gttttaccc    11161 aagacttcgc ctctaacata aattatagtt accaaatctg gcaaagggt tgaccggggg   11221 ggggggaaa gccacgttgt gtctcaaaat ctctgatgtt acattgcaca agataaaaat    11281
atatcatcat gaacaataaa actgtctgct tacataaaca gtaatacaag gggtgtt      11338
```

| | | | | | | | | | | | | | | | | |
|---|---|---|---|---|---|---|---|---|---|---|---|---|---|---|---|---|
| atg | agc | cat | att | caa | cgg | gaa | acg | tct | tgc | tcg | agg | ccg | cga | tta | aat | 11386 |
| Met | Ser | His | Ile | Gln | Arg | Glu | Thr | Ser | Cys | Ser | Arg | Pro | Arg | Leu | Asn | |
| | 865 | | | | 870 | | | | | 875 | | | | | | |

| tcc | aac | atg | gat | gct | gat | tta | tat | ggg | tat | aaa | tgg | gct | cgc | gat | aat | 11434 |
|---|---|---|---|---|---|---|---|---|---|---|---|---|---|---|---|---|
| Ser | Asn | Met | Asp | Ala | Asp | Leu | Tyr | Gly | Tyr | Lys | Trp | Ala | Arg | Asp | Asn | |
| 880 | | | | | 885 | | | | | 890 | | | | | 895 | |

| gtc | ggg | caa | tca | ggt | gcg | aca | atc | tat | cga | ttg | tat | ggg | aag | ccc | gat | 11482 |
|---|---|---|---|---|---|---|---|---|---|---|---|---|---|---|---|---|
| Val | Gly | Gln | Ser | Gly | Ala | Thr | Ile | Tyr | Arg | Leu | Tyr | Gly | Lys | Pro | Asp | |
| | | | | 900 | | | | | 905 | | | | | 910 | | |

| gcg | cca | gag | ttg | ttt | ctg | aaa | cat | ggc | aaa | ggt | agc | gtt | gcc | aat | gat | 11530 |
|---|---|---|---|---|---|---|---|---|---|---|---|---|---|---|---|---|
| Ala | Pro | Glu | Leu | Phe | Leu | Lys | His | Gly | Lys | Gly | Ser | Val | Ala | Asn | Asp | |
| | | | 915 | | | | | 920 | | | | | 925 | | | |

| gtt | aca | gat | gag | atg | gtc | aga | cta | aac | tgg | ctg | acg | gaa | ttt | atg | cct | 11578 |
|---|---|---|---|---|---|---|---|---|---|---|---|---|---|---|---|---|
| Val | Thr | Asp | Glu | Met | Val | Arg | Leu | Asn | Trp | Leu | Thr | Glu | Phe | Met | Pro | |
| | | | 930 | | | | | 935 | | | | | 940 | | | |

| ctt | ccg | acc | atc | aag | cat | ttt | atc | cgt | act | cct | gat | gat | gca | tgg | tta | 11626 |
|---|---|---|---|---|---|---|---|---|---|---|---|---|---|---|---|---|
| Leu | Pro | Thr | Ile | Lys | His | Phe | Ile | Arg | Thr | Pro | Asp | Asp | Ala | Trp | Leu | |
| 945 | | | | | 950 | | | | | 955 | | | | | | |

| ctc | acc | act | gcg | atc | ccc | ggg | aaa | aca | gca | ttc | cag | gta | tta | gaa | gaa | 11674 |
|---|---|---|---|---|---|---|---|---|---|---|---|---|---|---|---|---|
| Leu | Thr | Thr | Ala | Ile | Pro | Gly | Lys | Thr | Ala | Phe | Gln | Val | Leu | Glu | Glu | |
| 960 | | | | | 965 | | | | | 970 | | | | | 975 | |

| tat | cct | gat | tca | ggt | gaa | aat | att | gtt | gat | gcg | ctg | gca | gtg | ttc | ctg | 11722 |
|---|---|---|---|---|---|---|---|---|---|---|---|---|---|---|---|---|
| Tyr | Pro | Asp | Ser | Gly | Glu | Asn | Ile | Val | Asp | Ala | Leu | Ala | Val | Phe | Leu | |
| | | | | 980 | | | | | 985 | | | | | 990 | | |

| cgc | cgg | ttg | cat | tcg | att | cct | gtt | tgt | aat | tgt | cct | ttt | aac | agc | gat | 11770 |
|---|---|---|---|---|---|---|---|---|---|---|---|---|---|---|---|---|
| Arg | Arg | Leu | His | Ser | Ile | Pro | Val | Cys | Asn | Cys | Pro | Phe | Asn | Ser | Asp | |
| | | | 995 | | | | | 1000 | | | | | 1005 | | | |

| cgc | gta | ttt | cgt | ctc | gct | cag | gcg | caa | tca | cga | atg | aat | | aac | ggt | 11815 |
|---|---|---|---|---|---|---|---|---|---|---|---|---|---|---|---|---|
| Arg | Val | Phe | Arg | Leu | Ala | Gln | Ala | Gln | Ser | Arg | Met | Asn | | Asn | Gly | |
| | | 1010 | | | | | 1015 | | | | | 1020 | | | | |

| ttg | gtt | gat | gcg | agt | gat | ttt | gat | gac | gag | cgt | aat | ggc | tgg | cct | | 11860 |
|---|---|---|---|---|---|---|---|---|---|---|---|---|---|---|---|---|
| Leu | Val | Asp | Ala | Ser | Asp | Phe | Asp | Asp | Glu | Arg | Asn | Gly | Trp | Pro | | |
| | | | 1025 | | | | | 1030 | | | | | 1035 | | | |

| gtt | gaa | caa | gtc | tgg | aaa | gaa | atg | cat | aag | ctt | ttg | cca | ttc | tca | | 11905 |
|---|---|---|---|---|---|---|---|---|---|---|---|---|---|---|---|---|
| Val | Glu | Gln | Val | Trp | Lys | Glu | Met | His | Lys | Leu | Leu | Pro | Phe | Ser | | |
| | | | 1040 | | | | | 1045 | | | | | 1050 | | | |

```
ccg gat tca gtc gtc act cat ggt gat ttc tca ctt gat aac ctt      11950
Pro Asp Ser Val Val Thr His Gly Asp Phe Ser Leu Asp Asn Leu
        1055                1060                1065 att ttt gac gag ggg aaa tta ata ggt tgt att gat gtt gga cga      11995
Ile Phe Asp Glu Gly Lys Leu Ile Gly Cys Ile Asp Val Gly Arg
        1070                1075                1080 gtc gga atc gca gac cga tac cag gat ctt gcc atc cta tgg aac      12040
Val Gly Ile Ala Asp Arg Tyr Gln Asp Leu Ala Ile Leu Trp Asn
        1085                1090                1095 tgc ctc ggt gag ttt tct cct tca tta cag aaa cgg ctt ttt caa      12085
Cys Leu Gly Glu Phe Ser Pro Ser Leu Gln Lys Arg Leu Phe Gln
        1100                1105                1110 aaa tat ggt att gat aat cct gat atg aat aaa ttg cag ttt cat      12130
Lys Tyr Gly Ile Asp Asn Pro Asp Met Asn Lys Leu Gln Phe His
        1115                1120                1125 ttg atg ctc gat gag ttt ttc taa tcagaattgg ttaattggtt gtaacactgg  12184
Leu Met Leu Asp Glu Phe Phe
        1130 cagagcatta cgctgacttg acgggacggc ggctttgttg aataaatcga acttttgctg  12244 agttgaagga tcagatcacg catcttcccg acaacgcaga ccgttccgtg caaagcaaa   12304 agttcaaaat caccaactgg tccacctaca acaaagctct catcaaccgt ggctccctca  12364 ctttctggct ggatgatggg gcgattcagg atcacaggc agcaacgctc tgtcatcgtt   12424 acaatcaaca tgctaccctc cgcgagatca tccgtgtttc aaacccggca gcttagttgc  12484 cgttcttccg aatagcatcg gtaacatgag caaagtctgc cgccttacaa cggctctccc  12544 gctgacgccg tcccggactg atgggctgcc tgtatcgagt ggtgat              12590
```

<210> SEQ ID NO 217
<211> LENGTH: 638
<212> TYPE: PRT
<213> ORGANISM: Artificial sequence
<220> FEATURE:
<223> OTHER INFORMATION: Synthetic Construct

<400> SEQUENCE: 217

```
Met Ala Thr Ala Ala Ala Ala Ser Thr Ala Leu Thr Gly Ala Thr Thr
1               5                   10                  15

Ala Ala Pro Lys Ala Arg Arg Arg Ala His Leu Leu Ala Thr Arg Arg
            20                  25                  30

Ala Leu Ala Ala Pro Ile Arg Cys Ser Ala Ala Ser Pro Ala Met Pro
        35                  40                  45

Met Ala Pro Pro Ala Thr Pro Leu Arg Pro Trp Gly Pro Thr Asp Pro
    50                  55                  60

Arg Lys Gly Ala Asp Ile Leu Val Glu Ser Leu Glu Arg Cys Gly Val
65                  70                  75                  80

Arg Asp Val Phe Ala Tyr Pro Gly Gly Ala Ser Met Glu Ile His Gln
                85                  90                  95

Ala Leu Thr Arg Ser Pro Val Ile Ala Asn His Leu Phe Arg His Glu
            100                 105                 110

Gln Gly Glu Ala Phe Ala Ala Ser Gly Tyr Ala Arg Ser Ser Gly Arg
        115                 120                 125

Val Gly Val Cys Ile Ala Thr Ser Gly Pro Gly Ala Thr Asn Leu Val
    130                 135                 140

Ser Ala Leu Ala Asp Ala Leu Leu Asp Ser Val Pro Met Val Ala Ile
145                 150                 155                 160

Thr Gly Gln Val Pro Arg Arg Met Ile Gly Thr Asp Ala Phe Gln Glu
```

```
                    165                 170                 175
Thr Pro Ile Val Glu Val Thr Arg Ser Ile Thr Lys His Asn Tyr Leu
                180                 185                 190
Val Leu Asp Val Asp Asp Ile Pro Arg Val Val Gln Glu Ala Phe Phe
            195                 200                 205
Leu Ala Ser Ser Gly Arg Pro Gly Val Leu Val Asp Ile Pro Lys
        210                 215                 220
Asp Ile Gln Gln Gln Met Ala Val Pro Val Trp Asp Lys Pro Met Ser
225                 230                 235                 240
Leu Pro Gly Tyr Ile Ala Arg Leu Pro Lys Pro Ala Thr Glu Leu
                245                 250                 255
Leu Glu Gln Val Leu Arg Leu Val Gly Glu Ser Arg Arg Pro Val Leu
            260                 265                 270
Tyr Val Gly Gly Gly Cys Ala Ala Ser Gly Glu Glu Leu Arg Arg Phe
            275                 280                 285
Val Glu Leu Thr Gly Ile Pro Val Thr Thr Thr Leu Met Gly Leu Gly
            290                 295                 300
Asn Phe Pro Ser Asp Asp Pro Leu Ser Leu Arg Met Leu Gly Met His
305                 310                 315                 320
Gly Thr Val Tyr Ala Asn Tyr Ala Val Asp Lys Ala Asp Leu Leu Leu
                325                 330                 335
Ala Leu Gly Val Arg Phe Asp Asp Arg Val Thr Gly Lys Ile Glu Ala
            340                 345                 350
Phe Ala Ser Arg Ala Lys Ile Val His Val Asp Ile Asp Pro Ala Glu
            355                 360                 365
Ile Gly Lys Asn Lys Gln Pro His Val Ser Ile Cys Ala Asp Val Lys
        370                 375                 380
Leu Ala Leu Gln Gly Met Asn Ala Leu Leu Glu Gly Ser Thr Ser Lys
385                 390                 395                 400
Lys Ser Phe Asp Phe Gly Ser Trp Asn Asp Glu Leu Asp Gln Gln Lys
                405                 410                 415
Arg Glu Phe Pro Leu Gly Tyr Lys Thr Ser Asn Glu Glu Ile Gln Pro
                420                 425                 430
Gln Tyr Ala Ile Gln Val Leu Asp Glu Leu Thr Lys Gly Glu Ala Ile
            435                 440                 445
Ile Gly Thr Gly Val Gly Gln His Gln Met Trp Ala Ala Gln Tyr Tyr
            450                 455                 460
Thr Tyr Lys Arg Pro Arg Gln Trp Leu Ser Ser Ala Gly Leu Gly Ala
465                 470                 475                 480
Met Gly Phe Gly Leu Pro Ala Ala Ala Gly Ala Ser Val Ala Asn Pro
                485                 490                 495
Gly Val Thr Val Val Asp Ile Asp Gly Asp Gly Ser Phe Leu Met Asn
                500                 505                 510
Val Gln Glu Leu Ala Met Ile Arg Ile Glu Asn Leu Pro Val Lys Val
            515                 520                 525
Phe Val Leu Asn Asn Gln His Leu Gly Met Val Val Gln Trp Glu Asp
        530                 535                 540
Arg Phe Tyr Lys Ala Asn Arg Ala His Thr Tyr Leu Gly Asn Pro Glu
545                 550                 555                 560
Asn Glu Ser Glu Ile Tyr Pro Asp Phe Val Thr Ile Ala Lys Gly Phe
                565                 570                 575
Asn Ile Pro Ala Val Arg Val Thr Lys Lys Asn Glu Val Arg Ala Ala
            580                 585                 590
```

```
Ile Lys Lys Met Leu Glu Thr Pro Gly Pro Tyr Leu Leu Asp Ile Ile
        595                 600                 605

Val Pro His Gln Glu His Val Leu Pro Met Ile Pro Asn Gly Gly Ala
610                 615                 620

Phe Lys Asp Met Ile Leu Asp Gly Asp Gly Arg Thr Val Tyr
625                 630                 635
```

<210> SEQ ID NO 218
<211> LENGTH: 225
<212> TYPE: PRT
<213> ORGANISM: Artificial sequence
<220> FEATURE:
<223> OTHER INFORMATION: Synthetic Construct

<400> SEQUENCE: 218

```
Met Ala Ser Ser Glu Asn Val Ile Thr Glu Phe Met Arg Phe Lys Val
1               5                   10                  15

Arg Met Glu Gly Thr Val Asn Gly His Glu Phe Glu Ile Glu Gly Glu
            20                  25                  30

Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Thr His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ala Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```

<210> SEQ ID NO 219
<211> LENGTH: 271
<212> TYPE: PRT
<213> ORGANISM: Artificial sequence
<220> FEATURE:
<223> OTHER INFORMATION: Synthetic Construct

<400> SEQUENCE: 219

```
Met Ser His Ile Gln Arg Glu Thr Ser Cys Ser Arg Pro Arg Leu Asn
1               5                   10                  15

Ser Asn Met Asp Ala Asp Leu Tyr Gly Tyr Lys Trp Ala Arg Asp Asn
```

```
            20                  25                  30
Val Gly Gln Ser Gly Ala Thr Ile Tyr Arg Leu Tyr Gly Lys Pro Asp
         35                  40                  45

Ala Pro Glu Leu Phe Leu Lys His Gly Lys Gly Ser Val Ala Asn Asp
 50                  55                  60

Val Thr Asp Glu Met Val Arg Leu Asn Trp Leu Thr Glu Phe Met Pro
 65                  70                  75                  80

Leu Pro Thr Ile Lys His Phe Ile Arg Thr Pro Asp Asp Ala Trp Leu
                 85                  90                  95

Leu Thr Thr Ala Ile Pro Gly Lys Thr Ala Phe Gln Val Leu Glu Glu
                100                 105                 110

Tyr Pro Asp Ser Gly Glu Asn Ile Val Asp Ala Leu Ala Val Phe Leu
            115                 120                 125

Arg Arg Leu His Ser Ile Pro Val Cys Asn Cys Pro Phe Asn Ser Asp
130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
            195                 200                 205

Gly Lys Leu Ile Gly Cys Ile Asp Val Gly Arg Val Gly Ile Ala Asp
        210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270

<210> SEQ ID NO 220
<211> LENGTH: 39
<212> TYPE: DNA
<213> ORGANISM: Artificial sequence
<220> FEATURE:
<223> OTHER INFORMATION: A short oligo contains miR172 tag
<220> FEATURE:
<221> NAME/KEY: misc_RNA
<222> LOCATION: (10)..(30)
<223> OTHER INFORMATION: Nearly complementary to miR172

<400> SEQUENCE: 220
agctcgccgc tgcagcatca tcaggattcc cactgctag                    39

<210> SEQ ID NO 221
<211> LENGTH: 38
<212> TYPE: DNA
<213> ORGANISM: Artificial sequence
<220> FEATURE:
<223> OTHER INFORMATION: miR 319 tag
<220> FEATURE:
<221> NAME/KEY: misc_feature
<222> LOCATION: (10)..(29)
<223> OTHER INFORMATION: Nearly complementary to miR 319

<400> SEQUENCE: 221
agctggatgc agagctccct tcaatccaaa gagcctag                     38
```

```
<210> SEQ ID NO 222
<211> LENGTH: 39
<212> TYPE: DNA
<213> ORGANISM: Artificial sequence
<220> FEATURE:
<223> OTHER INFORMATION: miR 396a tag
<220> FEATURE:
<221> NAME/KEY: misc_feature
<222> LOCATION: (10)..(31)
<223> OTHER INFORMATION: complementary to miR 396a

<400> SEQUENCE: 222
agctgagggc agttcaataa agctgtggga aattgctag                                39

<210> SEQ ID NO 223
<211> LENGTH: 43
<212> TYPE: DNA
<213> ORGANISM: Artificial sequence
<220> FEATURE:
<223> OTHER INFORMATION: miR 398a tag
<220> FEATURE:
<221> NAME/KEY: misc_feature
<222> LOCATION: (11)..(31)
<223> OTHER INFORMATION: Nearly complementary to miR 398a

<400> SEQUENCE: 223
agctctcctc aagggtgac ctaagaacac caccaccacc tag                            43

<210> SEQ ID NO 224
<211> LENGTH: 40
<212> TYPE: DNA
<213> ORGANISM: Artificial sequence
<220> FEATURE:
<223> OTHER INFORMATION: miR 167 tag
<220> FEATURE:
<221> NAME/KEY: misc_feature
<222> LOCATION: (10)..(31)
<223> OTHER INFORMATION: Nearly complementary to miR 167d

<400> SEQUENCE: 224
agctccctgt tagatcaggc tggcagcttg tatttcctag                               40

<210> SEQ ID NO 225
<211> LENGTH: 20
<212> TYPE: RNA
<213> ORGANISM: Arabidopsis thaliana

<400> SEQUENCE: 225
ugacagaaga gagugagcac                                                     20

<210> SEQ ID NO 226
<211> LENGTH: 21
<212> TYPE: RNA
<213> ORGANISM: Arabidopsis thaliana

<400> SEQUENCE: 226
cgacagaaga gagugagcac a                                                   21

<210> SEQ ID NO 227
<211> LENGTH: 21
<212> TYPE: RNA
<213> ORGANISM: Arabidopsis thaliana

<400> SEQUENCE: 227
uugacagaag aaagagagca c                                                   21
```

```
<210> SEQ ID NO 228
<211> LENGTH: 21
<212> TYPE: RNA
<213> ORGANISM: Arabidopsis thaliana

<400> SEQUENCE: 228
uugacagaag auagagagca c                                              21

<210> SEQ ID NO 229
<211> LENGTH: 20
<212> TYPE: RNA
<213> ORGANISM: Arabidopsis thaliana

<400> SEQUENCE: 229
ucccaaaugu agacaaagca                                                20

<210> SEQ ID NO 230
<211> LENGTH: 21
<212> TYPE: RNA
<213> ORGANISM: Arabidopsis thaliana

<400> SEQUENCE: 230
uuuggauuga agggagcucu a                                              21

<210> SEQ ID NO 231
<211> LENGTH: 21
<212> TYPE: RNA
<213> ORGANISM: Arabidopsis thaliana

<400> SEQUENCE: 231
uuuggauuga agggagcucu u                                              21

<210> SEQ ID NO 232
<211> LENGTH: 21
<212> TYPE: RNA
<213> ORGANISM: Arabidopsis thaliana

<400> SEQUENCE: 232
uuuggauuga agggagcucc u                                              21

<210> SEQ ID NO 233
<211> LENGTH: 21
<212> TYPE: RNA
<213> ORGANISM: Arabidopsis thaliana

<400> SEQUENCE: 233
uugaaaguga cuacaucggg g                                              21

<210> SEQ ID NO 234
<211> LENGTH: 21
<212> TYPE: RNA
<213> ORGANISM: Arabidopsis thaliana

<400> SEQUENCE: 234
ucgauaaacc ucugcaucca g                                              21

<210> SEQ ID NO 235
<211> LENGTH: 21
<212> TYPE: RNA
<213> ORGANISM: Arabidopsis thaliana

<400> SEQUENCE: 235
uggagaagca gggcacgugc a                                              21
```

<210> SEQ ID NO 236
<211> LENGTH: 21
<212> TYPE: RNA
<213> ORGANISM: Arabidopsis thaliana

<400> SEQUENCE: 236
uggagaagca gggcacgugc g                                    21

<210> SEQ ID NO 237
<211> LENGTH: 21
<212> TYPE: RNA
<213> ORGANISM: Arabidopsis thaliana

<400> SEQUENCE: 237
ucggaccagg cuucaucccc c                                    21

<210> SEQ ID NO 238
<211> LENGTH: 21
<212> TYPE: RNA
<213> ORGANISM: Arabidopsis thaliana

<400> SEQUENCE: 238
ucggaccagg cuucauuccc c                                    21

<210> SEQ ID NO 239
<211> LENGTH: 21
<212> TYPE: RNA
<213> ORGANISM: Arabidopsis thaliana

<400> SEQUENCE: 239
uuaagcugcc agcaugaucu u                                    21

<210> SEQ ID NO 240
<211> LENGTH: 22
<212> TYPE: RNA
<213> ORGANISM: Arabidopsis thaliana

<400> SEQUENCE: 240
ugaagcugcc agcaugaucu gg                                   22

<210> SEQ ID NO 241
<211> LENGTH: 21
<212> TYPE: RNA
<213> ORGANISM: Arabidopsis thaliana

<400> SEQUENCE: 241
ucgcuuggug caggucggga a                                    21

<210> SEQ ID NO 242
<211> LENGTH: 21
<212> TYPE: RNA
<213> ORGANISM: Arabidopsis thaliana

<400> SEQUENCE: 242
cagccaagga ugacuugccg a                                    21

<210> SEQ ID NO 243
<211> LENGTH: 21
<212> TYPE: RNA
<213> ORGANISM: Arabidopsis thaliana

<400> SEQUENCE: 243
cagccaagga ugacuugccg g                                    21

```
<210> SEQ ID NO 244
<211> LENGTH: 21
<212> TYPE: RNA
<213> ORGANISM: Arabidopsis thaliana

<400> SEQUENCE: 244
ugagccaagg augacuugcc g                                            21

<210> SEQ ID NO 245
<211> LENGTH: 21
<212> TYPE: RNA
<213> ORGANISM: Arabidopsis thaliana

<400> SEQUENCE: 245
uagccaagga ugacuugccu g                                            21

<210> SEQ ID NO 246
<211> LENGTH: 21
<212> TYPE: RNA
<213> ORGANISM: Arabidopsis thaliana

<400> SEQUENCE: 246
ugauugagcc gugucaauau c                                            21

<210> SEQ ID NO 247
<211> LENGTH: 21
<212> TYPE: RNA
<213> ORGANISM: Arabidopsis thaliana

<400> SEQUENCE: 247
ugauugagcc gcgccaauau c                                            21

<210> SEQ ID NO 248
<211> LENGTH: 21
<212> TYPE: RNA
<213> ORGANISM: Arabidopsis thaliana

<400> SEQUENCE: 248
uugagccgug ccaauaucac g                                            21

<210> SEQ ID NO 249
<211> LENGTH: 22
<212> TYPE: RNA
<213> ORGANISM: Arabidopsis thaliana

<400> SEQUENCE: 249
uucgcuugca gagagaaauc ac                                           22

<210> SEQ ID NO 250
<211> LENGTH: 20
<212> TYPE: RNA
<213> ORGANISM: Arabidopsis thaliana

<400> SEQUENCE: 250
uuggacugaa gggagcuccc                                              20

<210> SEQ ID NO 251
<211> LENGTH: 20
<212> TYPE: RNA
<213> ORGANISM: Arabidopsis thaliana

<400> SEQUENCE: 251
```

```
uuggacugaa gggagcuccu                                              20

<210> SEQ ID NO 252
<211> LENGTH: 21
<212> TYPE: RNA
<213> ORGANISM: Arabidopsis thaliana

<400> SEQUENCE: 252
uccaaaggga ucgcauugau c                                            21

<210> SEQ ID NO 253
<211> LENGTH: 20
<212> TYPE: RNA
<213> ORGANISM: Arabidopsis thaliana

<400> SEQUENCE: 253
uuggcauucu guccaccucc                                              20

<210> SEQ ID NO 254
<211> LENGTH: 21
<212> TYPE: RNA
<213> ORGANISM: Arabidopsis thaliana

<400> SEQUENCE: 254
cugaaguguu uggggggaacu c                                           21

<210> SEQ ID NO 255
<211> LENGTH: 21
<212> TYPE: RNA
<213> ORGANISM: Arabidopsis thaliana

<400> SEQUENCE: 255
cugaaguguu ugggggggacu c                                           21

<210> SEQ ID NO 256
<211> LENGTH: 21
<212> TYPE: RNA
<213> ORGANISM: Arabidopsis thaliana

<400> SEQUENCE: 256
uuccacagcu uucuugaacu g                                            21

<210> SEQ ID NO 257
<211> LENGTH: 21
<212> TYPE: RNA
<213> ORGANISM: Arabidopsis thaliana

<400> SEQUENCE: 257
uuccacagcu uucuugaacu u                                            21

<210> SEQ ID NO 258
<211> LENGTH: 21
<212> TYPE: RNA
<213> ORGANISM: Arabidopsis thaliana

<400> SEQUENCE: 258
ucauugagug cagcguugau g                                            21

<210> SEQ ID NO 259
<211> LENGTH: 21
<212> TYPE: RNA
<213> ORGANISM: Arabidopsis thaliana

<400> SEQUENCE: 259
```

```
ucauugagug caucguugau g                                              21

<210> SEQ ID NO 260
<211> LENGTH: 21
<212> TYPE: RNA
<213> ORGANISM: Arabidopsis thaliana

<400> SEQUENCE: 260
uguguucuca ggucacccccu u                                             21

<210> SEQ ID NO 261
<211> LENGTH: 21
<212> TYPE: RNA
<213> ORGANISM: Arabidopsis thaliana

<400> SEQUENCE: 261
uguguucuca ggucacccccu g                                             21

<210> SEQ ID NO 262
<211> LENGTH: 21
<212> TYPE: RNA
<213> ORGANISM: Arabidopsis thaliana

<400> SEQUENCE: 262
ugccaaagga gauuugcccu g                                              21

<210> SEQ ID NO 263
<211> LENGTH: 21
<212> TYPE: RNA
<213> ORGANISM: Arabidopsis thaliana

<400> SEQUENCE: 263
ugccaaagga gaguugcccu g                                              21

<210> SEQ ID NO 264
<211> LENGTH: 21
<212> TYPE: RNA
<213> ORGANISM: Arabidopsis thaliana

<400> SEQUENCE: 264
ugccaaagga gauuugcccc g                                              21

<210> SEQ ID NO 265
<211> LENGTH: 21
<212> TYPE: RNA
<213> ORGANISM: Arabidopsis thaliana

<400> SEQUENCE: 265
ugccaaagga gauuugccuc g                                              21

<210> SEQ ID NO 266
<211> LENGTH: 21
<212> TYPE: RNA
<213> ORGANISM: Arabidopsis thaliana

<400> SEQUENCE: 266
ugccaaagga gauuugcccg g                                              21

<210> SEQ ID NO 267
<211> LENGTH: 20
<212> TYPE: DNA
<213> ORGANISM: Artificial sequence
<220> FEATURE:
```

```
<223> OTHER INFORMATION: miRNA-tag

<400> SEQUENCE: 267
agagctccct tcaatccaaa                                                    20

<210> SEQ ID NO 268
<211> LENGTH: 20
<212> TYPE: DNA
<213> ORGANISM: Artificial sequence
<220> FEATURE:
<223> OTHER INFORMATION: miR159

<400> SEQUENCE: 268
tttggattga agggagctct                                                    20

<210> SEQ ID NO 269
<211> LENGTH: 20
<212> TYPE: DNA
<213> ORGANISM: Artificial sequence
<220> FEATURE:
<223> OTHER INFORMATION: miRNA-tag

<400> SEQUENCE: 269
tgaagctgcc agcatgatct                                                    20

<210> SEQ ID NO 270
<211> LENGTH: 20
<212> TYPE: DNA
<213> ORGANISM: Artificial sequence
<220> FEATURE:
<223> OTHER INFORMATION: miR167

<400> SEQUENCE: 270
agatcatgct ggcagcttca                                                    20
```

METHODS CONTROLLING GENE EXPRESSION

RELATED APPLICATIONS

This application is a divisional application of U.S. application Ser. No. 11/918,554 filed Oct. 15, 2007, which is a national stage application (under 35 U.S.C. 371) of PCT/EP2006/061604 filed Apr. 13, 2006, which claims benefit of U.S. application 60/672,976 filed Apr. 19, 2005. The entire contents of each of these applications are hereby incorporated by reference herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074021_0072_01. The size of the text file is 159 KB, and the text file was created on Dec. 4, 2017.

FIELD OF THE INVENTION

The present invention is in the field of genetics, especially plant genetics, and provides agents capable of gene-specific silencing. The present invention specifically provides polycicstronic RNA molecules capable to generate double-stranded RNA (dsRNA) agents, methods for utilizing such molecules and cells and organism, especially plants, containing such molecules.

BACKGROUND OF THE INVENTION

Many factors affect gene expression in plants and other eukaryotic organisms. Recently, small RNAs, 21-26 nucleotides, have emerged as important regulators of eukaryotic gene expression. The known small regulatory RNAs fall into two basic classes. One class of small RNAs is the short interfering RNAs (siRNAs). These play essential roles in RNA silencing, a sequence-specific RNA degradation process that is triggered by double-stranded RNA (dsRNA) (see Vance and Vaucheret (2001) Science 292:2277-2280, and Zamore (2001) Nat Struct Biol 8:746-750 for recent reviews on RNA silencing in plants and animals, respectively). RNA silencing plays a natural role in defense against foreign nucleic acids including virus resistance in plants and control of transposons in a number of organisms. siRNAs are double-stranded with small 3' overhangs and derive from longer dsRNAs that induce silencing. They serve as guides to direct destruction of target RNAs and have been implicated as primers in the amplification of dsRNA via the activity of a cellular RNA dependent RNA polymerase. In plants, si-like RNAs have also been associated with dsRNA-induced transcriptional gene silencing (TGS), a process in which dsRNA with homology to promoter regions triggers DNA methylation and inhibits transcription. The TGS-associated small RNAs, unlike true siRNAs, are not involved in RNA degradation.

Another group of small RNAs are known generically as short temporal RNAs (stRNAs) and more broadly as microRNAs (miRNAs). miRNAs have emerged as evolutionarily conserved, RNA-based regulators of gene expression in animals and plants. miRNAs (approx. 21 to 25 nt) arise from larger precursors with a stem loop structure that are transcribed from non-protein-coding genes. miRNAs are single-stranded, and their accumulation is developmentally regulated and/or regulated by environmental stimuli. They derive from partially double-stranded precursor RNAs that are transcribed from genes that do not encode protein. The miRNAs appear to be transcribed as hairpin RNA precursors, which are processed to their mature, about 21 nt forms by Dicer (Lee R D, and Ambros, V. Science 294: 862-864 (2001)). miRNA targets a specific mRNA to suppress gene expression at post-transcriptional level (i.e. degrades mRNA) or at translational level (i.e. inhibits protein synthesis). microRNAs (miRNAs) have emerged as evolutionarily conserved. There are several hundred of miRNAs have been recently identified through computational analysis and experimental approaches from many plant and animal species. A body of miRNAs is well conserved within plant kingdom or animal kingdom, but some are species or genus specific.

miRNA genes are first transcribed by Pol II RNA polymerase resulting in pri-miRNA with Cap structure at 5' end and poly tail at 3' end. Pri-miRNA is subjected to cleavage by an RNase III-like enzyme, Dicer, to generate mature miRNA. miRNA is then recruited into RISC (RNA induced silencing complex) and targets a specific mRNA in cytoplasm to suppress gene expression at post-transcriptional level (i.e. degrades mRNA). MiRNA can also inhibit protein synthesis after targeting a mRNA in a sequence-specific manner. The mechanism of such translational inhibition is to be uncovered. It has been shown both in animal and plant, pairing of the miRNA 5' region to its target mRNA is crucial for miRNA actions (Mallory A et al., EMBO Journal 23:3356-3364, 2004; Doench J and Sharp P, Genes & Development 504-511, (2004)).

Thus, it was realized that small, endogenously encoded hairpin RNAs could stably regulate gene expression via elements of the RNAi machinery. Like stRNAs (and unlike siRNAs involved in RNA silencing), most of the miRNAs lack complete complementarity to any putative target mRNA. Although their functions are, as yet, not known, it is hypothesized that they regulate gene expression during development, perhaps at the level of development. However, given the vast numbers of these small regulatory RNAs, it is likely that they are functionally more diverse and regulate gene expression at more than one level. In plant, majority of miRNA target genes are transcription factors which are required for meristem identity, cell division, organ separation, and organ polarity. Some miRNAs have unique tissues-specific and/or temporal expression pattern. McManus et al. (RNA 8:842-850 (2002)) also studied miRNA mimics containing 19 nucleotides of uninterrupted RNA duplex, a 12-nucleotide loop length and one asymmetric stem-loop bulge composed of a single uridine opposing a double uridine. Synthetic miRNA can either be transfected into cells or expressed in the cell under the control of an RNA polymerase III promoter and cause the decreased expression of a specific target nucleotide sequence (McManus et al. (2002) RNA 8:842-850, herein incorporated by reference).

In plant, there have been increasing evidences that microRNAs target genes involved in many aspects of plant growth and development such as meristem identity, cell division, organ separation, and organ polarity. For example, miR164 targets NAC-domai genes, which encodes a family of transcription factors including (CUP-SHAPED COTYLEDON1, CUC1 and CUC2). Expression of miR164-resistant version of CUC1 mRNA from the CUC1 promoter causes alterations in *Arabidopsis* embryonic vegetative, and floral development (Mallory A et al., Current Biology 14:1035-1046, (2004)). MiR166 mediates leaf polarity in *Arabidopsis* and maize (Juarez M et al., Nature 428: 84-88, (2004) and Kidner C and Martlenssen R, Nature 428: 81-84, (2004)). MiR172 directs flower development through regulating APETALA2 gene expression (Chen X, Science, 303: 2022-2025 (2004)). MiRNAs also regulate plant gene expression in response to environmental stimuli such as abiotic stress. For example, the expression of miR395, the sulfurylase-targeting miRNA, is increased upon sulfate starvation (Jone-Rhoades M W and Bartel D, Molecular Cell 14: 787-799, (2004)). MiR319c expression is upregulated by cold but not dehydration, NaCl or ABA (Sunkar R and Zhu J K, The Plant Cell 16:2001:2019, (2004)). Some miRNAs have unique tissues-specific and/or temporal expression patterns. For example, miR398b is expressed predominantly in *Arabidopsis* leaf (Sunkar R and Zhu J K., The Plant Cell 16:2001:2019, 2004)

In animals, miRNAs also play a key role in growth and development. For example, in mammals, miR181 modulates hematopietic lineage differentiation (Chen C Z et al., Science 303:83-86, (2004)), and MiR196 direct cleavage of HOXB8 mRNA (Yekta S et al., Science 304:594-596, (2004)). In human, miR-124 is expressed only in brain with possible role in neuronal differentiation (Sempere L. F. et al., Genome Biology 5:R13 (2004)) while miR-1 is expressed in muscle (Lagos-Quintana. M et al., Current Biology, (2002))

In plant, so far disclosed applications of miRNAs are
1) overexpression and/or ectopic expression of a given miRNA to characterize its function or generate desired phenotypes (Palatnik J et al., Nature 425: 257-263, (2003));
2) engineering a miRNA precursor to produce new miRNA targeting gene-of-interest (WO2004009779;
3) engineering mRNA to be resistant to miRNA recognition and cleavage (i.e. silent mutation—by changing nucleotides in the codons for the same amino acid) (Palatnik J et al., Nature 425: 257-263, 2003; Mallory A et al., Current Biology 14:1035-1046, (2004)).

US 20040268441 describes microRNA precursor constructs that can be designed to modulate expression of any nucleotide sequence of interest, either an endogenous plant gene or alternatively a transgene.

One of the major obstacles in various field of biotechnology (including but not limited to gene therapy and plant biotechnology) is the difficulty to achieve cell or tissue specificity. Transcription is an essential process for every living organism to convert abstract genetic information into physical reality. Promoter is a major component to drive transcription. Some promoters are active in every tissue (e.g. actin promoters) while other promoters only active in limited tissues. It is quite often that a given promoter is predominantly active in one tissue type but weakly expressed in some other tissues, so called leaky promoters. Those promoters are undesirable for agriculture and pharmaceutical application because unintended expression of gene-of-interest resulted from leaky promoters could cause detrimental effects to crops or patients. It certainly would not meet requirement of regulatory agency.

For example plant-parasitic nematodes cause diseases in all crops of economic importance, resulting in an estimated US$100 billion annual losses to world agriculture. In US, soybean cyst nematode is No. 1 pest—infecting nearly all soybean production states (approx. 80 million acres) and causes up to 30% yield loss each year. Chemical control measures are inadequate and environmentally unfriendly. Transgenic-plant technology offers a great potential, however, no significant success has been made yet. One major problem is the leaky activities of nematode feeding site 'specific' promoter. Although such promoter (e.g. TobRB7) could drive phytotoxic molecules to 'kill' the feeding cells and alleviate nematode infection, leaky expression of these phytotoxic molecules in other tissues (e.g. flower) causes detrimental effects on the host plants. Thus, a novel approach to control leaky expression is in high demand.

For example a major problem in chemotherapy and radiation therapy for cancer is the difficulty in achieving tumor-specific cell killing. The inability of radiation or cytotoxic chemotherapeutic agents to distinguish between tumor cells and normal cells necessarily limits the dosage that can be applied. As a result, disease relapse due to residual surviving tumor cells is frequently observed, and thus there exists a clear need for alternative non-surgical strategies. Development of gene therapy techniques is approaching clinical realization for the treatment of neoplastic and metabolic diseases, and numerous genes displaying anti-tumor activity have been identified. However, the usefulness of gene therapy methods has been limited due to systemic toxicity of anti-tumor polypeptides encoded by gene therapy constructs (Spriggs & Yates (1992) in Bentler, ed., Tumor Necrosis Factor: The Molecules and Their Emerging Roles in Medicine, pp. 383-406 Raven Press, New York, N.Y.; Sigel & Puri (1991) J Clin Oncol 9:694-704; Ryffel (1997) Immunopathol 83:18-20). Problems with current state-of-the-art gene therapy strategies include the inability to deliver the therapeutic gene specifically to the target cells. This leads to toxicity in cells that are not the intended targets. For example, manipulation of-the p53 gene suppresses the growth of both tumor cells and normal cells, and intravenous administration of tumor necrosis factor alpha (TNF.alpha.) induces systemic toxicity with such clinical manifestations as fever and hypertension. Attempts have been made to overcome these problems. These include such strategies as the use of tissue-specific promoters to limit gene expression to specific tissues and the use of heat (Voellmy R., et al., Proc. Natl. Acad. Sci. USA, 82:4949-4953 (1985)) or ionizing radiation inducible enhancers and promoters (Trainman, R. H., et al., Cell 46: 567-574 (1986); Prowess, R., et al., Proc. Natl. Acad. Sci. USA 85, 7206-7210 (1988)) to enhance expression of the therapeutic gene in a temporally and spatially controlled manner.

Adenoviral vectors possess a number of attributes that render them useful gene delivery vehicles for systemic gene therapy. Ideally, such a system would be designed so that systemically administered vector would home specifically to tumor target cells without ectopic infection of normal cells. However, a major stumbling block to this approach is the fact that the majority of adenoviral vectors administered systemically are sequestered in the liver. Therefore measures that specifically control the distribution of delivered transgene expression must be superimposed on the basic vector for optimal applicability of adenoviral vectors.

Unfortunately, for most of the presently expression systems expression of the active ingredient is not restricted to the tumor sites due to the 'leakiness' of the available promoters thereby limiting efficiency of such approaches. Tissue specific promoters may add a further degree of transgene expression selectivity but there are few of these that have been validated in vivo and all are subject to some degree of non-specific activation or "leakiness". A versatile mechanism for controllable gene expression is therefore highly desired for gene therapy.

A mechanism for controlling gene expression should ideally include both spatial and temporal control of gene expression. One existing strategy employs a chemically regulated signal, for example the tetracycline-inducible gene expression system (Gossen & Bujard (1992) Proc Natl Acad Sci USA 89:5547-5551; Gossen & Bujard (1993) Nuc Acids Res 21(18):4411-4412; Gossen et al. (1995) Science 268: 1766-1769). A similar approach involves the provision of ionizing radiation to activate a radiosensitive promoter, e.g. the EGR-1 promoter (Weischelbaum et al. (1994) Cancer Res 54:4266-4269; Hallahan et al. (1995) Nat Med 1(8): 786-791; Joki et al. (1995) Hum Gen Ther 6:1507-1513). An alternative design relies on endogenous control of gene expression. For example, the CEA promoter is selectively expressed in cancer cells (Hauck & Stanners (1995) J Biol Chem 270:3602; Richards et al. (1995) Human Gene Ther 6:881-893).

In the past, several approaches have been attempted to solve leakiness problem in plant gene expression without much success. By conducting a series of deletion of promoter sequence, one might eliminate the sequence in the promoter region which contributes to the leaky expression. For example, a deleted version of TbRB7 promoter drives GUS reporter gene expression in nematode feeding cells in the root upon nematode infection. Leaky expression, however, in flower tissue is still unsolved (Opperman C H et al., Science 263:221-223, (1994)). By making a chimeric promoter, i.e. a minimal promoter (e.g. 35S promoter) plus tissues-specific regulatory elements, one might restrict gene expression in desired tissues. However, if tissue-specific regulatory elements are leaky, the chimeric promoter will be leaky as well.

US 20030045495 is disclosing modified inducible systems for selective expression of therapeutic genes by hyperthermia. However, hypothermia is also difficult to be applied to discrete cells or small tissue areas.

US 20010049828 is describing a method and system for controlling the expression of transgene products in specific tissues in a transgenic animal. The system is based on an interaction of various transactivators. The transcactivator activity is controlled by antisense which is under control of tissue-specific promoters, thereby suppressing expression in certain tissues. The system is rather complicated and relies on serveral expression constructs and transgenic transcription factors. A similar system is described in US 20020065243.

US 20020022018 described control of tissue-specificity by employing tissue-specific deletion or destruction of the expression-construct in the target organism by tissue-specific expression of a Cre recombinase. As a result of Cre recombinase expression, the same or another vector that expresses the transgene in that tissue will be cut by the action of the Cre recombinase into several pieces due to LoxP sites that are strategically placed within the vector backbone. Consequently, unwanted transgene as well as viral gene expression are prevented. However, due to leakiness of the promoter driving Cre expression, expression is expected to be lowered also in the target tissue itself, thereby decreasing overall efficiency of this approach.

Although each of the afore-mentioned systems display inducibility thereby solving problem with the temporal control of gene expression, the spatial precision of gene induction is still lacking. All systems disclosed in the art so far are either highly complex and/or also reducing efficient expression in the target cells. Thus, there remains substantial need for improvement of tissue-specificity or control of promoter leakiness. The present invention provides such means and methods thereby fulfilling this longstanding need and desire in the art.

SUMMARY OF THE INVENTION

A first embodiment of the invention relates to a method for transgenic expression with enhanced specificity in an eukaryotic organism said method comprising the steps of:

a) providing an expression construct comprising a promoter sequence functional in said eukaryotic organism and functionally linked thereto a nucleotide sequence to be expressed into a chimeric RNA sequence, said nucleotide sequence comprising
  i) at least one sequence capable to confer a preferred phenotype or beneficial effect to said eukaryotic organism, and
  ii) at least one sequence substantially complementary to a microRNA sequence naturally expressed in said eukaryotic organism, wherein said microRNA is naturally expressed in tissues, at times, and/or under environmental conditions, where expression is not desired, but is not or substantially less expressed in tissues, at times, and/or under environmental conditions, where such expression is desired, wherein at least one of sequence i) and sequence ii) are heterologous to each other, and
b) introducing said expression construct into an eukaryotic organism.

Preferably, said eukaryotic organism is a human, an animal or a plant.

Various positions are possible for the sequence being substantially complementary to the microRNA (hereinafter also the "microRNA tag") in the nucleotide sequence to be expressed. Preferably, the sequence being substantially complementary to the microRNA is positioned in a location of the nucleotide sequence to be expressed corresponding to the 5'-untranslated region or the 3'-untranslated region of said sequence.

The nucleotide sequence to be expressed may have various form and/or functions. For example, it may comprise an open reading frame encoding a protein. Alternatively, it may encode a functional RNA selected from the group consisting of antisense RNA, sense RNA, double-stranded RNA or ribozymes. Said functional RNA is preferably attenuating expression of an endogenous gene.

To allow for enhanced expression specificity, the microRNA (to which the sequence comprised in the nucleotide sequence to be expressed is substantially complementary) is preferably not constitutively expressed, but is varying in expression in at least one parameter selected from the group consisting of tissue, special, time, development, environmental or other exogenous factors. Preferably, the microRNA is tissue-specific expressed, spatially regulated, developmentally regulated, and/or regulated by biotic or abiotic stress factors.

The expression construct for the expression of the nucleotide sequence comprising the microRNA-tag can be RNA, RNA and can be single- or double-stranded. Preferably the expression construct is DNA, more preferably double-stranded DNA. The expression construct can be part or a larger vector construct. Preferably, the expression construct is in a plasmid.

Various promoters can be used for expression of the nucleotide sequence comprising the microRNA-tag. The promoters can—for example—be selected from the group consisting of constitutive promoters, tissue-specific or tissue-preferential promoters, and inducible promoters. A tissue-specific promoter in this context, does—preferably—mean which is leaky (i.e. having expression activity in other than the preferred or main tissue) to a small but measurable extent.

The invention has broad opportunities of application, both in the field of plants, human and animals.

In one preferred embodiment, the eukaryotic organism is a plant and the promoter is a promoter functional in plants.

For plants, the expressed nucleotide sequence preferably modulates expression of a gene involved in agronomic traits, disease resistance, herbicide resistance, and/or grain characteristics. The person skilled in art is aware of numerous nucleotide sequences which can be used in the context and for which a enhanced expression specificity is advantageous. For example, the expressed nucleotide sequence may modulate expression of a gene selected from the group consisting of genes involved in the synthesis and/or degradation of proteins, peptides, fatty acids, lipids, waxes, oils, starches, sugars, carbohydrates, flavors, odors, toxins, carotenoids, hormones, polymers, flavinoids, storage proteins, phenolic acids, alkaloids, lignins, tannins, celluloses, glycoproteins, and glycolipids.

Various applications in plants are contemplated herein for which modulation of the expression profile in certain directions is advantageous. This modulation is achieved by selection the microRNA-tag in a way, that the expression profile of the naturally occurring miRNA fits with the tissues, times, and/or under environmental conditions where no or lower expression should be achieved. For example, the microRNA has a natural expression profile in the plant selected from the group consisting of a) substantially constitutive expression but no expression in seed,
b) predominant expression in seeds but not in other tissues,
b) drought or other abiotic stress—induced expression,
c) plant pathogen—induced expression,
c) temporal expression (e.g., during early development, germination, pollination etc.), and
d) chemical induced expression.

Preferably, the microRNA is a plant microRNA selected from the group consisting of
a) the sequences as described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 225, 226, 227, 228, 229, 230, 231, 232, 233, 234, 235, 236, 237, 238, 239, 240, 241, 242, 243, 245, 245, 246, 247, 248, 249, 250, 251, 252, 253, 254, 255, 256, 257, 258, 259, 260, 261, 262, 263, 264, 265, and 266 and
b) derivatives of the sequences described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 225, 226, 227, 228, 229, 230, 231, 232, 233, 234, 235, 236, 237, 238, 239, 240, 241, 242, 243, 245, 245, 246, 247, 248, 249, 250, 251, 252, 253, 254, 255, 256, 257, 258, 259, 260, 261, 262, 263, 264, 265, and 266.

In one preferred embodiment, said derivate has an identity of at least 70%, preferably at least 80% or 85%, more preferably at least 90%, most preferably at least 95% to a sequence described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 225, 226, 227, 228, 229, 230, 231, 232, 233, 234, 235, 236, 237, 238, 239, 240, 241, 242, 243, 245, 245, 246, 247, 248, 249, 250, 251, 252, 253, 254, 255, 256, 257, 258, 259, 260, 261, 262, 263, 264, 265, and 266.

Other applications of the invention provide herein are used in animals (especially mammals) or human. Especially preferred are pharmaceutical applications. Thus, in another preferred embodiment of the invention the target organism is a mammal (more preferably a human being) and the promoter is a promoter functional in mammals (more preferably in humans). The expressed nucleotide sequence comprising the miRNA-tag preferably modulates (e.g., express, over-express, or suppress) expression of a gene selected from the group consisting of genes involved in a human or animal disease or is a therapeutic gene. Alternatively, exogenous genes or sequences may be expressed which have a curative effect on the target organism. The disease is preferably selected from the group of immunological diseases, cancer, diabetes, neurodegeneration, and metabolism diseases. The person skilled in the art is aware of numerous sequences, which can be used in this context. The modulated gene may be selected from the group consisting of retinoblastoma protein, p53, angiostatin, leptin, hormones, growth factors, cytokines, insulin, growth hormones, alpha-interferon, beta-glucocerebrosidase, serum albumin, hemoglobin, and collagen. Therapeutic genes may be selected from the group consisting of tumor necrosis factor alpha. In this context the invention disclosed herein is a improved method for gene therapy or nucleotide-mediated therapy.

Various promoters are currently used in the art to express sequences in animal, mammalian or human organism. Most of them are lacking tissue-specificity and can be advantageously combined with the teaching provided herein. For example the promoter may be selected from group consisting of the perbB2 promoter, whey acidic protein promoter, stromelysin 3 promoter, prostate specific antigen promoter, probasin promoter.

Various applications in animal, mammalian or human organisms are contemplated herein for which modulation of the expression profile in certain directions is advantageous. This modulation is achieved by selection the microRNA-tag in a way, that the expression profile of the naturally occurring miRNA fits with the tissues, times, and/or under environmental conditions where no or lower expression should be achieved. For example, the microRNA has a natural expression profile in the animal, mammalian or human organism selected from the group consisting of a) tissue-specific expression in a tissue selected from the group consisting of brain tissue, liver tissue, muscle tissue, neuron tissue, and tumor tissue.
b) stress-induced expression,
c) pathogen-induced expression,
d) neoplastic growth or tumorgenic growth induced expression, and
e) age-dependent expression.

Preferably, the microRNA is an animal, mammalian or human microRNA selected from the group consisting of
a) the sequences as described by SEQ ID NO: 56, 57, 58, 59, 60, 61, 62, and 63, and
b) derivatives of the sequences described by SEQ ID NO: 56, 57, 58, 59, 60, 61, 62, and 63, and
c) the complementary RNA sequence to a sequence as described by any of SEQ ID NO: 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, or 208, and
d) derivatives of RNA sequence complementary to a sequence as described by any of SEQ ID NO: 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, or 208.

In one preferred embodiment, said derivate has an identity of at least 70%, preferably at least 80% or 85%, more preferably at least 90%, most preferably at least 95% to a miRNA as described by any of SEQ ID NO: 56, 57, 58, 59, 60, 61, 62, and 63 or a RNA sequence complementary to a sequence as described by any of SEQ ID NO: 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, or 208.

The chimeric RNA expressed by the method of the invention (i.e. the RNA comprising the expressed miRNA-tag) is considered to be novel. Thus anther embodiment of the invention relates to a chimeric ribonucleotide sequence comprising
i) at least one sequence capable to confer a preferred phenotype or beneficial effect to a eukaryotic organism, and
ii) at least one sequence substantially complementary to a microRNA sequence naturally occurring in a eukaryotic organism,
wherein at least one of sequence i) and sequence ii) are heterologous to each other.

The sequences i) and/or ii) in said chimeric ribonucleotide sequence are preferably defined as above for the method of the invention.

Furthermore, the expression constructs for expression of said chimeric ribonucleotide sequence (which are employed in the method of the invention) are considered to be novel. Thus another embodiment of the invention relates to an expression construct comprising a promoter sequence functional in a eukaryotic organism and functionally linked thereto a nucleotide sequence to be expressed, said sequence comprising
i) at least one sequence capable to confer a preferred phenotype or beneficial effect to said eukaryotic organism, and
ii) at least one sequence substantially complementary to a microRNA sequence naturally occurring in said eukaryotic organism,
wherein at least one of sequence i) and sequence ii) are heterologous to each other.

The expression construct and its elements are preferably defined as above for the method of the invention.

Another embodiment of the invention relates to an expression vector comprising an expression construct of the invention. Preferably, the expression vector is an eukaryotic expression vector. More preferably the eukaryotic expression vector is a viral vector, a plasmid vector or a binary vector.

Yet another embodiment of the invention relates to a transformed cell or organism (preferably a non-human organism) comprising a chimeric ribonucleotide sequence, an expression construct or an expression vector of the invention. Preferably, said expression construct or expression vector are inserted (at least in part) into the genome of the cell or organism. Preferably, said cell or organism is selected from the group of mammalian, bacterial, fungal, nematode or plant cells and organism. Another embodiment of the invention relates to transformed seed of the plant of the invention.

Yet another embodiment of the invention relates to a pharmaceutically preparation of at least one expression construct, a chimeric ribonucelotide sequence, or a vector according to the invention.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

The GOI is only efficiently expressed in seeds, but its mRNA is broken down (symbolized by the pairs of scissors) in other tissues, where the endogenous miRNA159 is expressed.

Figure 4:
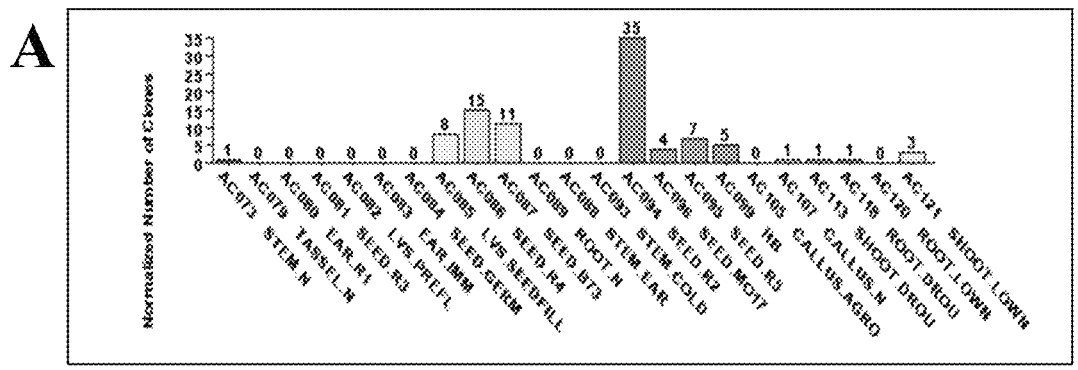
Figure 4:
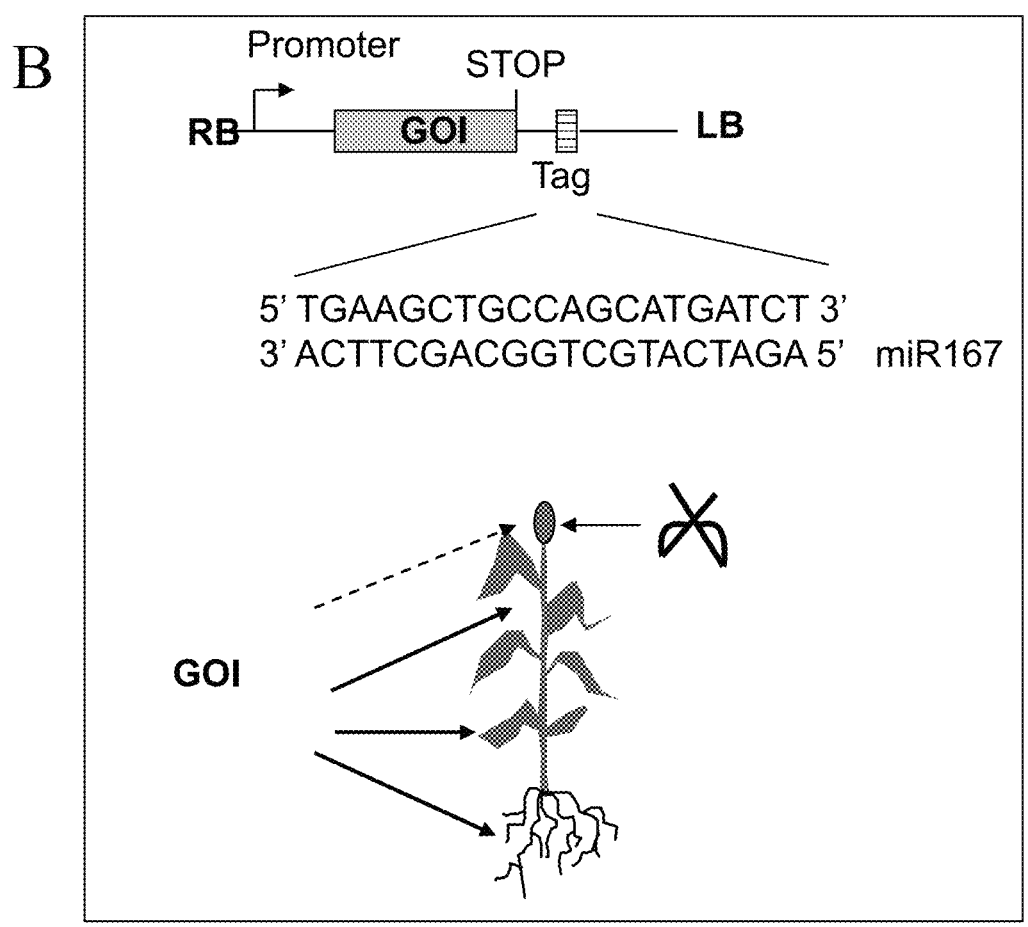

FIG. 4 Enhancing specificity of expression in non-seed tissues (preventing expression seeds)

Maize miR167 is predominantly expressed in seeds (FIG. 4-a). If the gene of interest (GOI) is NOT intended to express in seeds (e.g., genes conferring pesticide activities), but promoter used is leaky in seeds, one can incorporate a tag (5'-TGAAGCTGCCAGCATGATCT-3' (SEQ ID NO: 269), complementary to miR167 (SEQ ID NO: 270)) into the 3' UTR following the GOI to make a generic vector to control undesirable expression of the GOI in seeds by endogenous miR167 (FIG. 4-B). The GOI is only efficiently broken down in seeds (symbolized by the pair of scissors), where the endogenous miRNA167 is expressed, in other tissues the GOI is expressed.

Figure 5:
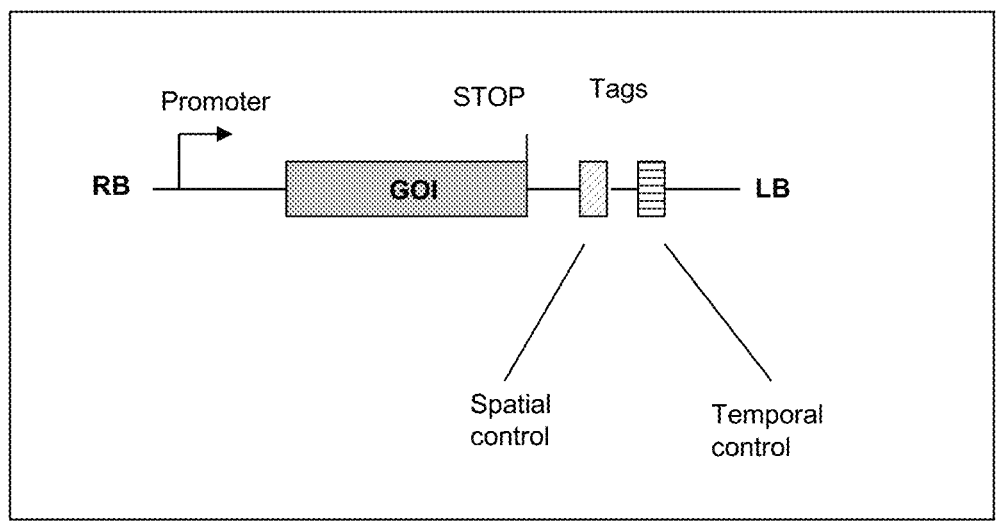

FIG. 5 A Generic Vector to Control Leakiness of GOI Expression

The invention disclosed herein can be employed to regulate transgene expression in spatial and/or temporal manner. Some traits (e.g. for animal feed) require the gene of interest (GOI) to express in certain stages (e.g. early or late embryos). Certain miRNAs could be regulated at different developmental stages. Therefore, one can incorporate miRNA target sites that are complementary to miRNA X (tissue-specific) and/or miRNA Y (developmental specific), so that expression of GOI can be controlled as a most desirable way.

DEFINITIONS

Abbreviations: BAP—6-benzylaminopurine; 2,4-D-2,4-dichlorophenoxyacetic acid; MS—Mura-shige and Skoog medium; NAA—1-naphtaleneacetic acid; MES, 2-(N-morpholinoethanesulfonic acid, IAA indole acetic acid; Kan: Kanamycin sulfate; GA3—Gibberellic acid; Timentin™: ticarcillin disodium/clavulanate potassium.

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Agronomically valuable trait: The term "agronomically valuable trait" refers to any phenotype in a plant organism that is useful or advantageous for food production or food products, including plant parts and plant products. Non-food agricultural products such as paper, etc. are also included. A partial list of agronomically valuable traits includes pest resistance, vigor, development time (time to harvest), enhanced nutrient content, novel growth patterns, flavors or colors, salt, heat, drought and cold tolerance, and the like. Preferably, agronomically valuable traits do not include selectable marker genes (e.g., genes encoding herbicide or antibiotic resistance used only to facilitate detection or selection of transformed cells), hormone biosynthesis genes leading to the production of a plant hormone (e.g., auxins, gibberllins, cytokinins, abscisic acid and ethylene that are used only for selection), or reporter genes (e.g. luciferase, glucuronidase, chloramphenicol acetyl transferase (CAT, etc.). Such agronomically valuable important traits may indude improvement of pest resistance (e.g., Melchers et al. (2000) Curr Opin Plant Biol 3(2):147-52), vigor, development time (time to harvest), enhanced nutrient content, novel growth patterns, flavors or colors, salt, heat, drought, and cold tolerance (e.g., Sakamoto et al. (2000) J Exp Bot 51(342):81-8; Saijo et al. (2000) Plant J 23(3): 319-327; Yeo et al. (2000) Mol Cells 10(3):263-8; Cushman et al. (2000) Curr Opin Plant Biol 3(2):117-24), and the like. Those of skill will recognize that there are numerous polynucleotides from which to choose to confer these and other agronomically valuable traits.

Alter: To "alter" or "modulate" the expression of a nucleotide sequence in a cell (e.g., a plant cell) means that the level of expression of the nucleotide sequence in a cell after applying a method of the present invention is different from its expression in the cell before applying the method. In a preferred embodiment, to alter expression means that the expression of the nucleotide sequence in the plant is reduced after applying a method of the present invention as compared to before applying the method. "Reduction of" or "to reduce" the expression of a target gene is to be understood in the broad sense and comprises the partial or essentially complete prevention or blocking of the expression of the target gene or the RNA, mRNA, rRNA, tRNA derived therefrom and/or of the protein product encoded by it in a cell, an organism or a part, tissue, organ, cell or seed thereof, which prevention or blockage may be based on different cell-biological mechanisms. The term "reduced" means herein lower, preferably significantly lower, more preferably the expression of the nucleotide sequence is not detectable. As used herein, "a reduction" of the level of an agent such as a protein or mRNA means that the level is reduced relative to a cell or organism lacking a chimeric RNA molecule of the invention capable of reducing the agent. As used herein, "at least a partial reduction" of the level of an agent (such as a RNA, mRNA, rRNA, tRNA expressed by the target gene and/or of the protein product encoded by it) means that the level is reduced at least 25%, preferably at least 50%, relative to a cell or organism lacking a chimeric RNA molecule of the invention capable of reducing said agent. As used herein, "a substantial reduction" of the level of an agent such as a protein or mRNA means that the level is reduced relative to a cell or organism lacking a chimeric RNA molecule of the invention capable of reducing the agent, where the reduction of the level of the agent is at least 75%, preferably at least 85%. As used herein, "an effective elimination" of an agent such as a protein or mRNA is relative to a cell or organism lacking a chimeric RNA molecule of the invention capable of reducing the agent, where the reduction of the level of the agent is greater than 95%, preferably greater than 98%. The reduction can be determined by methods with which the skilled worker is familiar. Thus, the reduction of the protein quantity can be determined for example by an immunological detection of the protein. Moreover, biochemical techniques such as Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed. Depending on the type of the reduced protein product, its activity or the effect on the phenotype of the organism or the cell may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254). In another preferred embodiment, to alter expression means that the expression of the nucleotide sequence in the plant is increased after applying a method of the present invention as compared to before applying the method.

Amino acid sequence: As used herein, the term "amino acid sequence" refers to a list of abbreviations, letters, characters or words representing amino acid residues. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Animal: The terms "animal" or "animal organism" refer to nonhuman vertebrates or invertebrates. Preferred vertebrates comprise, for example, fish species, nonhuman mammals such as cattle, horse, sheep, goat, mouse, rat or pig, and birds such as chicken or goose. Preferred animal cells comprise CHO, COS, HEK293 cells. Invertebrates comprise nematodes or other worms, and insects. Invertebrates comprise insect cells such as *Drosophila* S2 and *Spodoptera* Sf9 or Sf21 cells. Furthermore preferred are nematodes, which are capable of attacking animals or humans, such as those of the genera *Ancylostoma, Ascaridia, Ascaris, Bunostomum, Caenorhabditis, Capillaria, Chabertia, Cooperia, Dictyocaulus, Haemonchus, Heterakis, Nematodirus, Oesophagostomum, Ostertagia, Oxyuris, Parascaris, Strongylus, Toxascaris, Trichuris, Trichostrongylus, Tfhchonema, Toxocara* or *Uncinaria*. Furthermore preferred are those which are capable of attacking plant organisms such as, for example, *Bursaphalenchus, Criconemella, Diiylenchus, Ditylenchus, Globodera, Helicotylenchus, Heterodera, Longidorus, Melodoigyne, Nacobbus, Paratylenchus, Pratylenchus, Radopholus, Rotelynchus, Tylenchus* or *Xiphinema*. Preferred insects comprise those of the genera *Coleoptera, Diptera, Lepidoptera* and *Homoptera*.

Antiparallel: "Antiparallel" refers herein to two nucleotide sequences paired through hydrogen bonds between complementary base residues with phosphodiester bonds running in the 5'-3' direction in one nucleotide sequence and in the 3'-5' direction in the other nucleotide sequence.

Antisense: The term "antisense" refers to a nucleotide sequence that is inverted relative to its normal orientation for transcription and so expresses an RNA transcript that is complementary to a target gene mRNA molecule expressed within the host cell (e.g., it can hybridize to the target gene mRNA molecule through Watson-Crick base pairing). An antisense strand may be constructed in a number of different ways, provided that it is capable of interfering with the expression of a target gene. For example, the antisense strand can be constructed by inverting the coding region (or a portion thereof) of the target gene relative to its normal orientation for transcription to allow the transcription of its complement, (e.g., RNAs encoded by the antisense and sense gene may be complementary). Furthermore, the antisense oligonucleotide strand need not have the same intron or exon pattern as the target gene, and noncoding segments of the target gene may be equally effective in achieving antisense suppression of target gene expression as coding segments. In the context of gene silencing the term "antisense" is understood to mean a nucleic acid having a sequence complementary to a target sequence, for example a messenger RNA (mRNA) sequence the blocking of whose expression is sought to be initiated by hybridization with the target sequence.

Cell: The term "cell" or "plant cell" as used herein refers preferably to a single cell. The term "cells" refers to a population of cells. The population may be a pure population comprising one cell type. Likewise, the population may comprise more than one cell type. In the present invention, there is no limit on the number of cell types that a cell population may comprise. The cells may be synchronized or not synchronized. A cell within the meaning of this invention may be isolated (e.g., in suspension culture) or comprised in a tissue, organ or organism at any developmental stage.

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine and on the 3'-side by one of the three triplets which specify stop codons (i.e., TAA, TAG, TGA). In addition to containing introns, genomic forms of a gene may also include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. A "complement" of a nucleic acid sequence as used herein refers to a nucleotide sequence whose nucleic acids show total complementarity to the nucleic acids of the nucleic acid sequence.

Chromosomal DNA: The term "chromosomal DNA" or "chromosomal DNA-sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), and in situ PCR.

DNA shuffling: DNA shuffling is a method to rapidly, easily and efficiently introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA encodes an enzyme modified with respect to the enzyme encoded by the template DNA, and preferably has an altered biological activity with respect to the enzyme encoded by the template DNA.

Double-stranded RNA: A "double-stranded RNA" molecule, "RNAi molecule", or "dsRNA" molecule comprises a sense RNA fragment of a nucleotide sequence and an antisense RNA fragment of the nucleotide sequence, which both comprise nucleotide sequences complementary to one another, thereby allowing the sense and antisense RNA fragments to pair and form a double-stranded RNA molecule. Preferably the terms refer to a double-stranded RNA molecule capable, when introduced into a cell or organism, of at least partially reducing the level of an mRNA species present in a cell or a cell of an organism. As used herein, "RNA interference", "RNAi, and "dsRNAi" refer to gene-specific silencing that is induced by the introduction of a double-stranded RNA molecule.

Endogenous: An "endogenous" nucleotide sequence refers to a nucleotide sequence, which is present in the genome of the untransformed cell (e.g., a plant or mammalian cell).

Essential: An "essential" gene is a gene encoding a protein such as e.g. a biosynthetic enzyme, receptor, signal transduction protein, structural gene product, or transport protein that is essential to the growth or survival of the organism or cell (e.g., a plant).

Exon: The term "exon" as used herein refers to the normal sense of the term as meaning a segment of nucleic acid molecules, usually DNA, that encodes part of or all of an expressed protein.

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In the case of antisense constructs, for example, expression may refer to the transcription of the antisense DNA only.

Expression construct/expression construct: "Expression construct" and "expression construct" as used herein are synonyms and mean a DNA sequence capable of directing expression of a particular nucleotide sequence in an appropriate host cell (e.g., a plant pr mammalian cell), comprising a promoter functional in said host cell into which it will be introduced, operatively linked to the nucleotide sequence of interest which is—optionally—operatively linked to termination signals. If translation is required, it also typically comprises sequences required for proper translation of the nucleotide sequence. The coding region may code for a protein of interest but may also code for a functional RNA of interest, for example antisense RNA, dsRNA, or a non-translated RNA, in the sense or antisense direction. The expression construct comprising the nucleotide sequence of interest may be chimeric, meaning that at least one of its components is heterologous with respect to at least one of its other components. The expression construct may also be one, which is naturally occurring but has been obtained in a recombinant form useful for heterologous expression. Typically, however, the expression construct is heterologous with respect to the host, i.e., the particular DNA sequence of the expression construct does not occur naturally in the host cell and must have been introduced into the host cell or an ancestor of the host cell by a transformation event. The expression of the nucleotide sequence in the expression construct may be under the control of a constitutive promoter or of an inducible promoter, which initiates transcription only when the host cell is exposed to some particular external stimulus. In the case of a multicellular organism, such as a plant, the promoter can also be specific to a particular tissue or organ or stage of development.

Foreign gene: The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, etc.) relative to the naturally-occurring gene.

Gene: The term "gene" refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

Genetically modified organism: The term "genetically-modified organism" or "GMO" refers to any organism that comprises heterologous DNA or a transgene. Exemplary organisms include plants, animals and microorganisms.

Genome and genomic DNA: The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

Hairpin RNA: As used herein "hairpin RNA" refers to any self-annealing double stranded RNA molecule. In its simplest representation, a hairpin RNA consists of a double stranded stem made up by the annealing RNA strands, connected by a single stranded RNA loop, and is also referred to as a "pan-handle RNA". However, the term "hairpin RNA" is also intended to encompass more complicated secondary RNA structures comprising self-annealing double stranded RNA sequences, but also internal bulges and loops. The specific secondary structure adapted will be determined by the free energy of the RNA molecule, and can be predicted for different situations using appropriate software such as FOLDRNA (Zuker and Stiegler (1981) Nucleic Acids Res 9(1):133-48; Zuker, M. (1989) Methods Enzymol. 180, 262-288).

Heterologous: The terms "heterologous" with respect to a nucleic acid or DNA refer to a nucleotide sequence which is ligated to, or is manipulated to become ligated to, a nucleic acid sequence to which it is not ligated in nature, or to which it is ligated at a different location in nature. A heterologous expression construct comprising a nucleic acid sequence and at least one regulatory sequence (such as an promoter or an transcription termination signal) linked thereto for example is a constructs originating by experimental manipulations in which either a) said nucleic acid sequence, or b) said regulatory sequence or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the nucleic acid sequence is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid sequence operably lined to a promoter, which is not the native promoter of this sequence, is considered to be heterologous with respect to the promoter. Preferably, heterologous DNA is not endogenous to or not naturally associated with the cell into which it is introduced, but has been obtained from another cell. Heterologous DNA also includes an endogenous DNA sequence, which contains some modification, non-naturally occurring multiple copies of a endogenous DNA sequence, or a DNA sequence which is not naturally associated with another DNA sequence physically linked thereto. Generally, although not necessarily, heterologous DNA encodes RNA and proteins that are not normally produced by the cell into which it is expressed.

Homologous DNA Sequence: a DNA sequence naturally associated with a host cell or another DNA sequence.

Hybridization: The term "hybridization" as used herein includes "any process by which a strand of nucleic acid joins with a complementary strand through base pairing." (J. Coombs (1994) Dictionary of Biotechnology, Stockton Press, New York). Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids. As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm=81.5+0.41(\% G+C)$, when a nucleic acid is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6. Low stringency conditions when used in reference to nucleic acid hybridization comprise conditions equivalent to binding or hybridization at 68° C. in a solution consisting of 5×SSPE (43.8 g/L NaCl, 6.9 g/L $NaH_2PO_4 \cdot H_2O$ and 1.85 g/L EDTA, pH adjusted to 7.4 with NaOH), 1% SDS, 5×Denhardt's reagent [50×Denhardt's contains the following per 500 mL 5 g Ficoll (Type 400, Pharmacia), 5 g BSA (Fraction V; Sigma)] and 100 µg/mL denatured salmon sperm DNA followed by washing (preferably for one times 15 minutes, more preferably two times 15 minutes, more preferably three time 15 minutes) in a solution comprising 1×SSC (1×SSC is 0.15 M NaCl plus 0.015 M sodium citrate) and 0.1% SDS at room temperature or—preferably 37° C.—when a DNA probe of preferably about 100 to about 1,000 nucleotides in length is employed. Medium stringency conditions when used in reference to nucleic acid hybridization comprise conditions equivalent to binding or hybridization at 68° C. in a solution consisting of 5×SSPE (43.8 g/L NaCl, 6.9 g/L $NaH_2PO_4 \cdot H_2O$ and 1.85 g/L EDTA, pH adjusted to 7.4 with NaOH), 1% SDS, 5×Denhardt's reagent [50×Denhardt's contains the following per 500 mL 5 g Ficoll (Type 400, Pharmacia), 5 g BSA (Fraction V; Sigma)] and 100 µg/mL denatured salmon sperm DNA followed by washing (preferably for one times 15 minutes, more preferably two times 15 minutes, more preferably three time 15 minutes) in a solution comprising 0.1×SSC (1×SSC is 0.15 M NaCl plus 0.015 M sodium citrate) and 1% SDS at room temperature or—preferably 37° C.—when a DNA probe of preferably about 100 to about 1,000 nucleotides in length is employed. High stringency conditions when used in reference to nucleic acid hybridization comprise conditions equivalent to binding or hybridization at 68° C. in a solution consisting of 5×SSPE, 1% SDS, 5×Denhardt's reagent and 100 µg/mL denatured salmon sperm DNA followed by washing (preferably for one times 15 minutes, more preferably two times 15 minutes, more preferably three time 15 minutes) in a solution comprising 0.1×SSC, and 1% SDS at 68° C., when a probe of preferably about 100 to about 1,000 nucleotides in length is employed. The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 80% to 90% homology to the first nucleic acid sequence, then another hybridization condition is said to be equivalent to the hybridization condition of interest if this other hybridization condition also results in hybridization of the first nucleic acid sequence with the other nucleic acid sequences that have from 80% to 90% homology to the first nucleic acid sequence. When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above-listed conditions. Those skilled in the art know that whereas higher stringencies may be preferred to reduce or eliminate non-specific binding, lower stringencies may be preferred to detect a larger number of nucleic acid sequences having different homologies.

"Identity": The term "identity" is a relationship between two or more polypeptide sequences or two or more nucleic acid molecule sequences, as determined by comparing the sequences. In the art, "identity" also means the degree of sequence relatedness between polypeptide or nucleic acid molecule sequences, as determined by the match between strings of such sequences. "Identity" as used herein can be measured between nucleic acid sequences of the same ribonucleic-type (such as between DNA and DNA sequences) or between different types (such as between RNA and DNA sequences). It should be understood that in comparing an RNA sequence to a DNA sequence, an "identical" RNA sequence will contain ribonucleotides where the DNA sequence contains deoxyribonucleotides, and further that the RNA sequence will contain a uracil at positions where the DNA sequence contains thymidine. In case an identity is measured between RNA and DNA sequences, uracil bases of RNA sequences are considered to be identical to thymidine bases of DNA sequences. "Identity" can be readily calculated by known methods including, but not limited to, those described in Computational Molecular Biology, Lesk, A. M., ed., Oxford University Press, New York (1988); Biocomputing: Informatics and Genome Projects, Smith, D. W., ed., Academic Press, New York, 1993; Computer Analysis of Sequence Data, Part I, Griffin, A. M. and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., Stockton Press, New York (1991); and Carillo, H., and Lipman, D., SIAM J. Applied Math, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., Nucleic Acids Research 12(1):387 (1984); suite of five BLAST programs, three designed for nucleotide sequences queries (BLASTN, BLASTX, and TBLASTX) and two designed for protein sequence queries (BLASTP and TBLASTN) (Coulson, Trends in Biotechnology, 12:76-80 (1994); Birren et al., Genome Analysis, 1:543-559 (1997)). The BLASTX program is publicly available from NCBI and other sources (BLAST Manual, Altschul, S., et al., NCBI NLM NIH, Bethesda, Md. 20894; Altschul, S., et al., J. Mol. Biol., 215:403-410 (1990)). The well-known Smith Waterman algorithm can also be used to determine identity. Parameters for polypeptide sequence comparison typically include the following:

Algorithm: Needleman and Wunsch, J. Mol. Biol., 48:443-453 (1970)

Comparison matrix: BLOSUM62 from Hentikoff and Hentikoff, Proc. Natl. Acad. Sci. USA, 89:10915-10919 (1992)

Gap Penalty: 12

Gap Length Penalty: 4

A program, which can be used with these parameters, is publicly available as the "gap" program from Genetics Computer Group, Madison, Wis. The above parameters along with no penalty for end gap are the default parameters for peptide comparisons. Parameters for nucleic acid molecule sequence comparison include the following:

Algorithm: Needleman and Wunsch, J. Mol. Bio. 48:443-453 (1970)

Comparison matrix: matches-+10; mismatches=0

Gap Penalty: 50

Gap Length Penalty: 3

As used herein, "% identity" is determined using the above parameters as the default parameters for nucleic acid molecule sequence comparisons and the "gap" program from GCG, version 10.2.

Infecting: The terms "infecting" and "infection" with a bacterium or virus refer to co-incubation of a target biological sample, (e.g., cell, tissue, etc.) with the bacterium or virus under conditions such that nucleic acid sequences contained within the bacterium or virus are introduced into one or more cells of the target biological sample.

Intron: The term "intron" as used herein refers to the normal sense of the term as meaning a segment of nucleic acid molecules, usually DNA, that does not encode part of or all of an expressed protein, and which, in endogenous conditions, is transcribed into RNA molecules, but which is spliced out of the endogenous RNA before the RNA is translated into a protein. The splicing, i.e., intron removal, occurs at a defined splice site, e.g., typically at least about 4 nucleotides, between cDNA and intron sequence. For example, without limitation, the sense and antisense intron segments illustrated herein, which form a double-stranded RNA contained no splice sites.

Isogenic: organisms (e.g., plants), which are genetically identical, except that they may differ by the presence or absence of a heterologous DNA sequence.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring polynucleotide or polypeptide present in a living animal is not isolated, but the same polynucleotide or polypeptide, separated from some or all of the coexisting materials in the natural system, is isolated. Such polynucleotides can be part of a vector and/or such polynucleotides or polypeptides could be part of a composition, and would be isolated in that such a vector or composition is not part of its original environment. Preferably, the term "isolated" when used in relation to a nucleic acid, as in "an isolated nucleic acid sequence" refers to a nucleic acid sequence that is identified and separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO:

1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and antisense strands (i.e., the nucleic acid sequence may be double-stranded).

Mammal: The terms "mammal" or "mammalian" are intended to encompass their normal meaning. While the invention is most desirably intended for efficacy in humans, it may also be employed in domestic mammals such as canines, felines, and equines, as well as in mammals of particular interest, e.g., zoo animals, farmstock and the like.

Mature protein: protein which is normally targeted to a cellular organelle, such as a chloroplast, and from which the transit peptide has been removed.

Minimal Promoter: promoter elements, particularly a TATA element, that are inactive or that have greatly reduced promoter activity in the absence of upstream activation. In the presence of a suitable transcription factor, the minimal promoter functions to permit transcription.

Non-coding: The term "non-coding" refers to sequences of nucleic acid molecules that do not encode part or all of an expressed protein. Non-coding sequences include but are not limited to introns, promoter regions, 3' untranslated regions, and 5' untranslated regions.

Nucleic acids and nucleotides: The terms "Nucleic Acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "polynucleotide". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. shRNAs also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Nucleotide sequence of interest: The term "nucleotide sequence of interest" refers to any nucleotide sequence, the manipulation of which may be deemed desirable for any reason (e.g., confer improved qualities), by one of ordinary skill in the art. Such nucleotide sequences include, but are not limited to, coding sequences of structural genes (e.g., reporter genes, selection marker genes, drug resistance genes, growth factors, etc.), and non-coding regulatory sequences which do not encode an mRNA or protein product, (e.g., promoter sequence, polyadenylation sequence, termination sequence, enhancer sequence, etc.). A nucleic acid sequence of interest may preferably encode for an agronomically valuable trait.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Operable linkage: The term "operable linkage" or "operably linked" is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. The distance between the promoter sequence and the nucleic acid sequence to be expressed recombinantly is preferably less than 200 base pairs, especially preferably less than 100 base pairs, very especially preferably less than 50 base pairs. In a preferred embodiment, the nucleic acid sequence to be transcribed is located behind the promoter in such a way that the transcription start is identical with the desired beginning of the chimeric RNA of the invention. Operable linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specifis cleavage sites for restriction enzymes, or as a signal peptide, may also be positioned between the two sequences. The insertion of sequences may also lead to the expression of fusion proteins. Preferably, the expression construct, consisting of a linkage of promoter and nucleic acid sequence to be expressed, can exist in a vector-integrated form and be inserted into a plant genome, for example by transformation.

Organ: The term "organ" with respect to a plant (or "plant organ") means parts of a plant and may include (but shall not limited to) for example roots, fruits, shoots, stem, leaves, anthers, sepals, petals, pollen, seeds, etc. The term "organ" with respect to an animal ("animal organ") means parts of an animal and may include (but shall not limited to) for example external organs (such as arms, legs, head, etc.) or internal organs (such as heart, kidney, liver, stomach, etc.).

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Plant: The terms "plant" or "plant organism" refer to any organism, which is capable of photosynthesis, and the cells, tissues, parts or propagation material (such as seeds or fruits) derived therefrom. Encompassed within the scope of the invention are all genera and species of higher and lower plants of the Plant Kingdom. Annual, perennial, monocotyledonous and dicotyledonous plants and gymnosperms are preferred. A "plant" refers to any plant or part of a plant at any stage of development. Mature plants refer to plants at any developmental stage beyond the seedling stage. Encompassed are mature plant, seed, shoots and seedlings, and parts, propagation material (for example tubers, seeds or fruits) and cultures, for example cell cultures or callus cultures,) derived therefrom. Seedling refers to a young, immature plant at an early developmental stage. Therein are also included cuttings, cell or tissue cultures and seeds. As used in conjunction with the present invention, the term "plant tissue" includes, but is not limited to, whole plants, plant cells, plant organs, plant seeds, protoplasts, callus, cell cultures, and any groups of plant cells organized into structural and/or functional units. Preferably, the term "plant" as used herein refers to a plurality of plant cells, which are largely differentiated into a structure that is present at any stage of a plant's development. Such structures include one or more plant organs including, but are not limited to, fruit, shoot, stem, leaf, flower petal, etc. More preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom. Preferred are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxifragaceae, Scrophulariaceae, Solanaceae, Tetragoniaceae. Annual, perennial, monocotyledonous and dicotyledonous plants are preferred host organisms for the generation of transgenic plants. The use of the recombination system, or method according to the invention is furthermore advantageous in all ornamental plants, forestry, fruit, or ornamental trees, flowers, cut flowers, shrubs or turf. Said plant may include—but shall not be limited to—bryophytes such as, for example, Hepaticae (hepaticas) and Musci (mosses); pteridophytes such as ferns, horsetail and clubmosses; gymnosperms such as conifers, cycads, ginkgo and Gnetaeae; algae such as Chlorophyceae, Phaeophyceae, Rhodophyceae, Myxophyceae, Xanthophyceae, Bacillariophyceae (diatoms) and Euglenophyceae. Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geraniums, Liliaceae such as Drachaena, Moraceae such as ficus, Araceae such as philodendron and many others. The transgenic plants according to the invention are furthermore selected in particular from among dicotyledonous crop plants such as, for example, from the families of the Leguminosae such as pea, alfalfa and soybean; the family of the Umbelliferae, particularly the genus *Daucus* (very particularly the species *carota* (carrot)) and *Apium* (very particularly the species *graveolens* var. dulce (celery)) and many others; the family of the Solanaceae, particularly the genus *Lycopersicon*, very particularly the species *esculentum* (tomato) and the genus *Solanum*, very particularly the species *tuberosum* (potato) and *melongena* (aubergine), tobacco and many others; and the genus *Capsicum*, very particularly the species *annum* (pepper) and many others; the family of the Leguminosae, particularly the genus *Glycine*, very particularly the species max (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, particularly the genus *Lactuca*, very particularly the species *sativa* (lettuce) and many others. The transgenic plants according to the invention are selected in particular among monocotyledonous crop plants, such as, for example, cereals such as wheat, barley, *sorghum* and millet, rye, triticale, maize, rice or oats, and sugarcane. Further preferred are trees such as apple, pear, quince, plum, cherry, peach, nectarine, apricot, papaya, mango, and other woody species including coniferous and deciduous trees such as poplar, pine, sequoia, cedar, oak, etc. Especially preferred are *Arabidopsis thaliana, Nicotiana tabacum*, oilseed rape, soybean, corn (maize), wheat, linseed, potato and *tagetes*.

Polynucleotide construct. The term "polynucleotide construct" refers to a nucleic acid at least partly created by recombinant methods. The term "DNA construct" is referring to a polynucleotide construct consisting of deoxyribonucleotides. The construct may be single- or—preferably—double stranded. The construct may be circular or linear. The skilled worker is familiar with a variety of ways to obtain one of a DNA construct. Constructs can be prepared by means of customary recombination and cloning techniques as are described, for example, in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Pub-lisher, Dordrecht, The Netherlands.

Polypeptide: The terms "polypeptide", "peptide", "oligopeptide", "polypeptide", "gene product", "expression product" and "protein" are used interchangeably herein to refer to a polymer or oligomer of consecutive amino acid residues.

Pre-protein: Protein, which is normally targeted to a cellular organelle, such as a chloroplast, and still comprising its transit peptide.

Promoter: The terms "promoter," "promoter element," or "promoter sequence" are equivalents and as used herein, refers to a DNA sequence which when ligated to a nucleotide sequence of interest is capable of controlling the transcription of the nucleotide sequence of interest into mRNA. A promoter is typically, though not necessarily, located 5' (i.e., up-stream) of a nucleotide sequence of interest (e.g., proximal to the transcriptional start site of a structural gene) whose transcription into mRNA it controls, and provides a site for specific binding by RNA polymerase and other transcription factors for initiation of transcription. A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host cells (e.g., plants or plant pathogens like plant viruses). If a promoter is an inducible promoter, then the rate of transcription increases in response to an inducing agent. In contrast, the rate of transcription is not regulated by an inducing agent if the promoter is a constitutive promoter. Also, the promoter may be regulated in a tissue-specific or tissue preferred manner such that it is only active in transcribing the associated coding region in a specific tissue type(s) such as leaves, roots or meristem. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., GUS activity staining or immunohistochemical staining. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. An purified nucleic acid sequence may be an isolated nucleic acid sequence.

Recombinant: The term "recombinant" with respect to polypeptides or proteins refer to polypeptides or proteins produced by recombinant DNA techniques, i.e., produced from cells transformed by an exogenous recombinant DNA construct encoding the desired polypeptide or protein. Recombinant nucleic acids and polypeptide may also comprise molecules, which as such does not exist in nature but are modified, changed, mutated or otherwise manipulated by man. Preferably, a "recombinant polypeptide" is a non-naturally occurring polypeptide that differs in sequence from a naturally occurring polypeptide by at least one amino acid residue. Preferred methods for producing said recombinant polypeptide and/or nucleic acid may comprise directed or non-directed mutagenesis, DNA shuffling or other methods of recursive recombination.

Sense: The term "sense" is understood to mean a nucleic acid having a sequence which is homologous or identical to a target sequence, for example a sequence which binds to a protein transcription factor and which is involved in the expression of a given gene. According to a preferred embodiment, the nucleic acid comprises a gene of interest and elements allowing the expression of the said gene of interest.

Significant Increase or Decrease: An increase or decrease, for example in enzymatic activity or in gene expression, that is larger than the margin of error inherent in the measurement technique, preferably an increase or decrease by about 2-fold or greater of the activity of the control enzyme or expression in the control cell, more preferably an increase or decrease by about 5-fold or greater, and most preferably an increase or decrease by about 10-fold or greater.

Stabilize: To "stabilize" the expression of a nucleotide sequence in a plant cell means that the level of expression of the nucleotide sequence after applying a method of the present invention is approximately the same in cells from the same tissue in different plants from the same generation or throughout multiple generations when the plants are grown under the same or comparable conditions.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Substantially identical: In its broadest sense, the term "substantially identical", when used herein with respect to a nucleotide sequence, means a nucleotide sequence corresponding to a reference or target nucleotide sequence, wherein the percentage of identity between the substantially identical nucleotide sequence and the reference or target nucleotide sequence is desirably at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially identical" to a reference nucleotide sequence hybridizes to the exact complementary sequence of the reference nucleotide sequence (i.e. its corresponding strand in a double-stranded molecule) under low stringency conditions, preferably medium stringency conditions, most preferably high stringency conditions (as defined above). Homologes of a specific nucleotide sequence include nucleotide sequences that encode an amino acid sequence that is at least 24% identical, more preferably at least 35% identical, yet more preferably at least 50% identical, yet more preferably at least 65% identical to the reference amino acid sequence, as measured using the parameters described above, wherein the amino acid sequence encoded by the homolog has the same biological activity as the protein encoded by the specific nucleotide. The term "substantially identical", when used herein with respect to a polypeptide, means a protein corresponding to a reference polypeptide, wherein the polypeptide has substantially the same structure and function as the reference protein, e.g. where only changes in amino acids sequence not affecting the polypeptide function occur. When used for a polypeptide or an amino acid sequence the percentage of identity between the substantially similar and the reference polypeptide or amino acid sequence desirably is at least 24%, more desirably at least 30%, more desirably at least 45%, preferably at least 60%, more preferably at least 75%, still more preferably at least 90%, yet still more preferably at least 95%, yet still more preferably at least 99%, using default GAP analysis parameters as described above. Homologes are amino acid sequences that are at least 24% identical, more preferably at least 35% identical, yet more preferably at least 50% identical, yet more preferably at least 65% identical to the reference polypeptide or amino acid sequence, as measured using the parameters described above, wherein the amino acid sequence encoded by the homolog has the same biological activity as the reference polypeptide.

Synthetic: As used herein, "synthetic" means made wholly by chemical means, e.g. through the annealing of chemically-synthesized complementary oligonucleotides rather than by biological means, e.g. through the amplification of a chemically-synthesized template using the polymerase chain reaction (PCR) or other enzyme-mediated biological reactions such as ligation or phosphorylation. In preferred embodiments, the oligonucleotides are synthesized using commercial oligonucleotide synthesis machines, including but not limited to the ABI 394 and ABI 3900 DNA/RNA Synthesizers available from Applied Biosystems, Inc. or other commercially-equivalent synthesizers.

Target gene: The terms "target", "target gene" and "target nucleotide sequence" are used equivalently. As used herein, a target gene can be any gene of interest present in an eukaryotic organism (such as a plant). A target gene may be endogenous or introduced. For example, a target gene is a gene of known function or is a gene whose function is unknown, but whose total or partial nucleotide sequence is known. Alternatively, the function of a target gene and its nucleotide sequence are both unknown. A target gene is a native gene of the eukaryotic cell or is a heterologous gene which has previously been introduced into the eukaryotic cell or a parent cell of said eukaryotic cell, for example by genetic transformation. A heterologous target gene is stably integrated in the genome of the eukaryotic cell or is present in the eukaryotic cell as an extrachromosomal molecule, e.g. as an autonomously replicating extrachromosomal molecule. A target gene may include polynucleotides comprising a region that encodes a polypeptide or polynucleotide region that regulates replication, transcription, translation, or other process important in expression of the target protein; or a polynucleotide comprising a region that encodes the target polypeptide and a region that regulates expression of the target polypeptide; or noncoding regions such as the 5' or 3' UTR or introns. A target gene may refer to, for example, an mRNA molecule produced by transcription a gene of interest. Furthermore, the term "correspond," as in "an chimeric RNA comprising a sequence that corresponds to a target gene sequence," means that the two sequences are complementary or homologous or bear such other biologically rational relationship to each other (e.g., based on the sequence of nucleomonomers and their base-pairing properties). The "target gene" to which an chimeric RNA molecule of the invention is directed may be associated with a pathological condition. For example, the gene may be a pathogen-associated gene, e.g., a viral gene, a tumor-associated gene, a defective gene (e.g., an abnormal cancer-causing gene), or an autoimmune disease-associated gene. The target gene may also be a heterologous gene expressed in a recombinant cell or a genetically altered organism. By determining or modulating (e.g., inhibiting) the function of such a gene, valuable information and therapeutic benefits in medicine, veterinary medicine, and biology may be obtained.

Tissue: The term "tissue" with respect to an organism (e.g., a plant; "plant tissue") means arrangement of multiple cells including differentiated and undifferentiated tissues of the organism. Tissues may constitute part of an organ (e.g., the epidermis of a plant leaf or an animal skin) but may also constitute tumor tissues (e.g., callus tissue) and various types of cells in culture (e.g., single cells, protoplasts, embryos, calli, protocorm-like bodies, etc.). The tissue may be in vivo (e.g., in planta), in organ culture, tissue culture, or cell culture.

Transformation: The term "transformation" as used herein refers to the introduction of genetic material (e.g., a transgene or heterologous nucleic acid molecules) into a cell, tissue or organism. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA), which detects the presence of a polypeptide encoded by one or more of the transgenes. Alternatively, transient transformation may be detected by detecting the activity of the protein (e.g., β-glucuronidase) encoded by the transgene (e.g., the uid A gene). The term "transient transformant" refers to a cell which has transiently incorporated one or more transgenes. In contrast, the term "stable transformation" or "stably transformed" refers to the introduction and integration of one or more transgenes into the genome of a cell, preferably resulting in chromosomal integration and stable heritability through meiosis. Stable transformation of a cell may be detected by Southern blot hybridization of genomic DNA of the cell with nucleic acid sequences, which are capable of binding to one or more of the transgenes. Alternatively, stable transformation of a cell may also be detected by the polymerase chain reaction of genomic DNA of the cell to amplify transgene sequences. The term "stable transformant" refers to a cell, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which may exhibit variable properties with respect to meiotic stability. Transformed cells, tissues, or plants are understood to encompass not only the end product of a transformation process, but also transgenic progeny thereof.

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to a cell, tissue or organisms means transformed, preferably stably transformed, with a recombinant DNA molecule that preferably comprises a suitable promoter operatively linked to a DNA sequence of interest.

Unaffected: As used herein, "essentially unaffected" refers to a level of an agent such as a protein or mRNA transcript that is either not altered by a particular event or altered only to an extent that does not affect the physiological function of that agent. In a preferred aspect, the level of the agent that is essentially unaffected is within 20%, more preferably within 10%, and even more preferably within 5% of the level at which it is found in a cell or organism that lacks a nucleic acid molecule capable of selectively reducing another agent. As used herein, "substantially unaffected" refers to a level of an agent such as a protein or mRNA transcript in which the level of the agent that is substantially unaffected is within 49%, more preferably within 35%, and even more preferably within 24% of the level at which it is found in a cell or organism that lacks a nucleic acid molecule capable of selectively reducing another agent. As used herein, "partially unaffected" refers to a level of an agent such as a protein or mRNA transcript in which the level of the agent that is partially unaffected is within 80%, more preferably within 65%, and even more preferably within 50% of the level at which it is found in a cell or organism that lacks a nucleic acid molecule capable of selectively reducing another agent.

Vector: As used herein, the term "vector" refers to a nucleic acid molecule capable of transporting another nucleic acid to which it has been linked. One type of vector is a genomic integrated vector, or "integrated vector", which can become integrated into the chromosomal DNA of the host cell. Another type of vector is an episomal vector, i.e., a nucleic acid capable of extra-chromosomal replication. Vectors capable of directing the expression of genes to which they are operatively linked are referred to herein as "expression vectors". In the present specification, "plasmid" and "vector" are used interchangeably unless otherwise clear from the context. Expression vectors designed to produce RNAs as described herein in vitro or in vivo may contain sequences under the control of any RNA polymerase, including mitochondrial RNA polymerase, RNA pol I, RNA pol II, and RNA pol III. These vectors can be used to transcribe the desired RNA molecule in the cell according to this invention. Vectors may be desirably designed to utilize an endogenous mitochondrial RNA polymerase (e.g., human mitochondrial RNA polymerase, in which case such vectors may utilize the corresponding human mitochondrial promoter). Mitochondrial polymerases may be used to generate capped (through expression of a capping enzyme) or uncapped messages in vivo. RNA pol I, RNA pol II, and RNA pol III transcripts may also be generated in vivo. Such RNAs may be capped or not, and if desired, cytoplasmic capping may be accomplished by various means including use of a capping enzyme such as a vaccinia capping enzyme or an alphavirus capping enzyme. The DNA vector is designed to contain one of the promoters or multiple promoters in combination (mitochondrial, RNA poll, II, or pollIII, or viral, bacterial or bacteriophage promoters along with the cognate polymerases). Preferably, where the promoter is RNA pol II, the sequence encoding the RNA molecule has an open reading frame greater than about 300 nts to avoid degradation in the nucleus. Such plasmids or vectors can include plasmid sequences from bacteria, viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. Thus, one exemplary vector is a single or double-stranded phage vector. Another exemplary vector is a single or double-stranded RNA or DNA viral vector. Such vectors may be introduced into cells as polynucleotides, preferably DNA, by well known techniques for introducing DNA and RNA into cells. The vectors, in the case of phage and viral vectors may also be and preferably are introduced into cells as packaged or encapsidated virus by well known techniques for infection and transduction. Viral vectors may be replication competent or replication defective. In the latter case, viral propagation generally occurs only in complementing host cells.

Wild-type: The term "wild-type", "natural" or of "natural origin" means with respect to an organism, polypeptide, or nucleic acid sequence, that said organism is naturally occurring or available in at least one naturally occurring organism which is not changed, mutated, or otherwise manipulated by man.

DETAILED DESCRIPTION OF THE INVENTION

A first embodiment of the invention relates to a method for transgenic expression with enhanced specificity in an eukaryotic organism said method comprising the steps of:
a) providing an expression construct comprising a promoter sequence functional in said eukaryotic organism and functionally linked thereto a nucleotide sequence to be expressed into a chimeric RNA sequence, said nucleotide sequence comprising
   i) at least one sequence capable to confer a preferred phenotype or beneficial effect to said eukaryotic organism, and
   ii) at least one sequence substantially complementary to a microRNA sequence naturally expressed in said eukaryotic organism, wherein said microRNA is naturally expressed in tissues, at times, and/or under environmental conditions, where expression is not desired, but is not or substantially less expressed in tissues, at times, and/or under environmental conditions, where such expression is desired,
   wherein at least one of sequence i) and sequence ii) are heterologous to each other, and
b) introducing said expression construct into a eukaryotic organism.

Preferably, said eukaryotic organism is a human, an animal or a plant.

It is not unusual that some 'tissue-specific' promoters having leakiness of expression in other tissues which could result in undesirable phenotype such as phytotoxicity. In other cases, it has been proved very challenge to generate tissue-specific promoter for certain application (e.g., 'syncytium-specific' promoters for achieving nematode resistance in plants). Given that some miRNAs have tissues-specific and/or temporal expression pattern, one could design a generic vector with a miRNA-tag (a short sequence substantially complementary or complementary to a given endogenous miRNA) at 3'UTR of an expression construct (e.g., comprised in a binary vector), so that leakiness of transgene expression in the tissues where miRNA are expressed will be reduced or eliminated.

The essential, inventive feature of the invention disclosed herein is the incorporation of "at least one sequence substantially complementary to a microRNA sequence naturally expressed in said eukaryotic organism" (i.e. the target organism, where the enhanced expression specificity should be achieved). Said sequence—hereinafter also the "microRNA tag"—suppress or lower expression or will lead to enhanced degradation (thereby suppressing or lowering expression) of the chimeric RNA sequence in tissues, at times, and/or under environmental conditions where the endogenous miRNA is expressed.

Without being limited to any specific functional mechanism of action, the endogenous miRNA is thought to interact with the miRNA-tag in the chimeric RNA sequence, thereby inducing its degradation (or gene silencing). This silencing is surprisingly found to be restricted to the tissue, time, and/or under environmental condition where the endogenous miRNA is naturally expressed and is found not to spread over the entire organism.

1. The miRNA-tag of the Invention
1.1 General Properties

The miRNA-tag a sequence, which is substantially complementary to a microRNA (miRNA) sequence naturally expressed in an eukaryotic organism (i.e. an endogenous miRNA). The terms naturally occurring miRNA (or microRNA) and endogenous miRNA (or micro RNA) have the same meaning and are used interchangeable herein.

The miRNA-tags of the invention are complementary or substantially complementary to an endogenous miRNA. While the invention does not depend on miRNA-tags of a particular size, the miRNA-tags will have a length similar to the length of the endogenous miRNAs, such miRNAs known in the art typically comprise between about 15 and 30 nucleotides. Thus, the miRNA-tag will preferably be a small sequence comprising about 15 to about 30 nucleotides, about 20 to about 28 nucleotides, more specifically about 21-24 nucleotides. Generally the miRNA-tag will be completely complementary to the endogenous miRNA, however, mismatches may be tolerated, thus it is contemplated that the miRNA-tag is substantially complementary to the miRNA naturally expressed in an eukaryotic organism. The term substantially complementary as used in this context (i.e. for the complementarity between the miRNA-tag and an endogenous miRNA) means, that generally from 1 to about 6 mismatches may occur, more specifically about 2 to 3 mismatched nucleotides may be included in the miRNA-tag in comparison to the endogenous miRNA sequence. Alternatively, the complement of the miRNA-tag may have and identity to the sequence of the endogenous miRNA of at least 60% or 70%, preferably at least 80% or 85%, more preferably at least 90%, most preferably at least 95%. While the mismatched nucleotides may occur throughout the miRNA sequence (i.e. in any position), preferably, they are located in the region near or in the 3' region of the endogenous miRNA. The 3'-region of the endogenous miRNA is complementary to the 5'-region of the miRNA tag. Accordingly, said mismatches are preferably in the 5'-region of the miRNA-tag. It has been demonstrated, that for example, 3 mismatches plus a G::U wobble can be engineered at 3' region of miRNA without affecting its function (Mallory et al., EMBO Journal, 23:3356-3364, (2004)). Accordingly, in the most preferred embodiment the term substantially complement means that 3.5 mismatches (i.e. 3 true mismatches plus one G:U wobble counted as 0.5) can occur between the miRNA-tag and the endogenous miRNA. In this manner, a miRNA sequence can be designed to modulate the expression of any target sequence.

1.2 Identification of Suitable miRNAs for Designing miRNA Tags

To allow for enhanced expression specificity, the microRNA (to which the sequence comprised in the nucleotide sequence to be expressed is substantially complementary) is preferably not constitutively expressed, but is varying in expression in at least one parameter selected from the group consisting of tissue, special, time, development, environmental or other exogenous factors. Preferably, the microRNA is tissue-specific or—preferentially expressed, spatially-regulated, developmental regulated, and/or regulated by other factors such as biotic or abiotic stress factors.

A tissue-tissue specific—or preferentially expressed miRNA is understood herein as an miRNA which is not expressed to the same extent in all tissues of an organism at a given specific time (such expression profile may or may not change over time (e.g., during development or aging) or under other conditions (exogenous factors such as stress). Preferably, the miRNA is expressed only in one or a few tissues, while it is not expressed to a significant amount (e.g., an amount which is readily detectable by standard RNA detection methods such as Northern blot) in other tissues.

A miRNA regulated by other factors may include miRNAs which are up- or downregulated (in one, more or all tissues) upon interaction of the organism with a factor, preferably an exogenous factor, more preferably a stress stimuli. Such stress stimuli may comprise abiotic and biotic stress factors. Given the fact that maize miR160 (see Examples for details) is a stress-induced microRNA, it is very possible that some other miRNAs are induced by a range of environmental stimuli (e.g. biotic stress, and chemicals). Using similar strategies proposed above, one can control transgene expression in response to environmental stimuli in certain tissues.

There are several approaches to identify and isolate miRNAs in various organism and tissues. For example, after total RNA is isolated from an organism or specific tissues or cell types, RNA is resolved on a denaturing 15% polyacrylamide gel. A gel fragment represents the size range of 15 to 26 nucleotides is excised, small RNA is eluted, and recovered. Subsequently, small RNA is ligated to 5' and 3' RNA/DNA chimeric oligonucleotide adapters. Reverse transcription reaction is performed using RT primer followed by PCR with appropriate primers. PCR products are then cloned into vector for sequencing (Sunkar R and Zhu J K, The Plant Cell 16:2001:2019, 2004) Several other techniques and methods have been applied to detect miRNA in an organism or tissues such as Northern blot analysis, ribonucleases protection-based PAGE, microarray-based miRNA profiling and qRT-PCR Taqman analysis.

There are various ways to "design" a miRNA-tag to achieve a certain expression profile. For example, first, one chooses miRNA expressed in the tissue(s) (or at times or under conditions) where there is leaky expression of gene-of-interest, which should be prevented. Second, one determines complementary sequence of miRNA and insert such short nucleotide sequences into the gene-of-interest (e.g., the 5'UTR region, 3' UTR region, or even the coding region without affecting the function of gene-of-interest).

1.2 Localization within the Expressed Chimeric RNA

Various positions are possible for the sequence being substantially complementary to the microRNA (hereinafter also the "microRNA tag") in the nucleotide sequence to be expressed. Preferably, the sequence being substantially complementary to the microRNA is positioned in a location of the nucleotide sequence to be expressed corresponding to the 5'-untranslated region or the 3'-untranslated region of said sequence 1.3 Production and/or Expression of the Chimeric RNA of the Invention The term "chimeric RNA" or "chimeric RNA molecule" or "chimeric ribonucleotide sequence" are used interchangeable herein and are intended to mean an polynucleotide molecule, which is at least in part consisting of ribonucleotides, which comprises i) at least one sequence substantially complementary to a microRNA sequence naturally occurring in a eukaryotic organism, and i) at least one other sequence (preferably a sequence capable to confer a preferred phenotype or beneficial effect to an eukaryotic organism), wherein at least one of sequence i) and sequence ii) are heterologous to each other (i.e. are not covalently linked in nature or in an natural (i.e. non-genetically modified) organism or cell).

The fact the chimeric RNA sequence of the invention is "at least in part consisting of ribonucleotides" means—for example—that the chimeric RNA sequence may comprise other than ribonucleotide bases. As described below, the chimeric RNA molecule of the invention may also be obtained by chemically synthesis. By this method, other than natural occurring ribonucleotide residues (e.g., modified residues) may be incorporated).

The chimeric RNA molecules expressed by the method of the invention (i.e. the RNA comprising the miRNA-tag) are as such considered to be novel and inventive. Not only there expression constructs can be used, but also the chimeric RNA molecules as such has strong potential for industrial applicability, especially in the field of pharmaceutical application, where activity of a RNA-based pharmaceutical is sought to act only on certain tissue, at certain times or under certain conditions.

Thus anther embodiment of the invention relates to a chimeric ribonucleotide sequence comprising i) at least one sequence capable to confer a preferred phenotype or beneficial effect to a eukaryotic organism, and ii) at least one sequence substantially complementary to a microRNA sequence naturally occurring in a eukaryotic organism, wherein at least one of sequence i) and sequence ii) are heterologous to each other.

The sequences i) and/or ii) in said chimeric ribonucleotide sequence are preferably defined as for the method of the invention.

The chimeric RNA molecule (i.e. the RNA molecule comprising the miRNA tag) can be produced and applied to the host cell or organism by various means, familiar to the person skilled in the art. The chimeric RNA molecules of the invention can be produced or synthesized by any method known in the art, e.g., using recombinant expression, enzymatic synthesis or chemical synthesis. The RNA molecules can be synthesized in vitro (e.g., using enzymatic synthesis and chemical synthesis) or in vivo (using recombinant DNA technology well known in the art).

For example, the chimeric RNA may be produced outside the eukaryotic target cell or may be produced recombinantly (e.g., by an expression construct) within the target cell. In one embodiment, the chimeric RNA molecule of the invention can be produced by enzymatic synthetic methods or chemical synthetic methods in vitro. In another embodiment, the chimeric RNA molecule may be generated in a recombinant culture, e.g., bacterial cells, isolated therefrom, and used in the methods discussed below. In another embodiment another agent (such as an expression construct or vector) generates the chimeric RNA molecule in vivo after delivery to the target cell or organism. The target cell or organism is preferably a mammalian, plant cell or animal (such as a nematode) cell or organism.

For example the chimeric RNA molecule can be
a) expressed from an expression construct or an expression vector in the target cell or organism, or
b) expressed from an expression construct in an in vivo or in vitro transcription system, wherein the chimeric RNA molecule is purified from said transcription system and introduced into the host cell or organism (e.g., by feeding or injection), or
c) chemical synthesis of the chimeric RNA molecule introduced into the host cell or organism (e.g., by feeding or injection).

1.3.1 Expression of the Chimeric RNA by Recombinant Expression

The chimeric RNA molecule of the invention can be made by recombinant expression. Thus, in one embodiment of the invention the chimeric RNA is produced in the cell by an expression construct or expression vector. The chimeric RNA molecule can be made (e.g., expressed) directly in the eukaryotic target cell or organism, where it can directly fulfill its function without the need of further introduction. Alternatively the chimeric RNA molecule can be expressed in another cell, optionally purified, and subsequently delivered into the target cell or organism. Thus, the RNA molecule of this invention can be made in a recombinant microorganism, e.g., bacteria and yeast or in a recombinant host cell or organism, e.g., plant or mammalian cells, and—optionally—isolated from the cultures thereof by conventional techniques. See, e.g., the techniques described in Sambrook et al, MOLECULAR CLONING, A LABORATORY MANUAL, 2nd Ed.; Cold Spring Harbor Laboratory Press, Cold Spring Harbor, N. Y., 1989, which is exemplary of laboratory manuals that detail these techniques, and the techniques described in U.S. Pat. Nos. 5,824,538; 5,877,159 and 65,643,771, incorporated herein by reference.

Where the RNA molecules of the invention are formed in vivo they are preferably produced employing an expression construct or expression vector. More preferably the expression construct or vector is comprising a nucleic acid sequence, preferably a double stranded DNA molecule, encoding at least one of the above-described chimeric RNA molecules of the invention, operably linked to a transcription regulating sequence (a promoter) which is capable to realize transcription of said nucleic acid sequence in the chosen host or target cell to produce a chimeric RNA of the invention. As discussed, a number of promoters can be used in the practice of the invention. The promoters can be selected based on the desired outcome. Thus, the nucleotide sequence for expression of the chimeric RNA can be combined with constitutive, tissue-preferred, inducible, developmental, or other promoters for expression in plants depending upon the desired outcome. Specific promoters are described below.

Such expression constructs for expression of said chimeric ribonucleotide sequence (which are employed in the method of the invention) are considered to be novel and inventive. Thus another embodiment of the invention relates to an expression construct comprising a promoter sequence functional in a eukaryotic organism and functionally linked thereto a nucleotide sequence to be expressed, said sequence comprising
i) at least one sequence capable to confer a preferred phenotype or beneficial effect to said eukaryotic organism, and
ii) at least one sequence substantially complementary to a microRNA sequence naturally occurring in said eukaryotic organism,
wherein at least one of sequence i) and sequence ii) are heterologous to each other.

The expression construct and its elements are preferably defined as above for the method of the invention.

Another embodiment of the invention relates to an expression vector comprising an expression construct of the invention. Preferably, the expression vector is an eukaryotic expression vector. More preferably the eukaryotic expression vector is a viral vector, a plasmid vector or a binary vector.

The use and production of an expression construct are known in the art (see also WO 97/32016; U.S. Pat. Nos. 5,593,874, 5,698,425, 5,712,135, 5,789,214, and 5,804,693; and the references cited therein).

For transcription from a transgene in vivo or an expression construct, a regulatory region (e.g., promoter, enhancer, silencer, splice donor and acceptor, polyadenylation) may be used to transcribe the chimeric RNA. Transcription may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. Various promoters can be used for expression of the nucleotide sequence comprising the microRNA-tag. The promoters can—for example—be selected from the group consisting of constitutive promoters, tissue-specific or tissue-preferential promoters, and inducible promoters. A tissue specific promoter in this context, does—preferably—mean which is leaky (i.e. having expression activity in other than the preferred or main tissue) to a small but measurable extent. More specific examples for preferred expression constructs are described below for the specific application.

The nucleotide sequence to be expressed to form a chimeric RNA molecule may have various form and/or functions. For example, it may comprise an open reading frame encoding a protein. Alternatively, it may encode a functional RNA selected from the group consisting of antisense RNA, sense RNA, double-stranded RNA or ribozymes. Said functional RNA is preferably attenuating expression of an endogenous gene. For expression of a function RNA, it is desirable that the sequences, which enable protein expression, e.g., Kozak regions, etc., are not included in these expression constructs of the invention. The expression construct for the expression of the nucleotide sequence comprising the microRNA-tag can be DNA, RNA and can be single- or double-stranded. Preferably the expression construct is DNA, more preferably double-stranded DNA. The expression construct can be part or a larger vector construct. Preferably, the expression construct is in a plasmid. The expression construct is preferably comprised in an expression vector. Thus another embodiment of the invention relates to an expression vector comprising an expression construct of the invention. The expression vector can be a DNA or RNA molecule, can be single stranded or double stranded, can be a plasmid or other type of vector (as defined above and specified for the various application and technical field below in detail). More preferably the expression vector is a double-stranded, circular plasmid DNA vector. A further embodiment of the invention relates to an expression vector comprising an expression construct of the invention. Examples of vectors (see above in the DEFINITION section for details) can be plasmids, cosmids, phages, viruses or else *Agrobacteria*. Preferably, the vector is a eukaryotic expression vector. More preferably, the eukaryotic expression vector is a viral vector or plasmid vector. In certain embodiments, the expression constructs or vectors are episomal, e.g., and transfection is transient. In other embodiments, the expression constructs or vectors are chromosomally integrated, e.g., to produce a stably transfected cell line. Preferred vectors for forming such stable cell lines are described in U.S. Pat. No. 6,025,192 and WO/9812339, which are incorporated by reference herein. Vectors for expression in *E. coli* are preferably pQE70, pQE60 and pQE-9 (QIAGEN, Inc.); pBluescript vectors, Phagescript vectors, pNH8A, pNH16a, pNH18A, pNH46A (Stratagene Cloning Systems, Inc.); ptrc99a, pKK223-3, pKK233-3, pDR540, pRIT5 (Pharmacia Biotech, Inc.).

As described above (and for specific organisms and cells below in more detail), the expression construct and vector may be introduced into organisms or cells. Yet another embodiment of the invention relates to a transformed cell or non-human organism comprising an expression construct or an expression vector of the invention. Preferably, said expression construct or expression vector is inserted into the genome (preferably the chromosomal or plastid DNA) of said cell or organism. Preferably, said cell or organism is selected from the group of mammalian, bacterial, fungal, nematode or plant cells and organism. Another embodiment of the invention relates to tissues, part and propagation material of the transformed organism of the invention. In case of transformed plants the propagation material is preferably transformed seed.

The expression construct can be inserted into the vector (preferably a plasmid vector) via a suitable restriction cleavage site. The resulting vector is first introduced into *E. coli*. Correctly transformed *E. coli* are selected, grown, and the recombinant vector is obtained by methods with which the skilled worker is familiar. Restriction analysis and sequencing can be employed for verifying the cloning step. Preferred vectors are those, which make possible a stable integration of the expression construct into the host genome. Suitable promoters and vector constructs are described in United States Patent Application No. 20040220130.

The vectors designed to produce the chimeric RNA of the invention may desirably be designed to generate two or more, including a number of different chimeric RNAs. This approach is desirable in that a single vector may produce many, independently operative chimeric RNAs rather than a single chimeric RNA molecule from a single transcription unit and by producing a multiplicity of different chimeric RNAs. Various means may be employed to achieve this, including autocatalytic sequences as well as sequences for cleavage to create random and/or predetermined splice sites.

The construction of polynucleotide constructs generally requires the use of vectors able to replicate in bacteria. A plethora of kits are commercially available for the purification of plasmids from bacteria. For their proper use, follow the manufacturers instructions (see, for example, Easy-Prep™, FlexiPrep™, both from Pharmacia Biotech; Strata-Clean™, from Stratagene; and, QIAprep™, Qiagen). The isolated and purified plasmids can then be further manipulated to produce other plasmids, used to transfect cells or incorporated into other vector systems (e.g., *Agrobacterium tumefaciens*) to infect and transform target cells or organism (preferably plants).

Still other suitable vector (or delivery agents) for introducing a chimeric RNA of the invention into a target cell include live, attenuated or killed, inactivated viruses, and particularly recombinant viruses carrying the required RNA polynucleotide sequence discussed above. Such viruses may be designed similarly to recombinant viruses presently used to deliver genes to cells for gene therapy and the like, but preferably do not have the ability to express a protein or functional fragment of a protein. Among useful viruses or viral sequences which may be manipulated to provide the required RNA molecule to the mammalian cell in vivo are, without limitation, alphavirus, adenovirus, adeno-associated virus, baculoviruses, delta virus, pox viruses, hepatitis viruses, herpes viruses, papova viruses (such as SV40), poliovirus, pseudorabies viruses, retroviruses, vaccinia viruses, positive and negative stranded RNA viruses, viroids, and virusoids, or portions thereof. These various viral delivery agents may be designed by applying conventional techniques such as described in M. Di Nocola et al, Cancer Gene Ther., 5(6):350-6 (1998), among others, with the teachings of the present invention. A viral construct packaged into a viral particle would accomplish both efficient introduction of an expression construct into the cell and transcription of chimeric RNA construct encoded by the expression construct.

Another delivery agent for providing the chimeric RNA molecules of the invention in the target cell or organism include live, attenuated or killed, inactivated donor cells which have been transfected or infected in vitro with a synthetic RNA molecule or an expression construct or vector as described above. These donor cells may then be administered or feed to the target organism (e.g., a mammal or a pathogen such as a nematode), as described in detail below, to stimulate the mechanism in the target organism which mediates this inhibitory effect. These donor cells are desirably eukaryotic cells, such as mammalian cells C127, 3T3, CHO, HeLa, human kidney 293, BHK cell lines, and COS-7 cells, and preferably are of the same mammalian species as the mammalian recipient, or plant cells. Such donor cells can be made using techniques similar to those described in, e.g., Emerich et al, J. Neurosci., 16: 5168-81 (1996). Even more preferred, the donor cells may be harvested from the specific mammal to be treated and made into donor cells by ex vivo manipulation, akin to adoptive transfer techniques, such as those described in D. B. Kohn et al, Nature Med. 4(7):775-80 (1998). Donor cells may also be from non-mammalian species, if desired.

1.3.2 Production of the Chimeric RNA of the Invention by Enzymatic Synthesis

The chimeric RNA molecule according to this invention may be delivered to the target cell or organism as a molecule, which was made in vitro by enzymatic synthesis.

Thus, another embodiment of the invention relates to a method for generating a chimeric RNA of the invention comprising:

(i) providing an in vitro transcription system including an expression construct for the chimeric RNA of the invention, and (ii) isolating said chimeric RNA of the invention.

Prokaryotic and—preferably—eukaryotic transcription systems can be employed. Furthermore, systems based on isolated enzymes and systems based on cellular extracts can be utilized. Eukaryotic, prokaryotic or bacteriophage RNA polymerases (such as, for example, T3, T7 or SP6 RNA polymerase) can be used for this purpose. Suitable methods for the in-vitro expression of RNA are described (WO 97/32016; U.S. Pat. Nos. 5,593,874; 5,698,425, 5,712,135, 5,789,214, 5,804,693). Enzymatic systems based on isolated enzymes can be used, for example, the bacteriophage T7, T3 or SP6 RNA polymerases according to the conventional methods described by such texts as the Promega Protocols and Applications Guide, (3rd ed. 1996), eds. Doyle, ISBN No. 1-882274-57-1.

Accordingly, the invention also provides a kit that includes reagents for attenuating the expression of a target gene in a cell. The kit contains a DNA template comprising a promoter (preferably a T7 promoter, a T3 promoter or an SP6 promoter) operably linked to a nucleotide sequence encoding a chimeric RNA of the invention. The kit optionally contains amplification primers for amplifying the DNA sequence from the DNA template and nucleotide triphosphates (i.e., ATP, GTP, CTP and UTP) for forming RNA. Also optionally, the kit contains a RNA polymerase, capable of binding to the promoter on the DNA template and causing transcription of the nucleotide sequence to which the promoter is operably linked; a purification column for purifying single stranded RNA, such as a size exclusion column; one or more buffers, for example a buffer for annealing single stranded RNAs to yield double stranded RNA; and RNAse A or RNAse T for purifying double stranded RNA.

In cases where an eukaryotic transcription system is employed (such as lysates from rabbit reticulocytes or wheat germ; see Movahedzadeh et al., "In vitro transcription and translation," in Methods in Molecular Biology, V. 235, N. Casali, A. Preston, Eds., Totowa, N.J.: Humana Press, p. 247-55; Lamla et al., Acta Biochim Pol, 48:453-65, 2001) correct removal of the removable RNA element is expected resulting in release of the chimeric RNA, which may be purified from the system.

Prior to introduction into a cell, tissue or organism, a chimeric RNA which has been synthesized in vitro, either chemically or enzymatically, can be purified either completely or in part from the reaction mixture, for example by extraction, precipitation, electrophoresis, chromatography or combinations of these methods.

1.3.3 Production of the Chimeric RNA of the Invention by Chemical Synthesis

The chimeric RNA molecules of the invention can also be synthesized—entirely or in part—by chemical synthesis. Chemical synthesis of linear oligonucleotides is well known in the art and can be achieved by solution or solid phase techniques. Preferably, synthesis is by solid phase methods. Suitable synthetic procedures include but are not limited to phosphoramidite, phosphite triester, H-phosphonate, and phosphotriester methods, typically by automated synthesis methods. Such oligonucleotide synthesis protocols can be found, e.g., in U.S. Pat. No. 5,830,653; WO 98/13526; Stec et al. 1984. J. Am. Chem. Soc. 106:6077; Stec et al. 1985. J. Org. Chem. 50:3908; Stec et al. J. Chromatog. 1985. 326:263; LaPlanche et al. 1986. Nuc. Acid. Res. 1986. 14:9081; Fasman G. D., 1989. Practical Handbook of Biochemistry and Molecular Biology. 1989. CRC Press, Boca Raton, Fla.; Lamone. 1993. Biochem. Soc. Trans. 21:1; U.S. Pat. Nos. 5,013,830; 5,214,135; 5,525,719; Kawasaki et al. 1993. J. Med. Chem. 36:831; WO 92/03568; U.S. Pat. Nos. 5,276,019; 5,264,423. Alternative methods for in vitro chemical synthetis of the RNA molecules of the invention are described [see, e.g., Xu et al, Nucl. Acids Res., 24(18): 3643-4 (1996); Naryshkin et al, Bioorg. Khim., 22(9):691-8 (1996); Grasby et al, Nucl. Acids Res., 21(19):4444-50 (1993); Chaix el al, Nucl. Acids Res., 17(18):7381-93 (1989); Chou et al, Biochem., 2(6):2422-35 (1989); Odai et al, Nucl. Acids Symp, Ser., 21:105-6 (1989); Naryshkin et al, Bioorg. Khim, 22(9):691-8 (1996); Sun et al, RNA, 3(11):1352-1363 (1997); X. Zhang et al, Nucl. Acids Res., 25(20):3980-3 (1997); Grvaznov et al, Nucl. Acids Res., 26 (18):4160-7 (1998); Kadokura et al, Nucl. Acids Symp Ser, 37:77-8 (1997); Davison et al, Biomed. Pept. Proteins, Nucl. Acids, 2(1):1-6 (1996); Mudrakovskaia et al, Bioorg. Khim., 17(6):819-22 (1991)].

The synthesis method selected can depend on the length of the desired oligonucleotide and such choice is within the skill of the ordinary artisan. For example, the phosphoramidite and phosphite triester method can produce oligonucleotides having 175 or more nucleotides while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, Chemical Reviews 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. Methods in Molecular Biology 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The chimeric RNA molecule of the invention may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms by dsRNA. Likewise, bases may be modified to block the activity of adenosine deaminase. In one embodiment of the invention the chimeric RNA molecule has end-blocks on one or both ends.

The chimeric RNA of the invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nuc. Acid Drug Dev. 1996. 6:267); predictable targeting (Biochemica Biophysica Acta. 1999. 1489:141); reliable activity in cells (Antisense & Nuc. Acid Drug Dev. 1997. 7:63); excellent sequence specificity (Antisense & Nuc. Acid Drug Dev. 1997. 7:151); minimal non-antisense activity (Biochemica Biophysica Acta. 1999. 1489:141); and simple osmotic or scrape delivery (Antisense & Nuc. Acid Drug Dev. 1997. 7:291). Morpholino oligonucleotides are also preferred because of their non-toxicity at high doses. A discussion of the preparation of morpholino oligonucleotides can be found in Antisense & Nuc. Acid Drug Dev. 1997. 7:187.

Another embodiment of the invention includes duplexes in which nucleomonomernucleomonomer mismatches are present in a sense 2'-O-methly strand (and are thought to be easier to unwind). As a further example, the use of 2'-O-methyl RNA may beneficially be used in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This RNA interference ("stealth RNAi") is useful for avoiding the interferon or other cellular stress responses, both in short RNAi (e.g., siRNA) sequences that induce the interferon response, and in longer RNAi sequences that may induce the interferon response. Other chemical modifications in addition to 2'-O-methylation may also achieve this effect.

In certain embodiments, the chimeric RNA molecules of the invention comprise 3' and 5' termini (except for circular molecules). In one embodiment, the 3' and 5' termini can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl, phosphate, hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures. Exemplary end-blocking groups include cap structures (e.g., a 7-methylguanosine cap), inverted nucleomonomers, e.g., with 3'-3' or 5'-5' end inversions (see, e.g., Ortiagao et al. 1992. Antisense Res. Dev. 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'-3' internucleotide linkage. For example, the alkyloxy radical can be methoxy, ethoxy, or isopropoxy, and preferably, ethoxy. Optionally, the 3'-3' linked nucleotide at the 3' terminus can be linked by a substitute linkage. To reduce nuclease degradation, the 5' most 3'-5' linkage can be a modified linkage, e.g., a phosphorothioate or a P-alkyloxyphosphotriester linkage. Optionally, the 5' terminal hydroxy moiety can be esterified with a phosphorus containing moiety, e.g., phosphate, phosphorothioate, or P-ethoxyphosphate.

In another embodiment of the invention the chimeric RNA molecule of the invention may comprise one or more flexible linker. Such linkers may be used to combine or fuse two or more smaller chimeric RNAs together to a larger chimeric RNA molecule. A linker is provided with functional groups at each end that can be suitably protected or activated. The functional groups are covalently attached to each RNA molecule, e.g., via an ether, ester, carbamate, phosphate ester or amine linkage to either the 5'-hydroxyl or the 3'-hydroxyl. Preferred linkages are phosphate ester linkages similar to typical oligonucleotide linkages. For example, hexaethyleneglycol can be protected on one terminus with a photolabile protecting group (i.e., NVOC or MeNPOC) and activated on the other terminus with 2-cyanoethyl-N,N-diisopropylamino-chlorophosphite to form a phosphoramidite. Other methods of forming ether, carbamate or amine linkages are known to those of skill in the art and particular reagents and references can be found in such texts as March, Advanced Organic Chemistry, 4th Ed., Wiley-Interscience, New York, N.Y., 1992. In general, the flexible linkers are non-nucleotide molecules including spacers, attachments, bioconjugates, chromophores, reporter groups, dye labeled RNAs, and non-naturally occurring nucleotide analogues. Preferred linkers, spacers, bioconjugates, attachments, and chromophores are more specifically described in US Patent Application No. 20040058886, herein incorporated by reference.

In one embodiment, a chimeric RNA molecule of the invention, which is sought to function in gene silencing, can include an agent which increases the affinity for its target sequence. The term "affinity enhancing agent" includes agents that increase the affinity of an chimeric RNA molecule of the invention for its target. Such agents include, e.g., intercalating agents and high affinity nucleomonomers. Intercalating agents interact strongly and nonspecifically with nucleic acids. Intercalating agents serve to stabilize RNA-DNA duplexes and thus increase the affinity of the chimeric RNA molecule of the invention for their targets. Intercalating agents are most commonly linked to the 3' or 5' end of oligonucleotides. Examples of intercalating agents include acridine, chlorambucil, benzopyridoquinoxaline, benzopyridoindole, benzophenanthridine, and phenazinium. The agents may also impart other characteristics to the oligonucleotide, for example, increasing resistance to endonucleases and exonucleases.

In one embodiment, a high affinity nucleomonomer is incorporated into an chimeric RNA molecule of the invention. The language "high affinity nucleomonomer" as used herein includes modified bases or base analogs that bind to a complementary base in a target nucleic acid molecule with higher affinity than an unmodified base, for example, by having more energetically favorable interactions with the complementary base, e.g., by forming more hydrogen bonds with the complementary base. For example, high affinity nucleomonomer analogs such as aminoethyoxy phenoxazine (also referred to as a G clamp), which forms four hydrogen bonds with guanine are included in the term "high affinity nucleomonomer." A high affinity nucleomonomer is illustrated below (see, e.g., Flanagan, et al., 1999. Proc. Natl. Acad. Sci. 96:3513). Other exemplary high affinity nucleomonomers are known in the art and include 7-alkenyl, 7-alkynyl, 7-heteroaromatic-, or 7-alkynylheteroaromatic-substituted bases or the like which can be substituted for adenosine or guanosine in oligonucleotides (see, e.g., U.S. Pat. No. 5,594,121). Also, 7-substituted deazapurines have been found to impart enhanced binding properties to oligonucleotides, i.e., by allowing them to bind with higher affinity to complementary target nucleic acid molecules as compared to unmodified oligonucleotides. High affinity nucleomonomers can be incorporated into the oligonucleotides of the instant invention using standard techniques.

In another embodiment, an agent that increases the affinity of a chimeric RNA molecule of the invention for its target comprises an intercalating agent. As used herein, the language "intercalating agent" includes agents which can bind to a DNA double helix. When covalently attached to a chimeric RNA molecule of the invention, an intercalating agent enhances the binding of the oligonucleotide to its complementary genomic DNA target sequence. The intercalating agent may also increase resistance to endonucleases and exonucleases. Exemplary intercalating agents are taught by Helene and Thuong (1989. Genome 31:413), and include e.g., acridine derivatives (Lacoste et al. 1997. Nucleic Acids Research. 25:1991; Kukreti et al. 1997. Nucleic Acids Research. 25:4264); quinoline derivatives (Wilson et al. 1993. Biochemistry 32:10614); benzo[f]quino[3,4-b]quinoxaline derivatives (Marchand et al. 1996. Biochemistry. 35:5022; Escude et al. 1998. Proc. Natl. Acad. Sci. 95:3591). Intercalating agents can be incorporated into a chimeric RNA molecule of the invention using any convenient linkage. For example, acridine or psoralen can be linked to the oligonucleotide through any available —OH or —SH group, e.g., at the terminal 5' position of the oligonucleotide, the 2' positions of sugar moieties, or an OH, NH2, COOH, or SH incorporated into the 5-position of pyrimidines using standard methods.

In one embodiment, the double-stranded duplex constructs of the invention can be further stabilized against nucleases by forming loop structures at the 5' or 3' end of the sense or antisense strand of the construct. Suitable loop-structure and other structures to stabilize an RNA molecule of the invention are for example described in US patent Application No. 20040014956.

The chimeric RNA molecule of the invention (or an expression construct or vector for its production) can be derivatized, chemically modified, combined with and/or linked to various agents to enhance its activity or specificity. Such agents include but are not limited to conjugation agents (e.g., for improvement of cellular uptake), protein carriers (e.g., for improvement of cellular uptake and greater cellular accumulation), encapsulating agents (such as liposomes; e.g., to facilitate the cellular uptake or targeting), complexing agents (such as cationic lipid, e.g., to increase cellular uptake), basic oligopeptides, transporting peptides (e.g., HIV TAT transcription factor, lactoferrin, Herpes VP22 protein), and targeting agents (for targeting to a cellular receptor). Suitable conjugation agents, protein carriers, encapsulating agents, complexing agents, basic oligopeptides, transporting peptides, and targeting agents are described for example in US Patent Application No. 20040014956. Additional ways to contact a chimeric RNA molecule of the invention with its target cell are described below in the context of pharmaceutical application. Alternatively, the chimeric RNA can be delivered to the target organism by ingestion or infection of a transgenic organism comprising an expression construct for the chimeric RNA. See e.g., U.S. Pat. No. 6,506,559. Methods for increase stability of the RNA molecules of the invention against nuclease degradation (e.g., by serum nucleases and cellular nucleases and nucleases found in other bodily fluids) are described in United States Patent Application No. 20040014956.

If synthesized chemically or by in vitro enzymatic synthesis, the chimeric RNA molecule of the invention may be purified prior to introduction into the cell. For example, RNA can be purified from a mixture by extraction with a solvent or resin, precipitation, electrophoresis (e.g., polyacrylamide gel electrophoresis), chromatography (e.g., gel chromatography and high pressure liquid chromatography) or a combination thereof. Alternatively, the chimeric RNA may be used with no or a minimum of purification to avoid losses due to sample processing. The chimeric RNA may be dried for storage or dissolved in an aqueous solution. The quality of the synthesized chimeric RNA molecules of the invention synthesized can be verified by capillary electrophoresis and denaturing strong anion HPLC (SAX-HPLC) using, e.g., the method of Bergot and Egan. 1992. J. Chrom. 599:35.

1.4 Introduction of the Chimeric RNA into Cells and Organism

The chimeric RNA of the invention or its delivery or production agents (e.g., expression constructs or vectors) (hereinafter together the "RNA agent") can be introduced into an organism or a cell in various ways with which the skilled worker is familiar. "To introduce" is to be understood in the broad sense and comprises, for the purposes of the present invention, all those methods which are suitable for directly or indirectly introducing, into an organism or a cell, compartment, tissue, organ or seed of same, a RNA agent of the invention, or generating it/them therein. The introduction can bring about the transient presence of a RNA agent, or else a stable presence.

Thus a further aspect of the invention relates to cells and organism (e.g., plant, animal, protozoan, virus, bacterium, or fungus), which comprise at least one chimeric RNA of the invention, or an RNA agent (e.g., an expression construct or expression vectors encoding said chimeric RNA molecule). In certain embodiments, the cell is suspended in culture; while in other embodiments the cell is in (or part of) a whole organism (e.g., a microorganism, plant or an animal, such as a non-human mammal). The cell can be prokaryotic or of eukaryotic nature. Preferably, the expression construct is comprised with the genomic DNA, more preferably within the chromosomal or plastidic DNA, most preferably in the chromosomal DNA of the cell.

The cell having the target gene may be from the germ line or somatic, totipotent or pluripotent, dividing or non-dividing, parenchyma or epithelium, immortalized or transformed, or the like. The cell can be a gamete or an embryo; if an embryo, it can be a single cell embryo or a constituent cell or cells from a multicellular embryo. The term "embryo" thus also includes fetal tissue. The cell having the target gene may be an undifferentiated cell, such as a stem cell, or a differentiated cell, such as from a cell of an organ or tissue, including fetal tissue, or any other cell present in an organism. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Preferred prokaryotes are mainly bacteria such as bacteria of the genus *Escherichia, Corynebacterium, Bacillus, Clostridium, Propionibacterium, Butyrivibrio, Eubacterium, Lactobacillus, Erwinia, Agrobacterium, Flavobacterium, Alcaligenes, Phaeodactylum, Colpidium, Mortierella, Entomophthora, Mucor, Crypthecodinium* or *Cyanobacteria*, for example of the genus *Synechocystis*. Microorganisms which are preferred are mainly those which are capable of infecting plants and thus of transferring the constructs according to the invention. Preferred microorganisms are those of the genus *Agrobacterium* and in particular the species *Agrobacterium tumefaciens* and *rhizogenes*.

Eukaryotic cells and organisms comprise plant and animal (preferably nonhuman) organisms and/or cells and eukaryotic microorganisms such as, for example, yeasts, algae or fungi. A corresponding transgenic organism can be generated for example by introducing the expression systems in question into a zygote, stem cell, protoplast or another suitable cell which is derived from the organism. A transgenic animal that expresses a chimeric RNA of the invention from a recombinant expression construct may be produced by introducing the construct into a zygote, an embryonic stem cell, or another multipotent cell derived from the appropriate organism. A viral construct packaged into a viral particle would accomplish both efficient introduction of an expression construct into the cell and transcription of RNA encoded by the expression construct. Suitable vector are will known in the art (see e.g., Shi, Y. 2003. Trends Genet 2003 January 19:9; Reichhart J M et al. Genesis. 2002. 34(1-2):160-4, Yu et al. 2002. Proc Natl Acad Sci USA 99:6047; Sui et al. 2002. Proc Natl Acad Sci USA 99:5515).

The plant may be a monocot, dicot or gymnosperm; the animal may be a vertebrate or invertebrate. Preferred animal and plant organisms are specified above in the DEFINITION section. Preferred fungi are *Aspergillus, Trichoderma, Ashbya, Neurospora, Fusarium, Beauveria* or further fungi described in Indian Chem Engr. Section B. Vol 37, No 1, 2 (1995), page 15, Table 6. Especially preferred is the filamentous *Hemiascomycete Ash bya gossypii*. Preferred yeasts are *Candida, Saccharomyces, Hansenula* or *Pichia*, especially preferred are *Saccharomyces cerevisiae* or *Pichia pastoris* (ATCC Accession No. 201178). Especially preferred animal organisms are nematodes.

Preferred as organisms are plant organisms. Preferred plants are selected in particular from among crop plants. Most preferred are
a) Plants which are suitable for oil production such as, for example, oilseed rape, sunflower, sesame, safflower (*Carthamus tinctorius*), olive tree, soybean, maize, peanut, castor-oil plant, oil palm, wheat, cacao shrub, or various nut species such as, for example, walnut, coconut or almond. Especially preferred among these, in turn, are dicotyledonous plants, in particular oilseed rape, soybean and sunflower.
b) Plants, which serve for the production of starch, such as, for example, maize, wheat or potato.
c) Plants, which are used as foodstuffs and/or feeding stuffs and/or useful plant and in which a resistance to pathogens would be advantageous such as, for example, barley, rye, rice, potato, cotton, flax, or linseed.
d) Plants, which can serve for the production of fine chemicals such as, for example, vitamins and/or carotenoids such as, for example, oilseed rape.

Plant varieties may be excluded, particularly registrable plant varieties according to Plant Breeders Rights. It is noted that a plant need not be considered a "plant variety" simply because it contains stably within its genome a transgene, introduced into a cell of the plant or an ancestor thereof. In addition to a plant, the present invention provides any clone of such a plant, seed, selfed or hybrid progeny and descendants, and any part or propagule of any of these, such as cuttings and seed, which may be used in reproduction or propagation, sexual or asexual. Also encompassed by the invention is a plant which is a sexually or asexually propagated off-spring, clone or descendant of such a plant, or any part or propagule of said plant, off-spring, clone or descendant. Genetically modified plants according to the invention, which can be consumed by humans or animals, can also be used as food or feedstuffs, for example directly or following processing known in the art. The present invention also provides for parts of the organism especially plants, particularly reproductive or storage parts. Plant parts, without limitation, include seed, endosperm, ovule, pollen, roots, tubers, stems, leaves, stalks, fruit, berries, nuts, bark, pods, seeds and flowers. In a particularly preferred embodiment of the present invention, the plant part is a seed.

The RNA agent (e.g., the chimeric RNA molecule of the invention) is typically is introduced or administered in an amount that allows delivery of at least one copy per cell. Higher amounts (for example at least 5, 10, 100, 500 or 1000 copies per cell) can, if appropriate, affect a more efficient phenotype (e.g., higher expression or higher suppression of the target genes). The amount of RNA agent administered to a cell, tissue, or organism depends on the nature of the cell, tissue, or organism, the nature of the target gene, and the nature of the RNA agent, and can readily be optimized to obtain the desired level of expression or inhibition.

Preferably at least about 100 molecules, preferably at least about 1000, more preferably at least about 10,000 of the RNA agent, most preferably at least about 100,000 of the RNA agent are introduced. In the case of administration of RNA agent to a cell culture or to cells in tissue, by methods other than injection, for example by soaking, electroporation, or lipid-mediated transfection, the cells are preferably exposed to similar levels of RNA agent in the medium.

For examples the RNA agent may be introduced into cells via transformation, transfection, injection, projection, conjugation, endocytosis, and phagocytosis. Preferred method for introduction comprise but are not limited to:
a) methods of the direct or physical introduction of the chimeric RNA molecule of the invention into the target cell or organism, and
b) methods of the indirect introduction of chimeric RNA of the invention into the target cell or organism (e.g., by a first introduction of an expression construct and a subsequent intracellular expression).

1.4.1 Direct and Physical Introduction of RNA into Target Cells or Organism

In case the chimeric RNA of the invention (or a RNA agent) is produced outside the target cell or organism, it can be contacted with (i.e., brought into contact with, also referred to herein as administered or delivered to) and taken up by one or more cell or the target organism (preferably human, pathogen or plant cells or organisms). The contact may be in vitro, e.g., in a test tube or culture dish, (and may or may not be introduced into a subject) or in vivo, e.g., in a subject such as a mammalian, pathogen or plant subject. The pathogen is preferably a nematode.

The chimeric RNA of the invention (or a RNA agent) may be directly introduced into the cell (i.e., intracellularly); or introduced extracellularly into a cavity, interstitial space, into the circulation of an organism, introduced orally, or may be introduced by bathing an organism in a solution containing the chimeric RNA of the invention (or a RNA agent). Methods for oral introduction include direct mixing of RNA with food of the organism, as well as engineered approaches in which a species that is used as food is engineered to express a chimeric RNA of the invention (or a RNA agent), then fed to the organism to be affected.

Physical methods of introducing nucleic acids include injection of a solution of the chimeric RNA of the invention (or a RNA agent) directly into the cell or extracellular injection into the organism. For example, in the case of an embryo or a cell, the chimeric RNA of the invention (or a RNA agent) is conveniently administered by microinjection; other methods of introducing nucleic acids into a cell include bombardment by particles covered by the chimeric RNA of the invention (or a RNA agent), soaking the cell or organism in a solution of the chimeric RNA of the invention (or a RNA agent), electroporation of cell membranes in the presence of the chimeric RNA of the invention (or a RNA agent), liposome-mediated delivery of chimeric RNA of the invention (or a RNA agent) and transfection mediated by chemicals such as calcium phosphate.

The chimeric RNA of the invention (or a RNA agent) agent may be introduced along with components that enhance RNA uptake by the cell, or otherwise increase its functionality. Delivery into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. Nucleic Acids Research. 21:3567). Also polyamine or polycation conjugates using compounds such as polylysine, protamine, or N1, N12-bis (ethyl) spermine (see, e.g., Bartzatt, R. et al. 1989. Biotechnol. Appl. Biochem. 11:133; Wagner E. et al. 1992. Proc. Natl. Acad. Sci. 88:4255) can be employed. In the case of a cell culture or tissue explant, the cells are conveniently incubated in a solution containing the chimeric RNA of the invention (or a RNA agent) or lipid-mediated transfection; in the case of a whole animal or plant, the chimeric RNA of the invention (or a RNA agent) is conveniently introduced by injection or perfusion into a cavity or interstitial space of an organism, or systemically via oral, topical, parenteral (including subcutaneous, intramuscular and intravenous administration), vaginal, rectal, intranasal, ophthalmic, or intraperitoneal administration.

In addition, the chimeric RNA of the invention (or a RNA agent) can be administered via an implantable extended release device. Methods for oral introduction include direct mixing of RNA with food of the organism, as well as engineered approaches in which a species that is used as food is engineered to express an RNA, then fed to the organism to be affected. The chimeric RNA of the invention (or a RNA agent) may be sprayed onto a plant or a plant may be genetically engineered to express the RNA in an amount sufficient to kill some or all of a pathogen known to infect the plant.

1.4.2 Indirect Introduction of RNA

Alternatively, the RNA agent can be supplied to a cell indirectly by introducing (e.g., by transformation or transfection) one or more expression constructs or expression vectors that encode the chimeric RNA molecule of the invention. The expression of the chimeric RNA of the invention can be transient or—for example after integration into the genome (for example using selection markers) of the organism—stable. Preferably for pharmaceutical application, the RA agent is introduced transiently, and not stably integrated into the genome. Preferably for applications in plants, the chimeric RNA expression system is integrated stably into the genome—for example the chromosomal DNA or the DNA of the organelles (for example the plastids (e.g., chloroplasts), mitochondria and the like)—of a cell. Integration into the chromosomal DNA is preferred.

Expression constructs and vectors are generally described above (see DEFINITION section and section 1.3.1). Preferred expression constructs are described in more detailed below for the specific applications the composition and methods of the present invention. Methods for supplying a cell with RNA by introducing an expression construct or vector from which it can be transcribed are set forth in WO 99/32619. Principally also all the methods for direct introduction of RNA molecules into cells as described above can be employed for introduction of the nucleic acid molecules resembling the expression construct or vector.

2. Applications of Chimeric RNA of the Invention

The invention has broad opportunities of application, preferably in the field of plants, human and animals. Generally, the methods and subject matter of the invention can be used to increase or decrease with higher specificity the expression of any gene or sequence of interest including therapeutic or immunogenic peptides and proteins, nucleic acids for controlling gene expression, genes to reproduce enzymatic pathways for chemical synthesis, genes to shunt an enzymatic pathway for enhanced expression of a particular intermediate or final product, industrial processes, and the like.

In one preferred embodiment, the eukaryotic organism is a plant and the promoter is a promoter functional in plants. For plants, the expressed nucleotide sequence preferably modulates expression of a gene involved in agronomic traits, disease resistance, herbicide resistance, and/or grain characteristics. The person skilled in art is aware of numerous nucleotide sequences which can be used in the context and for which a enhanced expression specificity is advantageous. The target nucleotide sequence comprises any nucleotide sequence or gene of interest, including genes, regulatory sequences, etc. Genes of interest include those encoding agronomic traits, insect resistance, disease resistance, herbicide resistance, sterility, grain characteristics, and the like. The genes may be involved in metabolism of oil, starch, carbohydrates, nutrients, etc. Genes or traits of interest include, but are not limited to, environmental- or stress-related traits, disease-related traits, and traits affecting agronomic performance. Target sequences also include genes responsible for the synthesis and/or degradation of proteins, peptides, fatty acids, lipids, waxes, oils, starches, sugars, carbohydrates, flavors, odors, toxins, carotenoids, hormones, polymers, flavonoids, storage proteins, phenolic acids, alkaloids, lignins, tannins, celluloses, glycoproteins, glycolipids, etc.

Various applications in plants are contemplated herein for which modulation of the expression profile in certain directions is advantageous. This modulation is achieved by selection the microRNA-tag in a way, that the expression profile of the naturally occurring miRNA fits with the tissues, times, and/or under environmental conditions where no or lower expression should be achieved. For example, the microRNA has a natural expression profile in the plant selected from the group consisting of a) substantially constitutive expression but no expression in seed,
b) predominant expression in seeds but not in other tissues,
c) drought or other abiotic stress—induced expression,
d) plant pathogen—induced expression,
e) temporal expression (e.g., during early development, germination, pollination etc.), and
f) chemical induced expression.

Preferably, the microRNA is a plant microRNA selected from the group consisting of a) the sequences as described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 225, 226, 227, 228, 229, 230, 231, 232, 233, 234, 235, 236, 237, 238, 239, 240, 241, 242, 243, 245, 245, 246, 247, 248, 249, 250, 251, 252, 253, 254, 255, 256, 257, 258, 259, 260, 261, 262, 263, 264, 265, and 266, and b) derivatives of the sequences described by SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 225, 226, 227, 228, 229, 230, 231, 232, 233, 234, 235, 236, 237, 238, 239, 240, 241, 242, 243, 245, 245, 246, 247, 248, 249, 250, 251, 252, 253, 254, 255, 256, 257, 258, 259, 260, 261, 262, 263, 264, 265, and 266.

A derivative is preferably a sequence, which fulfills the same functional endogenous purpose (e.g., certain gene control functions) in an organism of a different species (i.e. different from the specie where the disclosed miRNA is derived from). Said derivates may have certain mismatches with respect to the specifically disclosed sequences, preferably a derivative is characterized by having an identity of at least 70%, preferably at least 80% or 85%, more preferably at least 90%, most preferably at least 95% to a sequence described by any of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 225, 226, 227, 228, 229, 230, 231, 232, 233, 234, 235, 236, 237, 238, 239, 240, 241, 242, 243, 245, 245, 246, 247, 248, 249, 250, 251, 252, 253, 254, 255, 256, 257, 258, 259, 260, 261, 262, 263, 264, 265, and 266. The mismatches with the specified miRNA maybe throughout the entire sequence but are preferably in the 3' region of the miRNA (corresponding to the 5'-region of the complementary miRNA-tag). More specific applications in plants are described herein below.

Other applications of the invention provide herein are used in animals (especially mammals) or human. Especially preferred are pharmaceutical applications. Thus, in another preferred embodiment of the invention the target organism is a mammal (more preferably a human being) and the promoter is a promoter functional in mammals (more preferably in humans). The expressed nucleotide sequence comprising the miRNA-tag preferably modulates (e.g., express, over-express, or suppress) expression of a gene selected from the group consisting of genes involved in a human or animal disease or is a therapeutic gene. Alternatively, exogenous genes or sequences may be expressed which have a curative effect on the target organism. The disease is preferably selected from the group of immunological diseases, cancer, diabetes, neurodegeneration, and metabolism diseases. The person skilled in the art is aware of numerous sequences which can be used in this context. The modulated gene may be selected from the group consisting of retinoblastoma protein, p53, angiostatin, leptin, hormones, growth factors, cytokines, insulin, growth hormones, alpha-interferon, beta-glucocerebrosidase, serum albumin, hemoglobin, and collagen. Therapeutic genes may be selected from the group consisting of tumor necrosis factor alpha (ADD). In this context the invention disclosed herein is a improved method for gene therapy or nucleotide-mediated therapy.

Various promoters are currently used in the art to express sequences in animal, mammalian or human organism. Most of them are lacking tissue-specificity and can be advantageously combined with the teaching provided herein. For example the promoter may be selected from group consisting of the perbB2 promoter, whey acidic protein promoter, stromelysin 3 promoter, prostate specific antigen promoter, probasin promoter.

Various applications in animal, mammalian or human organisms are contemplated herein for which modulation of the expression profile in certain directions is advantageous. This modulation is achieved by selection the microRNA-tag in a way, that the expression profile of the naturally occurring miRNA fits with the tissues, times, and/or under environmental conditions where no or lower expression should be achieved. For example, the microRNA has a natural expression profile in the animal, mammalian or human organism selected from the group consisting of a) tissue specific expression in a tissue selected from the group consisting of brain tissue, liver tissue, muscle tissue, neuron tissue, and tumor tissue.
b) stress-induced expression,
c) pathogen-induced expression,
d) neoplastic growth or tumorgenic growth induced expression, and
e) age-dependent expression.

Preferably, the microRNA is an animal, mammalian or human microRNA. Hundreds of miRNAs have been cloned from mouse and human organs and cell lines, and numerous additional miRNAs have been predicted with computational algorithms (Lagos-Quintana M et al. *Science* 2001, 294:853-858; Lagos-Quintana M et al. *Curr Biol* 2002, 12:735-739; Lagos-Quintana M et al. *RNA* 2003, 9:175-179; Lim L P et al. *Science* 2003, 299:1540; Mourelatos Z et al. *Genes Dev* 2002, 16:720-728; Dostie J et al *RNA* 2003, 9:180-186). Various of these microRNAs and their expression profile are described in the art (see for example Sempere L F et al. *Genome Biology* 2004, 5:R13; electronically available online at genomebiology.com/2004/5/3/R13); hereby incorporated by reference entirely including the cited references therein). Sempere et al. characterized the expression of 119 miRNAs in adult organs from mouse and human using northern blot analysis. Of these, 30 miRNAs were specifically expressed or greatly enriched in a particular organ (brain, lung, liver or skeletal muscle). A total of 19 brain-expressed miRNAs (including lin-4 and let-7 orthologs) were coordinately upregulated in both human and mouse embryonal carcinoma cells during neuronal differentiation. Mouse and human miRNAs often demonstrate a high homology (about 90%) and may be interchangeable (see FIG. 5 in Sempere et al. 2004).

Figure 1:
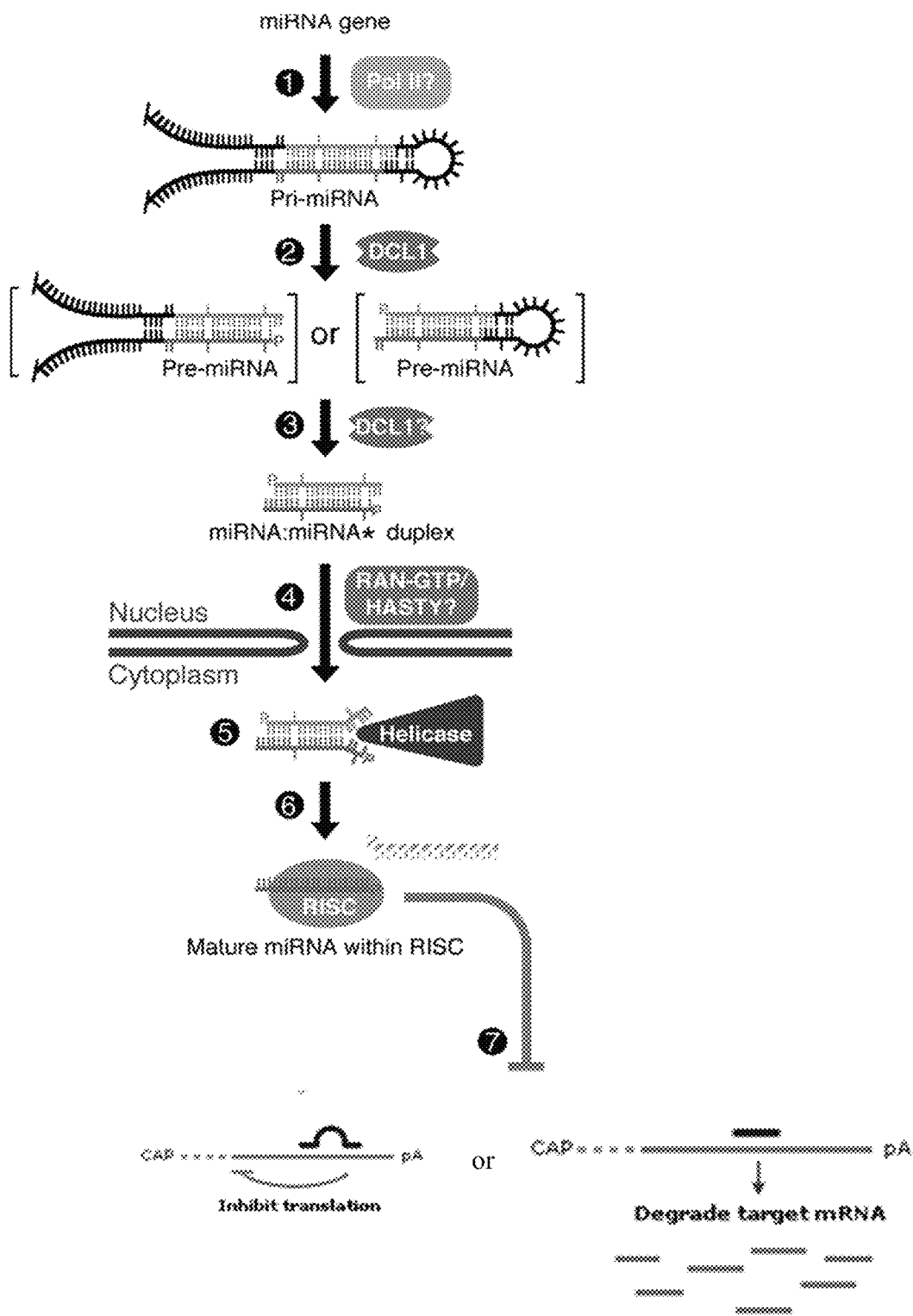
FIG. 1 Biogenesis and Mode of Action of miRNAs in Plant (Bartel D, Cell 116:281-297, 2004)
  Step 1: A miRNA gene is transcribed into Pri-miRNA by Pol II. There is an increasing evidence that, at least, some transcripts have Cap structure at 5' terminus and are polyadenylylated.at 3' terminus. The short-lived Pri-miRNA forms a stem-loop structure and quickly enters into Step 2.
  Step 2: Pri-miRNA is processed into Pre-miRNA by Dicer-1 resulting in exposure of one end of mature miRNA.
  Step 3: Pre-miRNA is processed into mature miRNA: miRNA* duplex (approx. 22 nt) by DCL1 or another gene.
  Step 4: miRNA is exported from nucleus into cytoplasm. Likely, HASTY, the plant orthologue of mammalian Exportin-5, is required for such exporting process.
  Step 5,6: A single-stranded miRNA is eventually incorporated into RISC (RNA-induced silencing complex) and binds specifically to target mRNA with perfect or near perfect sites complimentary to miRNA.
  Step 7: miRNA inhibits gene expression at post-transcription levels or translational levels.
Figure 2:
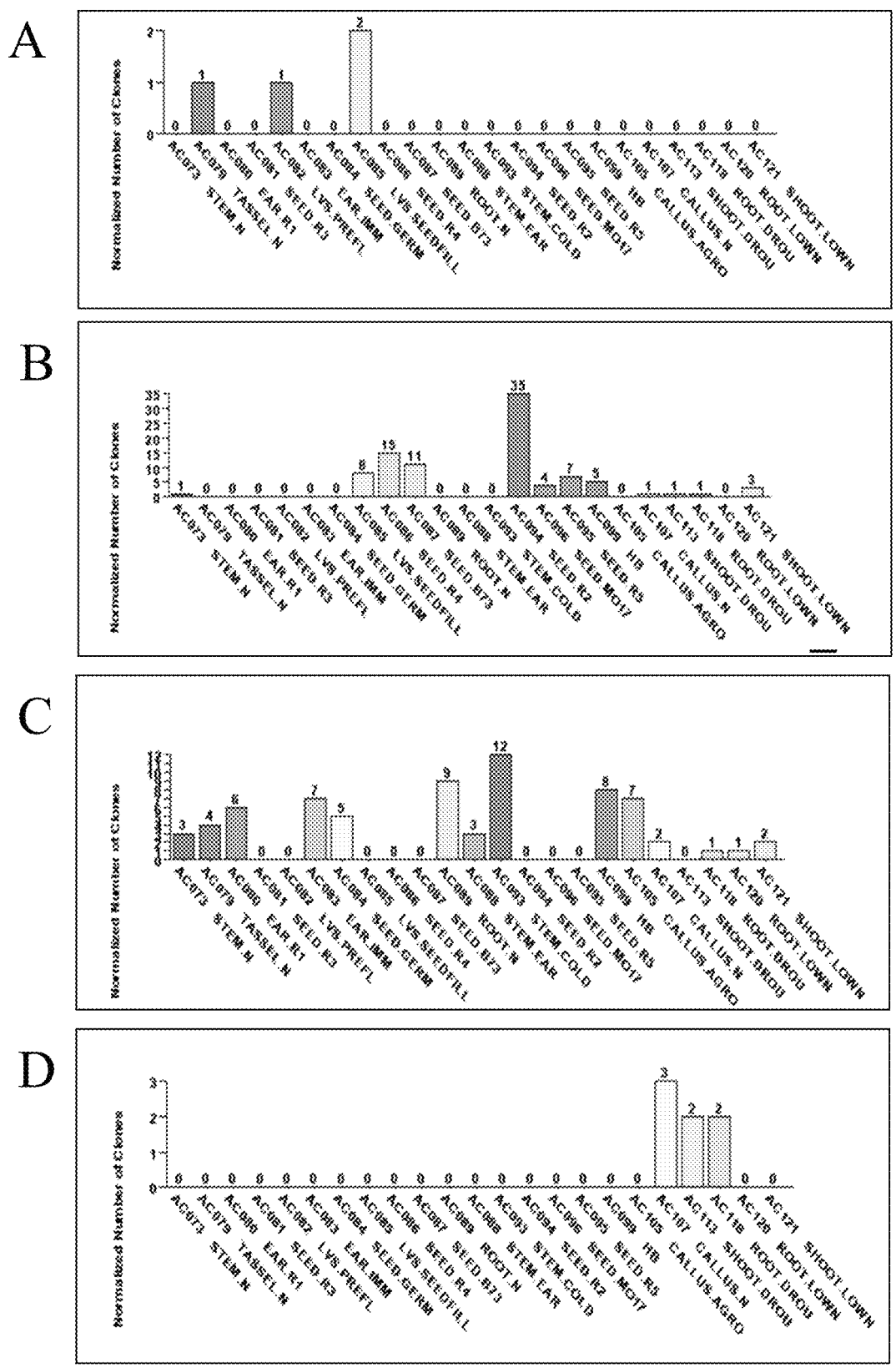
FIG. 2 Specific Expression Patterns of Maize microRNA precursors in Zea mays gene expression database.
  A: Expression of miR166 Precursor in Leaves and Tassel
  B: Predominate Expression of miR167 Precursor in Seeds
  C: Expression of miR159 Precursor in Everywhere but Seeds
  D: Stress Induced Expression of miR160 Precursor FIG. 3 Enhancing seed-specific expression
Maize miR159 is expressed in all tissues except (FIG. 3-A). If the gene of interest (GOI) is intended to express only in seeds with leaky 'seed-specific' promoter, one can incorporated a miRNA-tag (5'-AGAGCTCCCTTCAATCCAAA-3' (SEQ ID NO: 267), which is complementary to miR159 (SEQ ID NO: 268)) into 3'UTR following the GOI to make a generic binary vector to control leaky expression of the GOI in non-seed tissues by endogenous miR159 (FIG. 3-B).
Figure 3:
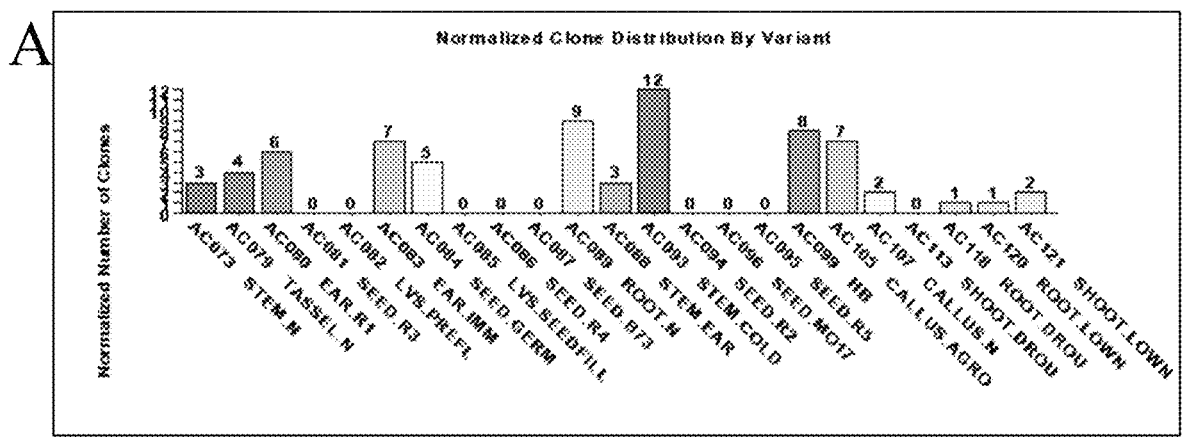
Figure 3:
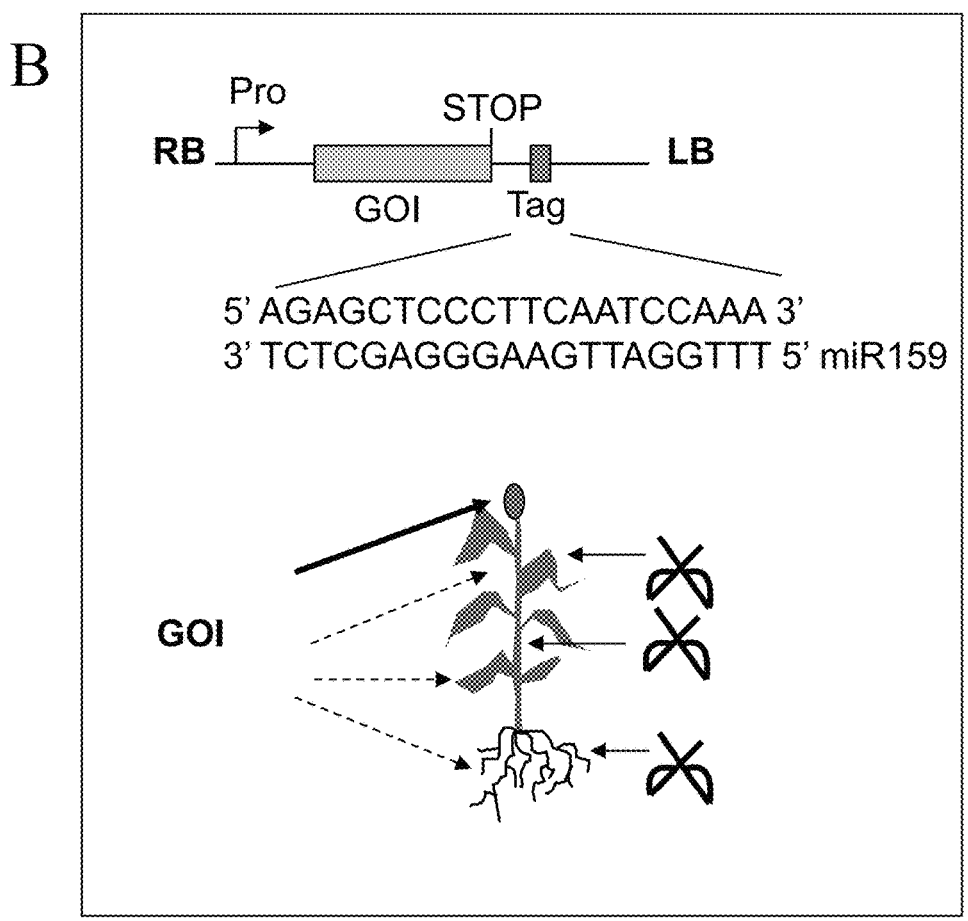

A total of 17 of the expressed miRNAs were detected exclusively in a particular mouse organ; these included: seven brain-specific miRNAs (miR-9, -124a, -124b, -135, -153, -183, -219), six lung-specific miRNAs (miR-18, -19a, -24, -32, -130, -213), two spleen-specific miRNAs (miR-189, -212), one liverspecific miRNA (miR-122a), and one heart-specific miRNA (miR-208) (Sempere et al. 2004; FIG. 2). Most of the indicated mouse brain-, liver and heart-specific miRNAs were also detected in the human counterpart organs. Among the 75 miRNAs that were detected in two or more mouse organs, the levels of 14 of these were detected in a particular mouse organ at levels at least two-fold higher than in any other organ; these included: seven brain-enriched miRNAs (miR-9*, -125a, -125b, -128, -132, -137, -139), three skeletal muscle-enriched miRNAs (miR-1d, -133, -206), two kidney-enriched miRNAs (miR-30b, -30c), and one spleen-enriched miRNA (miR-99a). All brain-enriched and skeletal muscle-enriched miRNAs had similar elevated levels in the human counterpart organs. There is a high conservation of expression of these organ-specific and organ-enriched miRNAs between mouse and human.

A group of six miRNAs was expressed primarily in mouse spleen (miR-127, -142-a, -142-s, -151, -189, -212). A group of five miRNAs was expressed in mouse and human liver (miR-122a, -152, -194, -199, -215) with some scattered expression in other organs including lung and kidney.

A group of seven miRNAs was expressed in mouse lung and kidney (miR-18, -20, -24, -32, -141, -193, -200b). Together, the last two groups might reflect a role of miRNAs in an epithelial cell type since liver, lung, and kidney are organs containing epithelial tissues.

A group of 17 miRNAs was expressed in mouse and human brain (miR-7, -9, -9*, -124a, -124b, -125a, -125b, -128, -132, -135, -137, -139, -153, -149, -183, -190, -219) with scattered expression in other organs.

A group of six miRNAs was expressed in mouse and human skeletal muscle and heart: miR-1b, -1d, -133 and -206 had elevated expression in heart and skeletal muscle with low expression in other organs and miR-143 and -208 were almost exclusively detected in heart and skeletal muscle.

A group of five miRNAs showed abundant expression across organs (let-7a, -7b, miR-30b, -30c).

The miRNA sequences are well known in the art and described for example in Sempere et al. 2004 and the additional electronically available data for this paper. For example some of the miRNA-tags are specified herein: hsa-miR-19a (SEQ ID NO: 90), hsa-let7b (SEQ ID NO: 91), hsa-miR-100 (SEQ ID NO: 92), hsa-miR-103-1 (SEQ ID NO: 93), hsa-miR-107 (SEQ ID NO: 94), hsa-miR-10a (SEQ ID NO: 95), hsa-miR-124b (SEQ ID NO: 96), hsa-miR-129a (SEQ ID NO: 97), hsa-miR-139 (SEQ ID NO: 98), hsa-miR-147 (SEQ ID NO: 99), hsa-miR-148 (SEQ ID NO: 100), hsa-miR-15a (SEQ ID NO: 101), hsa-miR-16 (SEQ ID NO: 102), hsa-miR-18 (SEQ ID NO: 103), hsa-miR-192 (SEQ ID NO: 104), hsa-miR-196 (SEQ ID NO: 105), hsa-miR-199a (SEQ ID NO: 106), hsa-let7a (SEQ ID NO: 107), hsa-miR-24 (SEQ ID NO: 108), hsa-miR-20 (SEQ ID NO: 109), hsa-miR-208 (SEQ ID NO: 110), hsa-miR-210 (SEQ ID NO: 111), hsa-miR-212 (SEQ ID NO: 112), hsa-miR-213 (SEQ ID NO: 113), hsa-miR-214 (SEQ ID NO: 114), hsa-miR-215 (SEQ ID NO: 115), hsa-miR-216 (SEQ ID NO: 116), hsa-miR-217 (SEQ ID NO: 117), hsa-miR-218 (SEQ ID NO: 118), hsa-miR-219 (SEQ ID NO: 119), hsa-miR-22 (SEQ ID NO: 120), hsa-miR-220 (SEQ ID NO: 121), hsa-miR-221 (SEQ ID NO: 122), hsa-miR-222 (SEQ ID NO: 123), hsa-miR-23a (SEQ ID NO:124), hsa-miR-19b (SEQ ID NO: 125), hsa-miR-96 (SEQ ID NO: 126), hsa-miR-26b (SEQ ID NO: 127), hsa-miR-27a (SEQ ID NO: 128), hsa-miR-28 (SEQ ID NO: 129), hsa-miR-29 (SEQ ID NO: 130), hsa-miR-29b (SEQ ID NO: 131), hsa-miR-30a (SEQ ID NO: 132), hsa-miR-30c (SEQ ID NO: 133), hsa-miR-30d (SEQ ID NO: 134), hsa-miR-30e (SEQ ID NO: 135), hsa-miR-32 (SEQ ID NO: 136), hsa-miR-33 (SEQ ID NO: 137), hsa-miR-7 (SEQ ID NO: 138), hsa-miR-91 (SEQ ID NO: 139), hsa-miR-92 (SEQ ID NO: 140), hsa-miR-93 (SEQ ID NO: 141), hsa-miR-95 (SEQ ID NO: 142), hsa-miR-98 (SEQ ID NO: 143), hsa-miR-26a (SEQ ID NO: 144). These sequences specify the potential miRNA-tag. The corresponding miRNA is the complementary sequence in RNA.

Preferably, the microRNA is an animal, mammalian or human microRNA selected from the group consisting of
a) the sequences as described by SEQ ID NO: 56, 57, 58, 59, 60, 61, 62, and 63, and
b) derivatives of the sequences described by SEQ ID NO: 56, 57, 58, 59, 60, 61, 62, and 63, and
c) the complementary RNA sequence to a sequence as described by any of SEQ ID NO: 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, or 208, and
d) derivatives of RNA sequence complementary to a sequence as described by any of SEQ ID NO: 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, or 208.

A derivative is preferably a sequence, which fulfills the same functional endogenous purpose (e.g., certain gene control functions) in an organism of a different species (i.e. different from the specie where the disclosed miRNA is derived from). Said derivates may have certain mismatches with respect to the specifically disclosed sequences, preferably a derivative is characterized by having an identity of at least 70%, preferably at least 80% or 85%, more preferably at least 90%, most preferably at least 95% to a sequence described by any of SEQ ID NO: 56, 57, 58, 59, 60, 61, 62, and 63 or a RNA sequence complementary to a sequence as described by any of SEQ ID NO: 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, or 208. The mismatches with the specified miRNA maybe throughout the entire sequence but are preferably in the 3' region (corresponding to the 5'-region of the miRNA tag).

Another embodiment of the invention relates to a pharmaceutically preparation of at least one expression construct, a chimeric ribonucleotide sequence, or a vector according to the invention.

More specific applications in animals and humans, especially in the field of pharmaceutical applications are described herein below.

As mentioned above the method and subject matter of the invention can be employed to increase specificity of expression for chimeric nucleotide sequence, which may encode
i) a protein (i.e. by comprising an open reading frame (ORF),
ii) a functional RNA (e.g., a antisense, sense, double-stranded or ribozyme RNA), which is preferably employed in a gene silencing approach.

2.1 Expression with Enhanced Specificity

The method for expression or over-expression of nucleotide sequences in various organism is well known to the person skilled in the art (Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; see section 3.3 for some details).

2.2 Gene Silencing with Enhanced Specificity

The chimeric RNA molecules of the invention, the expression constructs and the expression vectors for their expression, and the transgenic organism comprising said molecules could be utilized in gene silencing (i.e. to attenuate, reduce or suppress expression of target genes in target cells or organism). For this the chimeric RNA may comprise sequences, which are capable to provide an antisense RNA (for antisense RNA mediated gene silencing), double-stranded RNA (for dsRNA interference gene silencing) or senseRNA (for co-suppression gene silencing)

The methods of the invention will lead to better results and/or higher efficiencies when compared to the methods using conventional sense, antisense, or double-stranded RNA nucleotide sequences.

Another embodiment of the invention relates to composition for altering, preferably reducing or attenuating, expression of a target gene, comprising at least one chimeric RNA of the invention. Yet another embodiment of the invention relates to a method for attenuating (or reducing or suppressing) expression of at least one target gene in an eukaryotic cell, comprising introducing a chimeric RNA molecule of the invention (or an expression construct or vector encoding the same) into the cells in an amount sufficient to attenuate expression of the target gene, wherein the chimeric RNA molecule comprises at least one ribonucleotide sequence that is substantially identical to at least a part of the nucleotide sequence of the target gene.

Any gene being expressed in a cell (preferably an eukaryotic cell) can be targeted. A gene that is expressed in the cell is one that is transcribed to yield a RNA (e.g., a mRNA) and, optionally, a protein. Preferably the target gene is a eukaryotic gene, more preferably a mammalian, nematode, fungal or plant gene. Preferably the target gene is an endogenous gene of the cell or a heterologous gene relative to the genome of the cell, such as a pathogen gene. Preferably, the gene of a pathogen is from a pathogen capable to infect an eukaryotic organism. Most preferably, said pathogen is selected from the group of virus, bacteria, fungi and nematodes.

The chimeric RNA may be produced outside the cell (i.e. the host cell in which gene silencing should be achieved), or may be recombinantly produced by an expression construct or expression vector within the cell. The host cell is preferably eukaryotic cell, more preferably a nematode, mammalian cell or a plant cell.

Preferably, the target gene expression is attenuated (or reduced or suppressed) by at least about 10%, preferably at least about 30%, more preferably at least about 50%, even more preferably at least about 70%, most preferably at least about 90%.

To achieve gene silencing the chimeric RNA of the invention comprises at least one ribonucleotide sequence that is substantially identical (as defined above), preferably identical, to at least a part of at least one target gene. Preferably, said part of a target gene having substantial identity to said ribonucleotide sequence has a length of at least 15 nucleotides, preferably at least 19 nucleotides, more preferably at least 50 nucleotides, even more preferably at least 100 nucleotides, most preferably at least 250 nucleo-tides. More preferably, said nucleotide sequence has an identity of at least 65%, preferably at least 80%, more preferably at least 90%, most preferably 95%, even more preferably 100% to a sequence of at least 15 nucleotides, preferably at least 19 nucleotides, more preferably at least 50 nucleotides, even more preferably 100 nucleotides, most preferably at least 250 nucleotides of at least one target gene. Preferably, said first ribonucleotide sequence hybridizes (preferably under stringent conditions, more preferably under low stringency conditions, most preferably under high stringency conditions) to a sequence of the target gene.

In a preferred embodiment the nucleotide sequence is substantially identical, preferably identical, to a part of the coding sequence or the non-coding sequence of the target gene (preferably an eukaryotic gene, such as a mammalian or plant gene). The non-coding sequence can be the 5'- or 3'-untranslated sequence or the introns but can also be a nontranscribed sequence. Non-coding sequences as target sequence are preferred in cases where the target gene encodes a member of a gene family (i.e. different genes encoding very similar proteins).

The target gene can be an endogenous gene or an exogenous or foreign gene (i.e., a transgene or a pathogen gene). For example, a transgene that is present in the genome of a cell as a result of genomic integration of the viral delivery construct can be regulated using chimeric RNA according to the invention. The foreign gene can be integrated into the host genome (preferably the chromosomal DNA), or it may be present on an extrachromosomal genetic construct such as a plasmid or a cosmid. For example, the target gene may be present in the genome of the cell into which the chimeric RNA is introduced, or in the genome of a pathogen, such as a virus, a bacterium, a fungus or a protozoan, which is capable of infecting such organism or cell.

The eukaryotic cell or organism to which the chimeric RNA of the invention can be delivered can be derived from any eukaryotic organism, such as for example without limitation, plants or animals, such as mammals, insects, nematodes, fungi, algae, fish, and birds. Likewise, the chimeric RNA molecule of the invention or the expression constructs or vectors for its expression can be used to suppress or reduce any target gene in any eukaryotic organism. In some embodiments of the invention also prokaryotic organism comprising the chimeric RNA of the invention are useful. For example prokaryotic cells and organism can be used to produce or amplify the chimeric RNA of the invention or an expression construct or vector encoding the same. Furthermore, prokaryotic organism can be utilized as vehicles to introduce the chimeric RNA of the invention into animals e.g. by feeding. Also, prokaryotic organisms, for example *Agrobacteria*, can advantageously be employed as vehicles for the transformation of, for example, plant organisms.

Thus a further aspect of the invention relates to cells and organism (e.g., plant, animal, protozoan, virus, bacterium, or fungus), which comprise at least one chimeric RNA of the invention, or an expression construct or expression vectors encoding said chimeric RNA molecule (as defined above in more detail).

Another embodiment of the present invention relates to a method for attenuating (or reducing) expression of at least one target gene in an eukaryotic cell, comprising introducing a chimeric RNA molecule of the invention into the cell in an amount sufficient to attenuate expression of the target gene, wherein the chimeric RNA molecule comprises at least one ribonucleotide sequence that is substantially identical, preferably identical, to at least part of the nucleotide sequence of the target gene. Depending on the particular target gene and the dose of chimeric RNA delivered, the method may partially or completely inhibit expression of the gene in the cell. Preferably the chimeric RNA of the invention is capable of effectively eliminating, substantially reducing, or at least partially reducing the level of a RNA (preferably mRNA) transcript or protein encoded by the target gene (or gene family). Preferably, the expression of the target gene (as measured by the expressed RNA or protein) is reduced, inhibited or attenuated by at least 10%, preferably at least 30% or 40%, preferably at least 50% or 60%, more preferably at least 80%, most preferably at least 90% or 95%. The levels of target products such as transcripts or proteins may be decreased throughout an organism such as a plant or mammal, or such decrease in target products may be localized in one or more specific organs or tissues of the organism. For example, the levels of products may be decreased in one or more of the tissues and organs of a plant including without limitation: roots, tubers, stems, leaves, stalks, fruit, berries, nuts, bark, pods, seeds and flowers. A preferred organ is a seed of a plant.

The expression of two or more genes can be attenuated concurrently by introducing two or more chimeric RNAs or one RNA capable to provide (e.g., by subsequent RNA processing) more than one chimeric RNA molecule into the cell in amounts sufficient to attenuate expression of their respective target genes.

To overcome the sequence-independent protein kinase PKR stress-response triggered by dsRNA, modifications are made to a chimeric RNA molecule, which would normally activate the interferon pathway such that the interferon pathway is not activated. In certain embodiments, the cells can be treated with an agent(s) that inhibits the general dsRNA response(s) by the host cells, such as may give rise to sequence-independent apoptosis. For instance, the cells can be treated with agents that inhibit the dsRNA-dependent protein kinase known as PKR (protein kinase RNA-activated). Likewise, overexpression of agents, which ectopically activate eIF2α□ can be used. Other agents, which can be used to suppress the PKR response, include inhibitors of IκB phosphorylation of IκB, inhibitors of IκB ubiquitination, inhibitors of I□B degradation, inhibitors of NFκB nuclear translocation, and inhibitors of NF-□B interaction with κB response elements. Other inhibitors of sequence-independent dsRNA response in cells include the gene product of the vaccinia virus E3L. The E3L gene product contains two distinct domains. A conserved carboxyterminal domain has been shown to bind dsRNA and inhibit the antiviral dsRNA response by cells. Expression of at least that portion of the E3L gene in the host cell, or the use of polypeptide or peptidomimetics thereof, can be used to suppress the general dsRNA response. Caspase inhibitors sensitize cells to killing by dsRNA. Accordingly, ectopic expression or activation of caspases in the host cell can be used to suppress the general dsRNA response.

3. Specific Applications

The subsequent application of compositions and methods according to the invention may be mentioned by way of example, but not by limitation:

3.1 Applications in Plant Biotechnology

The method according to the invention is preferably employed for the purposes of plant biotechnology for generating plants with advantageous properties. Thus, the suitability of the plants or their seeds as foodstuff or feeding stuff can be improved, for example via a modification of the compositions and/or the content of metabolites, in particular proteins, oils, vitamins and/or starch. Also, growth rate, yield or resistance to biotic or abiotic stress factors can be increased. The subsequent applications in the field of plant biotechnology are particularly advantageous.

A further aspect of the invention relates to a transgenic plant or plant cell comprising a chimeric RNA of the invention, or an expression construct or expression vector for expression of said chimeric RNA. Another embodiment relates to the use of the transgenic organism according to the invention (e.g., the transgenic plant) and of the cells, cell cultures, parts—such as, for example, in the case of transgenic plant organisms roots, leaves and the like—derived from them and transgenic propagation material such as seeds or fruits for the production of foodstuffs or feeding stuffs, pharmaceuticals or fine chemicals, such as, for example, enzymes, vitamins, amino acids, sugars, fatty acids, natural or synthetic flavorings, aromas and colorants. Especially preferred is the production of triacylglycerides, lipids, oils, fatty acids, starches, tocopherols and tocotrienols and carotenoids. Genetically modified plants according to the invention which can be consumed by humans and animals can also be used as foodstuffs or feeding stuffs, for example directly or after undergoing a processing which is known per se.

3.1.1 Plant Target Genes for Expression with Enhanced Specificity 3.1.1.1. Herbicide Resistance The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP Synthase enzymes. The deh gene encodes the enzyme dalapon dehalogenase and confers resistance to the herbicide dalapon. The bxn gene codes for a specific nitrilase enzyme that converts bromoxynil to a non-herbicidal degradation product.

For this application either a miRNA-tag, which allows for enhanced specific expression in green leafs is preferred for designing the miRNA-tag. For example, *Arabidopsis* miR160b expressed in root and flower, but not in the leafs is good for such application.

3.1.1.2 Insect Resistance

An important aspect of the present invention concerns the introduction of insect resistance-conferring genes into plants. Potential insect resistance genes which can be introduced include *Bacillus thuringiensis* crystal toxin genes or Bt genes (Watrud 1985). Bt genes may provide resistance to lepidopteran or coleopteran pests such as European Corn Borer (ECB) and corn rootworm (CRW). Preferred Bt toxin genes for use in such embodiments include the CryIA(b) and CryIA(c) genes. Endotoxin genes from other species of *B. thuringiensis* which affect insect growth or development may also be employed in this regard. Protease inhibitors may also provide insect resistance (Johnson 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes which encode inhibitors of the insects' digestive system, or those that encode enzymes or co-factors that facilitate the production of inhibitors, may also be useful. This group may be exemplified by cystatin and amylase inhibitors, such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock 1990; Czapla & Lang, 1990). Lectin genes contemplated to be useful include, for example, barley and wheat germ agglutinin (WGA) and rice lectins (Gatehouse 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated, that the expression of juvenile hormone esterase, directed towards specific insect pests, may also result in insecticidal activity, or perhaps cause cessation of metamorphosis (Hammock 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn 1981). The introduction of genes that can regulate the production of maysin, and genes involved in the production of dhurrin in *sorghum*, is also contemplated to be of use in facilitating resistance to earworm and rootworm, respectively.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson & Guss, 1972).

Further genes encoding proteins characterized as having potential insecticidal activity may also be used as transgenes in accordance herewith. Such genes include, for example, the cowpea trypsin inhibitor (CpTI; Hilder 1987) which may be used as a rootworm deterrent; genes encoding avermectin (Campbell 1989; Ikeda 1987) which may prove particularly useful as a corn rootworm deterrent; ribosome inactivating protein genes; and even genes that regulate plant structures. Transgenic maize including anti-insect antibody genes and genes that code for enzymes that can covert a non-toxic insecticide (proinsecticide) applied to the outside of the plant into an insecticide inside the plant are also contemplated.

For this application either a miRNA-tag, which allows for enhanced specific expression in tissue, which presents the interaction or entry side for the insect (or other pathogen) (e.g., the epidermis) or a miRNA-tag corresponding to an miRNA, which is endogenously suppressed by the insect or pathogen induced stress factor is preferred to be employed for designing the miRNA-tag. For example, maize miR167 is predominantly expressed in seed, use of Zm miR167 tag in a transgene construct expressing insecticidal molecules can prevent leaky expression of such molecules in the seeds. Some of them (e.g. lectin) is a potential allergen for human.

3.1.1.3 Environment or Stress Resistance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Benefits may be realized in terms of increased resistance to freezing temperatures through the introduction of an "antifreeze" protein such as that of the Winter Flounder (Cutler 1989) or synthetic gene derivatives thereof. Improved chilling tolerance may also be conferred through increased expression of glycerol-3-phosphate acetyltransferase in chloroplasts (Murata 1992; Wolter 1992). Resistance to oxidative stress (often exacerbated by conditions such as chilling temperatures in combination with high light intensities) can be conferred by expression of superoxide dismutase (Gupta 1993), and may be improved by glutathione reductase (Bowler 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically-active solutes can impart protection against drought. Within this class of genes are DNAs encoding mannitol dehydrogenase (Lee and Saier, 1982) and trehalose-6-phosphate synthase (Kaasen 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski 1992).

Similarly, the efficacy of other metabolites in protecting either enzyme function (e.g. alanopine or propionic acid) or membrane integrity (e.g., alanopine) has been documented (Loomis 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson 1992), sorbitol, dulcitol (Karsten 1992), glucosylglycerol (Reed 1984; Erdmann 1992), sucrose, stachyose (Koster & Leopold 1988; Blackman 1992), ononitol and pinitol (Vernon & Bohnert 1992), and raffinose (Bernal-Lugo & Leopold 1992). Other osmotically active solutes which are not sugars include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure 1989). All three classes of these proteins have been demonstrated in maturing (i.e., desiccating) seeds. Within these 3 types of proteins, the Type-11 (dehydrin-type) have generally been implicated in drought and/or desiccation tolerance in vegetative plant parts (e.g. Mundy and Chua, 1988; Piatkowski 1990; Yamaguchi-Shinozaki 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor-induced promoter (such as the promoters for the turgor-induced genes described in Guerrero et al. 1990 and Shagan 1993). Spatial and temporal expression patterns of these genes may enable maize to better withstand stress.

Expression of genes that are involved with specific morphological traits that allow for increased water extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan 1995).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Improved protection of the plant to abiotic stress factors such as drought, heat or chill, can also be achieved—for example—by overexpressing antifreeze polypeptides from Myoxocephalus Scorpius (WO 00/00512), Myoxocephalus octodecemspinosus, the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREB1A factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

For this application either a miRNA-tag, which allows for enhanced specific expression in stress-sensitive tissue (e.g., young seedling or embryo) or a miRNA-tag corresponding to an miRNA, which is endogenously suppressed by the stress factor is preferred to be employed for designing the miRNA-tag.

3.1.1.4 Disease Resistance

It is proposed that increased resistance to diseases may be realized through introduction of genes into plants period. It is possible to produce resistance to diseases caused, by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo 1988, Hemenway 1988, Abel 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol 1990). Included amongst the PR proteins are β-1,3-glucanases, chitinases, and osmotin and other proteins that are believed to function in plant resistance to disease organisms. Other genes have been identified that have antifungal properties, e.g., UDA (stinging nettle lectin) and hevein (Broakgert 1989; Barkai-Golan 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

Furthermore, a resistance to fungi, insects, nematodes and diseases, can be achieved by by targeted accumulation of certain metabolites or proteins. Such proteins include but are not limited to glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, a-amylase inhibitor or protease inhibitors (cowpea trypsin inhibitor), lectins such as wheatgerm agglutinin, RNAses or ribozymes. Further examples are nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents of these. The accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77). The expression of synthetic cryIA(b) and cryIA(c) genes, which encode lepidoptera-specific *Bacillus thuringiensis* D-endotoxins can bring about a resistance to insect pests in various plants (Goyal R K et al. (2000) Crop Protection 19(5):307-312). Further target genes which are suitable for pathogen defense comprise "polygalacturonaseinhibiting protein" (PGIP), thaumatine, invertase and antimicrobial peptides such as lactoferrin (Lee T J et al. (2002) J Amer Soc Horticult Sci 127(2):158-164).

For this application either a miRNA-tag, which allows for enhanced specific expression in tissue, which presents the interaction or entry side for the pathogen (e.g., the epidermis) or a miRNA-tag corresponding to an miRNA, which is endogenously suppressed by the pathogen induced stress factor is preferred to be employed for designing the miRNA-tag. For example, maize miR167 is predominantly expressed in seeds, use of a Zm miR167 tag in a transgene construct expressing anti-pathogene molecules can prevent leaky expression of such molecules in the seeds.

3.1.1.5 Mycotoxin Reduction/Elimination

Production of mycotoxins, including aflatoxin and fumonisin, by fungi associated with plants is a significant factor in rendering the grain not useful. These fungal organisms do not cause disease symptoms and/or interfere with the growth of the plant, but they produce chemicals (mycotoxins) that are toxic to animals. Inhibition of the growth of these fungi would reduce the synthesis of these toxic substances and, therefore, reduce grain losses due to mycotoxin contamination. Novel genes may be introduced into plants that would inhibit synthesis of the mycotoxin without interfering with fungal growth. Expression of a novel gene which encodes an enzyme capable of rendering the mycotoxin nontoxic would be useful in order to achieve reduced mycotoxin contamination of grain. The result of any of the above mechanisms would be a reduced presence of mycotoxins on grain.

For this application either a miRNA-tag, which allows for enhanced specific expression in tissue, which presents the interaction or entry side for the fungal pathogen (e.g., the epidermis) or a miRNA-tag corresponding to an miRNA, which is endogenously suppressed by the fungal pathogen induced stress factor is preferred to be employed for designing the miRNA-tag. Alternatively, a miRNA-tag, which ensures enhanced seed-specific or preferential expression can be employed. For example, maize miR156 is expressed everywhere but seeds, use of miR156 tag could enhance seed-specific expression.

3.1.1.6 Grain Composition or Quality

Genes may be introduced into plants, particularly commercially important cereals such as maize, wheat or rice, to improve the grain for which the cereal is primarily grown. A wide range of novel transgenic plants produced in this manner may be envisioned depending on the particular end use of the grain.

For example, the largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes but in no way provide an exhaustive list of possibilities.

The protein of many cereal grains is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after the grain is supplemented with other inputs for feed formulations. For example, when the grain is supplemented with soybean meal to meet lysine requirements, methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway which are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyse steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. DNA may be introduced that decreases the expression of members of the zein family of storage proteins. This DNA may encode ribozymes or antisense sequences directed to impairing expression of zein proteins or expression of regulators of zein expression such as the opaque-2 gene product. The protein composition of the grain may be modified through the phenomenon of cosuppression, i.e., inhibition of expression of an endogenous gene through the expression of an identical structural gene or gene fragment introduced through transformation (Goring 1991). Additionally, the introduced DNA may encode enzymes which degrade zeines. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable energy content and density of the seeds for uses in feed and food. The introduced genes may encode enzymes that remove or reduce rate-limitations or regulated steps in fatty acid or lipid biosynthesis. Such genes may include, but are not limited to, those that encode acetyl-CoA carboxylase, ACPacyltransferase, 3-ketoacyl-ACP synthase, plus other well-known fatty acid biosynthetic activities. Other possibilities are genes that encode proteins that do not possess enzymatic activity such as acyl carrier protein. Additional examples include 2-acetyltransferase, oleosin pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo. Genes may be introduced that alter the balance of fatty acids present in the oil providing a more healthful or nutritive feedstuff. The introduced DNA may also encode sequences that block expression of enzymes involved in fatty acid biosynthesis, altering the proportions of fatty acids present in the grain such as described below.

Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA which blocks or eliminates steps in pigment production pathways.

Feed or food comprising some cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. For example, maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase which enhances phytic acid breakdown. These genes would increase levels of available phosphate in the diet, reducing the need for supplementation with mineral phosphate.

Numerous other examples of improvement of cereals for feed and food purposes might be described. The improvements may not even necessarily involve the grain, but may, for example, improve the value of the grain for silage. Introduction of DNA to accomplish this might include sequences that alter lignin production such as those that result in the "brown midrib" phenotype associated with superior feed value for cattle.

In addition to direct improvements in feed or food value, genes may also be introduced which improve the processing of grain and improve the value of the products resulting from the processing. The primary method of processing certain grains such as maize is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, Theological properties, and the like. To accomplish these changes in properties, genes that encode granule-bound or soluble starch synthase activity or branching enzyme activity may be introduced alone or combination. DNA such as antisense constructs may also be used to decrease levels of endogenous activity of these enzymes. The introduced genes or constructs may possess regulatory sequences that time their expression to specific intervals in starch biosynthesis and starch granule development. Furthermore, it may be advisable to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn and other grains, the value of which may be improved by introduction and expression of genes. The quantity of oil that can be extracted by wetmilling may be elevated by approaches as described for feed and food above. Oil properties may also be altered to improve its performance in the production and use of cooking oil, shortenings, lubricants or other oil-derived products or improvement of its health attributes when used in the food-related applications. Novel fatty acids may also be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids.

Improvements in the other major cereal wetmilling products, gluten meal and gluten feed, may also be achieved by the introduction of genes to obtain novel plants. Representative possibilities include but are not limited to those described above for improvement of food and feed value.

In addition it may further be considered that the plant be used for the production or manufacturing of useful biological compounds that were either not produced at all, or not produced at the same level, in the plant previously. The novel plants producing these compounds are made possible by the introduction and expression of genes by transformation methods. The possibilities include, but are not limited to, any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance gamma-zein synthesis, popcorn with improved popping, quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

For seed-based applications, a miRNA-tag, which ensures enhanced seed-specific or preferential expression can be employed.

3.1.1.7 Tuber or Seed Composition or Quality

Various traits can be advantegously expressed especially in seeds or tubers to improve composition or quality. Such traits include but are not lifted to:

Expression of metabolic enzymes for use in the food-and-feed sector, for example of phytases and cellulases. Especially preferred are nucleic acids such as the artificial cDNA which encodes a microbial phytase (GenBank Acc. No.: A19451) or functional equivalents thereof.

Expression of genes which bring about an accumulation of fine chemicals such as of tocopherols, tocotrienols or carotenoids. An example is phytoene desaturase. Preferred are nucleic acids which encode the *Narcissus pseudonarcissus* photoene desaturase (GenBank Acc. No.: X78815) or functional equivalents thereof.

Production of nutraceuticals such as, for example, polyunsaturated fatty acids (for example arachidonic acid, eicosapentaenoic acid or docosahexaenoic acid) by expression of fatty acid elongases and/or desaturases, or production of proteins with improved nutritional value such as, for example, with a high content of essential amino acids (for example the high-methionine 2S albumin gene of the brazil nut). Preferred are nucleic acids which encode the Bertholletia excelsa high-methionine 2S albumin (GenBank Acc. No.: AB044391), the *Physcomitrella patens* Δ6-acyl-lipid desaturase (GenBank Acc. No.: AJ222980; Girke et al. (1998) Plant J 15:39-48), the *Mortierella alpina* Δ6-desaturase (Sakuradani et al. 1999 Gene 238:445-453), the *Caenorhabditis elegans* Δ5-desaturase (Michaelson et al. 1998, FEBS Letters 439:215-218), the *Caenorhabditis elegans* Δ5-fatty acid desaturase (des-5) (GenBank Acc. No.: AF078796), the *Mortierella alpina* Δ5-desaturase (Michaelson et al. JBC 273: 19055-19059), the *Caenorhabditis elegans* Δ6-elongase (Beaudoin et al. 2000, PNAS 97:6421-6426), the *Physcomitrella patens* Δ6-elongase (Zank et al. 2000, Biochemical Society Transactions 28:654-657), or functional equivalents of these.

Production of high-quality proteins and enzymes for industrial purposes (for example enzymes, such as lipases) or as pharmaceuticals (such as, for example, antibodies, blood clotting factors, interferons, lymphokines, colony stimulation factor, plasminogen activators, hormones or vaccines, as described by Hood E E, Jilka J M (1999) Curr Opin Biotechnol 10(4):382-6; Ma J K, Vine N D (1999) Curr Top Microbiol Immunol 236:275-92). For example, it has been possible to produce recombinant avidin from chicken albumen and bacterial b-glucuronidase (GUS) on a large scale in transgenic maize plants (Hood et al. (1999) Adv Exp Med Biol 464:127-47. Review).

Obtaining an increased storability in cells which normally comprise fewer storage proteins or storage lipids, with the purpose of increasing the yield of these substances, for example by expression of acetyl-CoA carboxylase. Preferred nucleic acids are those which encode the *Medicago sativa* acetyl-CoA carboxylase (ACCase) (GenBank Acc. No.: L25042), or functional equivalents thereof.

Reducing levels of α-glucan L-type tuber phosphorylase (GLTP) or .α-glucan H-type tuber phosphorylase (GHTP) enzyme activity preferably within the potato tuber (see U.S. Pat. No. 5,998,701). The conversion of starches to sugars in potato tubers, particularly when stored at temperatures below 7° C., is reduced in tubers exhibiting reduced GLTP or GHTP enzyme activity. Reducing cold-sweetening in potatoes allows for potato storage at cooler temperatures, resulting in prolonged dormancy, reduced incidence of disease, and increased storage life. Reduction of GLTP or GHTP activity within the potato tuber may be accomplished by such techniques as suppression of gene expression using homologous antisense or double-stranded RNA, the use of co-suppression, regulatory silencing sequences. A potato plant having improved cold-storage characteristics, comprising a potato plant transformed with an expression cassette having a TPT promoter sequence operably linked to a DNA sequence comprising at least 20 nucleotides of a gene encoding an α-glucan phosphorylase selected from the group consisting of α-glucan L-type tuber phosphorylase (GLTP) and α-glucan H-type phosphorylase (GHTP).

Further examples of advantageous genes are mentioned for example in Dunwell J M, Transgenic approaches to crop improvement, J Exp Bot. 2000; 51 Spec No; pages 487-96.

For seed-based applications, a miRNA-tag, which ensures enhanced seed or tuber-specific or preferential expression can be employed. For example, maize miR156 is expressed everywhere but seeds, use of miR156 tag could enhance seed-specific expression.

3.1.1.8 Plant Agronomic Characteristics

Two of the factors determining where plants can be grown are the average daily temperature during the growing season and the length of time between frosts. Within the areas where it is possible to grow a particular plant, there are varying limitations on the maximal time it is allowed to grow to maturity and be harvested. The plant to be grown in a particular area is selected for its ability to mature and dry down to harvestable moisture content within the required period of time with maximum possible yield. Therefore, plant of varying maturities are developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. Genes that influence maturity and/or dry down can be identified and introduced into plant lines using transformation techniques to create new varieties adapted to different growing locations or the same growing location but having improved yield to moisture ratio at harvest. Expression of genes that are involved in regulation of plant development may be especially useful, e.g., the liguleless and rough sheath genes that have been identified in plants.

Genes may be introduced into plants that would improve standability and other plant growth characteristics. For example, expression of novel genes which confer stronger stalks, improved root systems, or prevent or reduce ear droppage would be of great value to the corn farmer. Introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilate into the grain and thus increase yield. Overexpression of genes within plants that are associated with "stay green" or the expression of any gene that delays senescence would be advantageous. For example, a non-yellowing mutant has been identified in *Festuca pratensis* (Davies 1990). Expression of this gene as well as others may prevent premature breakdown of chlorophyll and thus maintain canopy function.

3.1.1.9 Nutrient Utilization

The ability to utilize available nutrients and minerals may be a limiting factor in growth of many plants. It is proposed that it would be possible to alter nutrient uptake, tolerate pH extremes, mobilization through the plant, storage pools, and availability for metabolic activities by the introduction of novel genes. These modifications would allow a plant to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

For seed-based applications, a miRNA-tag, which ensures enhanced seed-specific or preferential expression can be employed. For example, maize miR156 is expressed everywhere but seeds, use of miR156 tag could enhance seed-specific expression.

3.1.1.10 Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani 1990). For example, a number of mutations were discovered in maize that confers cytoplasmic male sterility. One mutation in particular, referred to as T cytoplasm, also correlates with sensitivity to Southern corn leaf blight. A DNA sequence, designated TURF-13 (Levings 1990), was identified that correlates with T cytoplasm. It would be possible through the introduction of TURF-13 via transformation to separate male sterility from disease sensitivity. As it is necessary to be able to restore male fertility for breeding purposes and for grain production, it is proposed that genes encoding restoration of male fertility may also be introduced.

For this application, a miRNA-tag, which ensures enhanced pollen-specific or preferential expression can be employed.

3.1.2 Plant Target Genes for Gene Silencing with Enhanced Specificity

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA or double-stranded RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Expression of antisense-RNA or double-stranded RNA by one of the expression cassettes of the invention is especially preferred. Also expression of sense RNA can be employed for gene silencing (co-suppression). This RNA is preferably a non-translatable RNA. Gene regulation by double-stranded RNA ("double-stranded RNA interference"; dsR-NAi) is well known in the arte and described for various organism including plants (e.g., Matzke 2000; Fire A et al 1998; WO 99/32619; WO 99/53050; WO 00/68374; WO 00/44914; WO 00/44895; WO 00/49035; WO 00/63364).

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants which possess them. The transgenic plants may possess reduced levels of polypeptides including but not limited to the polypeptides cited above that may be affected by antisense RNA.

It is also possible that genes may be introduced to produce novel transgenic plants which have reduced expression of a native gene product by a mechanism of cosuppression. It has been demonstrated in tobacco, tomato, and *petunia* (Goring 1991; Smith 1990; Napoli 1990; van der Krol 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

The possible target genes stated are to be understood by way of example, but not by limitation:

3.1.2.1 Improved protection against abiotic stress factors (heat, chill, drought, increased moisture, environmental toxins, UV radiation). It is preferred to reduce the expression of genes, which are involved in stress reactions.

For this application either a miRNA-tag, which allows for enhanced specific expression in sensitive tissue (young seedling, embryo) or a miRNA-tag corresponding to an miRNA, which is endogenously suppressed by the stress factor is preferred to be employed for designing the miRNA-tag.

3.1.2.2 Modification of the Composition and/or the Content of Fatty Acids, Lipids or Oils A modification of the fatty acid contents or the fatty acid composition, preferably in an oil crop such as oilseed rape or sunflower, can be achieved, for example, by reducing the gene expression of fatty acid biosynthesis genes, preferably those selected from the group consisting of genes encoding acetyl transacylases, acyl transport proteins ("acyl carrier protein"), desaturases such as stearyl desaturases or microsomal D12-desaturases, in particular Fad2-1 genes, malonyl transacylase, β-ketoacyl-ACP synthetases, 3-keto-ACP reductases, enoyl-ACP hydrases, thioesterases such as acyl-ACP thioesterases, enoyl-ACP reductases. Various further advantageous approaches for modifying the lipid composition are described (Shure M et al. (1983) Cell 35:225-233; Preiss et al. (1987) Tailoring Genes for Crop Improvement (Bruening et al., eds.), Plenum Press, S. 133-152; Gupta et al. (1988) Plant Mol Biol. 10:215-224; Olive et al. (1989) Plant Mol Biol 12:525-538; Bhattacharyya et al. (1990) Cell 60:155-122; Dunwell J M (2000) J Exp Botany 51Spec No:487-96; Brar D S et al. (1996) Biotech Genet Eng Rev 13:167-79; Kishore G M and Somerville C R (1993) Curr Opin Biotech 4(2):152-8). Preferred are, in particular, Fad2 genes (for example those described by Genbank Acc. No.: AF124360 (*Brassica carinata*), AF042841 (*Brassica rapa*), L26296 (*Arabidopsis thaliana*), A65102 (*Corylus avellana*)). Further advantageous genes and methods for modifying the lipid content are described, for example, in U.S. Pat. No. 5,530,192 and WO 94/18337. Elevated lipid content can also be achieved by reducing the starch content, for example as the result of the reduced expression of enzymes of the carbohydrate metabolism (for example ADP-glucose pyrophosphorylases).

For this application either a miRNA-tag, which allows for enhanced specific expression in seeds is preferred for designing the miRNA-tag. For example, maize miR156 is expressed everywhere but seeds, use of miR156 tag could enhance seed-specific expression.

3.1.2.3 Modification of the Carbohydrate Composition

A modification of the carbohydrate composition can be achieved for example by reducing the gene expression of carbohydrate metabolism genes or of carbohydrate biosynthesis genes, for example genes of the biosynthesis of amylose, pectins, cellulose or cell wall carbohydrates. A multiplicity of cellular processes (maturation, storability, starch composition or starch content and the like) can thereby be influenced in an advantageous manner. Target genes which may be mentioned by way of example, but not by limitation, are phosphorylases, starch synthetases, 0-enzymes, sucrose-6-phosphate synthetases, sucrose-6-phosphate phosphatases, ADP-glucose pyrophosphorylases, branching enzymes, debranching enzymes and various amylases. The corresponding genes are described (Dunwell J M (2000) J Exp Botany 51Spec No:487-96; Brar D S et al. (1996) Biotech Genet Eng Rev 13:167-79; Kishore G M and Somerville C R (1993) Curr Opin Biotech 4(2):152-8). Advantageous genes for influencing the carbohydrate metabolism—in particular starch biosynthesis—are described in WO 92/11375, WO 92/11376, U.S. Pat. No. 5,365,016 and WO 95/07355.

For this application either a miRNA-tag, which allows for enhanced specific expression in seeds is preferred for designing the miRNA-tag. For example, maize miR156 is expressed everywhere but seeds, use of miR156 tag could enhance seed-specific expression.

3.1.2.4 Modification of the Color or Pigmentation

A modification of the color or pigmentation, preferably of ornamentals, can be achieved for example by reducing the gene expression of flavonoid biosynthesis genes such as, for example, the genes of chalcone synthases, chalcone isomerases, phenylalanine ammonia lyases, dehydrokaempferol (flavone) hydroxylases such as flavanone 3-hydroxylases or flavanone 2-hydroxylases, dihydroflavonol reductases, dihydroflavanol 2-hydroxylases, flavonoid 3'-hydroxylases, flavonoid 5'-hydroxylases, flavonoid glycosyltransferases (for example glucosyltransferases such as UDPG:flavonoid 3-O-glucosyltransferases, UDPG:flavonol 7-O-glucosyltransferases or rhamnosyltransferases), flavonoid methyltransferases (such as, for example, SAM:anthocyanidin-3-(p-coumaroyl)rutinoside-5-glucoside-3',5'-O-methyltransferases) and flavonoid acyltransferases (Hahlbrock (1981) Biochemistry of Plants, Vol. 7, Conn (Ed.); Weiring and de Vlaming (1984) "Petunia", K C Sink (Ed.), Springer-Verlag, New York). Particularly suitable are the sequences described in EP-A1 522 880.

For this application either a miRNA-tag, which allows for enhanced specific expression in flowers and its part is preferred for designing the miRNA-tag. For example, rice miR156I is expressed in root and shoot, use of miR156I tag can enhance specific expression of gene-of-interest in flowers.

3.1.2.5. Reduction of the Storage Protein Content

The reduction of the gene expression of genes encoding storage proteins (SP hereinbelow) has a large number of advantages such as, for example, the reduction of the allergenic potential or modification in the composition or quantity of other metabolites. Storage proteins are described, inter alia, in EP-A 0 591 530, WO 87/47731, WO 98/26064, EP-A 0 620 281; Kohno-Murase J et al. (1994) Plant Mol Biol 26(4): 1115-1124. SP serve for the storage of carbon, nitrogen and sulfur, which are required for the rapid heterotrophic growth in the germination of seeds or pollen. In most cases, they have no enzymatic activity. SP are synthesized in the embryo only during seed development and, in this process, accumulate firstly in protein storage vacuoles (PSV) of differently differentiated cells in the embryo or endosperm. Storage proteins can be classified into subgroups, as the function of further characteristic properties, such as, for example, their sedimentation coefficient or the solubility in different solutions (water, saline, alcohol). The sedimentation coefficient can be determined by means of ultracentrifugation in the manner with which the skilled worker is familiar (for example as described in Correia J J (2000) Methods in Enzymology 321:81-100). In total, four large gene families for storage proteins can be assigned, owing to their sequences: 2S albumins (napin-like), 7S globulins (phaseolin-like), 11S/12S globulins (legumin/cruciferin-like) and the zein prolamins.

2S albumins are found widely in seeds of dicots, including important commercial plant families such as Fabaceae (for example soybean), Brassicaceae (for example oilseed rape), Euphorbiaceae (for example castor-oil plant) or Asteraceae (for example sunflower). 2S albumins are compact globular proteins with conserved cysteine residues which frequently form heterodimers. 7S globulins occur in trimeric form and comprise no cysteine residues. After their synthesis, they are cleaved into smaller fragments and glycosylated, as is the case with the 2S albumins. Despite differences in polypeptide size, the different 7S globulins are highly conserved and can probably be traced to a shared precursor protein, as is the case with the 2S albumins. Only small amounts of the 7S globulins are found in monocots. In dicots, they always amount to less than the 11S/12S globulins. 11S/12S globulins constitute the main fraction of the storage proteins in dicots, in addition to the 2S albumins. The high degree of similarity of the different 11S globulins from different plant genera, in turn, allow the conclusion of a shared precursor protein in the course of evolution. The storage protein is preferably selected from the classes of the 2S albumins (napin-like), 7S globulins (phaseolin-like), 11S/12S globulins (legumin/cruciferin-like) or zein prolamins. Especially preferred 11S/12S globulins comprise preferably 11S globulins from oilseed rape, soybean and *Arabidopsis*, sunflower, linseed, sesame, safflower, olive tree, soybean or various nut species. Especially preferred zein prolamins preferably comprise those from monocotyledonous plants, in particular maize, rice, oats, barley or wheat.

For this application either a miRNA-tag, which allows for enhanced specific expression in seeds is preferred for designing the miRNA-tag. For example, maize miR156 is expressed everywhere but seeds, use of miR156 tag could enhance seed-specific expression.

3.1.2.6. Obtaining a Resistance to Plant Pathogens

The methods and means of the invention will be especially suited for obtaining pathogen (e.g., virus or nematode) resistance, in eukaryotic cells or organisms, particularly in plant cells and plants. It is expected that the chimeric RNA molecules (or the dsRNA molecules derived therefrom) produced by transcription in a host organism (e.g., a plant), can spread systemically throughout the organism. Thus it is possible to reduce the phenotypic expression of a nucleic acid in cells of a non-transgenic scion of a plant grafted onto a transgenic stock comprising the chimeric genes of the invention (or vice versa) a method which may be important in horticulture, viticulture or in fruit production.

A resistance to plant pathogens such as arachnids, fungi, insects, nematodes, protozoans, viruses, bacteria and diseases can be achieved by reducing the gene expression of genes which are essential for the growth, survival, certain developmental stages (for example pupation) or the multiplication of a certain pathogen. A suitable reduction can bring about a complete inhibition of the above steps, but also a delay of same. This may be plant genes which, for example, allow the pathogen to enter, but may also be pathogenhomologous genes. Preferably, the chimeric RNA (or the dsRNA derived therefrom) is directed against genes of the pathogen. For example, plants can be treated with suitable formulations of abovementioned agents, for example sprayed or dusted, the plants themselves, however, may also comprise the agents in the form of a transgenic organism and pass them on to the pathogens, for example in the form of a stomach poison. Various essential genes of a variety of pathogens are known to the skilled worker (for example for nematode resistance: WO 93/10251, WO 94/17194).

Thus, an aspect of this invention provides a method where the target gene for suppression encodes a protein in a plant pathogen (e.g., an insect or nematode). In an aspect, a method comprises introducing into the genome of a pathogen-targeted plant a nucleic acid construct comprising DNA which is transcribed into a chimeric RNA that forms at least one dsRNA molecule which is effective for reducing expression of a target gene within the pathogen when the pathogen (e.g., insect or nematode) ingests or infects cells from said plant. In a preferred embodiment, the gene suppression is fatal to the pathogen.

Most preferred as pathogen are fungal pathogens such as *Phytophthora infestans, Fusarium nivale, Fusarium graminearum, Fusarium culmorum, Fusarium oxysporum, Blumeria graminis, Magnaporthe grisea, Sclerotinia sclerotium, Septoria nodorum, Septoria tritici, Alternaria brassicae, Phoma lingam,* bacterial pathogens such as *Corynebacterium sepedonicum, Erwinia carotovora, Erwinia amylovora, Streptomyces scabies, Pseudomonas syringae* pv. *tabaci, Pseudomonas syringae* pv. *phaseolicola, Pseudomonas syringae* pv. *tomato, Xanthomonas campestris* pv. *malvacearum* and *Xanthomonas campestris* pv. *oryzae,* and nematodes such as *Globodera rostochiensis, G. paffida, Heterodera schachtii, Heterodera avenae, Ditylenchus dipsaci, Anguina tritici* and *Meloidogyne hapla.*

Resistance to viruses can be obtained for example by reducing the expression of a viral coat protein, a viral replicase, a viral protease and the like. A large number of plant viruses and suitable target genes are known to the skilled worker. The methods and compositions of the present invention are especially useful to obtain nematode resistant plants (for target genes see e.g., WO 92/21757, WO 93/10251, WO 94/17194).

Also provided by the invention is a method for obtaining pathogen resistant organisms, particularly plants, comprising the steps of providing cells of the organism with an chimeric RNA molecule of the invention, said chimeric RNA molecule capable to provide in an eukaryotic cell an at least partially double-stranded RNA molecule, said chimeric RNA molecule comprising a) at least one first ribonucleotide sequence that is substantially identical to at least a part of a target nucleotide sequence of at least one gene of a pathogen, and b) at least one second ribonucleotide sequence which is substantially complementary to said first nucleotide sequence and is capable to hybridizes to said first nucleotide sequence to form a double-stranded RNA structure, and c) at least one third ribonucleotide sequence located between said first and said second ribonucleotide sequence comprising at least one removable RNA element, which can be removed by the RNA processing mechanism of an eukaryotic cell without subsequently covalently joining the resulting sequences comprising said first and said secand ribonucleotide sequence, respectively.

Preferably, said first ribonucleotide sequence has between 65 and 100% sequence identity, preferably, between 75 and 100%, more preferably between 85 and 100%, most preferably between 95 and 100%, with at least part of the nucleotide sequence of the genome of a pathogen. More preferably the pathogen is selected from the group of virus, bacteria, fungi, and nematodes.

For this application either a miRNA-tag, which allows for enhanced specific expression in tissue, which functions as entry-site for the pathogen (e.g., epidermis) or a miRNA-tag corresponding to an miRNA, which is endogenously suppressed by the pathogen-induced stress is preferred to be employed for designing the miRNA-tag.

3.1.2.7. Prevention of Stem Break

A reduced susceptibility to stem break can be obtained for example by reducing the gene expression of genes of the carbohydrate metabolism (see above). Advantageous genes are described (WO 97/13865, inter alia) and comprise tissue-specific polygalacturonases or cellulases.

For this application either a miRNA-tag, which allows for enhanced specific expression in stem is preferred for designing the miRNA-tag. For example, maize miR166 is expressed in leafs and tassel, use of miR166 tag can enhance specific expression of gene-of-interest in stem.

3.1.2.8. Delay of Fruit Maturation

Delayed fruit maturation can be achieved for example by reducing the gene expression of genes selected from the group consisting of polygalacturonases, pectin esterases, β-(1-4)glucanases (cellulases), β-galactanases (β-galactosidases), or genes of ethylene biosynthesis, such as 1-aminocyclopropane-1-carboxylate synthase, genes of carotenoid biosynthesis such as, for example, genes of prephytoene or phytoene biosynthesis, for example phytoene desaturases. Further advantageous genes are, for example, in WO 91/16440, WO 91/05865, WO 91/16426, WO 92/17596, WO 93/07275 or WO 92/04456, U.S. Pat. No. 5,545,366).

For this application either a miRNA-tag, which allows for enhanced specific expression in fruits is preferred for designing the miRNA-tag.

3.1.2.9. Achieving male sterility. Suitable target genes are described in WO 94/29465, WO89/10396, WO 92/18625, inter alia. A particular application for reduction of the phenotypic expression of a transgene in a plant cell, inter alia, has been described for the restoration of male fertility, the latter being obtained by introduction of a transgene comprising a male sterility DNA (WO 94/09143, WO 91/02069). The nucleic acid of interest is specifically the male sterility DNA.

For this application either a miRNA-tag, which allows for enhanced specific expression in pollen is preferred for designing the miRNA-tag.

3.1.2.10. Reduction of undesired or toxic plant constituents such as, for example, glucosinolates. Suitable target genes are described (in WO 97/16559, inter alia). For this application either a miRNA-tag, which allows for enhanced specific expression in seeds is preferred for designing the miRNA-tag. For example, maize miR156 is expressed everywhere but seeds, use of miR156 tag could enhance seed-specific expression.

3.1.2.11. Delay of senescence symptoms. Suitable target genes are, inter alia, cinnamoyl-CoA:NADPH reductases or cinnamoyl alcohol dehydrogenases. Further target genes are described (in WO 95/07993, inter alia).

3.1.2.12. Modification of the lignification and/or the lignin content, mainly in tree species. Suitable target genes are described in WO 93/05159, WO 93/05160, inter alia.

3.1.2.13. Modification of the fiber content in foodstuffs, preferably in seeds, by reducing the expression of coffeic acid O-methyltransferase or of cinnamoyl alcohol dehydrogenase.

3.1.2.14. Modification of the fiber quality in cotton. Suitable target genes are described in U.S. Pat. No. 5,597,718, inter alia.

3.1.2.15. Reduction of the susceptibility to bruising of, for example, potatoes by reducing for example polyphenol oxidase (WO 94/03607) and the like.

3.1.2.16. Enhancement of vitamin E biosynthesis, for example by reducing the expression of genes from the homogentisate catabolic pathway such as, for example, homogentisate 1,2-dioxygenase (HGD; EC No.: 1.13.11.5), maleylacetoacetate isomerase (MAAI; EC No.: 5.2.1.2.) or fumaryl-acetoacetate hydrolase (FAAH; EC No.: 3.7.1.2).

3.1.2.17. Reduction of the nicotine content for example in tobacco by reduced expression of, for example, N-methylputrescin oxidase and putrescin N-methyltransferase.

3.1.2.18. Reduction of the caffeine content in coffee bean (e.g., *Coffea arabica*) by reducing the gene expression of genes of caffeine biosynthesis such as 7-methylxanthine 3-methyltransferase.

3.1.2.19. Reduction of the theophylline content in tea (*Camellia sinensis*) by reducing the gene expression of genes of theophylline biosynthesis such as, for example, 1-methylxanthine 3-methyltransferase.

3.1.2.20. Increase of the methionine content by reducing threonine biosynthesis, for example by reducing the expression of threonine synthase (Zeh M et al. (2001) Plant Physiol 127(3):792-802).

Furthermore the method and compounds of the invention can be used for obtaining shatter resistance (WO 97/13865), for obtaining modified flower color patterns (EP 522 880, U.S. Pat. No. 5,231,020), for reducing the presence of unwanted (secondary) metabolites in organisms, such as glucosinolates (WO97/16559) or chlorophyll content (EP 779 364) in plants, for modifying the profile of metabolites synthesized in a eukaryotic cell or organisms by metabolic engineering e.g. by reducing the expression of particular genes involved in carbohydrate metabolism (WO 92/11375, WO 92/11376, U.S. Pat. No. 5,365,016, WO 95/07355) or lipid biosynthesis (WO 94/18337, U.S. Pat. No. 5,530,192) etc. Further examples of advantageous genes are mentioned for example in Dunwell J M, Transgenic approaches to crop improvement, J Exp Bot. 2000; 51 Spec No; pages 487-96.

Each of the abovementioned applications can be used as such on its own. Naturally, it is also possible to use more than one of the abovementioned approaches simultaneously. If, in this context, all approaches are used, the expression of at least two differing target genes as defined above is reduced. In this context, these target genes can originate from a single group of genes which is preferred for a use, or else be assigned to different use groups.

3.1.3 Plant Transformation & Expression Technology

A chimeric RNA of the invention can be expressed within a plant cell using conventional recombinant DNA technology. Generally, this involves inserting a nucleotide sequence encoding the chimeric RNA of the invention into an expression construct or expression vector using standard cloning procedures known in the art.

3.1.3.1. Requirements for Construction of Plant Expression Constructs

The expression construct or expression construct of the invention comprises one or more genetic control sequences (or regulatory sequences) operably linked to a nucleic acid sequence encoding the chimeric RNA of the invention. These genetic control sequences regulate expression of the chimeric RNA in host cells. Genetic control sequences are described, for example, in "Goeddel; Gene Expression Technology: Methods in Enzymology 185, Academic Press, San Diego, Calif. (1990)" or "Gruber and Crosby, in: Methods in Plant Molecular Biology and Biotechnolgy, CRC Press, Boca Raton, Fla., eds.: Glick and Thompson, Chapter 7, 89-108" and the references cited therein. Sequences intended for expression in plants are first operatively linked to a suitable promoter functional in plants. Such expression constructs optionally comprise further sequences required or selected for the expression of the transgene. Such sequences include, but are not restricted to, transcription terminators, extraneous sequences to enhance expression. These expression constructs are easily transferred to the plant transformation vectors described infra.

3.1.3.1.1. Promoters

The nucleic acid sequence encoding the chimeric RNA of the invention is preferably operably linked to a plant-specific promoter. The term "plant-specific promoter" means principally any promoter which is capable of governing the expression of genes, in particular foreign nucleic acid sequences or genes, in plants or plant parts, plant cells, plant tissues, plant cultures. In this context, the expression specificity of said plant-specific promoter can be for example constitutive, tissue-specific, inducible or development-specific. The following are preferred:

3.1.3.1.1.1 Constitutive Promoters

Where expression of a gene in all tissues of a transgenic plant or other organism is desired, one can use a "constitutive" promoter, which is generally active under most environmental conditions and states of development or cell differentiation. Useful promoters for plants also include those obtained from Ti- or Ri-plasmids, from plant cells, plant viruses or other organisms whose promoters are found to be functional in plants. Bacterial promoters that function in plants, and thus are suitable for use in the methods of the invention include the octopine synthetase promoter, the nopaline synthase promoter, and the mannopine synthetase promoter. The promoter controlling expression of the chimeric RNA of the invention (and/or selection marker) can be constitutive. Suitable constitutive promoters for use in plants include, for example, the cauliflower mosaic virus (CaMV) 35S transcription initiation region (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228), the 19S transcription initiation region (U.S. Pat. No. 5,352,605 and WO 84/02913), and region VI promoters, the 1'- or 2'-promoter derived from T-DNA of *Agrobacterium tumefaciens*, and other promoters active in plant cells that are known to those of skill in the art. Other suitable promoters include the full-length transcript promoter from Figwort mosaic virus, actin promoters (e.g., the rice actin promoter; McElroy et al. (1990) Plant Cell 2: 163-171), histone promoters, tubulin promoters, or the mannopine synthase promoter (MAS). Other constitutive plant promoters include various ubiquitin or poly-ubiquitin promoters (Sun and Callis (1997) Plant J 11(5): 1017-1027, Cristensen et al. (1992) Plant Mol Biol 18:675-689; Christensen et al. (1989) Plant Mol. Biol. 12: 619-632; Bruce et al. (1989) Proc Natl Acad Sci USA 86:9692-9696; Holtorf et al. (1995) Plant Mol Biol 29:637-649), the mas, Mac or DoubleMac promoters (U.S. Pat. No. 5,106,739; Comai et al. (1990) Plant Mol Biol 15:373-381), the ubiquitin promoter (Holtorf et al. (1995) Plant Mol Biol 29:637-649), Rubisco small subunit (SSU) promoter (U.S. Pat. No. 4,962,028), the legumin B promoter (GenBank Acc. No. X03677), the promoter of the nopaline synthase (NOS) from *Agrobacterium*, the TR dual promoter, the octopine synthase (OCS) promoter from *Agrobacterium*, the Smas promoter, the cinnamyl alcohol dehydrogenase promoter (U.S. Pat. No. 5,683,439), the promoters of the vacuolar ATPase subunits, the pEMU promoter (Last et al. (1991) Theor. Appl. Genet. 81, 581-588); the MAS promoter (Velten et al. (1984) EMBO J. 3(12): 2723-2730), the maize H3 histone promoter (Lepetit et al. (1992) Mol. Gen. Genet. 231: 276-285; Atanassova et al. (1992) Plant J 2(3): 291-300), □-conglycinin promoter, the phaseolin promoter, the ADH promoter, and heatshock promoters, the nitrilase promoter from *Arabidopsis thaliana* (WO 03/008596; GenBank Acc. No.: U38846, nucleotides 3,862 to 5,325 or else 5342), promoter of a proline-rich protein from wheat (WO 91/13991), the promoter of the *Pisum sativum* ptxA gene, and other transcription initiation regions from various plant genes known to those of skill in the art.

However, it has to be noted that because of the high efficiency of the chimeric RNA of the invention, the method of the current invention does not rely on the presence of strong promoter regions to drive the transcriptional production of the chimeric RNA. In other words, a whole range of promoters, particularly plant expressible promoters, is available to direct the transcription.

3.1.3.1.1.2 Tissue-Specific Promoters

Alternatively promoters can be employed which regulate expression in only one or some tissues or organs, such as leaves, roots, fruit, seeds, anthers, ovaries, pollen, meristem, stems or flowers, or parts thereof. For example, the tissue-specific E8 promoter from tomato is particularly useful for directing gene expression so that a desired gene product is located in fruits (see, e.g., Lincoln et al. (1988) Proc Natl Acad Sci USA 84:2793-2797; Deikman et al. (1988) EMBO J 7:3315-3320; Deikman et al. (1992) Plant Physiol 100: 2013-2017). Suitable seed specific promoters include those derived from the following genes: MAC1 from maize (Sheridan et al. (1996) Genetics 142:1009-1020), Cat3 from maize (GenBank No. L05934), the gene encoding oleosin 18 kD from maize (GenBank No. J05212) viviparous-1 from *Arabidopsis* (Genbank Acc.-No. U93215), the gene encoding oleosin from *Arabidopsis* (Genbank Acc.-No. Z17657), Atmyc1 from *Arabidopsis* (Urao et al. (1996) Plant Mol Biol 32:571-576), the 2S seed storage protein gene family from *Arabidopsis* (Conceicao et al. (1994) Plant 5:493-505) the gene encoding oleosin 20 kD from *Brassica napus* (GenBank No. M63985), napin from *Brassica napus* (GenBank No. J02798, Joseffson et al. (1987) J Biol Chem 262:12196-12201), the napin gene family (e.g., from *Brassica napus*; Sjodahl et al. (1995) Planta 197:264-271), U.S. Pat. No. 5,608,152; Stalberg et al. (1996) Planta 199:515-519), the gene encoding the 2S storage protein from *Brassica napus* (Dasgupta et al. (1993) Gene 133: 301-302), the genes encoding oleosin A (Genbank Acc.-No. U09118) and oleosin B (Genbank No. U09119) from soybean, the gene encoding low molecular weight sulphur rich protein from soybean (Choi et al. (1995) Mol Gen Genet 246:266-268), the phaseolin gene (U.S. Pat. No. 5,504,200, Bustos et al. (1989) Plant Cell 1(9):839-53; Murai et al. (1983) Science 23: 476-482; SenguptaGopalan et al. (1985) Proc. Nat'l Acad. Sci. USA 82: 3320-3324 (1985)), the 2S albumin gene, the legumin gene (Shirsat et al. (1989) Mol Gen Genet 215(2): 326-331), the USP (unknown seed protein) gene, the sucrose binding protein gene (WO 00/26388), the legumin B4 gene (LeB4; Fiedler et al. (1995) Biotechnology (NY) 13(10): 1090-1093), Bäumlein et al. (1992) Plant J 2(2):233-239; Bäumlein et al. (1991a) Mol Gen Genet 225(3):459-467; Bäumlein et al. (1991b) Mol Gen Genet 225:121-128), the *Arabidopsis* oleosin gene (WO 98/45461), the *Brassica* Bce4 gene (WO 91/13980), genes encoding the "high-molecular-weight glutenin" (HMWG), gliadin, branching enzyme, ADP-glucose pyrophosphatase (AGPase) or starch synthase. Furthermore preferred promoters are those which enable seed-specific expression in monocots such as maize, barley, wheat, rye, rice and the like. Promoters which may advantageously be employed are the promoter of the Ipt2 or Ipt1 gene (WO 95/15389, WO 95/23230) or the promoters described in WO 99/16890 (promoters of the hordein gene, the glutelin gene, the oryzin gene, the prolamine gene, the gliadin gene, the zein gene, the kasirin gene or the secalin gene). Further preferred are a leaf-specific and light-induced promoter such as that from cab or Rubisco (Timko et al. (1985) Nature 318: 579-582; Simpson et al. (1985) EMBO J 4:2723-2729); an anther-specific promoter such as that from LAT52 (Twell et al. (1989) Mol Gen Genet 217:240-245); a pollen-specific promoter such as that from ZmI3 (Guerrero et al. (1993) Mol Gen Genet 224:161-168); and a microspore-preferred promoter such as that from apg (Twell et al. (1983) Sex. Plant Reprod. 6:217-224). Further suitable promoters are, for example, specific promoters for tubers, storage roots or roots such as, for example, the class I patatin promoter (B33), the potato cathepsin D inhibitor promoter, the starch synthase (GBSS1) promoter or the sporamin promoter, and fruit-specific promoters such as, for example, the tomato fruit-specific promoter (EP-A 409 625). Promoters which are furthermore suitable are those which ensure leaf-specific expression. Promoters which may be mentioned are the potato cytosolic FBPase promoter (WO 98/18940), the Rubisco (ribulose-1,5-bisphosphate carboxylase) SSU (small subunit) promoter or the potato ST-LSI promoter (Stockhaus et al. (1989) EMBO J 8(9):2445-2451). Other preferred promoters are those which govern expression in seeds and plant embryos. Further suitable promoters are, for example, fruit-maturation-specific promoters such as, for example, the tomato fruit-maturation-specific promoter (WO 94/21794), flower-specific promoters such as, for example, the phytoene synthase promoter (WO 92/16635) or the promoter of the P1-rr gene (WO 98/22593) or another node-specific promoter as described in EP-A 249676 may be used advantageously. The promoter may also be a pithspecific promoter, such as the promoter isolated from a plant TrpA gene as described in WO 93/07278.

3.1.3.1.1.3 Chemically Inducible Promoters

An expression constructs may also contain a chemically inducible promoter (review article: Gatz et al. (1997) Annu Rev Plant Physiol Plant Mol Biol 48:89-108), by means of which the expression of the nucleic acid sequence encoding the chimeric RNA of the invention in the plant can be controlled at a particular point in time. Such promoters such as, for example, a salicylic acid-inducible promoter (WO 95/19443), a benzenesulfonamide-inducible promoter (EP 0 388 186), a tetracycline-inducible promoter (Gatz et al. (1991) Mol Gen Genetics 227:229-237), an abscisic acid-inducible promoter EP 0 335 528) or an ethanol-cyclo-hexanone-inducible promoter (WO 93/21334) can likewise be used. Also suitable is the promoter of the glutathione-S transferase isoform II gene (GSTII-27), which can be activated by exogenously applied safeners such as, for example, N,N-diallyl-2,2-dichloroacetamide (WO 93/01294) and which is operable in a large number of tissues of both monocotyledonous and dicotyledonous. Further exemplary inducible promoters that can be utilized in the instant invention include that from the ACE1 system which responds to copper (Mett et al. PNAS 90: 4567-4571 (1993)); or the In2 promoter from maize which responds to benzenesulfonamide herbicide safeners (Hershey et al. (1991) Mol Gen Genetics 227:229-237; Gatz et al. (1994) Mol Gen Genetics 243:32-38). A promoter that responds to an inducing agent to which plants do not normally respond can be utilized. An exemplary inducible promoter is the inducible promoter from a steroid hormone gene, the transcriptional activity of which is induced by a glucocorticosteroid hormone (Schena et al. (1991) Proc Nat'l Acad Sci USA 88:10421). Other preferred promoters are promoters induced by biotic or abiotic stress, such as, for example, the pathogen-inducible promoter of the PRP1 gene (Ward et al. (1993) Plant Mol Biol 22:361-366), the tomato heat-inducible hsp80 promoter (U.S. Pat. No. 5,187,267), the potato chill-inducible alpha-amylase promoter (WO 96/12814) or the wound-induced pinII promoter (EP-A1 0 375 091).

3.1.3.1.1.4 Stress- or Pathogen-Inducible Promoters

One can use a promoter that directs expression environmental control. Examples of environmental conditions that may affect transcription by inducible promoters include biotic or abiotic stress factors or other environmental conditions, for example, pathogen attack, anaerobic conditions, ethylene or the presence of light.

Promoters inducible by biotic or abiotic stress include but are not limited to the pathogen-inducible promoter of the PRP1 gene (Ward et al. (1993) Plant Mol Biol 22:361-366), the heat-inducible hsp70 or hsp80 promoter from tomato (U.S. Pat. No. 5,187,267), the chill-inducible alpha-amylase promoter from potato (WO 96/12814), the light-inducible PPDK promoter or the wounding-inducible pinII promoter (EP375091). Pathogen-inducible promoters comprise those of genes which are induced as the result of attack by pathogens such as, for example, genes of PR proteins, SAR proteins, b-1,3-glucanase, chitinase and the like (for example Redolfi et al. (1983) Neth J Plant Pathol 89:245-254; Uknes, et al. (1992) The Plant Cell 4:645-656; Van Loon (1985) Plant Mol Viral 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968(1989)). Also comprised are wounding-inducible promoters such as that of the pinII gene (Ryan (1990) Ann Rev Phytopath 28:425-449; Duan et al. (1996) Nat Biotech 14:494-498), of the wun1 and wun2 gene (U.S. Pat. No. 5,428,148), of the win1 and win2 gene (Stanford et al. (1989) Mol Gen Genet 215:200-208), of systemin (McGurl et al. (1992) Science 225:1570-1573), of the WIP1 gene (Rohmeier et al. (1993) Plant Mol Biol 22:783-792; Eckelkamp et al. (1993) FEBS Letters 323:73-76), of the MPI gene (Corderok et al. (1994) The Plant J 6(2):141-150) and the like.

3.1.3.1.1.5 Development-Dependent Promoters

Further suitable promoters are, for example, fruit-maturation-specific promoters, such as, for example, the fruit-maturation-specific promoter from tomato (WO 94/21794, EP 409 625). Development-dependent promoters include partly the tissue-specific promoters described above since individual tissues are, naturally, formed as a function of the development. A development-regulated promoter is, inter alia, described (Baerson and Lamppa (1993) Plant Mol Biol 22(2):255-67).

3.1.3.1.1.6 Other Suitable Promoter and Promoter Elements

Promoters may also encompass further promoters, promoter elements or minimal promoters capable of modifying the expression-governing characteristics. Thus, for example, the tissue-specific expression may take place in addition as a function of certain stress factors, owing to genetic control sequences. Such elements are, for example, described for water stress, abscisic acid (Lam and Chua (1991) J Biol Chem 266(26):17131-17135) and heat stress (Schoffl et al. (1989) Molecular & General Genetics 217(2-3):246-53).

3.1.3.1.2 Other Genetic Control Elements

Genetic control sequences are furthermore to be understood as those permitting removal of the inserted sequences from the genome. Methods based on the cre/lox (Dale and Ow (1991) Proc Nat'l Acad Sci USA 88:10558-10562; Sauer (1998) Methods 14(4):381-92; Odell et al. (1990) Mol Gen Genet 223:369-378), FLP/FRT (Lysnik et al. (1993) NAR 21:969-975), or Ac/Ds system (Lawson et al. (1994) Mol Gen Genet 245:608-615; Wader et al. (1987) in TOMATO TECHNOLOGY 189-198 (Alan R. Liss, Inc.); U.S. Pat. No. 5,225,341; Baker et al. (1987) EMBO J 6: 1547-1554) permit a—if appropriate tissue-specific and/or inducible—removal of a specific DNA sequence from the genome of the host organism. Control sequences may in this context mean the specific flanking sequences (e.g., lox sequences), which later allow removal (e.g., by means of cre recombinase).

3.1.3.1.2.1 Transcriptional Terminators

A variety of transcriptional terminators are available for use in expression constructs. These are responsible for the termination of transcription beyond the transgene and its correct polyadenylation. Appropriate transcriptional terminators are those that are known to function in plants and include the CaMV 35S terminator, the tml terminator, the OCS (octopin synthase) terminator and the NOS (nopalin synthase) terminator and the pea rbcS E9 terminator. These can be used in both monocotyledons and dicotyledons.

3.1.3.1.2.2 Sequences for the Enhancement or Regulation of Expression

Genetic control sequences furthermore also comprise the 5'-untranslated regions, introns or noncoding 3' region of genes, such as, for example, the actin-1 intron, or the Adh1-S introns 1, 2 and 6 (general reference: The Maize Handbook, Chapter 116, Freeling and Walbot, Eds., Springer, New York (1994)). It has been demonstrated that they can play a significant role in the regulation of gene expression and have been shown to enhance expression, particularly in monocotyledonous cells. Thus, it has been demonstrated that 5'-untranslated sequences can enhance the transient expression of heterologous genes. An example which may be mentioned of such translation enhancers is the tobacco mosaic virus 5' leader sequence (Gallie et al. (1987) Nucl Acids Res 15:8693-8711) and the like. They can furthermore promote tissue specificity (Rouster J et al. (1998) Plant J 15:435-440).

3.1.3.2. Construction of Plant Transformation Vectors

The expression construct for expression of the chimeric RNA molecule of the invention is preferably comprised in an expression vector. Numerous transformation vectors for plant transformation are known to the person skilled in the plant transformation arts. The selection of vector will depend upon the preferred transformation technique and the target species for transformation.

3.1.3.2.1 Vector Elements

Expression constructs and the vectors derived therefrom may comprise further functional elements. The term functional element is to be understood in the broad sense and means all those elements, which have an effect on the generation, multiplication or function of the expression constructs, vectors or transgenic organisms according to the invention. The following may be mentioned by way of example, but not by limitation:

3.1.3.2.1.1. Selectable Marker Genes

Selectable marker genes are useful to select and separate successfully transformed cells. Preferably, within the method of the invention one marker may be employed for selection in a prokaryotic host, while another marker may be employed for selection in a eukaryotic host, particularly the plant species host. The marker may confer resistance against a biocide, such as antibiotics, toxins, heavy metals, or the like, or may function by complementation, imparting prototrophy to an auxotrophic host. Preferred selectable marker genes for plants may include but are not be limited to the following:

3.1.3.2.1.1.1. Negative Selection Markers

Negative selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Especially preferred negative selection markers are those which confer resistance to herbicides. These markers can be used—beside their function as a marker—to confer a herbicide resistance trait to the resulting plant. Examples, which may be mentioned, are:

Phosphinothricin acetyltransferases (PAT; also named Bialophos resistance; bar; de Block et al. (1987) EMBO J 6:2513-2518; EP 0 333 033; U.S. Pat. No. 4,975,374)

5-enolpyruvylshikimate-3-phosphate synthase (EPSPS; U.S. Pat. No. 5,633,435) or glyphosate oxidoreductase gene (U.S. Pat. No. 5,463,175) conferring resistance to Glyphosate (Nphosphonomethyl glycine) (Shah et al. (1986) Science 233: 478)

Glyphosate degrading enzymes (Glyphosate oxidoreductase; gox),

Dalapon inactivating dehalogenases (deh)

Sulfonylurea- and imidazolinone-inactivating acetolactate synthases (for example mutated ALS variants with, for example, the S4 and/or Hra mutation Bromoxynil degrading nitrilases (bxn)

Kanamycin- or. G418-resistance genes (NPTII; NPTI) coding e.g., for neomycin phosphotransferases (Fraley et al. (1983) Proc Natl Acad Sci USA 80:4803), which expresses an enzyme conferring resistance to the antibiotic kanamycin and the related antibiotics neomycin, paromomycin, gentamicin, and G418, 2-Deoxyglucose-6-phosphate phosphatase (DOGR1-Gene product; WO 98/45456; EP 0 807 836) conferring resistance against 2-desoxyglucose (Randez-Gil et al. (1995) Yeast 11:1233-1240)

Hygromycin phosphotransferase (HPT), which mediates resistance to hygromycin (Vanden Elzen et al. (1985) Plant Mol Biol. 5:299).

Dihydrofolate reductase (Eichholtz et al. (1987) Somatic Cell and Molecular Genetics 13, 67-76)

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Svab et al. (1990) Plant Mol. Biol. 14:197; Jones et al. (1987) Mol. Gen. Genet. 210:86; Hille et al. (1986) Plant Mol. Biol. 7:171 (1986); Hayford et al. (1988) Plant Physiol. 86:1216).

Especially preferred are negative selection markers which confer resistance against the toxic effects imposed by D-amino acids like e.g., D-alanine and D-serine (WO 03/060133; Erikson et al. Nat Biotechnol. 22(4):455-8 (2004)). Especially preferred as negative selection marker in this contest are the daol gene (EC: 1.4. 3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603). Depending on the employed D-amino acid the D-amino acid oxidase markers can be employed as dual function marker offering negative selection (e.g., when combined with for example D-alanine or D-serine) or counter selection (e.g., when combined with D-leucine or D-isoleucine).

3.1.3.2.1.1.2. Positive Selection Marker

Positive selection markers are conferring a growth advantage to a transformed plant in comparison with a non-transformed one. Genes like isopentenyltransferase from *Agrobacterium tumefaciens* (strain:PO22; Genbank Acc.-No.: AB025109) may—as a key enzyme of the cytokinin biosynthesis—facilitate regeneration of transformed plants (e.g., by selection on cytokinin-free medium). Corresponding selection methods are described (Ebinuma et al. (2000a) Proc Natl Acad Sci USA 94:2117-2121; Ebinuma et al. (2000b) Selection of Marker-free transgenic plants using the oncogenes (ipt, rol A, B, C) of *Agrobacterium* as selectable markers, In Molecular Biology of Woody Plants. Kluwer Academic Publishers). Additional positive selection markers, which confer a growth advantage to a transformed plant in comparison with a non-transformed one, are described e.g., in EP-A 0 601 092. Growth stimulation selection markers may include (but shall not be limited to) □-Glucuronidase (in combination with e.g., cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

3.1.3.2.1.1.3. Counter Selection Marker

Counter selection markers are especially suitable to select organisms with defined deleted sequences comprising said marker (Koprek et al. (1999) Plant J 19(6): 719-726). Examples for counter selection marker comprise thymidine kinases (TK), cytosine deaminases (Gleave et al. (1999) Plant Mol Biol. 40(2):223-35; Perera et al. (1993) Plant Mol. Biol 23(4): 793-799; Stougaard (1993) Plant J 3:755-761), cytochrom P450 proteins (Koprek et al. (1999) Plant J 19(6): 719-726), haloalkan dehalogenases (Naested (1999) Plant J 18:571-576), iaaH gene products (Sundaresan et al. (1995) Gene Develop 9: 1797-1810), cytosine deaminase codA (Schlaman and Hooykaas (1997) Plant J 11:1377-1385), or tms2 gene products (Fedoroff and Smith (1993) Plant J 3:273-289).

3.1.3.2.1.2. Reporter Genes

Reporter genes encode readily quantifiable proteins and, via their color or enzyme activity, make possible an assessment of the transformation efficacy, the site of expression or the time of expression. Very especially preferred in this context are genes encoding reporter proteins (Schenborn and Groskreutz (1999) Mol Biotechnol 13(1):29-44) such as the green fluorescent protein (GFP) (Haseloff et al. (1997) Proc Natl Acad Sci USA 94(6):2122-2127; Sheen et al. (1995) Plant J 8(5):777-784; Reichel et al. (1996) Proc Natl Acad Sci USA 93(12):5888-5893; Chui et al. (1996) Curr Biol 6:325-330; Leffel et al. (1997) Biotechniques. 23(5):912-8; Tian et al. (1997) Plant Cell Rep 16:267-271; WO 97/41228), chloramphenicol transferase, a luciferase (Millar et al. (1992) Plant Mol Biol Rep 10:324-414; Ow et al. (1986) Science 234:856-859), the aequorin gene (Prasher et al. (1985) Biochem Biophys Res Commun 126(3):1259-1268), β-galactosidase, R locus gene (encoding a protein which regulates the production of anthocyanin pigments (red coloring) in plant tissue and thus makes possible the direct analysis of the promoter activity without addition of further auxiliary substances or chromogenic substrates (Dellaporta et al. (1988) In: Chromosome Structure and Function: Impact of New Concepts, 18th Stadler Genetics Symposium, 11:263-282; Ludwig et al. (1990) Science 247:449), with β-glucuronidase (GUS) being very especially preferred (Jefferson (1987b) Plant Mol. Bio. Rep., 5:387-405; Jefferson et al. (1987) EMBO J 6:3901-3907). β-glucuronidase (GUS) expression is detected by a blue color on incubation of the tissue with 5-bromo-4-chloro-3-indolyl-β-D-glucuronic acid, bacterial luciferase (LUX) expression is detected by light emission; firefly luciferase (LUC) expression is detected by light emission after incubation with luciferin; and galactosidase expression is detected by a bright blue color after the tissue was stained with 5-bromo-4-chloro-3-indolyl-β-D-galactopyranoside. Reporter genes may also be used as scorable markers as alternatives to antibiotic resistance markers. Such markers are used to detect the presence or to measure the level of expression of the transferred gene. The use of scorable markers in plants to identify or tag genetically modified cells works well only when efficiency of modification of the cell is high.

3.1.3.2.1.3. Origins of Replication.

Origins of replication which ensure amplification of the expression constructs or vectors ac-cording to the invention in, for example, E. coli. Examples which may be mentioned are ORI (origin of DNA replication), the pBR322 ori or the P15A ori (Maniatis T, Fritsch E F and Sambrook J (1989) Molecular Cloning: A Laboratory Manual, 2nd Ed., Cold Spring Harbor Laboratory, Cold Spring Harbor (N.Y.)). Additional examples for replication systems functional in E. coli, are ColE1, pSC101, pACYC184, or the like. In addition to or in place of the E. coli replication system, a broad host range replication system may be employed, such as the replication systems of the P-1 Incompatibility plasmids; e.g., pRK290. These plasmids are particularly effective with armed and disarmed Ti-plasmids for transfer of T-DNA to the plant host.

3.1.3.2.1.4. Elements, which are necessary for Agrobacterium-mediated transformation, such as, for example, the right and/or—optionally—left border of the T-DNA or the vir region.

3.1.3.2.1.5. Multiple cloning sites (MCS) to enable and facilitate the insertion of one or more nucleic acid sequences.

3.1.3.2.2 Vectors for Plant Transformation 3.1.3.2.2.1 Vectors Suitable for Agrobacterium Transformation If Agrobacteria are used, the expression construct is to be integrated into specific plasmids vectors, either into a shuttle, or intermediate, vector or into a binary vector. If a Ti or Ri plasmid is to be used for the transformation, at least the right border, but in most cases the right and the left border, of the Ti or Ri plasmid T-DNA is flanking the region with the expression construct to be introduced into the plant genome. It is preferred to use binary vectors for the Agrobacterium transformation. Binary vectors are capable of replicating both in E. coli and in Agrobacterium. They preferably comprise a selection marker gene and a linker or polylinker flanked by the right and—optionally—left T-DNA border sequence. They can be transformed directly into Agrobacterium (Holsters et al. (1978) Mol Gen Genet 163:181-187). A selection marker gene may be included in the vector which permits a selection of transformed Agrobacteria (e.g., the nptIII gene). The Agrobacterium, which acts as host organism in this case, should already comprise a disarmed (i.e., non-oncogenic) plasmid with the vir region. This region is required for transferring the T-DNA to the plant cell. The use of T-DNA for the transformation of plant cells has been studied and described extensively (EP 120 516; Hoekema, In: The Binary Plant Vector System, Offsetdrukkerij Kanters B.V., Alblasserdam, Chapter V; An et al. (1985) EMBO J 4:277-287). A variety of binary vectors are known and available for transformation using Agrobacterium, such as, for example, pBI101.2 or pBIN19 (Clontech Laboratories, Inc. USA; Bevan et al. (1984) Nucl Acids Res 12:8711), pBinAR, pPZP200 or pPTV.

3.1.3.2.2.2 Vectors Suitable for Non-Agrobacterium Transformation

Transformation without the use of Agrobacterium tumefaciens circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Typical vectors suitable for non-Agrobacterium transformation include pCIB3064, pSOG19, and pSOG35. (See, for example, U.S. Pat. No. 5,639,949).

3.1.3.3. Transformation Techniques 3.1.3.3.1 General Techniques

Once an expression construct or expression vector of the invention has be established, it can be transformed into a plant cell. A variety of methods for introducing nucleic acid sequences (e.g., vectors) into the genome of plants and for the regeneration of plants from plant tissues or plant cells are known (Plant Molecular Biology and Biotechnology (CRC Press, Boca Raton, Fla.), chapter 6/7, pp. 71-119 (1993); White F F (1993) Vectors for Gene Transfer in Higher Plants; in: Transgenic Plants, vol. 1, Engineering and Utilization, Ed.: Kung and Wu R, Academic Press, 15-38; Jenes B et al. (1993) Techniques for Gene Transfer, in: Transgenic Plants, vol. 1, Engineering and Utilization, Ed.: Kung and R. Wu, Academic Press, pp. 128-143; Potrykus (1991) Annu Rev Plant Physiol Plant Molec Biol 42:205-225; Halford N G, Shewry P R (2000) Br Med Bull 56(1):62-73).

Transformation methods may include direct and indirect methods of transformation. Suitable direct methods include polyethylene glycol induced DNA uptake, liposome-mediated transformation (U.S. Pat. No. 4,536,475), biolistic methods using the gene gun ("particle bombardment"; Fromm M E et al. (1990) Bio/Technology. 8(9):833-9; Gordon-Kamm et al. (1990) Plant Cell 2:603), electroporation, incubation of dry embryos in DNA-comprising solution, and microinjection. In the case of these direct transformation methods, the plasmid used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229f. The *Agrobacterium*-mediated transformation is best suited to dicotyledonous plants but has also be adopted to monocotyledonous plants. The transformation of plants by *Agrobacteria* is described (White F F, Vectors for Gene Transfer in Higher Plants; in Transgenic Plants, Vol. 1, Engineering and Utilization, edited by S. D. Kung and R. Wu, Academic Press, 1993, pp. 15-38; Jenes B et al. (1993) Techniques for Gene Transfer, in: Transgenic Plants, Vol. 1, Engineering and Utilization, edited by S. D. Kung and R. Wu, Academic Press, pp. 128-143; Potrykus (1991) Annu Rev Plant Physiol Plant Molec Biol 42:205-225).

Transformation may result in transient or stable transformation and expression. Although a nucleotide sequence of the present invention can be inserted into any plant and plant cell falling within these broad classes (as specified above in the DEFINITION section), it is particularly useful in crop plant cells.

Various tissues are suitable as starting material (explant) for the *Agrobacterium*-mediated transformation process including but not limited to callus (U.S. Pat. No. 5,591,616; EP-A1 604 662), immature embryos (EP-A1 672 752), pollen (U.S. Pat. No. 54,929,300), shoot apex (U.S. Pat. No. 5,164,310), or in planta transformation (U.S. Pat. No. 5,994,624). The method and material described herein can be combined with virtually all *Agrobacterium* mediated transformation methods known in the art. Preferred combinations include—but are not limited—to the following starting materials and methods:

TABLE 1

Plant Transformation Methods

| Variety | Material/Citation |
|---|---|
| Monocotyledonous plants: | Immature embryos (EP-A1 672 752) |
|  | Callus (EP-A1 604 662) |
|  | Embryogenic callus (U.S. Pat. No. 6,074,877) |
|  | Inflorescence (U.S. Pat. No. 6,037,522) |
|  | Flower (in planta) (WO 01/12828) |
| Banana | U.S. Pat. No. 5,792,935; EP-A1 731 632; U.S. Pat. No. 6,133,035 |
| Barley | WO 99/04618 |
| Maize | U.S. Pat. No. 5,177,010; U.S. Pat. No. 5,987,840 |
| Pineapple | U.S. Pat. No. 5,952,543; WO 01/33943 |
| Rice | EP-A1 897 013; U.S. Pat. No. 6,215,051; WO 01/12828 |
| Wheat | AU-B 738 153; EP-A1 856 060 |
| Beans | U.S. Pat. No. 5,169,770; EP-A1 397 687 |
| *Brassica* | U.S. Pat. No. 5,188,958; EP-A1 270 615; EP-A1 1,009,845 |
| Cacao | U.S. Pat. No. 6,150,587 |
| Citrus | U.S. Pat. No. 6,103,955 |
| Coffee | AU 729 635 |
| Cotton | U.S. Pat. No. 5,004,863; EP-A1 270 355; |
|  | U.S. Pat. No. 5,846,797; EP-A1 1,183,377; |
|  | EP-A1 1,050,334; EP-A1 1,197,579; EP-A1 1,159,436 |
|  | Pollen transformation (U.S. Pat. No. 5,929,300) |
|  | In planta transformation (U.S. Pat. No. 5,994,624) |
| Pea | U.S. Pat. No. 5,286,635 |
| Pepper | U.S. Pat. No. 5,262,316 |
| Poplar | U.S. Pat. No. 4,795,855 |
| Soybean | cotyledonary node of germinated soybean seedlings |
|  | shoot apex (U.S. Pat. No. 5,164,310) |
|  | axillary meristematic tissue of primary, or higher leaf node of |
|  | about 7 days germinated soybean seedlings |
|  | organogenic callus cultures |
|  | dehydrated embryo axes |
|  | U.S. Pat. No. 5,376,543; EP-A1 397 687; U.S. Pat. No. 5,416,011; |
|  | U.S. Pat. No. 5,968,830; U.S. Pat. No. 5,563,055; |
|  | U.S. Pat. No. 5,959,179; EP-A1 652 965; EP-A1 1,141,346 |
| Sugarbeet | EP-A1 517 833; WO 01/42480 |
| Tomato | U.S. Pat. No. 5,565,347 |

3.1.3.3.2. Plastid Transformation

In another preferred embodiment, a nucleotide sequence of the present invention (preferably an expression construct for the chimeric RNA molecule of the invention) is directly transformed into the plastid genome. Plastid expression, in which genes are inserted by homologous recombination into the several thousand copies of the circular plastid genome present in each plant cell, takes advantage of the enormous copy number advantage over nuclear-expressed genes to permit high expression levels. In a preferred embodiment, the nucleotide sequence is inserted into a plastid targeting vector and transformed into the plastid genome of a desired plant host. Plants homoplasmic for plastid genomes containing the nucleotide sequence are obtained, and are preferentially capable of high expression of the nucleotide sequence.

Plastid transformation technology is for example extensively described in U.S. Pat. Nos. 5,451,513, 5,545,817, 5,545,818, and 5,877,462 in PCT application no. WO 95/16783 and WO 97/32977, and in McBride et al. (1994) Proc. Natl. Acad. Sci. USA 91, 7301-7305, all incorporated herein by reference in their entirety. The basic technique for plastid transformation involves introducing regions of cloned plastid DNA flanking a selectable marker together with the nucleotide sequence into a suitable target tissue, e.g., using biolistic or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al. (1990) Proc. Natl. Acad. Sci. USA 87, 8526-8530; Staub et al. (1992) Plant Cell 4, 39-45). The presence of cloning sites between these markers allowed creation of a plastid targeting vector for introduction of foreign genes (Staub et al. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab et al. (1993) Proc. Natl. Acad. Sc. USA 90, 913-917). Other selectable markers useful for plastid transformation are known in the art and encompassed within the scope of the invention.

For using the methods according to the invention, the skilled worker has available well-known tools, such as expression vectors with promoters which are suitable for plants, and methods for the transformation and regeneration of plants.

3.1.3.4. Selection and Regeneration Techniques

To select cells which have successfully undergone transformation, it is preferred to introduce a selectable marker which confers, to the cells which have successfully undergone transformation, a resistance to a biocide (for example a herbicide), a metabolism inhibitor such as 2-deoxyglucose-6-phosphate (WO 98/45456) or an antibiotic. The selection marker permits the transformed cells to be selected from untransformed cells (McCormick et al. (1986) Plant Cell Reports 5:81-84). Suitable selection markers are described above.

Transgenic plants can be regenerated in the known manner from the transformed cells. The resulting plantlets can be planted and grown in the customary manner. Preferably, two or more generations should be cultured to ensure that the genomic integration is stable and hereditary. Suitable methods are described (Fennell et al. (1992) Plant Cell Rep. 11: 567-570; Stoeger et al (1995) Plant Cell Rep. 14:273-278; Jahne et al. (1994) Theor Appl Genet 89:525-533).

3.2 Pharmaceutical (Therapeutic or Prophylactic) Compositions and Methods

The specificity of compounds, compositions and methods of the invention can also be harnessed by those of skill in the art for therapeutic or prophylactic uses and are suitable for the preparation of pharmaceuticals for the treatment of human and animal diseases and for the production of pharmaceuticals.

Thus, the invention further provides a method for treating or preventing a disease or infection in an animal or human being, preferably a mammal. Yet another embodiment of the invention relates to a pharmaceutically preparation comprising at least one chimeric RNA of the invention. Preferably, said preparation gives rise to i) at least one protein which has a therapeutic or prophylactic effect on the target organism (preferably an animal or human) or ii) at least one functional RNA molecule, which to attenuates expression of at least one disease-related target gene.

Yet another embodiment relates a chimeric RNA of the invention, an expression construct or expression vector for its expression, or an organism (preferably a non-human organism) comprising said chimeric RNA molecule for use as a pharmaceutical, preferably for the treatment of one or more human or animal diseases. Yet another embodiment relates to the use of a chimeric RNA of the invention, an expression construct or expression vector for its expression, or a non-human organism comprising said chimeric RNA molecule for the preparation of a pharmaceutical, preferably for the treatment of one or more human or animal diseases.

The chimeric RNA of the invention (or a expression construct or vector for its expression) is administered to animal or human being (e.g., the mammal) in a therapeutically or prophylactically effective amount (e.g., an amount sufficient to attenuate expression of a target gene, the expression of which is associated with the disease or infection; or—in case of protein expression—an amount suitable to bring about the effect associated with the therapeutic protein). In case of disease gene suppression, the expression of the target gene (or alternatively the activity of the target protein expressed therefrom) is inhibited by at least about 10%, preferably by at least about 30%, more preferably by at least 50% or more.

A variety of disorders can be treated, including infections by heterologous pathogenic organisms, either extracellular or intracellular pathogens. Additionally, the compositions of this invention are useful in preventing infection with a pathogen, or preventing the occurrence of disorders caused by reactivation of a latent pathogen. These compositions are also useful for the treatment of pathogenically-induced cancers. The composition and methods of the invention are especially suitable to treat viral diseases (i.e., HIV, Hepatitis C). This especially applies for gene silencing approaches.

Thus, the methods of the present invention employ a gene therapy construct comprising a nucleic acid molecule that encodes a polypeptide having a therapeutic biological activity (also referred to herein as a "therapeutic polypeptide"), including but not limited to immunostimulatory molecules, tumor suppressor gene products/antigens, antimetabolites, suicide gene products, and anti-angiogenic factors. See Mackensen et al. (1997) Cytokine Growth Factor Rev 8(2):

119-128; Walther & Stein (1999) Mol Biotechnol 13(1):21-28; Kirk & Mule (2000) Hum Gene Ther 11(6):797-806; and references cited therein.

Furthermore other (not pathogen related) disorders and diseases can be treated. Examples of diseases that can be treated by oligonucleotide compositions include: cancer, retinopathies, autoimmune diseases, inflammatory diseases (i.e., ICAM-1 related disorders, Psoriasis, Ulcerative Colitus, Crohn's disease), cardiovascular diseases (such as hypertension), diseases of the central or peripheral nervous system such as Alzheimer's disease, Parkinson's disease or multiple sclerosis, and autosomal dominant genetic disease such as Huntington's chorea (For example, see U.S. Pat. No. 6,506,559; US 2002/0,173,478 A1; US 2002/0,086,356 A1; Shuey, et al., "RNAi: gene-silencing in therapeutic intervention." Drug Discov. Today 2002 Oct. 15; 7(20):1040-6; Aoki, et al., "Clin. Exp. Pharmacol. Physiol. 2003 January; 30(1-2):96-102; Cioca, et al., "RNA interference is a functional pathway with therapeutic potential in human myeloid leukemia cell lines. Cancer Gene Ther. 2003 February; 10(2):125-33). There are numerous medical conditions for which gene silencing therapy is reported to be suitable (see, e.g., U.S. Pat. No. 5,830,653) as well as respiratory syncytial virus infection (WO 95/22,553) influenza virus (WO 94/23, 028), and malignancies (WO 94/08,003). Other examples of clinical uses of antisense sequences are reviewed, e.g., in Glaser. 1996. Genetic Engineering News 16:1. Exemplary targets for cleavage by oligonucleotides include, e.g., protein kinase Ca, ICAM-1, c-raf kinase, p53, c-myb, and the bcr/abl fusion gene found in chronic myelogenous leukemia. The method of the invention can further be used to reduce or prevent the rejection response to transplant tissue (e.g., by silencing MHC proteins). A chimeric RNA hat attenuates the expression of a gene in the transplant tissue that can elicit an immune response in the recipient is administered to the transplant tissue.

Also, the method according to the invention makes possible the parallel treatment of more than one disease, such as, for example, a cardiovascular disease and a disease of the central nervous system, which is not generally possible when traditional approaches are used. Such approaches are advantageous especially in the case of multiple diseases as occur frequently with advanced age. An example which may be mentioned is the parallel treatment of hypertension and, for example, Alzheimer's disease or senile dementia.

The compounds and compositions of the invention can be utilized in pharmaceutical compositions by adding an effective amount of the compound or composition to a suitable pharmaceutically acceptable diluent or carrier. Use of the oligomeric compounds and methods of the invention may also be useful prophylactically.

3.2.1 Diseases and Disorders Preferred to be Treated by Compositions and Methods of the Invention The method according to the invention is particularly suitable for the treatment of the below mentioned diseases and disorders.

3.2.1.1 Pathogen Infections

Infection with pathogens, such as, for example, viral or bacterial diseases, in which case the chimeric RNA (or the dsRNA derived therefrom) attenuates the expression of a bacterial or viral gene. Specifically some of the more desirable viruses to treat with this method include, without limitation, viruses of the species Retrovirus, Herpesvirus, Hepadenovirus, Poxvirus, Parvovirus, Papillomavirus, and Papovavirus, espcially HIV, HBV, HSV, CMV, HPV, HTLV and EBV. The chimeric RNA used in this method provides to the cell (e.g., of an mammal) an at least partially double-stranded RNA molecule as described above, which is substantially identical to a target polynucleotide which is a virus polynucleotide sequence necessary for replication and/or pathogenesis of the virus in an infected mammalian cell. Among such target polynucleotide sequences are protein-encoding sequences for proteins necessary for the propagation of the virus, e.g., the HIV gag, env, gp41, and pol genes, the HPV6 L1 and E2 genes, the HPV11 L1 and E2 genes, the HPV16 E6 and E7 genes, the HPV18 E6 and E7 genes, the HBV surface antigens, the HBV core antigen, HBV reverse transcriptase, the HSV gD gene, the HSVvp16 gene, the HSV gC, gH, gL and gB genes, the HSV ICPO, ICP4 and ICP6 genes, Varicella zoster gB, gC and GH genes, and the BCR-abl chromosomal sequences, and non-coding viral polynucleotide sequences which provide regulatory functions necessary for transfer of the infection from cell to cell, e.g., the HIV LTR, and other viral promoter sequences, such as HSV vp16 promoter, HSV-ICPO promoter, HSV-ICP4, ICP6 and gD promoters, the HBV surface antigen promoter, the HBV pre-genomic promoter, among others. The composition (e.g., an dsRNA agent such as the chimeric RNA molecule of the invention) is administered with an polynucleotide uptake enhancer or facilitator and an optional pharmaceutically acceptable carrier. The amount or dosage which is administered to the mammal is effective to reduce or inhibit the function of the viral sequence in the cells of the mammal.

The method can be used to treat animals (e.g., mammals) already infected with a virus in order to shut down or inhibit a viral gene function essential to virus replication and/or pathogenesis. In still another embodiment of this invention, the compositions described above can be employed in a method to prevent viral infection (e.g., in a mammal). When the chimeric RNA of the invention is administered prior to exposure of the mammal to the virus, it is expected that the exogenous RNA molecule remains in the mammal and work to inhibit any homologous viral sequence which presents itself to the mammal thereafter. Thus, the compositions of the present invention may be used to inhibit or reduce the function of a viral polynucleotide sequence for vaccine use. Still an analogous embodiment of the above "anti-viral" methods of the invention includes a method for treatment or prophylaxis of a virally induced cancer in a mammal (such cancers include HPV E6/E7 virusinduced cervical carcinoma, and EBV induced cancers).

The compositions of this invention can also be employed for the treatment or prophylaxis of infection by a non-viral pathogen, either intracellular or extracellular. As used herein, the term "intracellular pathogen" is meant to refer to a virus, bacteria, protozoan or other pathogenic organism that, for at least part of its reproductive or life cycle, exists within a host cell and therein produces or causes to be produced, pathogenic proteins. Intracellular pathogens which infect cells which include a stage in the life cycle where they are intracellular pathogens include, without limitation, *Listeria, Chlamydia, Leishmania, Brucella, Mycobacteria, Shigella*, and as well as Plasmodia, e.g., the causative agent of malaria, *P. falciparum*. Extracellular pathogens are those which replicate and/or propagate outside of the mammalian cell, e.g., *Gonorrhoeae*, and *Borrellia*, among others. According to this embodiment, such infection by an pathogen may be treated or possibly prevented by administering to a mammalian subject, either already infected or anticipating exposure to the pathogen, with a composition as described above with an optional second agent that facilitates polynucleotide uptake in a cell, in a pharmaceutically acceptable carrier. In this case, the RNA molecule of the composition has a polynucleotide sequence which is substantially identical to a target polynucleotide sequence of the pathogen that is necessary for replication and/or pathogenesis of the pathogen in an infected mammal or mammalian cell. As above, the amount of the composition administered is an amount effective to reduce or inhibit the function of the pathogenic sequence in the mammal. The dosages, timing, routes of administration and the like are as described below.

Thus one embodiment of the invention related to a method for reducing the susceptibility of host cells or host organisms to infection by pathogen, comprising introducing a chimeric RNA of the invention into said host cells or host organisms in an amount sufficient to attenuate expression of one or more genes necessary for expression by said pathogen. Preferably, the pathogen is a virus, a fungus or a nematode. Preferably, the host cell is a plant or an animal, preferably a mammalian, more preferably a human cell.

One of skill in the art, given this disclosure can readily select viral families and genera, or pathogens including prokaryotic and eukaryotic protozoan pathogens as well as multicellular parasites, for which therapeutic or prophylactic compositions according to the present invention can be made. See, e.g., the tables of such pathogens in general immunology texts and in U.S. Pat. No. 5,593,972, incorporated by reference herein.

3.2.1.2 Cancer

Treatment of cancer (for example solid tumors and/or leukemias) and inherited disorders. Among conditions particularly susceptible to treatment or prophylaxis according to this invention are those conditions which are characterized by the presence of an aberrant polynucleotide sequence, the function of which is necessary to the initiation or progression of the disorder, but can be inhibited without causing harm or otherwise unduly adversely impacting the health of the organism (e.g. the mammal). Mammalian cancers which are characterized by the presence of abnormal and normal polynucleotide sequences (for details see, e.g., WO94/13793) include chronic myelogenous leukemia (CML) and acute lymphoblastic leukemia (ALL), where the abnormal sequence is a fusion of two normal genes, i.e., bcr-abl. In such cancers or diseases, such as CML, the afflicted mammal also possesses a normal copy of the polynucleotide sequence or gene, and the differences between the abnormal and normal sequences or genes are differences in nucleotide sequence. For example, for CML, the abnormal sequence is the bcr-abl fusion, while the normal sequence is bcr and abl. Thus, the method above can be employed with the target polynucleotide sequence being the sequence which spans the fusion. A method of treatment or prophylaxis of such a cancer in a mammal comprises administering to the mammal a composition of this invention wherein the target polynucleotide is a polynucleotide sequence of an abnormal cancer-causing gene in a mammal which also possesses a normal copy of the gene, and wherein the differences between the abnormal gene and the normal gene are differences in polynucleotide sequence. The skilled worker is familiar with a large number of potential target genes for cancer therapy (for example oncogenes such as ABL1, BCL1, BCL2, BCL6, CBFA2, CBL, CSF1R, ERBA, ERBB, EBRB2, FGR, FOS, FYN, HRAS, JUN, LCK, LYN, MYB, MYC, NRAS, RET or SRC; tumor suppressor genes such as BRCA1 or BRCA2; adhesion molecules; cyclin kinases and their inhibitors). An exemplary list of potential target genes, including developmental genes, oncogenes, and enzymes, and a list of cancers that can be treated according to the present invention can be found in WO 99/32619. A candidate target gene derived from a pathogen might, for example, cause immunosuppression of the host or be involved in replication of the pathogen, transmission of the pathogen, or maintenance of the infection.

Another embodiment of the invention provides a method for the treatment of cancer (e.g., local and metastatic breast, ovarian, or porostate cancer) comprising: administration to the patient expression construct or vector (or a variant thereof) of the invention containing a cytotoxic gene.

Angiogenesis and suppressed immune response play a central role in the pathogenesis of malignant disease and tumor growth, invasion, and metastasis. Thus, preferably, the therapeutic polypeptide has an ability to induce an immune response and/or an anti-angiogenic response in vivo. In one embodiment, a gene therapy construct of the present invention encodes a therapeutic gene that displays both immunostimulatory and anti-angiogenic activities, for example, IL12 (see Dias et al. (1998) Int J Cancer 75(1):151-157, and references cited herein below), interferon-alpha (O'Byrne et al. (2000) Eur J Cancer 36(2):151-169, and references cited therein), or a chemokine (Nomura & Hasegawa (2000) Anticancer Res 20(6A):4073-4080, and references cited therein). In another embodiment, a gene therapy construct of the present invention encodes a gene product with immunostimulatory activity and a gene product having anti-angiogenic activity. See, e.g. Narvaiza et al. (2000) J Immunol 164:3112-3122. In another embodiment, the invention comprises a gene therapy construct encoding an IL2 polypeptide. IL12 is an immunostimulatory molecule that shows therapeutic activity in a variety of cancers, including renal cancer, breast cancer, bladder cancer, and malignant melanoma. The anti-tumor activity of IL2 is related to its capacity to expand and activate NK cells and T cells that express IL2 receptors. See, e.g., Margolin (2000) Semin Oncol 27(2):194-203; Gore (1996) Cancer Biother Radiopharm 11 (5):281-283; Deshmukh et al. (2001) J Neurosurgery 94(2):287-292; Larchian et al. (2000) Clin Cancer Res 6(7):2913-2920; Horiguchi et al. (2000) Gene Ther 7(10):844-851; and references cited therein. IL2 has also been used successfully when co-administered with anti-tumor vaccines. See Overwijk et al. (2000) Cancer J Sci Am 6 Suppl 1:S76-80, and references cited therein.

3.2.2 Formulations and Administration

The chimeric RNA of the invention may be used and applied directly to an animal or human in need of therapy or prophylaxis or may be applied indirectly by means of an expression vector or construct.

3.2.2.1 Viral Gene Therapy Vectors

The present invention also provides gene therapy constructs or vectors. The particular vector employed in accordance with the methods of the present invention is not intended to be a limitation of the method for heat-induced expression of therapeutic genes by hyperthermia. Thus, any suitable vector for delivery of the gene therapy construct can be used.

The vector can be a viral vector or a non-viral vector. Suitable viral vectors include adenoviruses, adeno-associated viruses (AAVs), retroviruses, pseudotyped retroviruses, herpes viruses, vaccinia viruses, Semiliki forest virus, and baculoviruses. Suitable non-viral vectors comprise plasmids, water-oil emulsions, polethylene imines, dendrimers, micelles, microcapsules, liposomes, and cationic lipids. Polymeric carriers for gene therapy constructs can be used as described in Goldman et al (1997) Nat Biotechnol 15:462 and U.S. Pat. Nos. 4,551,482 and 5,714,166. Peptide carriers are described in U.S. Pat. No. 5,574,172. Where appropriate, two or more types of vectors can be used together. For example, a plasmid vector can be used in conjunction with liposomes. Currently, a preferred embodiment of the present invention envisions the use of an adenovirus, a plasmid, or a liposome, each described further herein below.

As desired, vectors, especially viral vectors, can be selected to achieve integration of the nucleic acid of the construct of the invention, into the genome of the cells to be transformed or transfected. Including a ligand in the complex having affinity for a specific cellular marker can also enhance delivery of the complexes to a target in vivo. Ligands include antibodies, cell surface markers, viral peptides, and the like, which act to home the complexes to tumor vasculature or endothelial cells associated with tumor vasculature, or to tumor cells themselves. A complex can comprise a construct or a secreted therapeutic polypeptide encoded by a construct. An antibody ligand can be an antibody or antibody fragment specific towards a tumor marker such as Her2/neu (v-erb-b2 avian erythroblastic leukemia viral oncogene homologue 2), CEA (carcinoembryonic antigen), ferritin receptor, or a marker associated with tumor vasculature (integrins, tissue factor, or beta.-fibronectin isoform). Antibodies or other ligands can be coupled to carriers such as liposomes and viruses, as is known in the art. See, e.g., Neri et al. (1997) Nat BioTechnology 15:1271; Kirpotin et al. (1997) Biochemistry 36:66; Cheng (1996) Human Gene Therapy 7:275; Pasqualini et al. (1997) Nat Biotechnology 15:542; Park et al. (1997) Proc Am Ass Canc Res 38:342 (1997); Nabel (1997) "Vectors for Gene Therapy" in Current Protocols in Human Genetics on CD-ROM, John Wiley & Sons, New York, N.Y.; U.S. Pat. No. 6,071,890; and European Patent No. 0 439 095. Alternatively, pseudotyping of a retrovirus can be used to target a virus towards a particular cell (Marin et al. (1997) Mol Med Today 3:396).

Viral vectors of the invention are preferably disabled, e.g. replication-deficient. That is, they lack one or more functional genes required for their replication, which prevents their uncontrolled replication in vivo and avoids undesirable side effects of viral infection. Preferably, all of the viral genome is removed except for the minimum genomic elements required to package the viral genome incorporating the therapeutic gene into the viral coat or capsid. For example, it is desirable to delete all the viral genome except the Long Terminal Repeats (LTRs) or Invented Terminal Repeats (ITRs) and a packaging signal. In the case of adenoviruses, deletions are typically made in the E1 region and optionally in one or more of the E2, E3 and/or E4 regions. In the case of retroviruses, genes required for replication, such as env and/or gag/pol can be deleted. Deletion of sequences can be achieved by recombinant means, for example, involving digestion with appropriate restriction enzymes, followed by religation. Replication-competent self-limiting or selfdestructing viral vectors can also be used.

Nucleic acid constructs of the invention can be incorporated into viral genomes by any suitable means known in the art. Typically, such incorporation will be performed by ligating the construct into an appropriate restriction site in the genome of the virus. Viral genomes can then be packaged into viral coats or capsids by any suitable procedure. In particular, any suitable packaging cell line can be used to generate viral vectors of the invention. These packaging lines complement the replication-deficient viral genomes of the invention, as they include, typically incorporated into their genomes, the genes which have been deleted from the replication-deficient genome. Thus, the use of packaging lines allows viral vectors of the invention to be generated in culture.

Suitable packaging lines for retroviruses include derivatives of PA317 cells, .psi.-2 cells, CRE cells, GRIP cells, E-86-GP cells, and 293GP cells. Line 293 cells can be used for adenoviruses and adeno-associated viruses.

Suitable methods for introduction of a gene therapy construct into cells include direct injection into a cell or cell mass, particle-mediated gene transfer, electroporation, DEAEDextran transfection, liposome-mediated transfection, viral infection, and combinations thereof. A delivery method is selected based considerations such as the vector type, the toxicity of the encoded gene, and the condition to be treated.

3.2.2.2 Suitable Expression Constructs

Various promoters can be employed to express the chimeric RNA molecule of the invention to achieve a beneficial therapeutic or prophylactic effect. By the methods and subject matter of the invention provided herein the expression becomes more specific, which is preferably enhancing the beneficial effects and decreasing the side effects.

Various promoters are currently used in the art to express sequences in animal, mammalian or human organism. Most of them are lacking tissue-specificity and can be advantageously combined with the teaching provided herein. For example the promoter may be selected from group consisting of the perbB2 promoter, whey acidic protein promoter, stromelysin 3 promoter, prostate specific antigen promoter, probasin promoter.

The promoter may be a heat or light inducible promoter, or chemically inducible promoter (e.g., a promoter inducible by antibiotic (tetracycline or its derivatives), acting on a fusion protein with a tetracycline-responsive element).

The constructs may also comprise a heat-inducible promoter. Any heat-inducible promoter can be used in accordance with the methods of the present invention, including but not limited to a heat-responsive element in a heat shock gene (e.g., hsp20-30, hsp27, hsp40, hsp60, hsp70, and hsp90). See Easton et al. (2000) Cell Stress Chaperones 5(4):276-290; Csermely et al. (1998) Pharmacol Ther 79(2): 129-168; Ohtsuka & Hata (2000) Int J Hyperthermia 16(3): 231-245; and references cited therein. Sequence similarity to heat shock proteins and heat-responsive promoter elements have also been recognized in genes initially characterized with respect to other functions, and the DNA sequences that confer heat inducibility are suitable for use in the disclosed gene therapy vectors. For example, expression of glucose-responsive genes (e.g., grp94, grp78, mortalin/grp75) (Merrick et al. (1997) Cancer Lett 119(2):185-190; Kiang et al. (1998) FASEB J 12(14):1571-16-579), calreticulin (Szewczenko-Pawlikowski et al. (1997) Mol Cell Biochem 177 (1-2):145-152); clusterin (Viard et al. (1999) J Invest Dermatol 112(3):290-296; Michel et al. (1997) Biochem J 328(Ptl):45-50; Clark & Griswold (1997) J Androl 18(3): 257-263), histocompatibility class I gene (HLA-G) (Ibrahim et al. (2000) Cell Stress Chaperones 5(3):207-218), and the Kunitz protease isoform of amyloid precursor protein (Shepherd et al. (2000) Neuroscience 99(2):317-325) are up-regulated in response to heat.

In the case of clusterin, a 14 base pair element that is sufficient for heat-inducibility has been delineated (Michel et al. (1997) Biochem J 328(Pt1):45-50). Similarly, a twosequence unit comprising a 10- and a 14-base pair element in the calreticulin promoter region has been shown to confer heat-inducibility (Szewczenko-Pawlikowski et al. (1997) Mol Cell Biochem 177(1-2):145-152).

Other promoter responsive to non-heat stimuli that can be used. For example, the mortalin promoter is induced by low doses of ionizing radiation (Sadekova (1997) Int J Radiat Biol 72(6):653-660), the hsp27 promoter is activated by 17.beta.-estradiol and estrogen receptor agonists (Porter et al. (2001) J Mol Endocrinol 26(1):31-42), the HLA-G promoter is induced by arsenite, hsp promoters can be activated by photodynamic therapy (Luna et al. (2000) Cancer Res 60(6):1637-1644).

A suitable promoter can incorporate factors such as tissue-specific activation. For example, hsp70 is transcriptionally impaired in stressed neuroblastoma cells (Drujan & De Maio (1999) 12(6):443-448). The mortalin promoter, which is up-regulated in human brain tumors (Takano et al. (1997) Exp Cell Res 237(1):38-45). A promoter employed in methods of the present invention can show selective up-regulation in tumor cells as described, for example, for mortalin (Takano et al. (1997) Exp Cell Res 237(1):38-45), hsp27 and calreticulin (Szewczenko-Pawlikowski et al. (1997) Mol Cell Biochem 177(1-2):145-152; Yu et al. (2000) Electrophoresis 21(14):3058-3068), grp94 and grp78 (Gazit et al. (1999) Breast Cancer Res Treat 54(2):135-146), hsp27, hsp70, hsp73, and hsp90 (Cardillo et al. (2000) Anticancer Res 20(6B):4579-4583; Strik et al. (2000) Anticancer Res 20(6B):4457-4552).

3.2.2.3 Formulations for Uptake of RNA and DNA

For the purpose of pharmaceutical applications it is preferred that the chimeric RNA molecule of the invention is applied or administered to the target cell or organism directly. Various means for application of RNA as pharmaceutical active ingredient are described in the art.

As used herein "administration" refers to contacting cells (e.g., either in isolated form or comprised in an organism) with the pharmaceutical agent and can be performed in vitro or in vivo. With respect to in vivo applications, the formulations of the present invention can be administered to a patient in a variety of forms adapted to the chosen route of administration, e.g., parenterally, orally, or intraperitoneally. Parenteral administration, which is preferred, includes administration by the following routes: intravenous; intramuscular; interstitially; intraarterially; subcutaneous; intra ocular; intrasynovial; trans epithelial, including transdermal; pulmonary via inhalation; ophthalmic; sublingual and buccal; topically, including ophthalmic; dermal; ocular; rectal; and nasal inhalation via insufflation. Preferably pharmaceutical preparations for the various ways of administration (such as parenteral, transmucosal, transdermal, oral, or topical application) are well known in the art and for example described in US Patent Application No. 20040014956. The pharmaceutical agent of the invention may be administered systemically to a subject. Systemic absorption refers to the entry of drugs into the blood stream followed by distribution throughout the entire body. Administration routes which lead to systemic absorption include: intravenous, subcutaneous, intraperitoneal, and intranasal. The chosen method of delivery will result in entry into cells. Preferred delivery methods include liposomes (10-400 nm), hydrogels, controlled-release polymers, and other pharmaceutically applicable vehicles, and microinjection or electroporation (for ex vivo treatments). Drug delivery vehicles can be chosen e.g., for in vitro, for systemic, or for topical administration. These vehicles can be designed to serve as a slow release reservoir or to deliver their contents directly to the target cell. An advantage of using some direct delivery drug vehicles is that multiple molecules are delivered per uptake. Some examples of such specialized drug delivery vehicles which fall into this category are liposomes, hydrogels, cyclodextrins, biodegradable nanocapsules, and bioadhesive microspheres. In one embodiment, in vitro treatment of cells with oligonucleotides can be used for ex vivo therapy of cells removed from a subject (e.g., for treatment of leukemia or viral infection) or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein.

Compositions for pharmaceutical use of this invention desirably contain a chimeric RNA molecule, or an expression construct for its production (hereinafter the "pharmaceutical agent"). Any of the pharmaceutical agents can be used alone or in conjunction with a pharmaceutically acceptable carrier and with additional optional components for pharmaceutical delivery. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Suitable pharmaceutically acceptable carriers facilitate administration of the polynucleotide compositions of this invention, but are physiologically inert and/or nonharmful. Carriers may be selected by one of skill in the art. Such carriers include but are not limited to, sterile saline, phosphate, buffered saline, dextrose, sterilized water, glycerol, ethanol, lactose, sucrose, calcium phosphate, gelatin, dextran, agar, pectin, peanut oil, olive oil, sesame oil, and water and combinations thereof Additionally, the carrier or diluent may include a time delay material, such as glycerol monostearate or glycerol distearate alone or with a wax. In addition, slow release polymer formulations can be used. The formulation should suit not only the form of the delivery agent, but also the mode of administration. Selection of an appropriate carrier in accordance with the mode of administration is routinely performed by those skilled in the art. Additional components for the carrier may include but are not limited to adjuvants, preservatives, chemical stabilizers, or other antigenic proteins. Suitable exemplary preservatives include chlorobutanol, potassium sorbate, sorbic acid, sulfur dioxide, propyl gallate, the parabens, ethyl vanillin, glycerin, phenol, and parachlorophenol. Suitable stabilizing ingredients which may be used include, for example, casamino acids, sucrose, gelatin, phenol red, N-Z amine, monopotassium diphosphate, lactose, lactalbumin hydrolysate, and dried milk. A conventional adjuvant is used to attract leukocytes or enhance an immune response. Such adjuvants include, among others, Ribi, mineral oil and water, aluminum hydroxide, Amphigen, Avridine, L121/squalene, D-lactide-polylactide/glycoside, pluronic plyois, muramyl dipeptide, killed *Bordetella*, and saponins, such as Quil A.

The pharmaceutical agent may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types. Liposomes can be prepared by any of a variety of techniques that are known in the art. See e.g., Betageri et al. (1993) Liposome Drug Delivery Systems, Technomic Publishing, Lancaster; Gregoriadis, ed.

(1993) Liposome Technology, CRC Press, Boca Raton, Fla.; Janoff, ed. (1999) Liposomes: Rational Design, M. Dekker, New York, N.Y.; Lasic & Martin (1995) Stealth Liposomes, CRC Press, Boca Raton, Fla.; Nabel (1997) "Vectors for Gene Therapy" in Current Protocols in Human Genetics on CD-ROM, John Wiley & Sons, New York, N.Y.; and U.S. Pat. Nos. 4,235,871; 4,551,482; 6,197,333; and 6,132,766. Entrapment of an active agent within liposomes of the present invention can also be carried out using any conventional method in the art. In preparing liposome compositions, stabilizers such as antioxidants and other additives can be used. Other lipid carriers can also be used in accordance with the claimed invention, such as lipid microparticles, micelles, lipid suspensions, and lipid emulsions. See, e.g., Labat-Moleur et al. (1996) Gene Therapy 3:1010-1017; U.S. Pat. Nos. 5,011,634; 6,056,938; 6,217886; 5,948,767; and 6,210,707.

The composition of the invention may also involve lyophilized polynucleotides, which can be used with other pharmaceutically acceptable excipients for developing powder, liquid or suspension dosage forms, including those for intranasal or pulmonary applications. See, e.g., Remington: The Science and Practice of Pharmacy, Vol. 2, 19.sup.th edition (1995), e.g., Chapter 95 Aerosols; and International Patent Application No. PCT/US99/05547, the teachings of which are hereby incorporated by reference.

In some preferred embodiments, the pharmaceutical compositions of the invention are prepared for administration to mammalian subjects in the form of, for example, liquids, emulsions, powders, aerosols, tablets, capsules, enteric coated tablets or capsules, or suppositories. The optimal course of administration or delivery of the pharmaceutical agent may vary depending upon the desired result and/or on the subject to be treated.

The pharmaceutical preparations of the present invention may be prepared and formulated as emulsions or microemulsions. Emulsions are usually heterogenous systems of one liquid dispersed in another in the form of droplets usually exceeding 0.1 μm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase. Suitable examples for emulsifiers and preservatives are given in US Patent Application No. 20040014956. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system. Suitable examples for surfanctants and cosurfactants are described in US Patent Application No. 20040014956. Microemulsions are particularly of interest from the standpoint of drug solubilization and the enhanced absorption of drugs. Lipid based microemulsions (both oil/water and water/oil) have been proposed to enhance the oral bioavailability of drugs. It is expected that the microemulsion compositions and formulations of the present invention will facilitate the increased systemic absorption of pharmaceutical agents of the invention from the gastrointestinal tract, as well as improve the local cellular uptake of oligonucleotides within the gastrointestinal tract, vagina, buccal cavity and other areas of administration.

In an embodiment, the present invention employs various penetration enhancers to effect the efficient delivery of the pharmaceutical agents of the invention (especially nucleic acids, particularly oligonucleotides) to the skin of humans and animals. Suitable penetration enhancer are described in US Patent Application NO. 20040146902, herein incorporated by reference.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. The dosage of the pharmaceutical agent may be adjusted to optimally reduce expression from the target gene, e.g., as measured by a readout of RNA stability or by a therapeutic response, without undue experimentation. The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms. For example, the compositions of the present invention, when used as pharmaceutical compositions, can comprise about 1 ng to about 20 mgs of the pharmaceutical agent of the invention (e.g., the synthetic RNA molecules or the delivery agents which can be DNA molecules, plasmids, viral vectors, recombinant viruses, and mixtures thereof). The compositions of the present invention in which the delivery agents are donor cells or bacterium can be delivered in dosages of between about 1 cell to about $10^7$ cells/dose. Similarly, where the delivery agent is a live recombinant virus, a suitable vector-based composition contains between $1 \times 10^2$ pfu to $1 \times 10^{12}$ pfu per dose.

The pharmaceutical agent of the invention may be combined with any other drug, preferably for the same medicinal indication. For example for pharmaceutical agents which have anti-cancer properties the agent may be combined with one or more chemotherapeutic agents (e.g., such as daunorubicin, idarubicin, mitomycin C, 5-fluorouracil (5-FU), methotrexate (MTX), taxol, vincristine, and cisplatin) that function by a non-antisense mechanism.

Additional suitable teachings for pharmaceutical compositions and their preparation, administration and dosing in relation to oligonucleotide compounds which may be utilized within the scope of the present invention are given in US Patent Application No. 20040146902

In one embodiment, the pharmaceutical agents of the invention (e.g., oligonucleotides) can be administered to subjects. Examples of subjects include mammals, e.g., humans and other primates; cows, pigs, horses, and farming (agricultural) animals; dogs, cats, and other domesticated pets; mice, rats, and transgenic non-human animals.

3.3. Biotechnological Applications

The methods and compositions according to the invention can be applied advantageously in biotechnological applications and methods, including but not limited to optimization of metabolic pathways e.g., in yeasts, fungi or other eukaryotic microorganisms or cells which are used in fermentation for the production of fine chemicals such as amino acids (for example lysin or methionin), vitamins (such as vitamin B2, vitamin C, vitamin E), carotenoids, oils and fats, polyunsaturated fatty acids, biotin and the like.

Preferred vectors for expression in eukaryotes comprise pWLNEO, pSV2CAT, pOG44, pXT1 and pSG (Stratagene Inc.); pSVK3, pBPV, pMSG and pSVL (Pharmacia Biotech, Inc.). Inducible vectors which may be mentioned are pTet-tTak, pTet-Splice, pcDNA4/TO, pcDNA4/TO/LacZ, pcDNA6/TR, pcDNA4/TO/Myc-His/LacZ, pcDNA4/TO/Myc-His A, pcDNA4/TO/Myc-His B, pcDNA4/TO/Myc-His C, pVgRXR (Invitrogen, Inc.) or the pMAM series (Clontech, Inc.; GenBank Accession No.: U02443). These vectors already provide the inducible regulatory control element, for example for a chemically inducible expression of a DSBI enzyme. The nucleic acid sequence encoding a DSBI enzyme can be inserted directly into these vectors. Vectors for expression in yeast comprise for example pYES2, pYD1, pTEFI/Zeo, pYES2/GS, pPICZ, pGAPZ, pGAPZalph, pPIC9, pPIC3.5, PHIL-D2, PHIL-SI, pPIC3SK, pPIC9K and PA0815 (Invitrogen, Inc.). In principle, for the transformation of animal cell or of yeast cells, similar methods as the "direct" transformation of plant cells are to be applied. In particular, methods such as the calcium-phosphate- or liposome-mediated transformation or else electroporation are preferred. Selection markers which can be used are, in principle, many of the selection systems which are also preferred for plants. Especially preferred are for mammalian cell the neomycin (G418) resistance, the hygromycin resistance, the zeocin resistance or the puromycin resistance. The ampicillin resistance, the kanamycin resistance or the tetracycline resistant are especially preferred for prokaryotes.

Depending on the host organism, the organisms used in the method are grown or cultured in a manner with which the skilled worker is familiar. As a rule, microorganisms are grown in a liquid medium comprising a carbon source, usually in the form of sugars, a nitrogen source, usually in the form of organic nitrogen sources such as yeast extracts or salts such as ammonium sulfate, trace elements such as salts of iron, manganese and magnesium, and, if appropriate, vitamins, at temperatures of between 0° C. and 100° C., preferably between 10° C. to 60° C., while passing in oxygen. The pH of the liquid medium can be kept at a constant value, that is to say regulated during the culturing period, or else not. The culture can be batchwise, semibatchwise or continuous. Nutrients can be provided at the beginning of the fermentation or fed in semicontinuously or continuously.

4. Exemplification

Those skilled in the art will recognize, or be able to ascertain using no more than routine experimentation, many equivalents to the specific embodiments of the invention described herein. Such equivalents are intended to be encompassed by the following claims. The entire contents of all patents, published patent applications and other references cited herein are hereby expressly incorporated herein in their entireties by reference.

The invention, now being generally described, will be more readily understood by reference to the following examples, which are included merely for purposes of illustration of certain aspects and embodiments of the present invention and are not intended to limit the invention.

EXAMPLES

General Methods

Unless otherwise specified, all chemicals are obtained from Fluka (Buchs), Merck (Darmstadt), Roth (Karlsruhe), Serva (Heidelberg) and Sigma (Deisenhofen). Restriction enzymes, DNA-modifying enzymes and molecular biology kits were from AmershamPharmacia (Freiburg), Biometra (Göttingen), Roche (Mannheim), New England Biolabs (Schwalbach), Novagen (Madison, Wis., USA), Perkin-Elmer (Weiterstadt), Qiagen (Hilden), Stratagen (Amsterdam, Netherlands), Invitrogen (Karlsruhe) and Ambion (Cambridgeshire, United Kingdom). The reagents used were employed in accordance with the manufacturer's instructions.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, J. et al. (Cold Spring Harbor Laboratory Press (1989)); Short Protocols in Molecular Biology, 3rd Ed., ed. by Ausubel, F. et al. (Wiley, N.Y. (1995)); DNA Cloning, Volumes I and II (D. N. Glover ed., 1985); Oligonucleotide Synthesis (M. J. Gait ed. (1984)); Mullis et al. U.S. Pat. No. 4,683,195; Nucleic Acid Hybridization (B. D. Hames & S. J. Higgins eds. (1984)); the treatise, Methods In Enzymology (Academic Press, Inc., N.Y.); Immunochemical Methods In Cell And Molecular Biology (Mayer and Walker, eds., Academic Press, London (1987)); Handbook Of Experimental Immunology, Volumes I-IV (D. M. Weir and C. C. Blackwell, eds. (1986)); and Miller, J. Experiments in Molecular Genetics (Cold Spring Harbor Press, Cold Spring Harbor, N.Y. (1972)).

The chemical synthesis of oligonucleotides can be carried out for example in the known manner using the phosphoamidite method (Voet, Voet, 2nd edition, Wiley Press New York, pages 896-897). The cloning steps carried out for the purpose of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, propagation of phages and sequence analysis of recombinant DNA, are carried out as described in Sambrook et al. (1989) Cold Spring Harbor Laboratory Press; ISBN 0-87969-309-6. Recombinant DNA molecules are sequenced using an ABI laser fluorescence DNA sequencer by the method of Sanger (Sanger et al. (1977) Proc Natl Acad Sci USA 74:5463-5467).

Example 1: *Agrobacterium*-Mediated Transformation in Dicotyledonous and Monocotyledonous Plants 1.1 Transformation and Regeneration of Transgenic *Arabidopsis thaliana* (Columbia) Plants To generate transgenic *Arabidopsis* plants, *Agrobacterium tumefaciens* (strain C58C1 pGV2260) is transformed with various ptxA or SbHRGP3 promoter/GUS vector constructs. The agrobacterial strains are subsequently used to generate transgenic plants. To this end, a single transformed *Agrobacterium* colony is incubated overnight at 28° C. in a 4 mL culture (medium: YEB medium with 50 µg/mL kanamycin and 25 µg/mL rifampicin). This culture is subsequently used to inoculate a 400 mL culture in the same medium, and this is incubated overnight (28° C., 220 rpm) and spun down (GSA rotor, 8,000 rpm, 20 min). The pellet is resuspended in infiltration medium (1/2 MS medium; 0.5 g/L MES, pH 5.8; 50 g/L sucrose). The suspension is introduced into a plant box (Duchefa), and 100 mL of SILWET L-77 (heptamethyltrisiloxan modified with polyalkylene oxide; Osi Specialties Inc., Cat. P030196) was added to a final concentration of 0.02%. In a desiccator, the plant box with 8 to 12 plants is exposed to a vacuum for 10 to 15 minutes, followed by spontaneous aeration. This is repeated twice or 3 times. Thereupon, all plants are planted into flowerpots with moist soil and grown under long-day conditions (daytime temperature 22 to 24° C., nighttime temperature 19° C.; relative atmospheric humidity 65%). The seeds are harvested after 6 weeks.

As an alternative, transgenic *Arabidopsis* plants can be obtained by root transformation. White root shoots of plants with a maximum age of 8 weeks are used. To this end, plants which are kept under sterile conditions in 1 MS medium (1% sucrose; 100 mg/L inositol; 1.0 mg/L thiamine; 0.5 mg/L pyridoxine; 0.5 mg/L nicotinic acid; 0.5 g MES, pH 5.7; 0.8% agar) are used. Roots are grown on callus-inducing medium for 3 days (1× Gamborg's B5 medium; 2% glucose; 0.5 g/L mercaptoethanol; 0.8% agar; 0.5 mg/L 2,4-D (2,4-dichlorophenoxyacetic acid); 0.05 mg/L kinetin). Root sections 0.5 cm in length are transferred into 10 to 20 mL of liquid callus-inducing medium (composition as described above, but without agar supplementation), inoculated with 1 mL of the above-described overnight agrobacterial culture (grown at 28° C., 200 rpm in LB) and shaken for 2 minutes. After excess medium has been allowed to run off, the root explants are transferred to callus-inducing medium with agar, subsequently to callus-inducing liquid medium without agar (with 500 mg/L betabactyl, SmithKline Beecham Pharma GmbH, Munich), incubated with shaking and finally transferred to shoot-inducing medium (5 mg/L 2-isopentenyladenine phosphate; 0.15 mg/L indole-3-acetic acid; 50 mg/L kanamycin; 500 mg/L betabactyl). After 5 weeks, and after 1 or 2 medium changes, the small green shoots are transferred to germination medium (1 MS medium; 1% sucrose; 100 mg/L inositol; 1.0 mg/L thiamine; 0.5 mg/L pyridoxine; 0.5 mg/L nicotinic acid; 0.5 g MES, pH 5.7; 0.8% agar) and regenerated into plants.

1.2 Transformation and Regeneration of Crop Plants

The *Agrobacterium*-mediated plant transformation using standard transformation and regeneration techniques may also be carried out for the purposes of transforming crop plants (Gelvin & Schilperoort (1995) Plant Molecular Biology Manual, 2nd Edition, Dordrecht: Kluwer, Academic Publ. ISBN 0-7923-2731-4; Glick & Thompson (1993) Methods in Plant Molecular Biology and Biotechnology, Boca Raton: CRC Press, ISBN 0-8493-5164-2)

For example, oilseed rape can be transformed by cotyledon or hypocotyl transformation (Moloney et al. (1989) Plant Cell Reports 8: 238-242, de Block et al. (1989) Plant Physiol. 91:694-701) The use of antibiotics for the selection of *Agrobacteria* and plants depends on the binary vector and the *Agrobacterium* strain used for the transformation. The selection of oilseed rape is generally carried out using kanamycin as selectable plant marker. The *Agrobacterium*-mediated gene transfer in linseed (*Linum usitatissimum*) can be carried out using for example a technique described by Mlynarova et al. ((1994), Plant Cell Report 13: 282-285). The transformation of soya can be carried out using, for example, a technique described in EP-A1 0424 047 or in EP-A1 0397 687, U.S. Pat. Nos. 5,376,543, 5,169,770. The transformation of maize or other monocotyledonous plants can be carried out using, for example, a technique described in U.S. Pat. No. 5,591,616.

The transformation of plants using particle bombardment, polyethylene glycol-mediated DNA uptake or via the silicon carbonate fiber technique is described, for example, by Freeling & Walbot (1993) "The maize handbook" ISBN 3-540-97826-7, Springer Verlag New York).

Example 2: Detection of Reporter Gene Expression

These experiments are performed by bombardment of plant tissues or culture cells (Example 2.1), by PEG-mediated (or similar methodology) introduction of DNA to plant protoplasts (Example 2.2), or by *Agrobacterium*-mediated transformation (Example 2.3). The target tissue for these experiments can be plant tissues (e.g. leaf tissue has been described to best support IRES-mediated translation (Urwin, et al., 2000), cultured plant cells (e.g. maize BMS), or plant embryos for *Agrobacterium* protocols.

2.1 Transient Assay Using Microprojectile Bombardment

The plasmid constructs are isolated using Qiagen plasmid kit (cat #12143). DNA is precipitated onto 0.6 µM gold particles (Bio-Rad cat #165-2262) according to the protocol described by Sanford et al. (1993) and accelerated onto target tissues (e.g. two week old maize leaves, BMS cultured cells, etc.) using a PDS-1000/He system device (Bio-Rad). All DNA precipitation and bombardment steps are performed under sterile conditions at room temperature.

Two mg of gold particles (2 mg/3 shots) are resuspended in 100% ethanol followed by centrifugation in a Beckman Microfuge 18 Centrifuge at 2000 rpm in an Eppendorf tube. The pellet is rinsed once in sterile distilled water, centrifuged, and resuspended in 25 µL of 1 µg/µL total DNA. The following reagents are added to the tube: 220 µL $H_2O$, 250 µL 2.5M $CaCl_2$, 50 µL 0.1M spermidine, freebase. The DNA solution is briefly vortexed and placed on ice for 5 min followed by centrifugation at 500 rpm for 5 min in a Beckman Microfuge 18 Centrifuge. The supernatant is removed. The pellet is resuspended in 600 µL ethanol followed by centrifugation for 1 min at 14,000 rpm. The final pellet is resuspended in 36 µL of ethanol and used immediately or stored on ice for up to 4 hr prior to bombardment. For bombardment, two-week-old maize leaves are cut in approximately 1 cm in length and located on 2 inches diameter sterilized Whatman filter paper. In the case of BMS cultured cells, 5 mL of one-week-old suspension cells are slowly vacuum filtered onto the 2 inches diameter filter paper placed on a filter unit to remove excess liquid. The filter papers holding the plant materials are placed on osmotic induction media (N6 1-100-25, 0.2 M mannitol, 0.2 M sorbitol) at 27° C. in darkness for 2-3 hours prior to bombardment. A few minutes prior to shooting, filters are removed from the medium and placed onto sterile opened Petri dishes to allow the calli surface to partially dry. To keep the position of plant materials, a sterilized wire mesh screen is laid on top of the sample. Each plate is shot with 10 µL of gold-DNA solution once at 2,200 psi for the leaf materials and twice at 1100 psi for the BMS cultured cells. Following bombardment, the filters holding the samples are transferred onto MS basal media and incubated for 2 days in darkness at 27° C. prior to transient assays. Transient expression levels of the reporter gene are determined quantification of expression of reporter genes or RT-PCR using the protocols in the art in order to determine potentially strong and tight terminator candidates.

2.2 Transient Assay Using Protoplasts

Isolation of protoplasts is conducted by following the protocol developed by Sheen (1990). Maize seedlings are kept in the dark at 25° C. for 10 days and illuminated for 20 hours before protoplast preparation. The middle part of the leaves are cut to 0.5 mm strips (about 6 cm in length) and incubated in an enzyme solution containing 1% (w/v) cellulose RS, 0.1% (w/v) macerozyme R10 (both from Yakult Honsha, Nishinomiya, Japan), 0.6 M mannitol, 10 mM Mes (pH 5.7), 1 mM CaCl$_2$, 1 mM MgCl$_2$, 10 mM β-mercaptoethanol, and 0.1% BSA (w/v) for 3 hr at 23° C. followed by gentle shaking at 80 rpm for 10 min to release protoplasts. Protoplasts are collected by centrifugation at 100×g for 2 min, washed once in cold 0.6 M mannitol solution, centrifuged, and resuspended in cold 0.6 M mannitol (2×10$^6$/mL). A total of 50 µg plasmid DNA in a total volume of 100 µL sterile water is added into 0.5 mL of a suspension of maize protoplasts (1×10$^6$ cells/mL) and mix gently. 0.5 mL PEG solution (40% PEG 4000, 100 mM CaNO$_3$, 0.5 mannitol) is added and prewarmed at 70° C. with gentle shaking followed by addition of 4.5 mL MM solution (0.6 M mannitol, 15 mM MgCl$_2$, and 0.1% MES). This mixture is incubated for 15 minutes at room temperature. The protoplasts are washed twice by pelleting at 600 rpm for 5 min and resuspending in 1.0 mL of MMB solution[0.6 M mannitol, 4 mM Mes (pH 5.7), and brome mosaic virus (BMV) salts (optional)] and incubated in the dark at 25° C. for 48 hr. After the final wash step, collect the protoplasts in 3 mL MMB medium, and incubate in the dark at 25° C. for 48 hr. Transient expression levels of the reporter gene are determined quantification of expression of reporter genes or RT-PCR using the protocols in the art in order to determine potentially strong and tight terminator candidates.

2.3 Detection of GUS Reporter Gene

To identify the characteristics of the promoter and the essential elements of the latter, which bring about its tissue specificity, it is necessary to place the promoter itself and various fragments thereof before what is known as a reporter gene, which allows the determination of the expression activity. An example, which may be mentioned, is the bacterial β-glucuronidase (Jefferson et al. EMBO J 6:3901-3907 (1987). The β-glucuronidase activity can be detected in-planta by means of a chromogenic substrate such as 5-bromo-4-chloro-3-indolyl-β-D-glucuronic acid in an activity staining (Jefferson et al. Plant Mol Biol Rep 5:387-405 (1987)). To study the tissue specificity, the plant tissue is cut, embedded, stained and analyzed as described (for example Bäumlein et al. (1991a) Mol Gen Genet 225(3): 459-467, Bäumlein et al. (1991b) Mol Gen Genet 225:121-128).

A second assay permits the quantitative determination of the GUS activity in the tissue studied. For the quantitative activity determination, MUG (4-methylumbelliferyl-β-D-glucuronide) is used as substrate for β-glucuronidase, and the MUG is cleaved into MU (methylumbelliferone) and glucuronic acid.

To do this, a protein extract of the desired tissue is first prepared and the substrate of GUS is then added to the extract. The substrate can be measured fluorimetrically only after the GUS has been reacted. Samples that are subsequently measured in a fluorimeter are taken at various points in time. This assay may be carried out for example with linseed embryos at various developmental stages (21, 24 or 30 days after flowering). To this end, in each case one embryo is ground into a powder in a 2 mL reaction vessel in liquid nitrogen with the aid of a vibration-grinding mill (Type: Retsch MM 2000). After addition of 100 µL of EGL buffer (0.1 M KPO$_4$, pH 7.8; 1 mM EDTA; 5% glycerol; 1 M DTT), the mixture is centrifuged for 10 minutes at 25° C. and 14,000×g. The supernatant is removed and recentrifuged. Again, the supernatant is transferred to a new reaction vessel and kept on ice until further use. 25 µL of this protein extract are treated with 65 µL of EGL buffer (without DTT) and employed in the GUS assay. 10 µL of the substrate MUG (10 mM 4-methylumbelliferyl-β-D-glucuronide) are now added, the mixture is vortexed, and 30 µL are removed immediately as zero value and treated with 470 µL of Stop buffer (0.2 M Na$_2$CO$_3$). This procedure is repeated for all of the samples at an interval of 30 seconds. The samples taken were stored in the refrigerator until measured. Further readings were taken after 1 h and after 2 h. A calibration series which contained concentrations from 0.1 mM to 10 mM MU (4-methylumbelliferone) was established for the fluorimetric measurement. If the sample values were outside these concentrations, less protein extract was employed (10 µL, 1 µL, 1 µL from a 1:10 dilution), and shorter intervals were measured (0 h, 30 min, 1 h). The measurement was carried out at an excitation of 365 nm and an emission of 445 nm in a Fluoroscan II apparatus (Labsystem). As an alternative, the substrate cleavage can be monitored fluorimetrically under alkaline conditions (excitation at 365 nm, measurement of the emission at 455 nm; Spectro Fluorimeter BMG Polarstar+) as described in Bustos et al. (1989) Plant Cell 1(9):839-53. All the samples were subjected to a protein concentration determination by the method of Bradford (1976) Anal. Biochem. 72:248-254, thus allowing an identification of the promoter activity and promoter strength in various tissues and plants.

2.4 Detection of Fluorescent Protein Gene

Several fluorescent protein genes, e.g. DsRed, ZsGreen, ZsYellow, ZsCyan and AcGFP (BD Biosciences) are derived from new species of reef coral and jelly fish. It has been shown that these fluorescent proteins can be used as reporters in multiple plant species (Wenck A. et al., Plant Cell Report, 22:244-251, 2003). The plant materials (e.g. leaves and roots) carrying fluorescent proteins can be visualized using epifluoresecnce microscope with appropriate filter sets. Furthermore, the intensity of fluorescent protein, which indicates the expression level of the protein, is analyzed by a fluorescence imaging instrument such as Typhoon 9400 (Amersham Biosciences) in a quantitative manner following the instruction recommended by the manufacturer.

Example 3: Expression Analysis for microRNAs

Analysis is performed on RNA-level (e.g., by Northern blot analysis or real time qPCR). Alternatively expression profiles can be evaluated by the representation of specific miRNA sequences in non-normalized tissue-specific cDNA libraries and can—for example—be assessed in silico by "counting" the number of cDNA sequences for a specific miRNA in said library.

3.1 Northern Hybridization:

A suitable method for determining the amount of transcription of a gene is to carry out a Northern blot analysis (by way of reference, see Ausubel et al. (1988) Current Protocols in Molecular Biology, Wiley: New York, or the above-mentioned example section), where a primer which is designed in such a way that it binds to the gene of interest is labeled with a detectable label (usually a radioactive label or chemiluminescent label) so that, when the total RNA of a culture of the organism is extracted, separated on a gel, transferred to a stable matrix and incubated with this probe, the binding and the extent of the binding of the probe indicate the presence and also the amount of the mRNA for this gene. This information also indicates the degree of transcription of the transformed gene. Cellular total RNA can be prepared from cells, tissues or organs in a plurality of methods, all of which are known in the art, such as, for example, the method described by Bormann, E. R., et al. (1992) Mol. Microbiol. 6:317-326.

To carry out the RNA hybridization, 20 µg of total RNA or 1 µg of poly(A)+ RNA are separated by means of gel electrophoresis in agarose gels with a strength of 1.25% using formaldehyde, as described in Amasino (1986, Anal. Biochem. 152, 304), capillary-blotted to positively charged nylon membranes (Hybond N+, Amersham, Braunschweig) using 10×SSC, immobilized by means of UV light and prehybridized for 3 hours at 68° C. using hybridization buffer (10% dextran sulfate w/v, 1 M NaCl, 1% SDS, 100 mg herring sperm DNA). The DNA probe was labeled with the Highprime DNA labeling kit (Roche, Mannheim, Germany) during the prehybridization, using alpha-$^{32}$P-dCTP (Amersham Pharmacia, Braunschweig, Germany). After the labeled DNA probe had been added, the hybridization was carried out in the same buffer at 68° C. overnight. The washing steps were carried out twice for 15 minutes using 2×SSC and twice for 30 minutes using 1×SSC, 1% SDS, at 68° C. The sealed filters were exposed at −70° C. over a period of 1 to 14 days.

3.2 RT-qPCR

After total RNA is isolated from an organism or specific tissues or cell types, RNA is resolved on a denaturing 15% polyacrylamide gel. A gel fragment represents the size range of 15 to 26 nucleotides was excised, small RNA was eluted, and recovered. Subsequently, small RNA is ligated to 5' and 3' RNA/DNA chimeric oligonucleotide adapters. Reverse transcription reaction was performed using RT primer followed by PCR with appropriate primers. PCR products are then cloned into vector for sequencing (Sunkar R and Zhu J K, The Plant Cell 16:2001:2019, 2004)

3.3 Results

The following tables present some of the expression profiles found for various miRNAs both in plant and animal or mammalian species. During cloning and subsequent sequencing of miRNA, some miRNA-clones have shown different nucleotides at the ends (especially 3'-end), which are represented herein by small letters. The 3' end of miRNA is usually less important.

TABLE 2 miRNAs identified from Arabidopsis thaliana libraries.

| At pri-miRNA ID | | At miR319b | At miR160b | At miR163 | At miR167a | At miR172b |
|---|---|---|---|---|---|---|
| At miRNA sequence | | UUG-GACUGAAGG GAGCUCCC | UGCCUGCUCC CUGUAUGCCA | UUGAAGAGGAC-UUGGAACU-UCGAU | UGAA-GCUGCCAG-CAUGAUCUA | AGAAUCUUGAU GAUGCUGCAU |
| SEQ ID NO: | | 5 | 1 | 2 | 3 | 4 |
| Hyseq clone ID | | 65631003 | 65987305 | 65613288 | 64879045 | Contig1562 |
| Library Name | Library Synonym Description | Relative Expression | Relative Expression | Relative Expression | Relative Expression | Relative Expression |
| AC103 | seedfill Developing siliques with seeds 1 to 14 d post anthesis | 0 | 0 | 0 | 0.667 | 0 |
| AC104 | shoot Normal rosettes prior to bolting | 0 | 0 | 0 | 0 | 0 |
| AC108 | shoot Rosettes inoculated with conidia of Erysiphe cichoracearum, Blumeria f.sp. Hordei, Alternaria alternata, or A. brassicicloa for 12, 24, 48, 73 H | 0 | 0.059 | 0 | 0 | 0 |
| AC109 | flower Normal flower bud and seed development | 0.333 | 0.235 | 0.714 | 0.333 | 0.778 |
| AC114 | stress Mixed treatment: 1. 2 H dessication, 2. up to 6 H 300 mM NaCl, 3. Cold at -2 C., or 0 C. | 0 | 0.176 | 0.286 | 0 | 0 |

TABLE 2-continued miRNAs identified from Arabidopsis thaliana libraries.

| | | | | | | |
|---|---|---|---|---|---|---|
| | | or 6 C., 4. 20 mM hydrogen peroxide. (1, 2, 3) had some treatments allowing recovery. (1, 2) entire plants harvested, (3, 4) only shoots harvested. | | | | |
| AC115 | callus | Callus (Initiated from seeds) minimally induced to form either roots (5 mg/L NAA + 0.1 iP) or shoots (1 mg/L NAA + 0.1iP) | 0.667 | 0.176 | 0 | 0 |
| AC117 | root.mix | Roots from aerated hydroponics (continuous) with varying nutrient strength. | 0 | 0.353 | 0 | 0.111 |
| AC119 | RNA Mix | Mixed mRNA from all Arabidopsis libraris. | 0 | 0 | 0 | 0.111 |
| Preferred Use | | | Prevent leakiness in leaf tissue | Prevent leakiness in root and flowers | Prevent leakiness in flowers | Prevent leakiness in seeds and flowers | Prevent leakiness in flowers |

Table 3-A: miRNAs identified from Oryza sativa libraries.

| Os pri-miRNA ID | | Os miR167g | Os miR168a | Os miR169g | Os miR169i | Os miR171b | Os miR397b | Os miR398a | Os miR399k | Os miR156l | Os miR159b |
|---|---|---|---|---|---|---|---|---|---|---|---|
| Os miRNA sequence | | UGAAGCU GCCAGCA UGAUCUg | UCGCUUG GUGCAGA UCGGGAC | UAGCCAA GGAUGAC UUgccua | UAGCCAA GGAUGAC UUgccug | UGAUUGA GCCGUG CCAAUAUC | UUAUUGA GUGCAGC GUUGAUG | UGUGUUC UCAGGUC ACCCCUU | UGCCAAA GGAAAUU UGCCCCG | CGACAGA AGAGAGU GAGCAUA | UUUGGAU UGAAGGG AGCUCUG |
| SEQ ID NO: | | 14 | 15 | 16 | 17 | 18 | 19 | 20 | 21 | 7 | 8 |
| Hyseq clone ID | | Contig6503 | Contig2277 | Contig17418 | 3282464 | 37697372 | Contig16437 | 37947875 | Contig10310 | 35003089 | Contig4124 |
| Library Name | Library Synonym | Description | Relative Expression | Relative Expression | Relative Expression | Relative Expression | Relative Expression | Relative Expression | Relative Expression | Relative Expression | Relative Expression | Relative Expression |
| AC003 | shoot | Shoots | 0.033 | 0.056 | 0.176 | 0.333 | 0 | 0.094 | 0 | 0.014 | 0 | 0.022 |
| AC004 | shoot | Shoot meristems | 0 | 0.062 | 0.235 | 0 | 0 | 0.019 | 0 | 0.007 | 0.5 | 0.267 |
| AC005 | root | Roots | 0.067 | 0.025 | 0.118 | 0 | 0 | 0 | 0 | 0.007 | 0.5 | 0.022 |
| AC007 | seedling | Seedling, shoots and roots | 0.033 | 0.056 | 0.059 | 0.333 | 0 | 0 | 0 | 0 | 0 | 0.089 |
| AC008 | flower | Flowers, male and female organs | 0.067 | 0.087 | 0.059 | 0 | 0 | 0.038 | 0 | 0.007 | 0 | 0.022 |
| AC009 | shoot | Cold shoots (3, 6, 12, 24, 48) | 0.067 | 0.193 | 0.059 | 0 | 0 | 0.075 | 0 | 0.028 | 0 | 0 |
| AC010 | shoot | Salt shoots (6, 12, 24, 48 H) | 0 | 0.118 | 0 | 0 | 0 | 0.094 | 0 | 0.007 | 0 | 0.022 |
| AC011 | shoot | Shoots (2 + 8 H dark) | 0 | 0.056 | 0 | 0 | 0 | 0.075 | 0 | 0.056 | 0 | 0 |
| AC012 | root | Salt roots (6, 12, 24, 48 H) | 0.133 | 0.006 | 0 | 0 | 0 | 0 | 0 | 0.007 | 0 | 0 |
| AC013 | seed | Seedlings, seed and small shoot & root | 0.033 | 0.043 | 0 | 0 | 0.333 | 0 | 0 | 0.014 | 0 | 0.111 |
| AC014 | shoot | Flooding shoots (5, 24, 48, 72 + 24, 48 H) | 0.033 | 0.012 | 0 | 0 | 0 | 0.019 | 0 | 0.084 | 0 | 0 |

-continued

| | | | | | | | | | | | |
|---|---|---|---|---|---|---|---|---|---|---|---|
| AC015 | root | Flooding roots (5, 24, 48 + 24, 48 H) | 0.033 | 0.025 | 0 | 0 | 0.333 | 0.019 | 0.083 | 0.007 | 0 | 0 |
| AC016 | shoot | Drought shoots (24, 48 + 6, 12 H) | 0.133 | 0.031 | 0.059 | 0 | 0 | 0.019 | 0.417 | 0.308 | 0 | 0.044 |
| AC018 | root | Drought roots (24, 48 + 6, 12 H) | 0 | 0.043 | 0 | 0.333 | 0 | 0.019 | 0.083 | 0 | 0 | 0.022 |
| AC019 | panicle | Panicles (pooled over 20 days) | 0 | 0.043 | 0 | 0 | 0.333 | 0 | 0 | 0 | 0 | 0.267 |
| AC020 | embryo | Immature embryos and endosperm | 0 | 0 | 0 | 0 | 0 | 0 | 0 | 0 | 0 | 0 |
| AC021 | shoot | Nipponbare biotic stress 1 | 0 | 0.037 | 0 | 0 | 0 | 0.094 | 0 | 0.098 | 0 | 0 |
| AC022 | flower | Head flowers (1-5, 10 15 Days) | 0.1 | 0.012 | 0 | 0 | 0 | 0.075 | 0 | 0 | 0 | 0.022 |
| AC024 | shoot | Cypress shoots | 0.133 | 0.012 | 0.118 | 0 | 0 | 0.283 | 0 | 0.014 | 0 | 0 |
| AC025 | shoot | Nipponbare biotic stress 3 | 0.033 | 0.019 | 0.059 | 0 | 0 | 0.038 | 0.417 | 0.049 | 0 | 0.067 |
| AC026 | shoot | Nopponbare biotic stress 2 | 0.1 | 0.037 | 0.059 | 0 | 0 | 0.038 | 0 | 0.042 | 0 | 0 |
| AC027 | flower | Cypress flowers | 0.033 | 0.012 | 0 | 0 | 0 | 0 | 0 | 0.021 | 0 | 0.022 |
| AC092 | RNA mix | Combined mRNA long clone library | 0 | 0.012 | 0 | 0 | 0 | 0 | 0 | 0.231 | 0 | 0 |

Table 3-B (cont. from Table 3-A): miRNAs identified from Oryza sativa libraries.

| Pre-ferred Use | Prevent leakiness in every-where but embryo | Prevent leakiness in root and shoot | Prevent leakiness in shoot and root under flood condition | Prevent leakiness in shoot uder drought and bacteria infection | Prevent leakiness in shoot and root | Prevent leakiness in shoot and root |
|---|---|---|---|---|---|---|
| Os pri-miRNA ID | Os 156<sup>a</sup> | Os miR160f | Os miR162a | Os miR164a | Os miR164d | Os miR166a |
| Os miRNA sequence | UGACAGAAGA GAGUGAGCACA | UGCCUGGCUC CCUGAAUGCCA | UCGAUAAACC UCUGCAUCCAG | UGGAGAAGCA GGGCACGUGCA | UGGAGAAGCA GGGCACGUGCU | UCGGACCAGG CUUCAUUCCCC |
| SEQ ID NO: | 6 | 9 | 10 | 11 | 12 | 13 |
| Hyseq clone ID | 35003089 | 35420108 | 39760468 | 34256080 | 34832815 | 35093513 |

| Library Name | Library Synonym | Description | Relative Expression | Relative Expression | Relative Expression | Relative Expression | Relative Expression | Relative Expression |
|---|---|---|---|---|---|---|---|---|
| AC003 | shoot | Shoots | 0 | 0 | 0 | 0 | 0 | 0 |
| AC004 | shoot | Shoot meristems | 0.5 | 0 | 0.158 | 0.286 | 0 | 0.069 |
| AC005 | root | Roots | 0.5 | 0 | 0.158 | 0.143 | 0.333 | 0.241 |
| AC007 | seedling | Seedling, shoots and roots | 0 | 0 | 0.053 | 0 | 0 | 0 |
| AC008 | flower | Flowers, male and female organs | 0 | 0.25 | 0 | 0 | 0 | 0 |
| AC009 | shoot | Cold shoots (3, 6, 12, 24, 48) | 0 | 0 | 0 | 0 | 0.333 | 0 |
| AC010 | shoot | Salt shoots (6, 12, 24, 48 H) | 0 | 0 | 0 | 0 | 0 | 0 |
| AC011 | shoot | Shoots (2 + 8 H dark) | 0 | 0 | 0 | 0.143 | 0 | 0 |
| AC012 | root | Salt roots (6, 12, 24, 48 H) | 0 | 0 | 0 | 0 | 0 | 0.034 |
| AC013 | seed | Seedlings, seed and small shoot & root | 0 | 0 | 0.105 | 0 | 0 | 0.241 |

| | | | Prevent leakiness in root and shoot | Prevent leakiness in flower | Prevent leakiness in panicle and shoot | Prevent leakiness in shoot tip and panicle | Prevent leakiness in root, shoot (cold condition) and cypress flowers |
|---|---|---|---|---|---|---|---|
| AC014 | shoot | Flooding shoots (5, 24, 48, 72 + 24, 48 H) | 0 | 0 | 0.053 | 0 | 0 |
| AC015 | root | Flooding roots (5, 24, 48 + 24, 48 H) | 0 | 0 | 0 | 0 | 0.069 |
| AC016 | shoot | Drought shoots (24, 48 + 6, 12 H) | 0 | 0 | 0.053 | 0 | 0.138 |
| AC018 | root | Drought roots (24, 48 + 6, 12 H) | 0 | 0 | 0 | 0 | 0 |
| AC019 | panicle | Panicles (pooled over 20 days) | 0 | 0 | 0.263 | 0.286 | 0.103 |
| AC020 | embryo | Immature embryos and endosperm | 0 | 0 | 0 | 0.143 | 0 |
| AC021 | shoot | Nipponbare biotic stress 1 | 0 | 0 | 0 | 0 | 0 |
| AC022 | flower | Head flowers (1-5, 10 15 Days) | 0 | 0.125 | 0 | 0 | 0.034 |
| AC024 | shoot | Cypress shoots | 0 | 0 | 0 | 0 | 0.034 |
| AC025 | shoot | Nipponbare biotic stress 3 | 0 | 0 | 0.053 | 0 | 0.034 |
| AC026 | shoot | Nopponbare biotic stress 2 | 0 | 0 | 0.053 | 0 | 0 |
| AC027 | flower | Cypress flowers | 0 | 0.625 | 0 | 0 | 0.333 |
| AC092 | RNA mix | Combined mRNA long clone library | 0 | 0 | 0.053 | 0 | 0 |
| Preferred Use | | | | | | | |

TABLE 4 miRNAs identified from Zea mays sativa libraries.

| Zm pri-miRNA ID | | Zm miR156 | Zm miR159 | Zm miR160b | Zm miR166 | Zm miR167 | Zm miR171 |
|---|---|---|---|---|---|---|---|
| ZmmiRNA sequence | | UGACAGA AGAGAGU GAGCAC | UUUGGAU UGAAGGG AGCUCUA | UGCCUGGC UCCCUGUA UGCCA | UCCGACCAG GCUUCAUUC CCC | UGAAGCUG CCAGCAUG AUCUGG | UGAUUGAGC CGCGCCAAU AUC |
| SEQ ID NO: | | 22 | 23 | 24 | 25 | 26 | 27 |
| Hyseq clone ID | | 58989601 | 62202898 | 65442307 | 57507158 | 62178918 | 61430017 |
| Library Name | Library Synonym | Description | Relative Expression | Relative Expression | Relative Expression | Relative Expression | Relative Expression | Relative Expression |
| AC073 | stem | underground stem with meristem | 0.015 | 0.176 | 0.056 | 0 | 0 | 0 |
| AC079 | roots | root only from young to mid-age plant | 0 | 0 | 0 | 0.25 | 0 | 0 |
| AC080 | tassel | Tassel development | 0 | 0 | 0 | 0 | 0 | 0 |
| AC081 | ear | Ear development | 0 | 0 | 0 | 0 | 0 | 0 |
| AC082 | Leaves | Leaves of mixed ages, all prior to seed-fill | 0.123 | 0 | 0 | 0.25 | 0 | 0 |
| AC083 | immature ears | Ear shoots from 2 cm (V13) up to and including silking (unpollinated). 51 to 70 dap. | 0.031 | 0.059 | 0 | 0 | 0 | 0 |
| AC084 | stem | Stem tissue near ear at tassel emergence and during seed-fill | 0 | 0 | 0 | 0 | 0 | 0 |
| AC085 | uppper leaves | 56 (pretasseling) and 84 dap and 23 dpp (R3). Upper leaves at seed-fill | 0.015 | 0 | 0 | 0.5 | 0 | 0 |
| AC086 | seed | Kernels at early dough stage (R4). Developing starch grains and well-formed embryo present. 30 d post pollination | 0 | 0 | 0 | 0 | 0.32 | 0 |
| AC087 | seed | B73 inbreds. Kernals at 9 and 19 d post pollination | 0 | 0 | 0 | 0 | 0 | 0 |
| AC089 | root | Roots only from young to mid-age plants | 0.062 | 0 | 0 | 0 | 0 | 0 |

TABLE 4-continued miRNAs identified from Zea mays sativa libraries.

| | | | Prevent leakiness everywhere but seeds | Prevent leakiness in stem | Prevent leakiness in leaves and tassel | Prevent leakiness in seeds | Prevent leakiness in stem, root and shoot |
|---|---|---|---|---|---|---|---|
| AC088 | seed | Kernel at 9 and 19 d post pollination | 0.077 | 0.059 | 0 | 0 | 0 |
| AC093 | stem | Shoot cold, 10 d in chamber at 10 C./4 C. | 0.062 | 0.471 | 0.056 | 0 | 0.2 |
| AC094 | seed | Very young kernels at blister stage | 0 | 0 | 0 | 0.32 | 0 |
| AC096 | seed | Mo17 inbreds. Kernals at 10 and 21 d post pollination | 0 | 0 | 0.056 | 0.16 | 0.2 |
| AC095 | seed | Kernals at early dent stage (R5) | 0 | 0 | 0 | 0.08 | 0 |
| AC099 | RNA mix | Combined mRNA long clone library | 0.031 | 0.235 | 0 | 0.08 | 0 |
| AC105 | callus | Callus from immature embros, infected with agrobacteriurm | 0.031 | 0 | 0 | 0 | 0 |
| AC107 | callus | Normal callus from immature embryos at 7, 14, 31, 44, 65 d after cultivation | 0.108 | 0 | 0.444 | 0 | 0 |
| AC113 | shoot | 3 sets: 1. Shoot, no water at V4 for 3, 7, 10 d +- 6 h recovery; 2. Shoot + root, dried 3, 6, 24 h +- 6 h water; 3. Shoot, no water at v15 for 6, 9, 13, 16 d +/- 6 h water | 0.246 | 0 | 0.111 | 0.04 | 0 |
| AC118 | root | 2 sets: 1. Root, no water at V4 for 3, 7, 10 d +/- 6 h recovery; 2. root, air-dried 3, 6, 24 h +/- 6 h rewater. | 0 | 0 | 0.167 | 0 | 0 |
| AC120 | root | Roots only | 0.169 | 0 | 0.111 | 0 | 0.2 |
| AC121 | shoot | Shoot only | 0.031 | 0 | 0 | 0 | 0.4 |
| Preferred use | | | | | | | |

TABLE 5

Mammalian miRNA, their miRNA-tags and their expression profiles

| miRNA ID | SEQ ID NO (for miRNA) | miRNA Sequence (miRNA Tag) | Length of miR-NA (nt) | Brain | Liver | Heart | Skeletal muscle |
|---|---|---|---|---|---|---|---|
| mmu-miR-1b | 56 | Tag: TACATACTTCTTTACATTCCA<br>miRNA: UGGAAUGUAAAGAAGUAUGUA | 21 | | | X | X |
| mmu-miR-9 | 57 | Tag: TCATACAGCTAGATAACCAAAGA-<br>miRNA: UCUUUGGUUAUCUAGCUGUAUGA | 23 | X | | | |
| mmu-miR-122a | 58 | Tag: ACAAACACCATTGTCACACTCCA<br>miRNA: UGGAGUGUGACAAUGGUGUUUGU | 23 | | X | | |
| mmu-miR-124a | 59 | Tag: TGGCATTCACCGCGTGCCTTAA<br>miRNA: UUAAGGCACGCGGUGAAUGCCA | 22 | X | | | |
| mmu-miR-128 | 60 | Tag: AAAAGAGACCGGTTCACTGTGA<br>miRNA: UCACAGUGAACCGGUCUCUUUU | 22 | X | | | X |
| mmu-miR-194 | 61 | Tag: TCCACATGGAGTTGCTGTTACA<br>miRNA: UGUAACAGCAACUCCAUGUGGA | 22 | | X | | |
| mmu-miR-206 | 62 | Tag: CCACACACTTCCTTACATTCCA<br>miRNA: UGGAAUGUAAGGAAGUGUGUGG | 22 | | | X | X |
| hsa-miR-218 | 63 | Tag: ACATGGTTAGATCAAGCACAA<br>miRNA: UUGUGCUUGAUCUAACCAUGU | 21 | X | | | |

Note:
Northern analysis on human tissues (Ref: Sempere LF et al., Genome Biology 2004, R13)

TABLE 6

Maize miRNAs Identified in Hyseq Database

| miRNA ID | SEQ ID NO: | miRNA Sequence | Length (nt) | Maize miRNA Precursors |
|---|---|---|---|---|
| miR167-like | 47 | UGAAGCUGCCAGCAUGAUCU | 20 | Contig9065<br>62178918ZM |
| miR171 | 53 | UGAUUGAGCCGCGCCAAUAUC | 21 | Contig5235<br>61430017ZM |
| miR167-like | 48 | UGAAGCUGCCAGCAUGAUCUG | 21 | Contig9065<br>62178918ZM |
| miR167 | 46 | UGAAGCUGCCAGCAUGAUCUGG | 22 | Contig9065<br>62178918ZM |
| miR167-like | 49 | UGAAGCUGCCAGCAUGAUCUAU | 22 | Contig9065<br>62178918ZM |
| miR171-like | 54 | UGAUUGAGCCGCGCCAAUAU | 20 | Contig5235<br>61430017ZM |
| miR167-like | 50 | AUGAAGCUGCCAGCAUGAUCUA | 22 | Contig9065<br>62178918ZM |
| miR390 | 55 | AAGCUCAGGAGGGAUAGCGCC | 21 | Contig4340<br>59283967ZM |
| miR167-like | 51 | GUGAAGCUGCCAGCAUGAUCUA | 22 | Contig9065<br>62178918ZM |
| miR166 | 42 | UCGGACCAGGCUUCAUUCCCC | 21 | 57507158.f_k09_1<br>57507158.f_k09_1 |
| miR156 | 31 | UGACAGAAGAGAGUGAGCAC | 20 | Contig3945<br>58989601ZM |
| miR159 | 35 | UUUGGAUUGAAGGGAGCUCUA | 21 | Contig9470<br>62202898ZM |
| miR160 | 39 | UGCCUGGCUCCCUGUAUGCCA | 21 | 65442307.f_l16_1<br>65442307.f_l16_1 |

TABLE 6-continued

Maize miRNAs Identified in Hyseq Database

| miRNA ID | SEQ ID NO: | miRNA Sequence | Length (nt) | Maize miRNA Precursors |
|---|---|---|---|---|
| miR156-like | 32 | UUGACAGAAGAGAGUGAGCAC | 21 | Contig3945 58989601ZM |
| ASRP754-like | 28 | AGCUCAGGAGGGAUAGCGCC | 20 | Contig4340 59283967ZM |
| miR166-like-1 | 43 | UCGGACCAGGCUUCAUUCCCCC | 22 | 57507158.f_k09_1 57507158.f_k09_1 |
| miR159-like | 36 | UUUGGAUUGAAGGGAGCUCUU | 21 | Contig9470 62202898ZM |
| miR160-like | 40 | UGCCUGGCUCCCUGUAUGCCAU | 22 | 65442307.f_l16_1 65442307.f_l16_1 |
| miR160-like | 41 | GCCUGGCUCCCUGUAUGCCA | 20 | 65442307.f_l16_1 65442307.f_l16_1 |
| miR159-like | 37 | UCUUUGGAUUGAAGGGAGCUC | 21 | Contig9470 62202898ZM |
| miR166-like | 44 | UUCGGACCAGGCUUCAUUCCCC | 22 | 57507158.f_k09_1 57507158.f_k09_1 |
| miR166-like | 45 | UUCGGACCAGGCUUCAUUCCC | 21 | 57507158.f_k09_1 57507158.f_k09_1 |
| miR156-like | 33 | GUGACAGAAGAGAGUGAGCAC | 21 | Contig3945 58989601ZM |
| ASRP754-like | 29 | AAGCUCAGGAGGGAUAGCGC | 20 | Contig4340 59283967ZM |
| miR159-like | 38 | UUUGGAUUGAAGGGAGCUCU | 20 | Contig9470 62202898ZM |
| miR170-like | 52 | UGAUUGAGCCGUGCCAAUAUC | 21 | 58229137.f_c06_1 58229137.f_c06_1 |
| miR156-like | 34 | UGACAGAAGAGAGUGAGCACA | 21 | Contig3945 58989601ZM |
| ASRP754-like | 30 | AGCUCAGGAGGGAUAGCGCCA | 21 | Contig4340 59283967ZM |

Example 4: Vector Construction for Plant Transformation

A typical plant transformation vector or binary vector contains two plant expression constructs: one for selection marker and the other for gene-of-interest. Each cassette consists of a promoter, a gene to be expressed and a terminator. The expression construct can be constructed into a binary vector via standard molecular cloning procedures, PCR or via Gateway system (Invitrogen, CA)

4.1 Isolation of Promoters

Genomic DNA from maize and rice is extracted using the Qiagen DNAeasy Plant Mini Kit (Qiagen). The promoter regions were isolated from genomic DNA using conventional PCR. Approximately 0.1 μg of digested genomic DNA was uses for the regular PCR reaction (see below). The primers were designed based on the maize or rice genomic DNA sequences upstream of the EST candidates, maize genomic sequences, or promoter sequences disclosed in the public database (e.g. rice caffeoyl CoA-O-methyltransferase [CCoAMT1], GenBank accession number AB023482; rice unknown protein, AP002818; maize hydroxyproline-rich glycoprotein [HRGP], AJ131535; maize lactate dehydrogenase [LDH], Z11754; rice Chloroplast Protein12-like, NP914106.1). 1 μL of the diluted digested genomic DNA was used as the DNA template in the primary PCR reaction. The reaction comprised forward (5') and reverse (3') primers in a mixture containing Buffer 3 following the protocol outlined by an Expand Long PCR kit (Cat #1681-842, Roche-Boehringer Mannheim). The isolated DNA is employed as template DNA in a PCR amplification reaction using the following primers:

TABLE 7

Primer sequences for isolation of the promoter region

| Promoter or Terminator* | Size (bp) | Primer Sequences Forward Primer (F) & Reverse Primer (R) |
|---|---|---|
| Oryza sativa Caffeoyl-CoA-O-methyltransferase Promoter (Os.CCoAMT1-p) | 1,035 | F: 5'-CAACTACTGCACGGTAAAAGTGATAGG-3' (SEQ ID NO: 64) <br> R: 5'-GCAGCTTGCTTCGATCTCTCGCTCGCC-3' (SEQ ID NO: 65) |
| Oryza sativa C-8,7-sterol-isomerase Promoter (Os.SI-p) | 813 | FP: 5'-TGCCTCGATTCGACCGTGTAATGGAAT-3' (SEQ ID NO: 66) <br> RP: 5'-ACTCCTGGCTTCCTTCCGATCTGGACT-3' (SEQ ID NO: 67) |
| Zea maize Hydroxyproline-rich glycoprotein Promoter (Zm.HRGP-p) | 1,263 | FP: 5'-CCGGTGACCTTCTTGCTTCTTCGATCG-3' (SEQ ID NO: 68) <br> RP: 5'-CCTCTCTCTCACACACACTCTCAGTAA-3' (SEQ ID NO: 69) |
| Zea maize Lactate-dehydrogenase promoter (Zm.LDH-p) | 1,061 | FP: 5'-AACAAATGGCGTACTTATATAACCACA-3' (SEQ ID NO: 70) <br> RP: 5'-CGGGCGGAATGGGATGGGATTACGTGT-3' (SEQ ID NO: 71) |
| Oryza sativa Chloroplast protein 12 Promoter (Os.CP12-p) | 998 | FP: 5'-TTTGTATTTAGGTCCCTAACGCCCTC-3' (SEQ ID NO: #72) <br> RP: 5'-TGTTGATGCGGATTTCTGCGTGTGAT-3' (SEQ ID NO: 73) |

The promoter regions are amplified in the reaction solution[1×PCR reaction buffer (Roche Diagnostics), 5 μL genomic DNA (corresponds to approximately 80 ng, 2.5 mM of each dATP, dCTP, dGTP and dTTP (Invitrogen: dNTP mix), 1 μL 5' primer (100 μM) 1 μL 3' primer (100 μM), 1 μL Taq DNA polymerase 5 U/μL (Roche Diagnostics), in a final volume of 100 μL] under the optimized PCR thermocycler program (T3 Thermocycler Biometra; 1 cycle with 180 sec at 95° C., 30 cycles with 40 sec at 95° C., 60 sec at 53° C. and 2 min at 72° C., and 1 cycle with 5 min at 72° C. before stop the reaction at 4° C.).

The PCR product was applied to a 1% (w/v) agarose gel and separated at 80V followed by excising from the gel and purified with the aid of the Qiagen Gel Extraction Kit (Qiagen, Hilden, Germany). If appropriate, the eluate of 50 μL can be evaporated. The PCR product was cloned directly into vector pCR4-TOPO (Invitrogen) following the manufacturer's instructions, i.e. the PCR product obtained is inserted into a vector having T overhangs with its A overhangs and a topoisomerase.

4.2 Isolation of Terminator of Interest Including the 3' Untranslated Region

Genomic DNA fragment containing the 3' untranslated regions of interest were isolated using sequence specific primers based on the sequences that disclosed in the public database (GenBank accession number AB023482, AJ131535, Z11754; Table 8). Plant genomic DNA isolation and conventional PCR amplification using sequence specific primers were conducted using the protocols in the art (Sambrook, 1987).

TABLE 8

Primer sequences for isolation of terminator region

| Terminator | Size (bp) | Primer Sequences Forward Primer (F) & Reverse Primer (R) |
|---|---|---|
| Oryza sativa Caffeoyl-CoA-O-methyltransferase Terminator (Os.CCoAMT1-t) | 1,092 | FP: 5'-GCCGATGCCCAAGAACTAGTCATTTTA-3' (SEQ ID NO: 74) <br> RP: 5'-ATTAACACGTCAACCAAACCGCCGTCC-3' (SEQ ID NO: 75) |
| Zea maize Hydroxyproline-rich glycoprotein Terminator (Zm.HRGP-t) | 541 | FP: 5'-AAAGCGATGCCTACCATACCACACTGC-3' (SEQ ID NO: 76) <br> RP: 5'-TGCCCACATTTATTATGGTTTTACACCC-3' (SEQ ID NO: 77) |
| Zea maize Lactate-dehydrogenase terminator (Zm.LDH-t) | 475 | FP: 5'-TGATCACATCACCGTCTCTCTTCATTAA-3' (SEQ ID NO: 78) <br> RP: 5'-TATCCCAGTCTCGATATTGTCATCCGCT-3' (SEQ ID NO: 79) |

The primer sequences given in the table abobe represent the 3'-part of the actual primer used. Said primers further comprised a SacI-restriction site adapter (5'-GAGCTC-3')

for the forward primer and a PmeI-resitrtiction site adapter (5'-GTTTAAAC-3') for the reverse primer (added to the sequence-specific primers for the further cloning purpose.

4.3 pUC Based Vector (Promoter of Interest::Intron (IME)::GUS::Terminator)

The base vector (pBPSMM270) comprises multiple cloning sites (MCS) followed by the first Zm.ubiquitin intron, the GUSint ORF (including the potato invertase [PIV]2 intron to prevent bacterial expression), and nopaline synthase (NOS) terminator in order (5' to 3'). Maize ubiquitin intron can be replaced with an intron of interest that functions in intronmeidated enhancement at BgII and XmaI.

The genomic DNA fragment containing promoter of interest (Os.CCoAMT1, Os.SI, Zm.HRGP, Zm.LDH, or Os.CP12 promoter) in the Topo vector (Invitrogen) was digested with PacI and AscI followed by subcloning upstream of the Zm.ubiquitin intron into the GUS construct.

The PCR fragment containing terminator of interest (e.g. 1,092 bp rice genomic DNA including CCoAMT1 terminator; 558 bp maize genomic DNA including HRGP terminator, 477 bp maize genomic DNA including LDH terminator) was digested with SacI and PmeI enzymes. Nopaline synthase terminator region was replaced with terminator of interest.

In order to include a miRNA tag in the terminator region, the complementary sequences (up to 21 bp) of the miRNAs of interest (Table 9) are chemically synthesized including a SacI restriction enzyme site at both 5' and 3'-ends of the sequence followed by suncloning between GUS gene and terminator of interest. The tag can be inserted into 5'UTR or 3'UTG or the coding region of gene-of-interest without affecting gene function.

TABLE 9

BPS miRNA tag sequences and the expression patterns

| miRNA tag [MRT] ID | SEQ ID NO | Tag sequence (5' to 3') | miRNA expression |
|---|---|---|---|
| BPS.MRT1 | 80 | ACAGATCATGCTGGCAGCTTCA | Predominantly in seed |
| BPS.MRT2 | 81 | TAGAGCTCCCTTCAATCCAAA | Non-seed tissues |

4.4 Transformation Binary Vector (Promoter Constructs without a miRNA Tag)

The GUS chimeric cassettes in the pUC-based vectors were digested with AscI or PacI (5') and PmeI (3') and subcloned into a monocot binary vector containing a plant selectable marker cassette (pBPSMM344) at AscI or PacI (5') and PmlI (3') sites to generate promoter constructs for plant transformation (Table 10).

TABLE 10

Promoter constructs without a miRNA tag in a binary vector

| Promoter construct | SEQ ID NO: | Composition [promoter (p) ::IME-intron (i) ::GUS ::terminator (t)] (Numbers are indicating the nucleotide position in the construct) |
|---|---|---|
| pBPSMM232 | 84 | Zm.ubiquitin-p::Zm.ubiquitin-i::GUS (PIV2)::NOS-t<br>Zm ubiquitin promoter and intron (1981 bp): 298-2278,<br>GUS (2001 bp): 2305-4305,<br>NOS terminator (253 bp): 4376-4628<br>MiRNA tag insertion site: 4365 (Sac I) |
| pBPSMM271 | 85 | Os.CCoAMT1-p::Zm.ubiquitin-i::GUS (PIV2)::NOS-t<br>Os CCoAMT1 promoter (1034 bp): 227-1260,<br>Zm ubiquitin intron (1051 bp): 1319-2369,<br>GUS (2001 bp): 2389-4389,<br>NOS terminator (253 bp).: 4461-4713<br>MiRNA tag insertion site: 4450 (Sac I) |
| pBPSMM272 | 86 | Zm.LDH-p::Zm.ubiquitin-i::GUS (PIV2)::NOS-t<br>Zm LDH Promoter (1062 bp): 255-1316,<br>ubiquitin Intron (1051 bp): 1355-2405,<br>GUS (2001 bp): 2425-4425,<br>NOS terminator (253 bp): 4497-4749<br>MiRNA tag insertion site: 4486 (SacI) |
| PBPSMM304 | 87 | Os.CP12-p::Zm.ubiquitin-i::GUS (PIV2)::NOS-t<br>Os CP12 promoter (998 bp): 3859-4856,<br>Zm ubiquitin intron (1051 bp): 2769-3819,<br>GUS (2001 bp): 749-2749,<br>NOS terminator (253 bp): 426-678<br>MiRNA tag insertion site: 694 (Sac I) |
| pBPSMM331 | 88 | Os.SI-p::Zm.ubiquitin-i::GUS (PIV2)::NOS-t<br>Os SI promoter (814 bp): 3912-4725,<br>Zm ubiquitin intron (1051 bp): 2824-3874,<br>GUS (2001 bp): 804-2804,<br>NOS terminator (253 bp): 481-733<br>MiRNA tag insertion site: 749 (Sac I) |
| pBPSMM325 | 89 | Os.CCoAMT1-p::Zm.ubiquitin-i:GUS (PIV2)::CCoAMT1-t<br>Os CCoAMT1 promoter (1034 bp): 305-1338,<br>Zm ubiquitin intron: (1051 bp) 1345-2395,<br>GUS (2001 bp): 2407-4407,<br>CCoAMT1 terminator (1104 bp): 4446-5549.<br>MiRNA tag insertion: 4793 (AgeI) |
| pBPSET003 | | Zm.HRGP-p::Zm.ubiquitin-i::GUS (PIV2)::Zm.HRGP-t |
| pBPSET007 | | Zm.LDH-p::Zm.ubiquitin-i::GUS (PIV2)::Zm.LDH-t |

The promoters described above are preferably improvement for higher promoter specificity with miRNA tags as follows: The Os CCoAMT promoter with ubiquitin intron (pBPSMM271) or the Zm LDH promoter with ubiquitin intron (pBPSMM272) are active strongly in roots and kernel. By use of a Zm miR167 tag, the expression in kernel is eliminated and gene-of-interest becomes predominantly expressed in roots.

The Os CP12 promoter with ubiquitin intron is active strongly in leafs, but medium in endosperm, no activity is observed in roots and embryos. By use of Zm miR167 tag, the expression in endosperm is eliminated and gene-of-interest becomes expressed predominantly in leaves. Alternatively, by use of a Zm miR166h tag, expression in leaves is reduced or eliminated and gene-of-interest is expressed predominantly in endosperm.

The Os SI promoter with ubiquitin intron is active strongly in roots and kernel, but weakly in leaves. By use of a Zm miR166h tag, expression in leaves is eliminated and the gene-of-interest is predominantly expressed in roots.

A miRNA tag can be introduced into the beginning of the terminator after the stop codon of GUS gene using PCR and standard cloning methods. For example, the insertion can be realized by utilizing a unique SacI site (Sac I and Pac I are unique sites to remove NOS terminator from pBPSMM271). The miRNA-tag for miR166h is incorporated into NOS terminator region by PCR with following primers:

```
Forward primer (SEQ ID NO: 209):
5'-GGGAGCTCGGGGAATGAAGCCTGGTCCGAgaatttccccgatcg ttcaaacatttggca
(The SacI-site is underlined; The miR166h-tag is
in bold letters.

Reverse primer (SEQ ID NO: 210):
5' TCGGACCGTTAATTAACACAAACTGAAGGC
The Pac I site is underlined.
```

The template DNA is the vector prior to insertion of the miRNA-tag. The PCR product is subsequently cut with restriction enzyme Sac I and Pac I. This fragment is then 'swaped' with Sac I-Pac I fragment in MM271 by subcloning. This strategy can be used to engineer miRNA tags into NOS terminator for other binary vectors such as pBPS MM 272, MM232 and MM304.

Example 5: Engineering Binary Vector with Tissue-Specific miRNA Tags to Target DsRed mRNA A binary vector, pBPSLM185 (SEQ ID NO: 212), contains a reporter gene expression construct: ScBV promoter (1398 bp), a full-length DsRed cDNA (678 bp) and a NOS terminator (253 bp). ScBV promoter was isolated from sugarcane bacilliform badnavirus (Schenk et al., Plant Mol Biol. 39:1221-1230, (2004))). DsRed is red fluorescent protein from Discosoma sp. reef coral (Baird, G. S., et al., Proc. Natl. Acas. Sci USA 97:11984-11989, (2000)). NOS terminator is 3' untranslated region of nopaline synthase gene isolated from *Agrobacterium*. In transgenic maize carrying LM185 construct, strong red fluorescence was readily detected through out plants by fluorescence microscopy analysis. The quantitative analysis of expression of DsRed was achieved by using an imaging instrument (Typhoon 9400, Amersham Biosciences). The ubiquitous expression of DsRed was resulted from ScBV promoter which is active in every maize tissues.

To reduce or eliminate expression of DsRed in maize leaf and tassel, a modified LM185 binary vector, PR100, is constructed. In vector PR100, a short nucleotide sequence or lag' is cloned into NOS terminator region by PCR using LM185 DNA as a template.

```
Forward primer (SEQ ID NO: 209):
5'-GGGAGCTCGGGGAATGAAGCCTGGTCCGAgaatttccccgatcg ttcaaacatttggca
(The SacI-site is underlined; The miR166h-tag is
in bold letters.

Reverse primer (SEQ ID NO: 211):
5' GATCTGGCCGGCCGGGCCCGAATTC
The FseI site is underlined.
```

The PCR product is subsequently cut with restriction enzyme Sac I and FseI. This fragment is then 'swaped' with Sac I-FseI fragment in LM185 by subcloning. The resulted PCR product contains 'tag 1' at the beginning of NOS terminator. The restriction sites at each end of PCR product facilitates subcloning such modified NOS terminator into binary vector following DsRed coding sequence. This strategy applies to introduce any miRNA tags into expression cassette. The 'tag 1' sequence, 5' GGGGAATGAAGCCTG-GTCCGA 3' (SEQ ID NO: 82) is completely complementary to maize miRNA miR166h, 5' TCGGACCAGGCTTCAT-TCCCC 3'. Transgenic maize carrying PR100 express DsRed mRNA with a 'tag 1' in every maize tissue. Because miR166h is only expressed in leaves and tassels, miR166h recognizes and binds to the lag' specifically in DsRed mRNA in the leaves and tassels. As a result, DsRed mRNA levels in these tissues are reduced or eliminated through miRNA-mediated gene silencing. The red fluorescence is reduced or undetectable in leaves and tassels but is not affected in other tissues.

It has been shown both in animal and plant, complementarity between 5' region of miRNA (e.g. position 2-8 nt) and miRNA target site is crucial for miRNA action (Mallory et al., EMBO Journal, 23:3356-3364, (2004), Doench J and Sharp P, Genes & Development 504-511, (2004)), while 3' region of miRNA (e.g. position 12-19 nt) can be mismatched to its target site. Such mismatch might reduce the efficacy of miRNA-mediated gene silencing.

A binary vector, PR101, is the same as PR100 except the 'tag 2' is used instead of 'tag 1'. The 'tag 2', 5' GGGGAAT-GAAGCgTGGaCCGA 3' (SEQ ID NO: 82) contains two mutations 'C to g' and 'T to a' comparing to 'tag 1'. This results in two mismatches between lag 2' and miR166h. Transgenic maize carrying PR101 has reduced red fluorescence in leaves and tassels. Furthermore, quantitative analysis on multiple events of transgenic maize carrying PR100 or PR101 using an imaging instrument (e.g. Typhoon 9400) shows that statistically the intensity of red fluorescence from PR100 maize is lower than that from PR101 maize in leaves and tassels. This is because perfect complementarity between 'tag 1' and miR166h in PR100 causing great reduction of DsRed expression, whereas mismatches between 'tag 2' and miR166h in PR101 causing less reduction of DsRed expression in leaves and tassels.

Example 6: Engineering Binary Vector with Tissue-Specific miRNA Tags to Target a Trait Gene or Selection Marker Seeds are the most relevant agronomical product, which is heavily used for feed and food purposes. However, expression of transgenes in seeds is in most cases neither necessary nor beneficial. For example, traits like herbicide resistance, resistance against insects, fungi, or nematode, cold or drought resistance do not need to be expressed in seeds, since expression is only required in roots or green tissues. Expression in seeds can have one or more of the following disadvantageous:

1. Unnecessary expression of traits in seeds may lead to lower germination rates or at least unnecessary consumption of transcription/translation capacity resulting in yield loss or negatively affecting composition of the seed.
2. Unnecessary expression of traits in seeds may raise higher hurdles in de-regulation proceedings (since a more substantial amount of the transgenic product is comprised in the feed or food materials).
3. Unnecessary expression of traits in seeds may negatively affect consumer acceptance.

Flowers comprise the plants reproductive organs (carpels and stamens). Expression in these tissues is for some traits also regarded as disadvantageous. For example, expression of the Bt protein (conferring resistance against corn root borer and other insect pests) under a strong constitutive promoter resulted in expression in pollen and was discussed to have a toxic effect on beneficial pollen transferring insects like the monarch butterflies.

A point mutation of a single nucleotide in AHAS (acetohydroxyacid synthase) gene generates resistance to herbicide imidazolinone. A mutated version of AHAS is also used as a selection marker for crop transformation towards commercial application. To eliminate AHAS marker in the seeds, a binary vector carrying miR-167 tag can be constructed. Maize miR167 is predominantly expressed in seeds including different stages of seed development. In a binary vector PR102, Ubi promoter drives AHAS expression. Following AHAS cDNA, a short nucleotide sequence or 'tag' is cloned into NOS terminator by PCR and standard cloning procedure. The 'tag 3' sequence, 5' ACAGATCATGCTGGCAGCTTCA 3' (SEQ ID NO: 80) is completely complementary to maize miRNA miR167, 5' TGAAGCTGCCAGCATGATCTGT 3'. Transgenic maize carrying PR102 express AHAS mRNA with a 'tag 3' in every maize tissue. Because miR167 is predominantly expressed in seeds, miR167 recognizes and binds to the 'tag' specifically in AHAS mRNA in the seeds. As a result, AHAS mRNA levels in seeds is reduced or eliminated through miRNA-mediated gene silencing. The AHAS expression in other tissues is largely unaffected determined by Western blot analysis using an antibody specifically recognize a mutated AHAS.

Example 7: From Constitutive Expression to Vegetative Tissue-Specific or Kernel-Specific Expression 7.1 Constitutive Expression [without a miRNA Tag]

In comparison with maize ubiquitin promoter (Zm.ubiquitin promoter::Zm.ubiquitin intron) and sugarcane bacilliform virus promoter (pBPSMM247), rice CCoAMT1 promoter in combination with Zm.ubiquitin intron and CCoAMT1 terminator (pBPSMM325) showed medium to strong constitutive and ubiquitous expression in all tissues and organs at different developmental stages. Strong ubiquitous expression can also be detected in in vitro plants.

TABLE 11

GUS expression controlled by monocot constitutive promoter candidates

| | Promoter (GUS expression levels) | | |
|---|---|---|---|
| Tissues/Developmental stages | pBPSMM232* | pBPSMM247* | pBPSMM325 |
| 3 days after co-cultivation | ++++ | +++ | +++ |
| Leaves at 5-leaf stage | +++++ | +++++ | ++++ |
| Roots at 5-leaf stage | +++++ | +++++ | ++++ |
| Leaves at flowering stage | +++++ | +++++ | +++ |
| Stem | +++ | +++ | +++ |
| Pre-pollination | +++++ | +++++ | ++ |
| 5 days after pollination [DAP] | +++++ | +++ (7 DAP) | ND |
| 30 DAP | +++++ | +++++ | ++ |
| Dry seeds | ND | +++ | ++ |
| Imbibition/germination | +++++ | ++++ | ND |

*Positive controls as a constitutive promoter (pBPSMM232 = Zm.ubiquitin promoter::Zm.ubiquitin intron:: GUS (PIV2)::NOS terminator; pBPSMM247 = sugarcane bacilliform virus promoter::GUS (PIV2) ::NOS terminator); pBPSMM325 = Os.CCoAMT1 promoter::Zm.ubiquitin intron::GUS (PIV)2::Os.CCoAMT1 terminator; a range of GUS expression levels measured by histochemical assay (− to +++++), ND: not determined yet 7.2 Vegetative Tissue-Specific or Kernel-Specific Expression Controlled by miRNA Tag in the Terminator Region To control either vegetative tissue-specific or kernel-specific expression, BPS.MRT1 or BPS.MRT2 is inserted between GUS gene and NOS terminator at SacI site in pBPSMM232, pBPSMM247, or pBPSMM235 to generate pBPSPR1 or pBPSPR002, pBPSPR003 or pBPSPR004, or pBPSPR005 or pBPSPR006, respectively. A chimeric construct composed of a miRNA tag can be transformed into monocotyledonous or dicotyledonous plants such as rice, barley, maize, wheat, ryegrass, *Arabidoposis*, canola, soybean, tobacco, but is not restricted to these plant species. Any methods for improving expression in monocotyledonous plants are applicable such as addition of intron or exon with intron in 5'UTR either non-spliced or spliced. Standard methods for transformation in the art can be used if required. Transformed plants are selected under the selection agent of interest and regenerated using known methods. Selection scheme is examined at early developmental stages of tissues or tissue culture cells. Gene expression levels can be determined at different stages of development and at different generations (T0 to T2 plants or further generations). Results of the evaluation in plants lead to determine appropriate genes to be used in this promoter construct.

Example 8: From Root and Kernel-Preferable Expression to Root or Kernel-Specific Expression

8.1 Root and Kernel-Preferable Expression [without a miRNA Tag]

The following four promoter constructs showed root and kernel-preferable expression in maize (Table 12). First, rice Caffeoyl-CoA-O-methyltransferase (CCoAMT1) promoter::ubiquitin-intron::NOS terminator (pBPSMM271) showed low expression in leaves and stem of T1 plants but strong expression in roots. GUS stain was also detected in kernel and pollen.

Second, OsC-8,7-sterol-isomerase promoter::Zm.ubiquitinintron::NOS terminator (pBPSMM331) showed weak expression in most parts of the plants but good expression in roots and kernels. Third, maize HRGP promoter containing the ubiquitin intron and the HRGP termiantor (pBPSET003) showed no expression in leaves but strong expression in roots and silk. In kernels expression is predominantly in the embryo and only weak in the endosperm. Fourth, maize Lactate-dehydrogenase (LDH) promoter::Zm.ubiquitinintron::NOS or LDH terminator (pBPSMM272 or pBPSET007, respectively) showed weak expression in leaves but good expression in roots and kernels.

TABLE 12

GUS expression controlled by monocot root and kernel-preferable promoter candidates

| Tissues & Developmental stages | pBPSMM232* | pBPSMM271 | pBPSMM331 | pBPSET003 | pBPSMM272 or pBPSET007 |
|---|---|---|---|---|---|
| 3 days after co-cultivation | ++++ | + | ND | ND | +++ |
| Leaves at 5-leaf stage | +++++ | + | + | − | ++ |
| Roots at 5-leaf stage | +++++ | ++++ | +++ | ++++ | ++++ |
| Leaves at flowering stage | +++++ | + | ++ | − | ++ |
| Stem | +++ | + | ND | ND | + |
| Pre-pollination | +++++ | +++ | ++++ | ND | +++ |
| 5 days after pollination [DAP] | +++++ | +++ | ND | ND | +++ |
| 30 DAP | ++++ | +++ | ++ | ++ | +++ |
| Dry seeds | ND | ND | ND | ND | ND |
| Imbibition/germination | +++++ | +++ | ND | ND | +++ |

*positive control as a constitutive promoter (pBPSMM232 = Zm.ubiquitin promoter::Zm.ubiquitin intron::GUS (PIV2)::NOS terminator); a range of GUS expression levels measured by histochemical assay (− to +++++), ND: not determined yet

8.2 Root or Kernel-Specific Expression Controlled by miRNA Tag in the Terminator Region To control either root-specific or kernel-specific expression, BPS.MRT1 or BPS.MRT2 is inserted between GUS gene and NOS terminator at SacI site in pBPSMM271, pBPSMM272, pBPSMM331, pBPSET003, or pBPSET007 to generate pBPSPR007 or pBPSPR008, pBPRPR009 or pBPSPR010, pBPRPR011 or pBPSPR012, pBPRPR013 or pBPSPR014, or pBPRPR015 or pBPSPR016, respectively. A chimeric construct composed of a miRNA tag can be transformed into monocotyledonous or dicotyledonous plants such as rice, barley, maize, wheat, ryegrass, Arabidoposis, canola, soybean, tobacco, but is not restricted to these plant species. Any methods for improving expression in monocotyledonous plants are applicable such as addition of intron or exon with intron in 5'UTR either non-spliced or spliced. Standard methods for transformation in the art can be used if required. Transformed plants are selected under the selection agent of interest and regenerated using known methods. Selection scheme is examined at early developmental stages of tissues or tissue culture cells. Gene expression levels can be determined at different stages of development and at different generations (T0 to T2 plants or further generations). Results of the evaluation in plants lead to determine appropriate genes to be used in this promoter construct.

Example 9: From Leaf and Endoperm-Preferable Expression to Leaf-Specific or Endosperm-Specific Expression

9.1 Leaf and Endosperm-Preferable Expression [without a miRNA Tag]

Os.CP12 promoter::Zm.ubiquitin intron::GUS (PIV2)::NOS terminator (pBPSMM304) showed strong expression in leaves and endosperm, but not in roots or embryo.

TABLE 13

GUS expression controlled by leaf and endosperm-preferable monocot promoter

| Tissues/Developmental stages | pBPSMM232* | pBPSMM304 |
|---|---|---|
| 3 days after co-cultivation | ++++ | + |
| In vitro leaves | +++++ | ++++ |
| In vitro roots | +++++ | − |
| Leaves | +++++ | ++++ |
| Roots | +++++ | − |
| Kernel pre-pollination | +++++ | + |
| Kernel 30 DAP - Endosperm | +++++ | ++++ |
| Kernel 30 DAP - Embryo | +++++ | − |
| Dry seeds | ++++ | ND |

*positive control as a constitutive promoter (pBPSMM232 = Zm.ubiquitin promoter::Zm.ubiquitin intron::GUS (PIV2)::NOS terminator); a range of GUS expression levels measured by histochemical assay (− to +++++),
ND: not determined yet

9.2 Leaf or Endosperm-Specific Expression Controlled by miRNA Tag in the Terminator Region To control either leaf-specific or endosperm-specific expression, BPS.MRT1 or BPS.MRT2 is inserted between GUS gene and NOS terminator at SacI site in pBPS304 to generate pBPSPR017 or pBPSPR018, respectively. A chimeric construct composed of a miRNA tag can be transformed into monocotyledonous or dicotyledonous plants such as rice, barley, maize, wheat, ryegrass, *Arabidoposis*, canola, soybean, tobacco, but is not restricted to these plant species. Any methods for improving expression in monocotyledonous plants are applicable such as addition of intron or exon with intron in 5'UTR either non-spliced or spliced. Standard methods for transformation in the art can be used if required. Transformed plants are selected under the selection agent of interest and regenerated using known methods. Selection scheme is examined at early developmental stages of tissues or tissue culture cells. Gene expression levels can be determined at different stages of development and at different generations (T0 to T2 plants or further generations). Results of the evaluation in plants lead to determine appropriate genes to be used in this promoter construct.

Example 10: Mature microRNA Profiling

Expression profiling of mature miRNAs in maize tissues was obtained using the 46 *Arabidopsis thaliana* (Ath) miRNA assays developed by Applied Biosystems (Chen et al. 2005, Nucleic Acids Research. 33:e179). Table 14 represents the 46 miRNA sequences that were used for the profiling.

Total RNA from 11 different maize samples (Table 14) was extracted with Trizol reagent following the instruction recommended by manufactory (Invitrogen 15596-026). Maize glyceraldehyde-3-phosphate dehydrogenase (GADPH) subunit C was used for an internal control to normalize miRNA expression among different tissue samples.

TABLE 14 miRNA sequence for the profiling

| Name | Sequence | SEQ ID NO |
|---|---|---|
| Ath-miR156 | UGACAGAAGAGAGUGAGCAC | 225 |
| Ath-miR156g | CGACAGAAGAGAGUGAGCACA | 226 |
| Ath-miR156h | UUGACAGAAGAAAGAGAGCAC | 227 |
| Ath-miR157 | UUGACAGAAGAUAGAGAGCAC | 228 |
| Ath-miR158 | UCCCAAAUGUAGACAAAGCA | 229 |
| Ath-miR159a | UUUGGAUUGAAGGGAGCUCUA | 230 |
| Ath-miR159b | UUUGGAUUGAAGGGAGCUCUU | 231 |
| Ath-miR159c | UUUGGAUUGAAGGGAGCUCCU | 232 |
| Ath-miR160 | UGCCUGGCUCCCUGUAUGCCA | 1 |
| Ath-miR161 | UUGAAAGUGACUACAUCGGGG | 233 |
| Ath-miR162 | UCGAUAAACCUCUGCAUCCAG | 234 |
| Ath-miR163 | UUGAAGAGGACUUGGAACUUCGAU | 2 |
| Ath-miR164 | UGGAGAAGCAGGGCACGUGCA | 235 |
| Ath-miR164c | UGGAGAAGCAGGGCACGUGCG | 236 |
| Ath-miR165 | UCGGACCAGGCUUCAUCCCCC | 237 |
| Ath-miR166 | UCGGACCAGGCUUCAUUCCCC | 238 |
| Ath-miR167 | UGAAGCUGCCAGCAUGAUCUA | 3 |
| Ath-miR167c | UUAAGCUGCCAGCAUGAUCUU | 239 |
| Ath-miR167d | UGAAGCUGCCAGCAUGAUCUGG | 240 |
| Ath-miR168 | UCGCUUGGUGCAGGUCGGGAA | 241 |
| Ath-miR169 | CAGCCAAGGAUGACUUGCCGA | 242 |
| Ath-miR169b | CAGCCAAGGAUGACUUGCCGG | 243 |
| Ath-miR169d | UGAGCCAAGGAUGACUUGCCG | 244 |
| Ath-miR169h | UAGCCAAGGAUGACUUGCCUG | 245 |
| Ath-miR170 | UGAUUGAGCCGUGUCAAUAUC | 246 |
| Ath-miR171 | UGAUUGAGCCGCGCCAAUAUC | 247 |
| Ath-miR171b | UUGAGCCGUGCCAAUAUCACG | 248 |
| Ath-miR172 | AGAAUCUUGAUGAUGCUGCAU | 4 |
| Ath-miR173 | UUCGCUUGCAGAGAGAAAUCAC | 249 |
| Ath-miR319 | UUGGACUGAAGGGAGCUCCC | 250 |
| Ath-miR319c | UUGGACUGAAGGGAGCUCCU | 251 |
| Ath-miR393a | UCCAAAGGGAUCGCAUUGAUC | 252 |
| Ath-miR394a | UUGGCAUUCUGUCCACCUCC | 253 |
| Ath-miR395a | CUGAAGUGUUUGGGGGAACUC | 254 |
| Ath-miR395b | CUGAAGUGUUUGGGGGACUC | 255 |
| Ath-miR396a | UUCCACAGCUUUCUUGAACUG | 256 |
| Ath-miR396b | UUCCACAGCUUUCUUGAACUU | 257 |
| Ath-miR397a | UCAUUGAGUGCAGCGUUGAUG | 258 |
| Ath-miR397b | UCAUUGAGUGCAUCGUUGAUG | 259 |
| Ath-miR398a | UGUGUUCUCAGGUCACCCCUU | 260 |
| Ath-miR398b | UGUGUUCUCAGGUCACCCCUG | 261 |
| Ath-miR399a | UGCCAAAGGAGAUUUGCCCUG | 262 |
| Ath-miR399b | UGCCAAAGGAGAGUUGCCCUG | 263 |
| Ath-miR399d | UGCCAAAGGAGAUUUGCCCCG | 264 |
| Ath-miR399e | UGCCAAAGGAGAUUUGCCUCG | 265 |
| Ath-miR399f | UGCCAAAGGAGAUUUGCCCGG | 266 |

TABLE 15

Maize materials used for miRNA profiling

| Library ID | Tissue | Description |
|---|---|---|
| AC094 | Kernel | 16 days post pollination. Kernels at blister stage R2 |

TABLE 15-continued

Maize materials used for miRNA profiling

| Library ID | Tissue | Description |
|---|---|---|
| AC081 | Kernel | 23 days post pollination. Kernels only (milk stage) |
| AC086 | Kernel | 30 days post pollination. Kernels at R4, early dough |
| AC095 | Kernel | 36 days post pollination. Kernels at beginning of dent stage, early R5 |
| AC089 | Root | Roots (only), 2 leaf to 9 leaf stages. From greenhouse plants, 12 dap (V2), 21 dap (V6), and 35 dap (V9). |
| AC118 | Root | Two samples were combined for the drought maize root library |
| AC085 | Upper leaf | 56 (pretasseling) and 84 dap and 23 dpp (R3). Upper leaves at seed-fill |
| AC082 | Lower leaf | Lower leaf tissue, from 12 dap (V2), 21 dap (V6), and 56 dap (pretassel). |
| AC080 | Ear | 1 and 9 days post pollination |
| AC079 | Tassel | Immature and mature tassels at 44, 51, 56, 70 dap(anthesis). Stages are 10-leaf, 13-leaf, just before tassel emergence, and anthesis (V10 to R1). |
|  | Callus | 21 days |

Several tissue-specific miRNAs were identified through the profiling (Table 16).

TABLE 16

Relative expression of miRNAs in different maize tissues.

| Average of relative expression level | lower leaf | upper leaf | root | root, drought | tassel | kernel, R2 | kernel, R3 | kernel, R4 | kernel, R5 | ear | callus |
|---|---|---|---|---|---|---|---|---|---|---|---|
| ath-miR156 | 0.05 | 0.06 | 36.29 | 0.36 | 9.72 | 0.12 | 1469.50 | 996.49 | 15.55 | 0.00 | 134.96 |
| ath-miR164 | 0.62 | 0.14 | 39.69 | 2.61 | 9.09 | 0.84 | 345.50 | 289.53 | 4.27 | 1.61 | 2.01 |
| ath-miR170 | 0.02 | 0.01 | 8.20 | 0.07 | 2.51 | 0.60 | 2112.79 | 1719.49 | 14.36 | 0.02 | 1.47 |
| ath-miR396b | 0.00 | 0.00 | 0.11 | 0.00 | 0.95 | 0.00 | 142.89 | 40.11 | 0.10 | 0.00 | 0.26 |
| ath-miR156g | 0.02 | 0.04 | 21.23 | 0.14 | 3.79 | 0.04 | 751.31 | 544.26 | 5.82 | 0.00 | 65.12 |
| ath-miR164c | 0.22 | 0.08 | 17.68 | 1.09 | 5.39 | 0.34 | 406.60 | 128.18 | 1.82 | 0.50 | 0.52 |
| ath-miR171 | 0.01 | 0.00 | 6.23 | 0.06 | 2.46 | 0.46 | 2024.72 | 1644.35 | 4.13 | 0.01 | 2.32 |
| ath-miR397a | 0.00 | 0.00 | 0.00 | 0.00 | 0.05 | 0.00 | 59.70 | 19.52 | 0.04 | 0.00 | 3.93 |
| ath-miR156h | 0.00 | 0.00 | 0.08 | 0.00 | 0.02 | 0.00 | 2.96 | 3.23 | 0.02 | 0.00 | 0.00 |
| ath-miR165 | 0.45 | 0.39 | 15.80 | 2.29 | 4.09 | 0.70 | 3660.80 | 1740.77 | 15.34 | 0.44 | 0.00 |
| ath-miR171b | 0.00 | 0.01 | 0.43 | 0.02 | 1.99 | 0.02 | 276.84 | 54.19 | 0.24 | 0.00 | 0.00 |
| ath-miR397b | 0.00 | 0.00 | 0.00 | 0.00 | 0.00 | 0.00 | 0.14 | 0.11 | 0.00 | 0.00 | 0.00 |
| ath-miR157 | 0.00 | 0.00 | 0.04 | 0.00 | 0.02 | 0.00 | 1.62 | 1.58 | 0.02 | 0.00 | 0.10 |
| ath-miR166 | 0.52 | 0.84 | 27.81 | 5.26 | 10.15 | 1.05 | 7512.02 | 3237.04 | 37.50 | 0.79 | 32.76 |
| ath-miR172 | 0.00 | 0.04 | 30.39 | 0.05 | 6.89 | 0.01 | 610.71 | 138.30 | 0.23 | 0.00 | 0.22 |
| ath-miR398a | 0.03 | 0.10 | 0.03 | 0.02 | 0.17 | 0.16 | 139.69 | 31.63 | 0.30 | 0.00 | 0.81 |
| ath-miR158 | 0.00 | 0.00 | 0.00 | 0.00 | 0.00 | 0.00 | 0.03 | 0.02 | 0.00 | 0.00 | 0.00 |
| ath-miR167 | 0.24 | 0.49 | 52.18 | 2.42 | 16.13 | 2.95 | 19579.50 | 15335.46 | 83.98 | 0.44 | 92.18 |
| ath-miR173 | 0.00 | 0.00 | 0.00 | 0.00 | 0.00 | 0.00 | 0.03 | 0.02 | 0.00 | 0.00 | 0.00 |
| ath-miR398b | 0.07 | 0.12 | 0.02 | 0.02 | 0.18 | 0.15 | 113.83 | 24.07 | 0.45 | 0.00 | 0.98 |
| ath-miR159a | 0.70 | 1.74 | 9.17 | 1.12 | 5.95 | 0.19 | 499.99 | 167.53 | 3.69 | 0.61 | 3.68 |
| ath-miR167c | 0.27 | 0.57 | 40.05 | 1.91 | 13.41 | 2.57 | 13523.59 | 8992.73 | 55.09 | 0.38 | 62.65 |
| ath-miR319 | 0.00 | 0.00 | 0.24 | 0.05 | 0.11 | 0.01 | 375.35 | 61.39 | 0.43 | 0.05 | 1.28 |
| ath-miR399a | 0.00 | 0.01 | 0.86 | 0.03 | 0.29 | 0.00 | 208.27 | 39.40 | 0.05 | 0.00 | 8.12 |
| ath-miR159b | 0.24 | 0.96 | 3.19 | 0.44 | 2.13 | 0.10 | 217.23 | 60.24 | 1.34 | 0.21 | 2.73 |
| ath-miR167d | 0.09 | 0.12 | 6.22 | 0.18 | 8.87 | 3.08 | 74431.14 | 37597.33 | 103.19 | 0.03 | 1.84 |
| ath-miR319c | 0.00 | 0.00 | 0.03 | 0.00 | 0.01 | 0.00 | 10.09 | 1.85 | 0.01 | 0.00 | 0.06 |
| ath-miR399b | 0.00 | 0.01 | 0.84 | 0.02 | 0.33 | 0.00 | 116.03 | 17.61 | 0.02 | 0.00 | 20.56 |
| ath-miR159c | 0.02 | 0.07 | 0.90 | 0.03 | 0.17 | 0.01 | 30.71 | 6.50 | 0.21 | 0.06 | 0.10 |
| ath-miR168 | 0.08 | 0.08 | 8.11 | 0.66 | 1.02 | 0.20 | 633.43 | 335.35 | 3.01 | 0.03 | 3.05 |
| ath-miR393a | 0.00 | 0.00 | 0.85 | 0.01 | 0.09 | 0.01 | 234.90 | 58.76 | 0.10 | 0.00 | 0.14 |
| ath-miR399d | 0.00 | 0.00 | 0.07 | 0.00 | 0.02 | 0.00 | 21.85 | 3.45 | 0.01 | 0.00 | 0.95 |
| ath-miR160 | 0.63 | 1.68 | 10.22 | 1.96 | 2.24 | 0.16 | 932.78 | 272.42 | 2.71 | 0.26 | 14.36 |
| ath-miR169 | 0.01 | 0.02 | 1.88 | 0.05 | 1.73 | 0.02 | 222.26 | 172.16 | 0.39 | 0.01 | 0.31 |
| ath-miR394a | 0.04 | 0.11 | 11.24 | 1.16 | 6.91 | 0.10 | 570.12 | 341.75 | 1.23 | 0.18 | 7.88 |
| ath-miR399e | 0.00 | 0.00 | 0.00 | 0.00 | 0.00 | 0.00 | 0.33 | 0.10 | 0.00 | 0.00 | 0.04 |
| ath-miR161 | 0.01 | 0.00 | 0.01 | 0.02 | 0.00 | 0.00 | 1.44 | 0.72 | 0.01 | 0.00 | 0.00 |
| ath-miR169b | 0.01 | 0.00 | 2.18 | 0.13 | 1.04 | 0.01 | 165.48 | 81.61 | 0.44 | 0.01 | 0.73 |
| ath-miR395a | 0.00 | 0.00 | 0.12 | 0.04 | 3.01 | 0.00 | 12.26 | 2.13 | 0.03 | 0.00 | 0.01 |
| ath-miR399f | 0.00 | 0.00 | 0.05 | 0.00 | 0.03 | 0.00 | 21.54 | 3.27 | 0.00 | 0.00 | 0.94 |
| ath-miR162 | 0.00 | 0.02 | 1.14 | 0.04 | 0.36 | 0.01 | 23.51 | 9.79 | 0.12 | 0.00 | 0.11 |
| ath-miR169d | 0.01 | 0.01 | 3.58 | 0.16 | 1.97 | 0.02 | 309.21 | 167.12 | 0.77 | 0.02 | 0.82 |
| ath-miR395b | 0.04 | 0.03 | 0.07 | 0.04 | 1.10 | 0.02 | 7.49 | 1.54 | 0.05 | 0.00 | 0.00 |
| ath-miR163 | 0.00 | 0.00 | 0.00 | 0.00 | 0.00 | 0.00 | 0.03 | 0.02 | 0.00 | 0.00 | 0.00 |
| ath-miR169h | 0.01 | 0.00 | 1.49 | 0.21 | 13.93 | 0.00 | 23.86 | 37.05 | 0.06 | 0.00 | 2.48 |
| ath-miR396a | 0.06 | 0.12 | 15.62 | 0.37 | 21.77 | 0.57 | 33028.58 | 9829.62 | 6.79 | 0.14 | 66.63 |

R2, R3, R4, and R5 represent different reproductive stages during kernel development: R2 stage (blister, 10-14 days after silking); R3 stage (milk, 18-22 days after silking); R4 stage (dough, 24-28 days after silking); R5 stage (dent, 35-42 days after silking). Callus represents embryogenic calli that were induced during regeneration process.

For example, miR319 and miR398a are expressed in kernel and callus (embryogenic calli). MiR167d and miR167 family members are highly expressed in different developmental stages of kernel. MiR172 has relatively high expression in root, tassel and kernel.

Example 11: Construction of Binary Vectors with miRNA Tags

Based on miRNA expression profiling, several binary vectors were constructed in such way that a short nucleotide sequence nearly complementary to miRNA was incorporated into 3' UTR of dsRed. RPR40 (SEQ ID NO: 216) was a negative control in which dsRed expression was under the control of ScBV promoter and NOS terminator. Two unique restriction enzyme sites, Sac I and Ava II, located between translation stop codon 'TAG' of dsRed and NOS terminator were used to insert a short nucleotide sequence to create RPR41, RPR42, RPR43, RPR44 and RPR45, respectively. Each short nucleotide sequence was determined by analyzing the region of mRNA potentially targeted by miRNA. For example, maize glossy 15 is targeted by miR172 in the region 5' CTGCAGCATCATCAGGATTCC 3' (i.e. miRNA tag) which is nearly complementary to miR172, 5' AGAAUCUUGAUGAUGCUGCAC 3'. A short oligo (SEQ ID NO: 220) containing miR172 target region plus 5 nt up and downstream, and Sac I and Ava II sites was chemically synthesized. This short oligo was then subcloned into RPR40 to create RPR42.

TABLE 17

Vectors and miRNA tags used for leakiness control

| Construct ID | MiRNA tag | Specific sequence containing miRNA tag | MiRNA Expression | Predicted DsRed2 expression |
|---|---|---|---|---|
| RPR40 (SEQ ID NO: 216) | None | N/A | N/A | Everywhere |
| RPR41 | MiR319 | SEQ ID NO: 221 | Kernel and callus | Everywhere but weak or no in kernel and callus |
| RPR42 | MiR172 | SEQ ID NO: 220 | Root, tassel, low in kernel | Everywhere but weak or no in root and tassel |
| RPR43 | MiR396a | SEQ ID NO: 222 | Kernel and callus | Everywhere but weak or no in kernel and callus |
| RPR44 | MiR398a | SEQ ID NO: 223 | Kernel | Everywhere but weak or no in kernel |
| RPR45 | MiR167d | SEQ ID NO: 224 | High in kernel, callus | Everywhere but weak or no in kernel and callus |

Example 12: Gene Silencing of miRNA Tagged DsRed2 in Maize Callus 12.1 Generation of Transgenic Calli Immature maize embryos were transformed with *Agrobacterium* containing either plasmids RPR40, RPR41, or RPR42. The transformation and selection procedures are modified from Ishida et al. (1996, Nature Biotech 14:745-749). Immature embryos were excised and placed into infection media. Infection media was removed and replaced with a suspension of *Agrobacterium* pre-induced for 1-4 hours in infection media containing 200 µM acetosyringone. *Agrobacterium* and embryos remained in liquid for 30 minutes for infection. Following infection, *Agrobacterium* solution was removed and embryos placed on co-culture media (modified from Ishida with the addition of 150 mg/L L-cysteine). Co-culture was allowed to occur for 2-3 days. Following co-culture, embryos were placed on a recovery media containing antibiotics to inhibit *Agrobacterium* growth for 7-10 days. Embryos that formed callus were placed on a selection media capable of suppressing growth of non-transformed tissue.

12.2 Identification of Transgenic Calli and Copy Number Analysis

The transgene copy number in maize calli transformed with RPR40 and RPR41 was determined by TaqMan analysis (Ingham et al., 2001, Biotechniques 31:132-4, 136-40). The TaqMan probe was chosen to target NOS terminator, which is located downstream of the DsRed2s as a common region in these three constructs. Only the transgenic maize calli were used for the following expression analysis for DsRed2.

12.3 Isolation of RNA from Transgenic Maize Callus

Callus tissues were ground with a mortar and pestle in liquid nitrogen followed by addition of 600 µL of lysis/binding solution (mirVana miRNA Isolation Kit, Ambion, Inc. Austin, Tex.) in order to extract total RNA based on the mirVana total RNA isolation protocol. The isolated RNA was DNase treated with DNA-free (Ambion, Inc) following the manufacture's protocol.

12.4 DsRed RNA Quantitation

DsRed2 and the endogenous maize GpC1 first strand cDNAs were synthesized from RNA isolated from RPR40 and RPR41 maize transgenic calli. RNA was reversed transcribed with the ImProm-II Reverse Transcription System (Promega, Madison, Wis.) using DsRed and GpC1 specific primers and following the manufacture's protocol. The relative levels of DsRed2 RNA from the RPR40 and RPR41 transgenic calli were determined by quantitative Taqman PCR using probes specific to DsRed2 and GpC1. First strand cDNA synthesized from callus total RNA was used as template. The TaqMan assay was performed essentially as for copy number analysis. To compare the relative amounts of DsRed2 RNA between calli, the data were first normalized to the internal GpC1 endogenous control. Quantitation of DsRed2 RNA was repeated 3 times for each RNA sample.

12.5 Fluorescence is Reduced in Maize Calli Expressing DsRed2 Tagged with the 319 and 172 miRNA Binding Sites Putative transgenic calli containing plasmids RPR40, RPR41, and RPR42 were examined for DsRed2 fluorescence under a microscope (Zeiss Stemi SV11) equipped with UV and rhodamine filter. The intensity of fluorescence was recorded as high, medium, low and none (see Table 18).

TABLE 18

DsRed2 fluorescent expression of transgenic calli

| Construct ID | High | Medium | Low | None | Total number of calli examined |
|---|---|---|---|---|---|
| RPR40 | 17 | 2 | 11 | 2 | 32 |
| RPR41 | 0 | 3 | 13 | 17 | 33 |
| RPR42 | 14 | 8 | 8 | 17 | 47 |

12.5 miRNA Tagged DsRed2 RNA is Significantly Reduced in Maize Calli

Each cluster of calli analyzed was confirmed to be transgenic by quantitative TaqMan PCR. This assay also provided a copy number of integrated DsRed2 constructs in each cluster of calli. To compare the relative levels of DsRed2 RNA in the RPR40 and RPR41 calli populations, RNA was isolated from individual transgenic positive calli and the amount of DsRed2 RNA determined by quantitative TaqMan analysis. The DsRed2 RNA is greatly reduced in RPR41 transgenic calli compared to RPR40 calli (Table 19). The difference in DsRed2 RNA levels between the RPR40 and RPR41 calli populations is significant with a p value of 0.0026.

TABLE 19

DsRed2 mRNA expression from transgenic calli

| callus # | plasmid | miRNA tag | copy number | Quantitation of DsRed2 RNA (3 repetitions) | | |
|---|---|---|---|---|---|---|
| | | | | A | B | C |
| 1 | RPR40 | none | 1 | 25.2 | 35.1 | 30.1 |
| 2 | RPR40 | none | 1 | 46.8 | 43.0 | 48.3 |
| 3 | RPR40 | none | 1 | 26.8 | 22.2 | 23.1 |
| 4 | RPR40 | none | 1 | 50.6 | 30.6 | 38.5 |
| 5 | RPR40 | none | 1 | 37.7 | 46.0 | 39.7 |
| 6 | RPR40 | none | 1 | 7.8 | 8.5 | 11.1 |
| 7 | RPR40 | none | 1 | 11.6 | 56.0 | 17.4 |
| 8 | RPR41 | mi319 | 3 | 8.9 | 8.6 | 9.6 |
| 9 | RPR41 | mi320 | 2 | 8.0 | 7.6 | 8.0 |
| 10 | RPR41 | mi321 | 1 | 1.1 | 1.0 | 1.4 |
| 11 | RPR41 | mi322 | 1 | 6.2 | 10.1 | 7.3 |
| 12 | RPR41 | mi323 | 1 | 11.5 | 12.5 | 14.3 |

We claim:

1. An expression construct comprising a promoter sequence functional in a monocotyledonous plant and functionally linked thereto a chimeric nucleotide sequence to be expressed, wherein said chimeric nucleotide sequence comprises:
   i) at least one sequence comprising an open reading frame encoding a protein that is capable of conferring an agronomically valuable trait in a monocotyledonous plant, wherein the agronomically valuable trait is selected from the group consisting of disease resistance, pest resistance, herbicide resistance, sterility, grain characteristics, vigor, time to harvest, enhanced nutrient content, novel growth patterns, flavors or colors, and salt, heat, drought, and/or cold tolerance, and
   ii) at least one sequence having at least 95% sequence complementarity to a tissue-specifically expressed microRNA sequence naturally occurring in said monocotyledonous plant, wherein the microRNA is a plant microRNA comprising:
      a) the nucleotide sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 225, 226, 227, 228, 229, 230, 231, 232, 233, 234, 235, 236, 237, 238, 239, 240, 241, 242, 243, 245, 245, 246, 247, 248, 249, 250, 251, 252, 253, 254, 255, 256, 257, 258, 259, 260, 261, 262, 263, 264, 265, or 266; or
      b) a nucleotide sequence having at least 95% sequence identity to the nucleotide sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 225, 226, 227, 228, 229, 230, 231, 232, 233, 234, 235, 236, 237, 238, 239, 240, 241, 242, 243, 245, 245, 246, 247, 248, 249, 250, 251, 252, 253, 254, 255, 256, 257, 258, 259, 260, 261, 262, 263, 264, 265, or 266;
   wherein the at least one sequence of i) and the at least one sequence of ii) are heterologous to each other.

2. The expression construct of claim 1, wherein said promoter is selected from the group consisting of constitutive promoters, tissue-preferential promoters, developmental promoters, and inducible promoters.

3. The expression construct of claim 1, wherein mismatches between the at least one sequence of ii) and the microRNA sequence naturally occurring in the plant are in the region corresponding to the 3'-region of said microRNA sequence.

4. The expression construct of claim 1, wherein the microRNA is tissue-specific expressed, spatially-regulated, developmental regulated, and/or regulated by biotic or abiotic stress factors.

5. The expression construct of claim 1, wherein said expression construct is in a plasmid.

6. The expression construct of claim 1, wherein the microRNA has an expression profile in the plant selected from the group consisting of:

a) expression in any tissue but no expression in seed;

b) expression in seeds but not in other tissues;

c) drought or other abiotic stress-induced expression;

d) plant pathogen-induced expression; and e) chemical induced expression.

7. The expression construct of claim 1, wherein the at least one sequence of ii) is positioned in a location of the nucleotide sequence to be expressed corresponding to the 5'-untranslated region or the 3'-untranslated region of said nucleotide sequence.

8. An expression vector comprising the expression construct of claim 1.

9. A transformed cell or a non-human organism comprising the expression construct of claim 1.

10. The transformed cell or non-human organism of claim 9, wherein said expression construct is inserted into its genome.

11. The transformed cell or non-human organism of claim 9, wherein said cell or organism is selected from the group consisting of mammalian, bacterial, fungal, nematode, and plant.

12. A transgenic monocot plant, plant cell or plant part comprising:

a) the expression construct of claim 1; or b) a vector comprising said expression construct of a).

13. A pharmaceutical preparation comprising:

a) the expression construct of claim 1; or b) a vector comprising said expression construct of a).

14. The expression construct of claim 1, wherein the plant microRNA comprises a nucleotide sequence having at least 95% sequence identity to the nucleotide sequence of SEQ ID NO: 22.

15. The expression construct of claim 1, wherein the plant microRNA comprises the nucleotide sequence of SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 225, 226, 227, 228, 229, 230, 231, 232, 233, 234, 235, 236, 237, 238, 239, 240, 241, 242, 243, 245, 245, 246, 247, 248, 249, 250, 251, 252, 253, 254, 255, 256, 257, 258, 259, 260, 261, 262, 263, 264, 265, or 266.

16. The expression construct of claim 1, wherein the microRNA comprises a nucleotide sequence identical to SEQ ID NO: 22.

* * * * *